US009458209B2

(12) United States Patent
Glass et al.

(10) Patent No.: US 9,458,209 B2
(45) **Date of Patent: *Oct. 4, 2016**

(54) METHODS AND COMPOSITIONS USING KLOTHO-FGF FUSION POLYPEPTIDES

(71) Applicant: NOVARTIS AG, Basel (CH)

(72) Inventors: David Glass, Cortland Manor, NY (US); Shou-Ih Hu, New Providence, NJ (US)

(73) Assignee: NOVARTIS AG, Basel (CH)

( * ) Notice: Subject to any disclaimer, the term of this patent is extended or adjusted under 35 U.S.C. 154(b) by 1 day.

This patent is subject to a terminal disclaimer.

(21) Appl. No.: 13/904,574

(22) Filed: May 29, 2013

(65) Prior Publication Data

US 2013/0324458 A1 Dec. 5, 2013

Related U.S. Application Data

(62) Division of application No. 12/360,970, filed on Jan. 28, 2009, now Pat. No. 8,481,031.

(60) Provisional application No. 61/063,015, filed on Jan. 28, 2008.

(51) Int. Cl.

| | |
|---|---|
| ***A61K 38/18*** | (2006.01) |
| ***A61K 39/395*** | (2006.01) |
| ***C07K 14/50*** | (2006.01) |
| ***C07K 16/00*** | (2006.01) |
| ***C12N 1/21*** | (2006.01) |
| ***C12N 5/10*** | (2006.01) |
| ***C07K 14/435*** | (2006.01) |
| ***C12N 9/24*** | (2006.01) |
| *A61K 38/00* | (2006.01) |

(52) U.S. Cl.

CPC ............. *C07K 14/435* (2013.01); *C07K 14/50* (2013.01); *C12N 9/2402* (2013.01); *C12Y 302/01031* (2013.01); *A61K 38/00* (2013.01); *C07K 2319/00* (2013.01)

(58) Field of Classification Search

None

See application file for complete search history.

(56) References Cited

U.S. PATENT DOCUMENTS

| | | | |
|---|---|---|---|
| 5,408,038 | A | 4/1995 | Smith et al. |
| 5,541,094 | A | 7/1996 | Anton et al. |
| 7,060,479 | B2 | 6/2006 | Dumas Milne Edwards et al. |
| 7,217,798 | B2 | 5/2007 | Hinton et al. |
| 7,223,563 | B2 | 5/2007 | Econs et al. |
| 7,259,248 | B2 | 8/2007 | Itoh et al. |
| 7,745,406 | B2 | 6/2010 | Econs et al. |
| 8,461,111 | B2 | 6/2013 | Blaber et al. |
| 2006/0160181 | A1 | 7/2006 | Luethy et al. |
| 2006/0281679 | A1 | 12/2006 | Itoh et al. |
| 2010/0298220 | A1 | 11/2010 | Blaber et al. |
| 2011/0195077 | A1 | 8/2011 | Glass et al. |
| 2011/0195895 | A1 | 8/2011 | Walker et al. |
| 2013/0122004 | A1 | 5/2013 | Glass et al. |
| 2014/0323396 | A1 | 10/2014 | Belouski et al. |
| 2016/0030585 | A1 | 2/2016 | Barnes et al. |

FOREIGN PATENT DOCUMENTS

| | | | |
|---|---|---|---|
| WO | 2009/095372 | A1 | 8/2009 |
| WO | 2009/117622 | A2 | 9/2009 |
| WO | 2011/092234 | A1 | 8/2011 |
| WO | 2015/200078 | A1 | 12/2015 |

OTHER PUBLICATIONS

Ito et al., Mech. Dev., 98:115-119 (2000).
Wu et al., J. Biol. Chem., 283(48):33304-33309 (2008).
Razzuae et al., Expert Opin. Ther. Patents, 20(6):1-5 (2010).
Carpenter et al., J. Clin. Endocrinol. Metab., 95:E352-E357 (2010).
Kuro-o, Pediatr. Nephrol., 25:583-590 (2010).
Drueke et al., Nephrol Dial. Transplant., 22:1524-1526 (2007).
White et al., Kidney International, 60:2079-2086 (2001).
Yu et al., Cytokine & Growth Factor Reviews, 16:221-232 (2005).
Kurosu et al., Journal of Biological Chemistry, 281(10:6120-6123 (2006).
Tohyama et al., Journal of Biological Chemistry, 279(11):9777-9784 (2004).
Torres et al., Kidney International, 71(8):730-737 (2007).
Wu et al., Journal of Biological Chemistry, 282(40:29069-29072 (2007).
Goetz et al., Mol. and Cell. Bio., pp. 3417 (2007).
Hessell et al., Nature, 449:101 (2007).
Lode et al., Proc. Nat. Acad. Sci. USA, 95:2475 (1998).
Ray, Sci. STKE, 2006(365):tw416 (2006).
Urakawa et al., Nature, 444:770 (2006).
The ADHR Consortium, Nature Genetics, 26:345-348 (2000).
Bai et al., The Journal of Biological Chemistry, 278(11):9843-9849 (2003).
Bai et al., Endocrinology, 145(11:5269-5279 (2004).
Bai et al., Am. J. Physiol. Endorinol. Metab., 296:E79-E88 (2009).
Ben-Dov et al., The Journal of Clinical Investigation—Research Article, 117(12):4003-4008 (2007).
Berndt et al., Pflugers Arch—Eur. J. Physiol., 454:615-623 (2007).
Shimada et al., Endocrinology, 143(8):3179-3182 (2002).
Strewler, PNAS—Commentary, 98(11):5945-5946 (2001).
Urakawa et al, Nature, 444:770-774 (2006) [Supplemental Data List; Supplemental Figures 1-6; Supplemental Discussion; Supplemental Methods and Supplemental Table].
Gasparian et al., "Overexpression in Escherichia coli and Purification of Human Fibroblast Growth Factor (FGF-2)", Biochemistry, 74(2):221-225 (2009).
Beenken et al., "The Structural Biology of the FGF19 Subfamily", Adv. Exp. Med. Biol. 728:1-24 (2012).

*Primary Examiner* — Christine J Saoud
(74) *Attorney, Agent, or Firm* — Hong-Van M. Le

(57) ABSTRACT

The present invention is directed to fusion polypeptides comprising a Klotho protein or an active fragment thereof and FGF23 or an active fragment thereof.

11 Claims, 8 Drawing Sheets

Figure 1A:
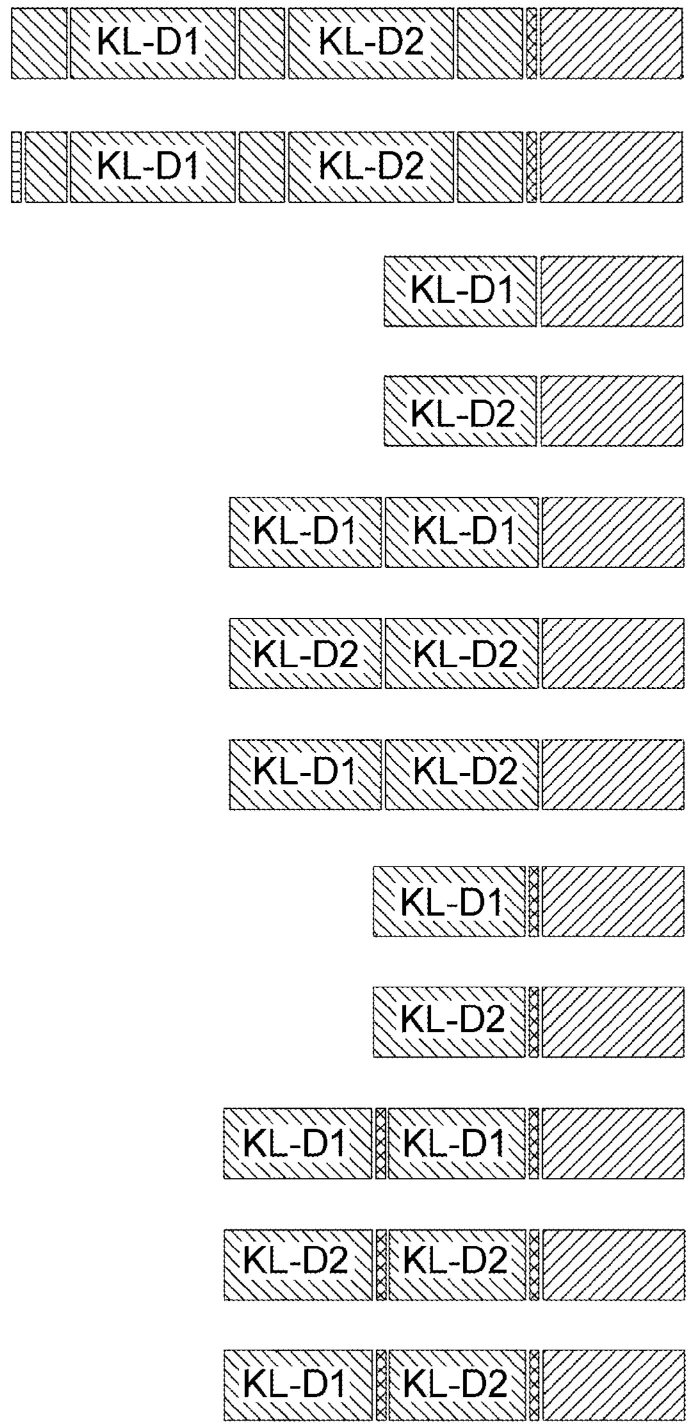

: Klotho (extracellular domain) or active fragment of Klotho;

: FGF23 (R179Q), FGF23, FGF 19, FGF21; : linker; : IgG signal peptide.

: Klotho (extracellular domain) or active fragment of Klotho;

: FGF23 (R179Q), FGF23, FGF 19, FGF21; : linker; : IgG signal peptide.

lane 1, Ctrl; lane 2, FGF23; lane 3, sKlotho; lanes 4-6, sKlotho-FGF23 lane 1, Ctrl; lane 2, FGF23; lane 3, sKlotho; lanes 4-6, sKlotho-FGF23 lane 1, purified sKlotho-FGF23-6xHis;
lane 2, molecular weight marker

METHODS AND COMPOSITIONS USING KLOTHO-FGF FUSION POLYPEPTIDES

This application is a divisional of U.S. application Ser. No. 12/360,970 filed Jan. 28, 2009, which claims priority to U.S. Provisional Application No. 61/063,015 filed Jan. 28, 2008, the contents of which are incorporated herein by reference in their entirety.

SEQUENCE LISTING

The instant application contains a Sequence Listing which has been submitted in ASCII format via EFS-Web and is hereby incorporated by reference in its entirety. Said ASCII copy, created on Aug. 13, 2013, is named PAT052377-US-DIV02_SL.txt and is 268,890 bytes in size.

1. BACKGROUND

The alpha-Klotho gene encodes a 130 kDa single pass type I transmembrane protein with an extracellular domain and a short cytoplasmic domain. The extracellular domain of alpha-Klotho protein comprises two subdomains termed, KL-D1 and KL-D2. These two subdomains share sequence homology to β-glucosidase of bacteria and plants. The extracellular domain of the alpha-Klotho protein may be bound to the cell surface by the transmembrane domain or may be cleaved and released into the extracellular milieu. Cleavage of the extracellular domain appears to be facilitated by local low extracellular $Ca^{2+}$ concentrations.

In addition to alpha-Klotho, a homolog of alpha-Klotho, beta-Klotho, has been identified (Ito et al., Mech. Dev. 98:115-9 (2000)). Beta-Klotho is also a single pass type I transmembrane protein with extracellular KL-D1 and KL-D2 subdomains.

Modulation of alpha-Klotho expression has been demonstrated to produce aging related characteristics in mammals. Mice homozygous for a loss of function mutation in the alpha-Klotho gene develop characteristics resembling human aging, including shortened lifespan, skin atrophy, muscle wasting, arteriosclerosis, pulmonary emphysema and osteoporosis (Kuro-o et al., Nature, 390:45-51 (1997)). In contrast, overexpression of the alpha-Klotho gene in mice extends lifespan and increases resistance to oxidative stress relative to wild-type mice (Kurosu et al., Science 309:1829-1833 (2005); Yamamoto et al., J. Biol. Chem. 280:38029-38034 (2005)).

Fibroblast growth factors (FGFs) constitute a family of homologous polypeptide growth factors expressed in many organisms (Ornitz and Itoh, Genome Biol. 2: reviews, 3005.1-3005.12 (2001)). Among vertebrate species, FGFs are highly conserved in both gene structure and amino-acid sequence, having between 13-71% amino acid identity with one another. In humans, there are 22 known members of the FGF family (FGF15 is the mouse ortholog of human FGF19, hence there is no human FGF15). During early development, FGFs regulate cell proliferation, migration, and differentiation, but in the adult organism, FGFs maintain homeostasis, function in tissue repair, and respond to injury.

FGFs function as growth factors by binding and thereby activating cell-surface FGF receptors. FGF receptors (FGFRs) are tyrosine kinase receptors that activate signal transduction through autophosphorylation of FGFR, phosphorylation of FRS2 (FGF receptor substrate 2) and ERK1/2 (extracellular signal-regulated protein kinase ½), and activating Egr-1 (early growth response-1). FGFs also have a high affinity for heparin sulfate proteoglycans. When bound to FGFs, heparin sulfate enhances the activation of FGFRs.

Recent studies have demonstrated strikingly similar biological characteristics between FGF23-deficient mice and alpha-Klotho-deficient mice (Shimada et al., J. Clin. Invest. 113:561-568 (2004); Yoshida et al. Endocrinology 143:683-689 (2002)), indicating functional crosstalk between FGF23 and alpha-Klotho. These studies led to the identification of alpha-Klotho as an obligatory partner of FGF23, in terms of both binding and signaling through its cognate FGF receptors (Urakawa et al., Nature 22:1524-6 (2007)). The alpha-Klotho gene is mainly expressed in kidney, parathyroid gland and choroid plexus. It is hypothesized that the tissue-specific expression of alpha-Klotho restricts activation of FGF23 signaling to those tissues.

Similar to FGF23/alpha-Klotho, beta-Klotho is an obligatory partner of FGF19 and FGF21, both in binding and in signaling through their respective cognate FGF receptors (Ogawa et al., Proc. Natl. Acad. Sci. USA 104:7432-7 (2007); Lin et al., J. Biol. Chem. 282:27227-84 (2007); and Wu et al., J. Biol. Chem. 282:29069-72 (2007)). Such studies have also demonstrated the involvement of beta-Klotho in regulating tissue-specific metabolic activity. Beta-Klotho was initially shown to act with FGF21 as a cofactor for regulating carbohydrate and lipid metabolism in adipose tissue. Beta-Klotho in conjunction with FGF19 regulates bile acid metabolism in liver, thus explaining elevated bile synthesis in beta-Klotho deficient mice (Ito et al., J Clin Invest. 2005 August; 115(8):2202-8).

U.S. Pat. No. 6,579,850 describes polypeptides and compositions comprising an alpha-Klotho polypeptide. Human and mouse alpha-Klotho polypeptides are disclosed. The patent also disclosed that compositions comprising the polypeptides are useful in treating a syndrome resembling premature aging, treating adult diseases, and suppressing aging.

U.S. Pat. No. 7,223,563 describes isolated nucleic acids encoding the FGF23 polypeptide sequence or recombinant cells comprising such an isolated nucleic acid. The patent further relates to methods of diagnosing and treating hypophosphatemic and hyperphosphatemic disorders, osteoporosis, dermatomyositis, and coronary artery disease.

U.S. Pat. No. 7,259,248 describes isolated nucleic acids encoding the FGF21 polypeptide sequence. The patent further relates to methods of diagnosing and treating liver disease, conditions related to thymic function, and methods of treating conditions of the testis.

2. SUMMARY OF THE INVENTION

The present invention is directed to methods, kits and compositions for preventing or treating age-related conditions or metabolic disorders with Klotho fusion polypeptides or soluble Klotho polypeptides. The Klotho fusion polypeptides of the present invention are formed of a Klotho protein or an active fragment thereof (e.g., sKlotho). In some embodiments, the present invention provides a Klotho fusion polypeptide comprising a Klotho protein or an active fragment thereof and a fibroblast growth factor or an active fragment thereof. In some embodiments, the fusion polypeptide comprises a Klotho polypeptide, a FGF (such as FGF23) and a modified Fc fragment. The Fc fragment can, for example, have decreased binding to Fc-gamma-receptor and increased serum half-life. Fusion proteins comprising sKlotho, FGF23 and FcLALA (a modified Fc fragment having decreased affinity for Fc-gamma-receptor and/or increased serum half-life) are described in SEQ ID NOs. 46, 47, 48, and 49. In some embodiments, the fusion polypeptide or protein comprises a FGF (e.g., FGF23) and a modified Fc fragment. Fusion proteins comprising FGF23 and FcLALA are described in SEQ ID NOs. 50, 51, 52 and 53.

In a first aspect, the invention provides a fusion polypeptide having at least one extracellular subdomain of a Klotho protein and a fibroblast growth factor or an active fragment thereof. In some embodiments, the fusion further comprises a modified Fc fragment having decreased affinity (e.g., decreased Ka or increased Kd) for Fc-gamma-receptor and/or increased serum half-life. The Klotho extracellular domain may be derived from either the alpha or beta Klotho isoforms. Further, although the FGF component of the Klotho fusion polypeptide is described primarily with reference to fibroblast growth factor-19, fibroblast growth factor-21 and fibroblast growth factor-23, it is contemplated that any of the twenty-three known FGFs can be used in practicing the invention. The reader of the instant application may assume that each of every combination of alpha or beta extracellular domain with each human FGF protein or an active fragment thereof are individually and specifically contemplated.

According to the present invention, the extracellular domain of the Klotho protein can include one or both of the KL-D1 and KL-D2 domains of a Klotho protein. In some embodiments, the Klotho fusion polypeptide of the invention has at least two extracellular subdomains of a Klotho protein. For example, the at least two extracellular subdomains can be at least two KL-D1 domains in tandem repeats, at least two KL-D2 domains in tandem repeats, or at least one KL-D1 domain and at least one KL-D2 domain. In one embodiment, the fusion polypeptide of the invention comprises amino acids 28-292 of the full length alpha Klotho protein. In another embodiment, the fusion polypeptide of the invention comprises amino acids 52-997 of the full length beta Klotho protein.

According to the present invention, the components of a fusion polypeptide comprising (1) at least one extracellular subdomain of a Klotho protein, (2) a FGF or an active fragment thereof, and (3) a modified Fc fragment having decreased affinity for Fc-gamma-receptor and/or increased serum half-life may be linked together covalently, for example, chemically linked or fused in frame by a peptide bond. They may also linked via a linker. Non-limiting examples of polypeptide linker are SEQ ID NOs:11, 12, 13, 14, 15, 16, 17, and 18. Such linkers may comprise at least one and up to about 30 repeats of SEQ ID NOs:11, 12, 13, 14, 15, 16, 17 and 18. In another non-limiting embodiment, the fusion comprises (2) a FGF or an active fragment thereof and (3) a modified Fc fragment. The various components of the fusion can be operatively linked in any order; the polypeptide (1) can be operatively linked to the N-terminus of the polypeptide for (2) or (3); the polypeptide for (2) can be operatively linked to the N-terminus of the polypeptide for (1) or (3); the polypeptide for (3) can be operatively linked to the N-terminus of the polypeptide for (1) or (2).

According to the present invention, the extracellular subdomain of a Klotho protein, the fibroblast growth factor and the (optional) modified Fc fragment having decreased affinity for Fc-gamma-receptor and/or increased serum half-life can be operatively linked to one another in a variety of orientations and manners. For example, the extracellular subdomain of the Klotho protein can be operatively linked to the N-terminus of the fibroblast growth factor or alternatively the fibroblast growth factor can be operatively linked to the N-terminus of an extracellular subdomain of the Klotho protein.

In one embodiment, the present invention provides a fusion polypeptide comprising a sKlotho of a Klotho protein and a linker. In another embodiment, the present invention provides a fusion polypeptide comprising a sKlotho of the alpha Klotho protein and a linker. In another embodiment, the present invention provides a fusion polypeptide comprising a sKlotho of the beta Klotho protein and a linker. In yet another embodiment, the present invention provides a human FGF protein or an active fragment thereof (e.g., without signal peptide) and a linker. Pharmaceutical compositions comprising the fusion proteins of the invention and their uses for treating or preventing age-related conditions or metabolic disorders are also encompassed by the present invention. In some embodiments, the fusion protein further comprises a modified Fc fragment having decreased affinity for Fc-gamma-receptor and/or increased serum half-life.

In one embodiment, the present invention provides a fusion polypeptide comprising a sKlotho of alpha Klotho protein with signal peptide fused (directly or indirectly via a linker) to FGF-23. In another embodiment, the present invention provides a fusion polypeptide comprising a sKlotho of alpha Klotho protein without signal peptide fused (directly or indirectly via a linker) to FGF-23. In another embodiment, the present invention provides sKlotho of alpha Klotho protein with signal peptide fused (directly or indirectly via a linker) to FGF-23 without signal peptide. In another embodiment, the present invention provides a fusion polypeptide comprising sKlotho of alpha Klotho protein without signal peptide fused (directly or indirectly via a linker) to FGF-23 without signal peptide. In some embodiments, the fusion protein further comprises a modified Fc fragment having decreased affinity for Fc-gamma-receptor and/or increased serum half-life.

In one embodiment, the present invention provides a fusion polypeptide comprising a sKlotho of alpha Klotho protein with signal peptide fused (directly or indirectly via a linker) to FGF-23 (R179Q) variant. In another embodiment, the present invention provides a fusion polypeptide comprising a sKlotho of alpha Klotho protein without signal peptide fused (directly or indirectly via a linker) to FGF-23 (R179Q) variant. In another embodiment, the present invention provides sKlotho of alpha Klotho protein with signal peptide fused (directly or indirectly via a linker) to FGF-23 (R179Q) variant without signal peptide. In another embodiment, the present invention provides a fusion polypeptide comprising sKlotho of alpha Klotho protein without signal peptide fused (directly or indirectly via a linker) to FGF-23 (R179Q) variant without signal peptide. In some embodiments, the fusion protein further comprises a modified Fc fragment having decreased affinity for Fc-gamma-receptor and/or increased serum half-life.

In one embodiment, the present invention provides a fusion polypeptide comprising (1) sKlotho of alpha Klotho protein with signal peptide; (2) a linker; and (3) FGF-23 (R179Q) variant without signal peptide. In another embodiment, the present invention provides a fusion polypeptide comprising (1) sKlotho of alpha Klotho protein without signal peptide; (2) a linker; and (3) FGF-23 (R179Q) variant without signal peptide. In some embodiments, the fusion polypeptides of the invention are glycosylated. In some embodiments, the fusion protein further comprises a modified Fc fragment having decreased affinity for Fc-gamma-receptor and/or increased serum half-life.

In one embodiment, the present invention provides a fusion polypeptide comprising (1) sKlotho of alpha Klotho protein with signal peptide (SEQ ID NO: 44 or SEQ ID NO:45); (2) a linker comprising SEQ ID NO:11; and (3)

FGF-23 (R179Q) variant without signal peptide (SEQ ID NO: 43). In another embodiment, the present invention provides a fusion polypeptide comprising (1) sKlotho of alpha Klotho protein without signal peptide (SEQ ID NO:7); (2) a linker comprising SEQ ID NO:11; and (3) FGF-23 (R179Q) variant without signal peptide (SEQ ID NO: 43). In one embodiment, the present invention provides a fusion polypeptide comprising the amino acid sequence of SEQ ID NO:19, 20, 40, or 41. In some embodiments, the fusion polypeptides of the invention are glycosylated.

In one embodiment, the present invention provides a fusion polypeptide comprising sKlotho of alpha Klotho protein with signal peptide (SEQ ID NO:44 or SEQ ID NO:45); and a linker comprising SEQ ID NO:11. In another embodiment, the present invention provides a fusion polypeptide comprising sKlotho of alpha Klotho protein without signal peptide (SEQ ID NO:7); and a linker comprising SEQ ID NO:11. In some embodiments, the fusion polypeptides of the invention are glycosylated. In some embodiments, the fusion protein further comprises a modified Fc fragment having decreased affinity for Fe-gamma-receptor and/or increased serum half-life.

In one embodiment, the present invention provides a fusion polypeptide comprising a human FGF protein or an active fragment thereof (e.g., without the signal peptide); and a linker comprising SEQ ID NO:11. In some embodiments, the fusion polypeptides of the invention are glycosylated. In some embodiments, the fusion protein further comprises a modified Fc fragment having decreased affinity for Fc-gamma-receptor and/or increased serum half-life.

In one embodiment, the present invention provides a pharmaceutical composition (e.g., in an intra-muscular administering form) comprising (e.g., as a sole pharmaceutically active ingredient) a fusion polypeptide (e.g., glycosylated or non-glycosylated) that comprises (1) sKlotho of alpha Klotho protein with signal peptide (SEQ ID NO: 44 or SEQ ID NO:45); (2) a linker comprising SEQ ID NO:11; and (3) FGF-23 (R179Q) variant without signal peptide (SEQ ID NO: 43); and (4) optionally, a modified Fc fragment having decreased affinity for Fc-gamma-receptor and/or increased serum half-life; and uses of the pharmaceutical composition for treating and/or preventing age-related conditions, such as muscular atrophy. In another embodiment, the present invention provides a pharmaceutical composition (e.g., in an intra-muscular administering form) comprising (e.g., as a sole pharmaceutically active ingredient) a fusion polypeptide (e.g., glycosylated or non-glycosylated) that comprises (1) sKlotho of alpha Klotho protein without signal peptide (SEQ ID NO:7); (2) a linker comprising SEQ ID NO:11; and (3) FGF-23 (R179Q) variant without signal peptide (SEQ ID NO: 43); and (4) optionally, a modified Fc fragment having decreased affinity for Fc-gamma-receptor and/or increased serum half-life; and uses of the pharmaceutical composition for treating and/or preventing age-related conditions, such as muscular atrophy. In one embodiment, the present invention provides a pharmaceutical composition (e.g., in an intra-muscular administering form) comprising (e.g., as a sole pharmaceutically active ingredient) a fusion polypeptide (e.g., glycosylated or non-glycosylated) comprising the amino acid sequence of SEQ ID NO:19, 20, 40, or 41; and uses of the pharmaceutical composition for treating and/or preventing age-related conditions, such as muscular atrophy.

In one embodiment, the present invention provides a pharmaceutical composition (e.g., in an intra-muscular administering form) comprising (e.g., as a sole pharmaceutically active ingredient) a fusion polypeptide (e.g., glycosylated or non-glycosylated) that comprises sKlotho of alpha Klotho protein with signal peptide (SEQ ID NO:44 or SEQ ID NO:45); and a linker comprising SEQ ID NO:11; and uses of the pharmaceutical composition for treating and/or preventing age-related conditions, such as muscular atrophy. In another embodiment, the present invention provides a pharmaceutical composition (e.g., in an intra-muscular administering form) comprising (e.g., as a sole pharmaceutically active ingredient) a fusion polypeptide (e.g., glycosylated or non-glycosylated) comprising sKlotho of alpha Klotho protein without signal peptide (SEQ ID NO:7); and a linker comprising SEQ ID NO:11; and uses of the pharmaceutical composition for treating and/or preventing age-related conditions, such as muscular atrophy. In some embodiments, the fusion protein further comprises a modified Fc fragment.

In one embodiment, the present invention provides a pharmaceuticals composition comprising (e.g., as a sole pharmaceutically active ingredient) a fusion polypeptide (e.g., glycosylated or non-glycosylated) that comprises a human FGF protein or an active fragment thereof (e.g., without the signal peptide); and a linker comprising SEQ ID NO:11.

Pharmaceutical compositions comprising the fusion proteins of the invention and their uses for treating or preventing age-related conditions (e.g., muscle atrophy) or metabolic disorders (e.g., diabete) are also encompassed by the present invention.

In one embodiment, the present invention provides a fusion polypeptide that is at least 85%, at least 90%, at least 91%, at least 92%, at least 93%, at least 94%, at least 95%, at least 96%, at least 96%, at least 97%, at least 98%, at least 99% identical to SEQ ID NO: 19. In another embodiment, the present invention provides a fusion polypeptide that is at least 85%, at least 90%, at least 91%, at least 92%, at least 93%, at least 94%, at least 95%, at least 96%, at least 96%, at least 97%, at least 98%, at least 99% identical to SEQ ID NO: 20.

In one embodiment, the present invention provides a fusion polypeptide that is at least 85%, at least 90%, at least 91%, at least 92%, at least 93%, at least 94%, at least 95%, at least 96%, at least 96%, at least 97%, at least 98%, at least 99% identical to SEQ ID NO: 40. In another embodiment, the present invention provides a fusion polypeptide that is at least 85%, at least 90%, at least 91%, at least 92%, at least 93%, at least 94%, at least 95%, at least 96%, at least 96%, at least 97%, at least 98%, at least 99% identical to SEQ ID NO: 41.

In one embodiment, the present invention provides a fusion polypeptide that is at least 85%, at least 90%, at least 91%, at least 92%, at least 93%, at least 94%, at least 95%, at least 96%, at least 96%, at least 97%, at least 98%, at least 99% or 100% identical to SEQ ID NO: 46. In another embodiment, the present invention provides a fusion polypeptide that is at least 85%, at least 90%, at least 91%, at least 92%, at least 93%, at least 94%, at least 95%, at least 96%, at least 96%, at least 97%, at least 98%, at least 99% or 100% identical to SEQ ID NO: 47.

In another embodiment, the present invention provides a fusion polypeptide that is at least 85%, at least 90%, at least 91%, at least 92%, at least 93%, at least 94%, at least 95%, at least 96%, at least 96%, at least 97%, at least 98%, at least 99% or 100% identical to SEQ ID NO: 48. In another embodiment, the present invention provides a fusion polypeptide that is at least 85%, at least 90%, at least 91%, at least 92%, at least 93%, at least 94%, at least 95%, at least 96%, at least 96%, at least 97%, at least 98%, at least 99% or 100% identical to SEQ ID NO: 49.

In one embodiment, the present invention provides a fusion polypeptide that is at least 85%, at least 90%, at least 91%, at least 92%, at least 93%, at least 94%, at least 95%, at least 96%, at least 96%, at least 97%, at least 98%, at least 99% or 100% identical to SEQ ID NO: 50. In another embodiment, the present invention provides a fusion polypeptide that is at least 85%, at least 90%, at least 91%, at least 92%, at least 93%, at least 94%, at least 95%, at least 96%, at least 96%, at least 97%, at least 98%, at least 99% or 100% identical to SEQ ID NO: 51.

In one embodiment, the present invention provides a fusion polypeptide that is at least 85%, at least 90%, at least 91%, at least 92%, at least 93%, at least 94%, at least 95%, at least 96%, at least 96%, at least 97%, at least 98%, at least 99% or 100% identical to SEQ ID NO: 52. In another embodiment, the present invention provides a fusion polypeptide that is at least 85%, at least 90%, at least 91%, at least 92%, at least 93%, at least 94%, at least 95%, at least 96%, at least 96%, at least 97%, at least 98%, at least 99% or 100% identical to SEQ ID NO: 53.

In one embodiment, the present invention provides a fusion polypeptide comprising a sKlotho of beta Klotho protein with signal peptide fused (directly or indirectly via a linker) to FGF-19 or an active fragment thereof. In some embodiments, the fusion further comprises a modified Fc fragment having decreased affinity for Fc-gamma-receptor and/or increased serum half-life. In another embodiment, the present invention provides a fusion polypeptide comprising a sKlotho of beta Klotho protein without signal peptide fused (directly or indirectly via a linker) to FGF-19 or an active fragment thereof. In another embodiment, the present invention provides a fusion polypeptide comprising a sKlotho of beta Klotho protein with signal peptide fused (directly or indirectly via a linker) to FGF-21 or an active fragment thereof. In another embodiment, the present invention provides a fusion polypeptide comprising a sKlotho of beta Klotho protein without signal peptide fused (directly or indirectly via a linker) to FGF-21 or an active fragment thereof.

The invention provides nucleic acid sequences encoding any of the Klotho fusion polypeptides described herein and host cells containing the nucleic acids. In some embodiments, the fusion further comprises a modified Fc fragment having decreased affinity for Fc-gamma-receptor and/or increased serum half-life.

The invention also provides composition having any of the Klotho fusion polypeptides contemplated herein. The compositions of the invention can further include heparin. In some embodiments, the fusion further comprises a modified Fc fragment having decreased affinity for Fc-gamma-receptor and/or increased serum half-life.

The invention also provides a method for treating or preventing an age-related condition in an individual. An individual (e.g., human) is administered a therapeutically effective dose of a pharmaceutical composition containing a Klotho fusion polypeptide, having at least one extracellular subdomain of a Klotho protein (e.g., alpha Klotho protein) and a fibroblast growth factor or an active fragment thereof so as to treat or prevent the age-related condition. In some embodiments, the fusion further comprises a modified Fc fragment having decreased affinity for Fc-gamma-receptor and/or increased serum half-life. In particular, the invention provides a method of treating or preventing muscle wasting comprising administering to an individual (e.g., human) an therapeutically effective amount of a fusion polypeptide having at least one extracellular subdomain of an alpha Klotho protein and a fibroblast growth factor (or an active fragment thereof).

Additionally, the invention provides a method for treating or preventing a metabolic disorder in an individual. An individual is administered a therapeutically effective dose of a pharmaceutical composition containing a fusion polypeptide of the invention, having at least one extracellular subdomain of a Klotho protein and a fibroblast growth factor (or an active fragment thereof) so as to treat the metabolic disorder. In some embodiments, the fusion further comprises a modified Fc fragment having decreased affinity for Fc-gamma-receptor and/or increased serum half-life. In particular, a fusion polypeptide of the invention having at least one extracellular subdomain of a beta-Klotho protein and a fibroblast growth factor 21 is useful for treating a metabolic disorder.

Klotho-FGF23 fusion polypeptides of the invention can be used for treating or preventing hyperphosphatemia or calcinosis in an individual. In some embodiments, the fusion further comprises a modified Fc fragment having decreased affinity for Fc-gamma-receptor and/or increased serum half-life. A pharmacologically effective dose of a pharmaceutical composition containing the Klotho fusion polypeptide of the invention, having at least one extracellular subdomain of a Klotho protein and a fibroblast growth factor, is administered to treat or prevent hyperphosphatemia or calcinosis. In particular, a Klotho fusion polypeptide of the invention having at least one extracellular subdomain of an alpha Klotho protein and a fibroblast growth factor 23 is useful for treating hyperphosphatemia or calcinosis.

Klotho-FGF23 fusion polypeptides of the invention can be used for treating or preventing chronic renal disease or chronic renal failure in an individual. In some embodiments, the fusion further comprises a modified Fc fragment having decreased affinity for Fc-gamma-receptor and/or increased serum half-life. A therapeutically effective dose of a pharmaceutical composition containing the Klotho fusion polypeptide of the invention, having at least one extracellular subdomain of a Klotho protein (e.g., alpha Klotho protein) and a fibroblast growth factor, is administered to treat or prevent chronic renal disease or chronic renal failure.

Klotho-FGF23 fusion polypeptides of the invention can be used for treating or preventing cancer (e.g., breast cancer) in an individual. In some embodiments, the fusion further comprises a modified Fc fragment having decreased affinity for Fc-gamma-receptor and/or increased serum half-life. A therapeutically effective dose of a pharmaceutical composition containing the Klotho fusion polypeptide of the invention, having at least one extracellular subdomain of a Klotho protein (e.g., alpha Klotho protein) and a fibroblast growth factor, is administered to treat or prevent cancer or breast cancer.

The present invention provides fusion polypeptides comprising at least one extracellular subdomain of Klotho protein and a FGF or an active fragment thereof for use in medicine. In some embodiments, the fusion further comprises a modified Fc fragment having decreased affinity for Fc-gamma-receptor and/or increased serum half-life. In one embodiment, the present invention provides fusion polypeptides comprising at least one extracellular subdomain of Klotho protein and a FGF or an active fragment thereof for use in treating or preventing muscle atrophy. The present invention also provides a method of treating or preventing an age related condition (e.g., muscle atrophy) comprising administering to an individual in need thereof a therapeutically effective dose of a pharmaceutical composition comprising a soluble Klotho protein.

The invention also includes kits for treating or preventing an age-related disorder or metabolic disorder in an individual. The kit includes instructions for use and a purified Klotho fusion polypeptide having at least one extracellular subdomain of a Klotho protein and a fibroblast growth factor. In some embodiments, the fusion further comprises a modified Fc fragment having decreased affinity for Fc-gamma-receptor and/or increased serum half-life.

The invention also provides a kit for producing a Klotho fusion polypeptide of the invention. The kit of the invention includes instructions for use and a nucleic acid encoding a Klotho fusion polypeptide, having at least one extracellular subdomain of Klotho protein and a fibroblast growth factor. In some embodiments, the fusion further comprises a modified Fc fragment having decreased affinity for Fc-gamma-receptor and/or increased serum half-life.

In one embodiment of the invention, the fusion polypeptide comprises: (a) a polypeptide comprising a fibroblast growth factor; and (b) a modified Fc fragment having decreased affinity for Fc-gamma-receptor and/or increased serum half-life In one embodiment of the invention, the polypeptide of (a) and the polypeptide of (b) are connected by a polypeptide linker. The linker can be repeated 1 to 30 times, or more.

In one embodiment of the invention, the polypeptide linker comprises an amino acid sequence selected from the group consisting of: SEQ ID NO:11, SEQ ID NO:12, SEQ ID NO:13, SEQ ID NO:14, SEQ ID NO:15, SEQ ID NO:16, SEQ ID NO:17, and SEQ ID NO:18.

In one embodiment of the invention, the polypeptide of (a) is connected by a peptide bond to the N-terminus of said polypeptide linker, and the polypeptide of (b) is connected by a peptide bond to the C-terminus of said polypeptide linker.

In one embodiment of the invention, the fusion polypeptide further comprises a signal peptide.

In one embodiment of the invention, the signal peptide is the IgG signal peptide.

In one embodiment of the invention, the fibroblast growth factor is fibroblast growth factor-23 or a fibroblast growth factor-23 variant (R179Q).

In one embodiment of the invention, the fibroblast growth factor is fibroblast growth factor-19 or fibroblast growth factor-21.

In one embodiment of the invention, fusion polypeptide comprises an amino acid sequence which is 95% or more identical to the amino acid sequence of SEQ ID NO: 51, or SEQ ID NO: 53.

In one embodiment of the invention, fusion polypeptide comprises the amino acid sequence of SEQ ID NO:51, or SEQ ID NO:53.

In one embodiment of the invention, fusion polypeptide comprises FcLALA.

3. BRIEF DESCRIPTION OF THE DRAWINGS

Figure 1B:
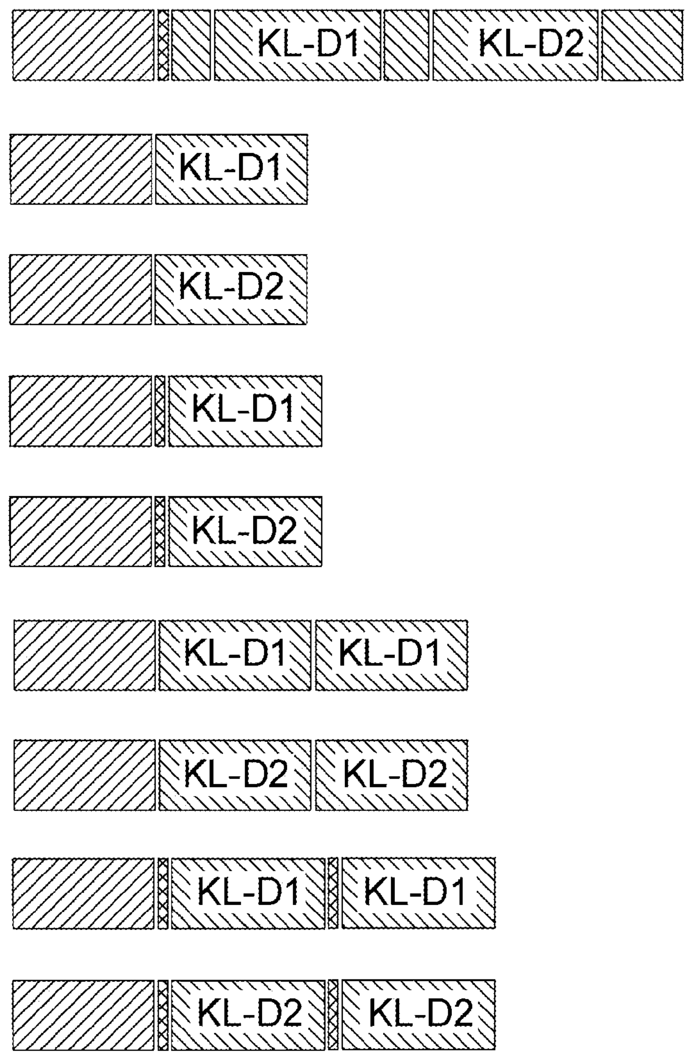

FIG. 1 illustrates several different embodiments of the Klotho fusion polypeptides of the invention. The represented fusion polypeptides include one or more Klotho extracellular subdomains operatively linked to a fibroblast growth factor. Polypeptides containing one or more Klotho extracellular subdomains include, for example, an extracellular domain of Klotho (e.g., a.a. 1 to 982 of human Klotho), or an active fragment of Klotho.

Figure 2A:
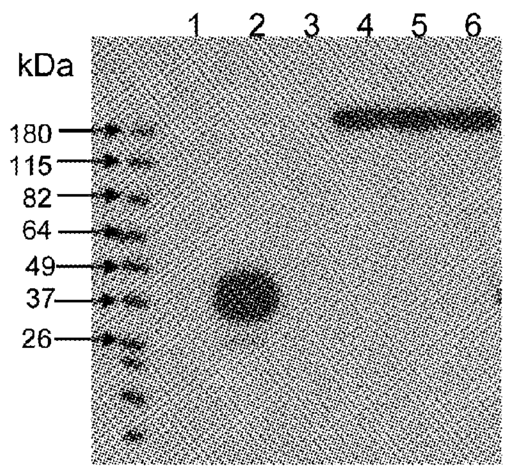
Figure 2B:
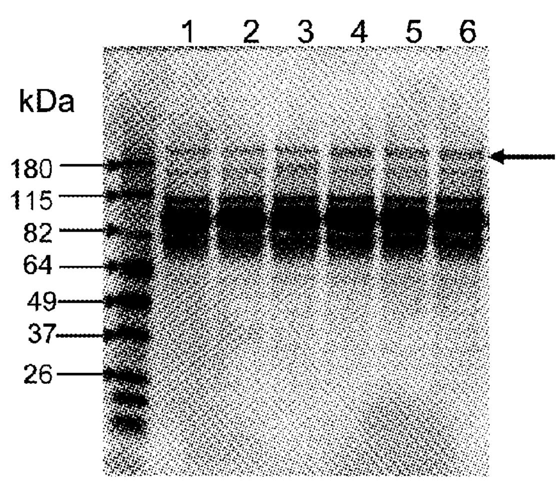
Figure 2C:
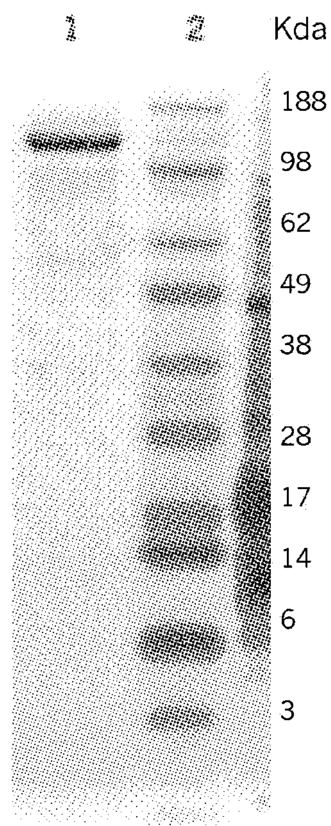

FIGS. 2A-2C depict protein expression of an sKlotho-FGF23 fusion protein. FIG. 2A shows that sKlotho-FGF23 fusion protein was detected in conditioned media by Western blotting with anti-FGF23 antibodies. FIG. 2B shows that sKlotho-FGF23 fusion protein was detected in conditioned media by SDS-PAGE and Coomassie blue staining FIG. 2C shows a highly purified sKlotho-FGF23-6×His fusion protein ("6×His" disclosed as SEQ ID No: 54), analyzed by SDS-PAGE and Coomassie blue staining.

Figure 3:
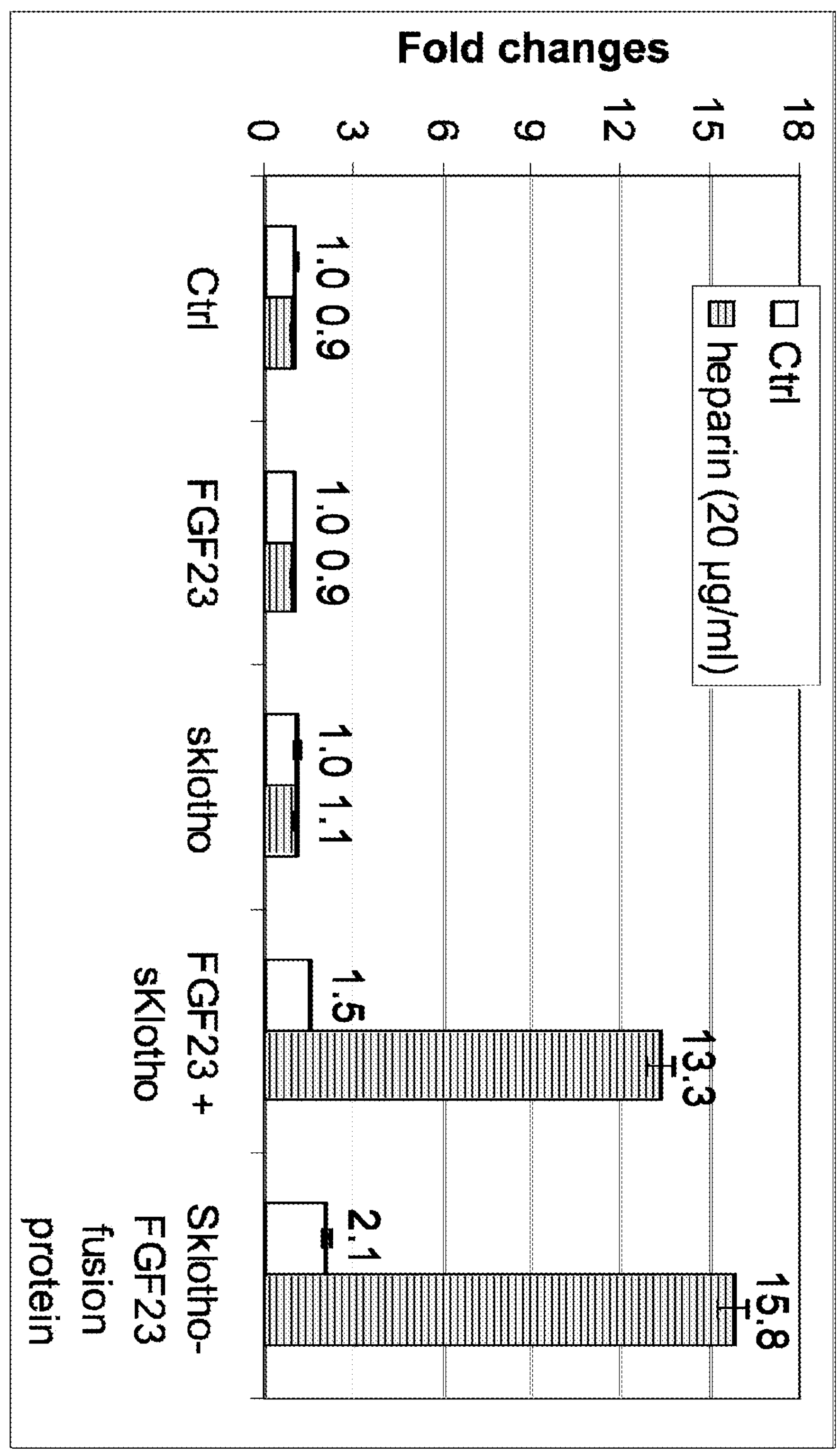

FIG. 3 illustrates the results of an Egr-1 luciferase assay comparing the activation level of Egr-1 in cells treated with conditioned media containing either a Klotho fusion polypeptide, a FGF23 polypeptide only, a soluble Klotho (sKlotho) polypeptide only, and a soluble Klotho polypeptide in combination with a FGF23 polypeptide in the absence or presence of heparin (20 μg/ml).

Figure 4A:
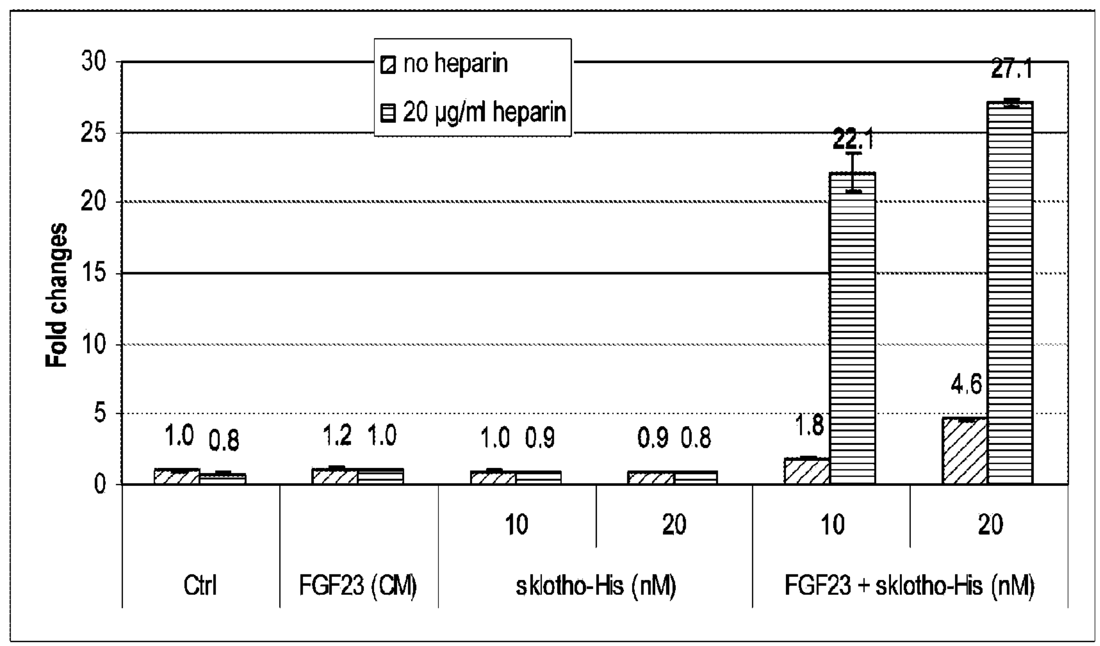
Figure 4B:
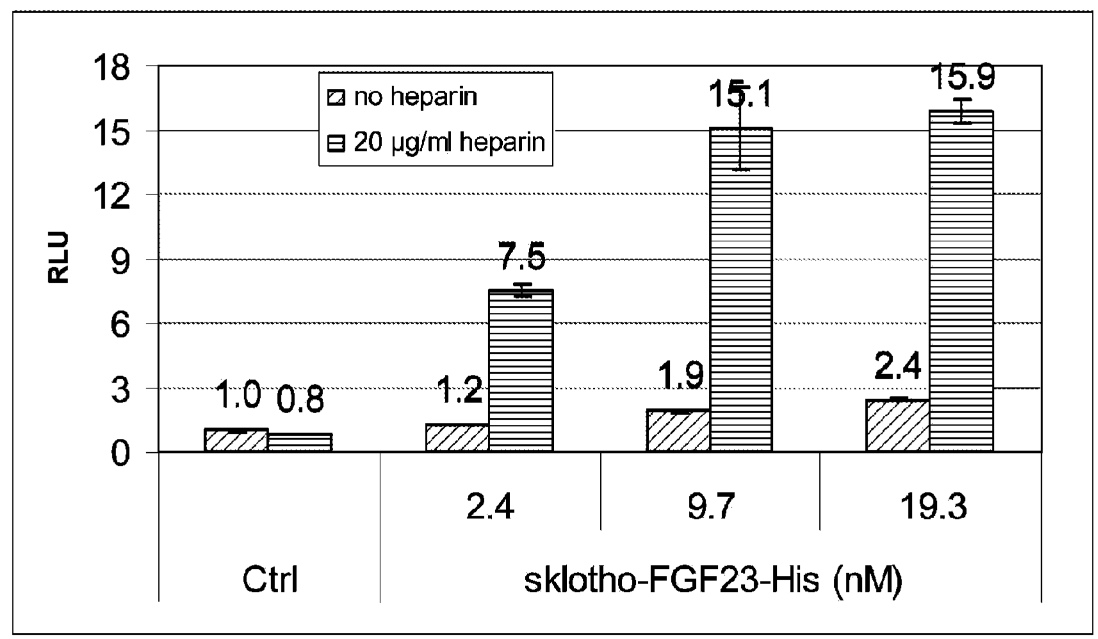

FIGS. 4A-4B depict the results of an Egr-1 luciferase assay comparing the activation level of Egr-1 in cells treated with purified Klotho fusion polypeptide, FGF23 polypeptide, or soluble Klotho polypeptide in the absence or presence of heparin. FIG. 4A shows an the results of an experiment comparing the activation level of Egr-1 in cells treated with FGF23 alone, sKlotho-His (10 nM or 20 nM) and a combination of FGF23 and sKlotho-His (10 nM or 20 nM) in the absence or presence of heparin (20 μg/ml). FIG. 4B shows Egr-1 luciferase reporter activity in cells treated with sKlotho-FGF23-His fusion (0 nM, 0.6 nM, 1.21 nM, 2.41 nM, 4.83 nM, 9.65 nM, and 19.3 nM).

Figure 5A:
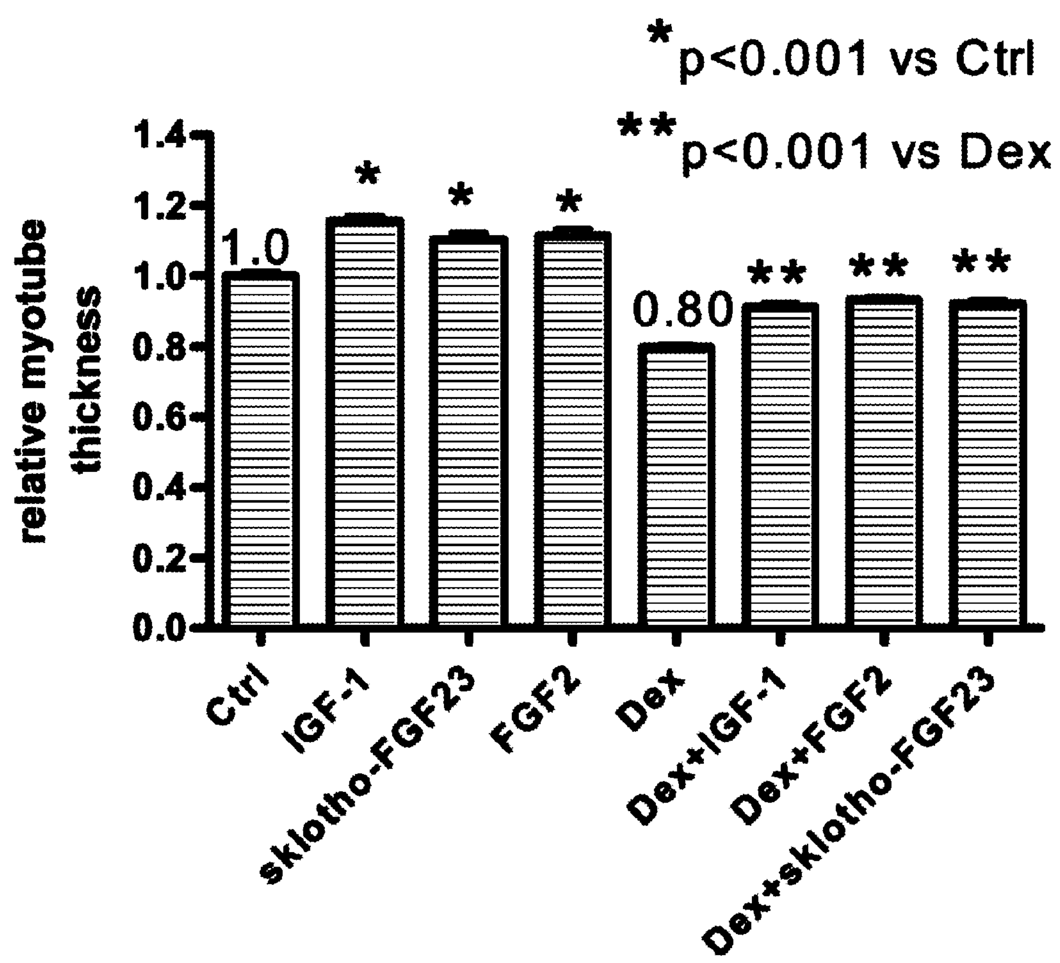
Figure 5B:
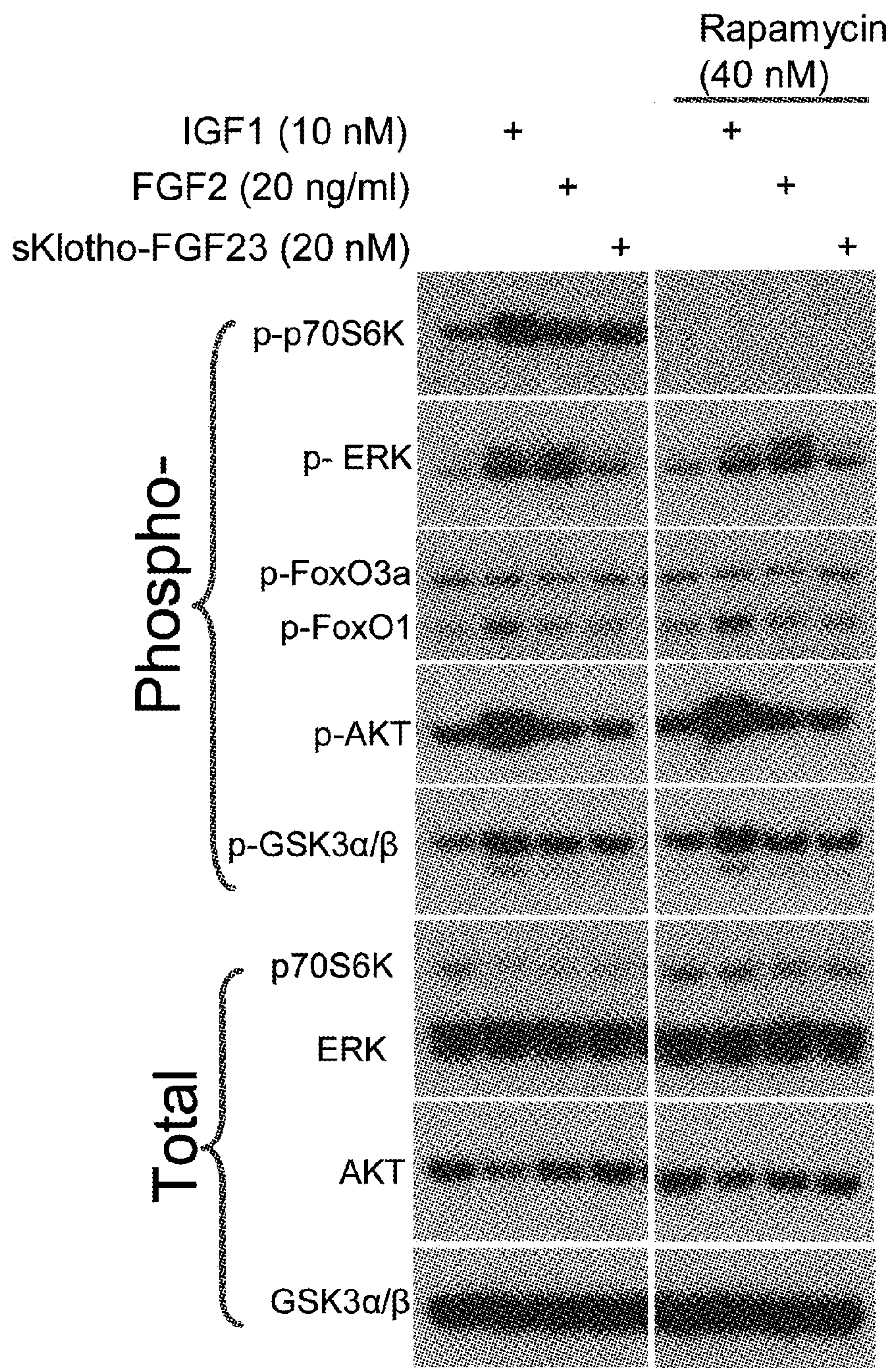

FIGS. 5A-5B illustrate the effect of treatment with a purified sKlotho fusion polypeptide on C2C12 muscle cells. FIG. 5A shows measurements of myotube diameter in C2C12 muscle cells treated with either IGF-1 (10 nM), FGF2 (20 ng/ml), or a purified Klotho fusion polypeptide (20 nM), in the absence or presence of dexamethasone (100 μM). FIG. 5B shows the phosphorylation of signaling pathway proteins in C2C12 muscle cells by IGF-1 (10 nM), FGF2 (20 ng/ml), or a purified Klotho fusion polypeptide (20 nM), in the absence or presence of rapamycin (40 nM).

4. DETAILED DESCRIPTION

The present invention is directed to methods, kits and compositions for preventing or treating age-related conditions and metabolic disorders. The fusion polypeptides of the invention include a Klotho protein or active fragment thereof. In some embodiments, the fusion polypeptides of the invention include a Klotho protein or an active fragment thereof operatively linked to a fibroblast growth factor polypeptide or active fragment thereof. In some embodiments, the fusion further comprises a modified Fc fragment with decreased ability to bind FcRn and/or increased stability in serum. In another embodiment, the fusion polypeptide comprises a FGF (e.g., FGF23) and a modified Fc fragment with decreased ability to bind FcRn and/or increased stability in serum.

The fusion proteins or sKlotho of the present invention are useful in the treatment and prevention of a variety of age-related conditions including sarcopenia, skin atrophy, muscle wasting, brain atrophy, atherosclerosis, arteriosclerosis, pulmonary emphysema, osteoporosis, osteoarthritis, immunologic incompetence, high blood pressure, dementia, Huntington's disease, Alzheimer's disease, cataracts, age-related macular degeneration, prostate cancer, stroke, diminished life expectancy, memory loss, wrinkles, impaired kidney function, and age-related hearing loss; and metabolic disorders including Type II Diabetes, Metabolic Syndrome, hyperglycemia, and obesity.

The present invention is based at least in part on the finding that despite the physical constraints (e.g., large size of both the Klotho and FGF polypeptides) the Klotho-FGF fusion polypeptides are highly effective in activating an FGF receptor. This finding is unexpected given that fusion of these two proteins would likely interfere with the heterodimerization and thus the activities of the proteins; e.g., the binding domains of the proteins may be perturbed by the fusion or the proteins may be mis-oriented spatially if put together in a "cis" formation.

The fusion polypeptides described herein are advantageous because they allow the administration of a single therapeutic protein that has enhanced activity compared to Klotho or FGF administered alone or together as separate polypeptides. The use of Klotho and FGF as a single fusion polypeptide rather than as two separate polypeptides (i.e., a Klotho polypeptide and a separate FGF polypeptide) is more effective at activating the FGF receptor.

Definitions

"Klotho polypeptide", "Klotho protein", or "Klotho" as used herein, includes active fragments, derivatives, mimetics, variants and chemically modified compounds or hybrids thereof of wild-type "Klotho". A Klotho active fragment has the ability to bind to an FGF polypeptide. Generally, a Klotho active polypeptide contains at least a Klotho subdomain (e.g., KL-D1 and KL-D2). Wild-type Klotho has the amino acid sequence as is found in nature. Exemplary Klotho polypeptides suitable for use with the present invention include alpha-Klotho (SEQ ID NO: 2) and beta-Klotho (SEQ ID NO: 4). Nucleotide and amino acid sequences of the alpha-Klotho and beta-Klotho are found in the GenBank database at Accession No. NM_004795; NP_004786 and NM_175737; NP_783864, respectively. Klotho polypeptides include those described in U.S. Pat. No. 6,579,850, the content of which is herein incorporated by reference in its entirety. The Klotho polypeptides include those from other species besides humans, including alpha-Klotho from mouse (NP_038851), rat (NP_112626), rabbit (NP_001075692) and beta-Klotho from mouse (NP_112457). Species predicted to have alpha-Klotho include chimpanzee (XP_522655), macaque (XP_001101127), horse (XP_001495662), cow (XP_001252500), platypus (XP_001510981), and chicken (XP_417105). Species predicted to have beta-Klotho include chimpanzee (XP_526550), macaque (XP_001091413), horse (XP_001495248), dog (XP_536257), rat (XP_001078178), platypus (XP_001512722), and chicken (XP_423224). The Klotho polypeptides have an amino acid sequence that is substantially identical to the amino acid sequence of SEQ ID NO: 2 or SEQ ID NO:4; i.e., at least 70%, 75%, 80%, 85%, 90%, 95%, 96%, 97%, 98%, 99% or more identical at the amino acid sequences of SEQ ID NO:2 or SEQ ID NO:4, or active fragment thereof.

"Fusion polypeptide" or "fusion protein", as used herein, shall mean a polypeptide comprising two or more different polypeptides or active fragments thereof that are not naturally present in the same polypeptide. In some embodiments, the two or more different polypeptides are operatively linked together covalently, e.g., chemically linked or fused in frame by a peptide bond. As used herein a "Klotho fusion polypeptide" is a fusion polypeptide which includes an amino acid sequence from a Klotho polypeptide or active fragment thereof. A fusion polypeptide can comprise, as non-limiting examples, Klotho (e.g., sKlotho), FGF (e.g., FG23), and (optionally) a modified Fc fragment (e.g., a modified Fc fragment with decreased binding affinity to FC-gamma-receptor and/or increased serum half-life). Examples of this type of fusion polypeptide are presented in SEQ ID NOs. 46 to 49. In another embodiment, the fusion proteins comprise FGF (e.g., FGF23) and a modified Fc (e.g., FcLALA). Fusion proteins comprising FGF23 and FcLALA are described in SEQ ID NOs. 50, 51, 52 and 53. FcLALA is a Fc fragment with a LALA mutation (L234A, L235A), which triggers ADCC with lowered efficiency, and binds and activates human complement weakly. Hessell et al. 2007 Nature 449:101-104.

"Fibroblast growth factor" and "FGF" are used interchangeably herein and shall refer to polypeptides that regulate cell proliferation, migration, differentiation, homeostasis, tissue repair and response to injury in an animal, including a human subject. FGFs have the ability to bind to a fibroblast growth factor receptor and regulate its activity, including autophosphorylation of FGFR, phosphorylation of FRS2 (FGF receptor substrate 2) and ERK1/2 (extracellular signal-regulated protein kinase ½), and activating Egr-1 (early growth response-1). The term "FGF" includes active fragments, derivatives, mimetics, variants and chemically modified compounds or hybrids thereof of wild-type "FGF", e.g., as known in the art and as described in U.S. Pat. No. 7,223,563 and U.S. Pat. No. 7,259,248, the contents of which are incorporated by reference in their entirety. Wild-type FGF has an amino acid sequence as is found in nature. Exemplary fibroblast growth factors suitable for use with the present invention include fibroblast growth factor-19 (FGF19; SEQ ID NO: 31), fibroblast growth factor-21 (FGF21; SEQ ID NO: 33), and fibroblast growth factor-23 (FGF23; SEQ ID NO: 35). The FGF polypeptides include those from other species besides humans, including murine FGFs. Generally, FGF polypeptides have an amino acid sequence that is substantially identical to the amino acid sequence of SEQ ID NO: 31, SEQ ID NO:33 or SEQ ID NO:35; i.e., having an amino acid sequence is which is at least 70%, 75%, 80%, 85%, 90%, 95%, 96%, 97%, 98%, 99% or more or 100% identical to the amino acid sequences of SEQ ID NO: 31 SEQ ID NO:33 or SEQ ID NO:35, or active fragments thereof. Additional non-limiting examples of FGF, particularly FGF23, are provided at aa 1002-1228 of SEQ ID NO:47; aa 1002-1228 of SEQ ID NO: 49; aa 1-251 of SEQ ID NO: 51, and aa 1-251 of SEQ ID NO:53; and sequences which are at least 70%, 75%, 80%, 85%, 90%, 95%, 96%, 97%, 98%, 99% or more or 100% identical to these sequences. Nucleotides encoding these sequences are provided in SEQ ID NOs: 46, 48, 50 and 52.

The term "FGF", includes active fragments of the full-length polypeptide. Active FGF fragments that are able to bind to their corresponding FGF receptors are known in the art and also contemplated for use in the present invention. One skilled in the art would appreciate, based on the sequences disclosed herein, that overlapping fragments of the FGFs can be generated using standard recombinant technology, for example, that described in Sambrook et al. (1989, Molecular Cloning: A Laboratory Manual, Cold Spring Harbor Laboratory Press, New York) and Ausubel et al. (1997, Current Protocols in Molecular Biology, Green & Wiley, New York). One skilled in the art would appreciate, based on the disclosure presented herein, that the biological activity of FGF fragments could be tested by methods well known in the art and described herein, including binding to the FGF receptor. Similarly, cell culture models which possess the necessary FGF signal transduction machinery (i.e. FGF receptor) may be transfected with FGF fragments and subsequently tested for alterations in FGF signaling, relative to wild type FGF.

FGFs are grouped into seven subfamilies based on the homology of the FGF core homology domain (approximately 120 amino acids long), which is flanked by N- and C-terminal sequences that are highly variable in both length and primary sequence, particularly among different FGF subfamilies (Goetz et al., Molecular and Cellular Biology, 2007, Vol. 27, 3417-3428). An FGF active polypeptide generally contains at least an FGF core homology domain. In some embodiments, an FGF active polypeptide may contain, in addition to an FGF core homology domain, flanking sequences which may confer additional specificity in binding FGF receptors. FGF19, FGF21, and FGF23 are grouped in the FGF19 subfamily because the core region of these ligands share high sequence identity relative to other FGFs (FGF19 v. FGF21: 38% identity; FGF19 v. FGF23: 36% identity). FGF19 subfamily members act analogously to signaling molecules of the endocrine system and regulate diverse physiological processes uncommon to classical FGFs (e.g., FGF19: energy and bile acid homeostasis; FGF21: glucose and lipid metabolism; and FGF 23: phosphate and vitamin D homeostasis).

"Fibroblast growth factor receptor" and "FGFR" as used herein refer to any one of FGFRs 1-4 known in the art, or splice variants thereof (e.g., FGFR1c). Exemplary fibroblast growth factor receptors suitable for use with the present invention include fibroblast growth factor receptor-19 (e.g., FGFR4-beta Klotho), fibroblast growth factor receptor-21 (e.g., FGFR1c-alpha Klotho), and fibroblast growth factor receptor-23 (e.g., FGFR1c-alpha Klotho, FGFR3-alpha Klotho, FGFR4-alpha Klotho).

"Extracellular domain", as used herein, refers to the fragment of a transmembrane protein existing outside of a cell (e.g., not including the intracellular or transmembrane region). The "extracellular domain of the Klotho protein", "soluble Klotho", or "sKlotho" (e.g., SEQ ID NO: 7; SEQ ID NO: 39), refers to an extracellular domain of the Klotho polypeptide that is capable of binding a fibroblast growth factor, and/or capable of enabling the binding of a fibroblast growth factor to a fibroblast growth factor receptor by binding to the fibroblast growth factor. The Klotho extracellular domain corresponds to amino acid residues 28-982 of the full length alpha Klotho sequence (SEQ ID NO: 2) and to amino acid residues 52-997 of the full length beta Klotho sequence (SEQ ID NO:4).

"Extracellular subdomain of Klotho protein" and "extracellular subdomain of Klotho protein" are used interchangeably herein and shall refer to a region in the extracellular domain of the Klotho polypeptide that is capable of binding a fibroblast growth factor, and/or is capable of enabling the binding of a fibroblast growth factor to a fibroblast growth factor receptor by binding to the fibroblast growth factor. In various embodiments, the fusion comprises a polypeptide comprising at least one extracellular subdomain of a Klotho protein; a polypeptide comprising a fibroblast growth factor; and, optionally, a modified Fc fragment having decreased affinity for Fc-gamma-receptor and/or increased serum half-life. The Klotho extracellular domain has two homologous subdomains that are repeated, i.e., KL-D1 (SEQ ID NO: 5) and KL-D2 (SEQ ID NO: 6). KL-D1 and KL-D2 correspond respectively to amino acid residues 58-506 and 517-953 of the full length alpha Klotho polypeptide (SEQ ID NO: 2) and respectively to amino acid residues 77-508 and 571-967 of the full length beta Klotho polypeptide (SEQ ID NO:4) and are suitable for use with the present invention. Generally, a polypeptide that contains at least one Klotho subdomain is a Klotho active polypeptide. The Klotho extracellular subdomain for use with the polypeptide of the invention may be an alpha Klotho or beta Klotho KL-D1 domain with an amino acid sequence that is substantially identical to the amino acid sequence of SEQ ID NO: 5 or SEQ ID NO: 37, respectively. Further, the Klotho KL-D1 domain may have an amino acid sequence that is at least 70%, 75%, 80%, 85%, 90%, 95%, 96%, 97%, 98%, 99% or more identical to the amino acid sequence of SEQ ID NO: 5 or SEQ ID NO: 37. The Klotho extracellular subdomain may also be an alpha or beta Klotho polypeptide KL-D2 domain that is substantially identical to the amino acid sequence of SEQ ID NO: 6 or SEQ ID NO: 38, respectively. In a further embodiment, the KL-D2 domain has an amino acid sequence that is at least at least 70%, 75%, 80%, 85%, 90%, 95%, 96%, 97%, 98%, 99% or more identical to the amino acid sequence of SEQ ID NO: 6 or SEQ ID NO: 38. In some embodiments, the fusion comprises at least two extracellular subdomains of the Klotho protein (e.g., KL-D1 and KL-D2; KL-D1 and KL-D1 in tandem repeats; KL-D2 and KL-D2 in tandem repeats, etc.).

"Modified Fc fragment", as used herein, shall mean an Fc fragment of an antibody comprising a modified sequence. The Fc fragment is a portion of an antibody comprising the CH2, CH3 and part of the hinge region. The modified Fc fragment can be derived from, for example, IgG1, IgG2, IgG3, or IgG4. FcLALA is a modified Fc fragment with a LALA mutation (L234A, L235A), which triggers ADCC with lowered efficiency, and binds and activates human complement weakly. Hessell et al. 2007 Nature 449:101-104. Additional modifications to the Fc fragment are described in, for example, U.S. Pat. No. 7,217,798. For example, in various modified Fc fragments: (a) amino acid residue 250 is glutamic acid and amino acid residue 428 is phenylalanine; or (b) amino acid residue 250 is glutamine and amino acid residue 428 is phenylalanine; or (c) amino acid residue 250 is glutamine and amino acid residue 428 is leucine. In some embodiments, amino acid residues 250 and 428 differ from the residues present in an unmodified Fc-fusion protein by amino acid residue 250 being glutamic acid or glutamine and amino acid residue 428 being leucine or phenylalanine, and wherein amino acid residues are numbered by the EU numbering system, as described in U.S. Pat. No. 7,217,798. In some embodiments, the modified Fc-fusion protein has a higher affinity for FcRn at pH 6.0 than at pH 8.0. Preferably, the modified Fc fragment has decreased affinity to FcRn and/or increased serum half-life. Non-limiting examples of modified Fc fragments include that at aa (amino acids) 1234-1459 of SEQ ID NO: 47; aa 1234 to 1450 of SEQ ID NO: 49; aa 257 to 482 of SEQ ID NO: 51; and aa 257 to 473 of SEQ ID NO: 53; and sequences which are at least 70%, 75%, 80%, 85%, 90%, 95%, 96%, 97%, 98%, 99% or more or 100% identical to these sequences. Nucleotides encoding these sequences are provided in SEQ ID NOs: 46, 48, 50 and 52.

"Signal peptide", as used herein, shall mean a peptide chain (3-60 amino acids long) that directs the post-translational transport of a protein to the endoplasmic reticulum and may be cleaved off. Exemplary signal peptides suitable for use with the present invention include the Klotho signal peptide (SEQ ID NO:19) and the IgG signal peptide (SEQ ID NO:20).

"Linker", as used herein, shall mean a functional group (e.g., chemical or polypeptide) that covalently attaches two or more polypeptides or nucleic acids so that they are connected with one another. As used herein, a "peptide linker" refers to one or more amino acids used to couple two proteins together (e.g., to couple the extracellular domain of Klotho and fibroblast growth factor-23). Peptide linkers suitable for use with the present invention include, but are not limited to, polypeptides with amino acid sequences represented by SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17 and SEQ ID NO:18. A polypeptide linker can comprise at least 1 and up to about 30 repeats of any of these amino acid sequences.

"Operatively linked", as used herein, shall mean the linking of two or more biomolecules so that the biological functions, activities, and/or structure associated with the biomolecules are at least retained. In reference to polypeptides, the term means that the linking of two or more polypeptides results in a fusion polypeptide that retains at least some of the respective individual activities of each polypeptide component. The two or more polypeptides may be linked directly or via a linker. In reference to nucleic acids, the term means that a first polynucleotide is positioned adjacent to a second polynucleotide that directs transcription of the first polynucleotide when appropriate molecules (e.g., transcriptional activator proteins) are bound to the second polynucleotide.

"Specifically binds", as used herein, shall refer to the ability of a first molecule to bind to a target molecule out of many, different types of molecules to which it may be exposed because of the ability of the first molecule to adopt a particular structure conducive to forming non-covalent interactions between itself and the other target molecule. The first molecule binds to the target forming a stable complex while there is substantially less recognition, contact, or complex formation of the first molecule with any other non-specific molecules.

"Polypeptide variant" or "protein variant", as used herein, refers to polypeptides in which one or more amino acids have been substituted by different amino acids from a reference sequence. It is well understood in the art that some amino acids may be substituted by others with broadly similar properties without changing the nature of the activity of the polypeptide (conservative substitutions) as described hereinafter. These terms also encompass polypeptides in which one or more amino acids have been added or deleted, or replaced with different amino acids, e.g., protein isoforms. An exemplary variant of fibroblast growth factor-23 suitable for use with the present invention is the fibroblast growth factor-23 variant (R179Q).

"Pharmaceutical composition", as used herein, shall mean a composition containing a compound (e.g., a fusion polypeptide of the invention) that may be administered to treat or prevent a disease or disorder in an individual.

"Individual" or "subject", as used herein, shall refer to a mammal, including, but not limited to, a human or non-human mammal, such as a bovine, equine, canine, ovine, or feline.

"Treat", as used herein, shall mean decrease, suppress, attenuate, diminish, arrest, or stabilize the development or progression of a disease. In the context of the invention, the administration of the polypeptides of the invention may be used to treat age-related conditions, including sarcopenia, skin atrophy, muscle wasting, brain atrophy, atherosclerosis, arteriosclerosis, pulmonary emphysema, osteoporosis, osteoarthritis, immunologic incompetence, high blood pressure, dementia, Huntington's disease, Alzheimer's disease, cataracts, age-related macular degeneration, prostate cancer, stroke, diminished life expectancy, memory loss, wrinkles, impaired kidney function, and age-related hearing loss; and metabolic disorders, including Type II Diabetes, Metabolic Syndrome, hyperglycemia, and obesity.

"Prevent", as used herein, shall refer to a decrease in the occurrence of a disorder or decrease in the risk of acquiring a disorder or its associated symptoms in a subject. In the context of the invention, the administration of the polypeptides of the invention may be used to prevent age-related conditions, including sarcopenia, skin atrophy, muscle wasting, brain atrophy, atherosclerosis, arteriosclerosis, pulmonary emphysema, osteoporosis, osteoarthritis, immunologic incompetence, high blood pressure, dementia, Huntington's disease, Alzheimer's disease, cataracts, age-related macular degeneration, prostate cancer, stroke, diminished life expectancy, memory loss, wrinkles, impaired kidney function, and age-related hearing loss; and metabolic disorders, including Type II Diabetes, Metabolic Syndrome, hyperglycemia, and obesity. The prevention may be complete, e.g., the total absence of an age-related condition or metabolic disorder. The prevention may also be partial, such that the likelihood of the occurrence of the age-related condition or metabolic disorder in a subject is less likely to occur than had the subject not received the present invention.

"Disease", as used herein, shall mean any condition or disorder that damages or interferes with the normal function of a cell, tissue, or organ.

"Age-related condition", as used herein, shall mean any disease or disorder whose incidence in a population or severity in an individual correlates with the progression of age. In one embodiment, the age-related condition is a disease or disorder whose incidence is at least 1.5 fold higher among human individuals greater than 60 years of age relative to human individuals between the ages of 30-40 and in a selected population of greater than 100,000 individuals. Age-related conditions relevant to the present invention include, but are not limited to, sarcopenia, skin atrophy, muscle wasting, brain atrophy, atherosclerosis, arteriosclerosis, pulmonary emphysema, osteoporosis, osteoarthritis, immunologic incompetence, high blood pressure, dementia, Huntington's disease, Alzheimer's disease, cataracts, age-related macular degeneration, prostate cancer, stroke, diminished life expectancy, memory loss, wrinkles, impaired kidney function, and age-related hearing loss.

"Metabolic disorder", as used herein, shall mean any disease or disorder that damages or interferes with normal function in a cell, tissue, or organ by affecting the production of energy in cells or the accumulation of toxins in a cell, tissue, organ, or individual. Metabolic disorders relevant to the present invention include, but are not limited to, Type II Diabetes, Metabolic Syndrome, hyperglycemia, and obesity.

An "effective dose" or "effective amount" is an amount sufficient to effect a beneficial or desired clinical result. In the context of the invention, it is an amount of a Klotho fusion polypeptide or sKlotho effective to produce the intended pharmacological, therapeutic or preventive result. A therapeutically effective dose results in the prevention or amelioration of the disorder or one or more symptoms of the disorder, (e.g., an age-related condition or metabolic disorder). Therapeutically effective doses will vary depending upon the subject and disease condition being treated, the weight and age of the subject, the severity of the disease condition, the manner of administration and the like which can be readily be determined by one of ordinary skill in the art.

"Klotho nucleic acid molecule", as used herein is a gene encoding a Klotho protein. An exemplary human Klotho gene is provided at GenBank Accession No. NM_004795 (SEQ ID NO:1). Additional non-limiting examples of Klotho are provided at aa 1-982 of SEQ ID NO:47 and aa 1-982 of SEQ ID NO: 49; and sequences which are at least 70%, 75%, 80%, 85%, 90%, 95%, 96%, 97%, 98%, 99% or more or 100% identical to these sequences.

"Fragment", as used herein, refers to a portion of a polypeptide or nucleic acid molecule. This portion contains, preferably, at least 10%, 20%, 30%, 40%, 50%, 60%, 70%, 80%, 90% or more of the entire length of the reference nucleic acid molecule or polypeptide. A fragment may contain 10, 20, 30, 40, 50, 60, 70, 80, 90, or 100, 200, 300, 400, 500, 600, 700, 800, 900, 1000 or up to 3000 nucleotides or amino acids.

The term "substantially identical" refers to a polypeptide or nucleic acid molecule exhibiting at least 50% identity to a reference amino acid sequence (for example, any one of the amino acid sequences described herein) or nucleic acid sequence (for example, any one of the nucleic acid sequences described herein). Preferably, such a sequence is at least 60%, 70%, 75%, 80% or 85%, 90%, 91%, 92%, 93%, 94%, 95%, 96%, 97%, 98%, 99% or more identical at the amino acid level or nucleic acid to the sequence used for comparison.

The present invention is directed to methods, kits and compositions for preventing or treating age-related conditions and metabolic disorders. In some embodiments, the invention provides a fusion polypeptide having at least one extracellular subdomain of a Klotho protein. In some embodiments, the fusion polypeptides further comprise a fibroblast growth factor or an active fragment thereof. In some embodiments, the fusion further comprises a modified Fc fragment having decreased affinity for Fc-gamma-receptor and/or increased serum half-life. In other embodiments, the fusion comprises an FGF (e.g., FGF19, FGF21, FGF23 or FGF23 variant R179Q) fused to a modified Fc (e.g., FcLALA). FcLALA is a Fc fragment with a LALA mutation (L234A, L235A), which triggers ADCC with lowered efficiency, and binds and activates human complement weakly. The Klotho extracellular domain may be derived from either the alpha or beta Klotho isoforms. Further, although the FGF component of the Klotho fusion polypeptide is described primarily with reference to fibroblast growth factor-19, fibroblast growth factor-21 and fibroblast growth factor-23, it is contemplated that any of the twenty-three known FGFs or an active fragment thereof can be used in practicing the invention.

The extracellular domain of the Klotho protein can include one or both of the KL-D1 and KL-D2 domains of a Klotho protein. In some embodiments, the Klotho fusion polypeptide has at least two extracellular subdomains of a Klotho protein. For example, the at least two extracellular subdomains can be at least two KL-D1 domains in tandem repeats, at least two KL-D2 domains in tandem repeats, or at least one KL-D1 domain and at least one KL-D2 domain.

The extracellular subdomain of a Klotho protein and the fibroblast growth factor (or an active fragment thereof) can be operatively linked to one another in a variety of orientations and manners. For example, the extracellular subdomain of the Klotho protein can be operatively linked to the N-terminus of the fibroblast growth factor or alternatively the fibroblast growth factor can be operatively linked to the N-terminus of the at least one extracellular subdomain of the Klotho protein.

The fusion polypeptide of the invention may include one or both of the Klotho extracellular domains, i.e., KL-D1 (SEQ ID NO: 5) and KL-D2 (SEQ ID NO: 6). KL-D1 and KL-D2 correspond respectively to amino acid residues 58-506 and 517-953 of the full length alpha Klotho polypeptide (SEQ ID NO: 2) and to amino acid residues 77-508 and 571-967 of the full length beta Klotho polypeptide (SEQ ID NO:4) and are suitable for use with the present invention. The Klotho fusion polypeptide may have a KL-D1 domain of an alpha Klotho polypeptide having an amino acid sequence that is substantially identical to the amino acid sequence of SEQ ID NO: 5 or of a beta Klotho polypeptide having an amino acid sequence that is substantially identical to the amino acid sequence of SEQ ID NO: 37. Specifically, the Klotho fusion polypeptide may have an amino acid sequence that is at least at least 70%, 75%, 80%, 85%, 90%, 95%, 96%, 97%, 98%, 99% or more identical to SEQ ID NO: 5 or SEQ ID NO: 37. The Klotho fusion polypeptide may have a KL-D2 domain of an alpha Klotho polypeptide with an amino acid sequence that is substantially identical to the amino acid sequence of SEQ ID NO: 6 or of a beta Klotho polypeptide having an amino acid sequence that is substantially identical to the amino acid sequence of SEQ ID NO: 38. Specifically, the Klotho fusion polypeptide may have an amino acid sequence that is at least at least 70%, 75%, 80%, 85%, 90%, 95%, 96%, 97%, 98%, 99% or more identical to SEQ ID NO: 6 or SEQ ID NO: 38, respectively.

In some embodiments, the Klotho fusion polypeptide of the invention is soluble and is capable of binding to an FGF receptor.

The Klotho fusion polypeptides of the invention can contain a polypeptide linker which connects the polypeptide having at least one extracellular subdomain of a Klotho protein and the fibroblast growth factor and the (optional) modified Fc fragment. Suitable linkers are well known in the art and generally contain several Gly and several Ser residues, e.g., $(Gly_4\ Ser)_3$ (SEQ ID NO: 11), $Gly_4$ Ser polypeptide (SEQ ID NO: 12), Gly (SEQ ID NO: 13), Gly Gly (SEQ ID NO: 14), Gly Ser (SEQ ID NO: 15), $Gly_2$ Ser (SEQ ID NO: 16), Ala (SEQ ID NO: 17), and Ala Ala (SEQ ID NO: 18). In some embodiments, the linker will have at least 2 and up to about 30 repeats of an amino acid sequence represented by any one of SEQ ID NO:12, SEQ ID NO:13, SEQ ID NO:14, SEQ ID NO:15, SEQ ID NO:16, SEQ ID NO:17, or SEQ ID NO:18.

When a polypeptide linker is present in the Klotho fusion polypeptide of the invention, the polypeptide having at least one extracellular subdomain of a Klotho protein may be connected by a peptide bond to the N-terminus of the linker polypeptide with the FGF connected by a peptide bond to the C-terminus of the polypeptide linker. Alternatively, the FGF may be connected by a peptide bond to the N-terminus of the linker polypeptide with the polypeptide having at least one extracellular subdomain of Klotho connected by a peptide bond to the C-terminus of the polypeptide linker A chemical linker can also be used to link the two polypeptides.

The Klotho fusion polypeptide of the invention may include a signal peptide. Exemplary signal peptides for use with the Klotho fusion polypeptide include, but are not limited to the Klotho signal peptide (SEQ ID NO: 8) and the IgG signal peptide (SEQ ID NO: 9).

In some embodiments, the invention provides a fusion between a FGF (e.g., FGF19, FGF21, FGF23, or FGF23 variant R179Q) and a modified Fc (e.g., FcLALA). The fusion can also optionally comprise linkers between the FGF and Fc portions. The fusion can also optionally comprise a signal peptide. In various embodiments, the invention encompasses nucleic acids encoding these fusion polypeptides, vectors comprising these nucleic acids, and host cells containing these nucleic acids.

4.1. Klotho and Fibroblast Growth Factor Polypeptides

The Klotho fusion polypeptides of the invention are expected to exhibit biological activities comparable to FGF in nature, such as binding to an FGF receptor and inducing the phosphorylation of an FGF receptor, FRS2 (FGF receptor substrate 2) and ERK1/2 (extracellular signal-regulated protein kinase ½) and activating Egr-1 (early growth response-1) gene. FGF is a secreted peptide growth factor that binds the FGF receptor. The amino acid and nucleic acid sequences of FGF are readily available to those of skill in the art. For example, exemplary nucleotide sequences for FGF19, FGF21, and FGF23 can be found in the GenBank database at Accession numbers: NM_005117, NM_019113, and NM_020638, respectively, and herein as SEQ ID NOs: 30, 32, and 34, respectively. Exemplary amino sequences for FGF19, FGF21, and FGF23 can be found in the GenBank database at Accession numbers: NP_005108, NP_061986, and NP_065689, respectively, and herein as SEQ ID NOs: 31, 35, and 35, respectively. Additionally, FGF may include one or more alterations which aid in the expression of the protein, e.g., the FGF23 (R179Q) variant (SEQ ID NO: 36).

The Klotho protein is a 130 kDa single pass type I transmembrane protein with an extracellular domain and a short cytoplasmic domain. The amino acid and nucleic acid sequences of Klotho are readily available to those of skill in the art. For example, exemplary nucleotide sequences for alpha-Klotho and beta-Klotho can be found in the GenBank database at Accession numbers: NM_004795 and NM_175737, respectively, and herein as SEQ ID NOs: 7 and 8, respectively. Exemplary amino acid sequences for alpha-Klotho and beta-Klotho can be found in the GenBank database at Accession numbers: NP_004786 and NP_783864, respectively, and herein as SEQ ID NOs: 2 and 4, respectively.

The Klotho fusion polypeptide of the invention can bind to a fibroblast growth factor receptor and has an alpha-Klotho or beta-Klotho extracellular domain operatively linked to either fibroblast growth factor-19 (SEQ ID NO: 31), fibroblast growth factor-21 (SEQ ID NO: 33), fibroblast growth factor-23 (SEQ ID NO: 35), or variants thereof (which include fibroblast growth factor-23 variant (R179Q) (SEQ ID NO: 36)).

Specifically, the Klotho fusion polypeptide of the invention may include an alpha-Klotho (SEQ ID NO: 2) which is operatively coupled to fibroblast growth factor-23 (SEQ ID NO: 35) or fibroblast growth factor-23 variant (R179Q) (SEQ ID NO: 36). Additionally, the Klotho fusion polypeptide of the invention may have beta-Klotho (SEQ ID NO: 4), which is operatively coupled to fibroblast growth factor-19 (SEQ ID NO: 31). The Klotho fusion polypeptide of the invention may include a beta-Klotho (SEQ ID NO: 4), which is operatively coupled to fibroblast growth factor-21 (SEQ ID NO: 33).

The invention includes homologs of the various Klotho and FGF genes and proteins encoded by those genes. A "homolog," in reference to a gene refers to a nucleotide sequence that is substantially identical over at least part of the gene or to its complementary strand or a part thereof, provided that the nucleotide sequence encodes a protein that has substantially the same activity/function as the protein encoded by the gene which it is a homolog of Homologs of the genes described herein can be identified by percent identity between amino acid or nucleotide sequences for putative homologs and the sequences for the genes or proteins encoded by them (e.g., nucleotide sequences for genes encoding Klotho and FGF or their complementary strands). Percent identity may be determined, for example, by visual inspection or by using various computer programs known in the art or as described herein. Sequence identity is typically measured using sequence analysis software (for example, Sequence Analysis Software Package of the Genetics Computer Group, University of Wisconsin Biotechnology Center, 1710 University Avenue, Madison, Wis. 53705, BLAST, BESTFIT, GAP, or PILEUP/PRETTYBOX programs). Such software matches identical or similar sequences by assigning degrees of homology to various substitutions, deletions, and/or other modifications. Conservative substitutions typically include substitutions within the following groups: glycine, alanine; valine, isoleucine, leucine; aspartic acid, glutamic acid, asparagine, glutamine; serine, threonine; lysine, arginine; and phenylalanine, tyrosine. In an exemplary approach to determining the degree of identity, a BLAST program may be used, with a probability score between $e^{-3}$ and $e^{-100}$ indicating a closely related sequence.

As used herein, the terms "homology" and "homologous" are not limited to designate proteins having a theoretical common genetic ancestor, but includes proteins which may be genetically unrelated that have, nonetheless, evolved to perform similar functions and/or have similar structures. Functional homology to the various proteins described herein also encompasses proteins that have an activity of the corresponding protein of which it is a homolog. For proteins to have functional homology, it is not required that they have significant identity in their amino acid sequences, but, rather, proteins having functional homology are so defined by having similar or identical activities. For example, with respect to a Klotho molecule, the polypeptide should have the functional characteristics of binding to an FGF polypeptide and enable the binding of the FGF to an FGFR. With respect to an FGF molecule, the polypeptide should have the functional characteristics of binding to an FGFR and causing the activation of FGFR (e.g., phosphorylation). Assays for assessing FGF binding to the FGF receptor and/or activation of the FGF signaling pathway are known in the art and described herein (See Example 2). Assays for assessing Klotho activity are also known in the art and described herein (e.g., binding to a FGF polypeptide). Proteins with structural homology are defined as having analogous tertiary (or quaternary) structure and do not necessarily require amino acid identity or nucleic acid identity for the genes encoding them. In certain circumstances, structural homologs may include proteins which maintain structural homology only at the active site or binding site of the protein.

In addition to structural and functional homology, the present invention further encompasses proteins having amino acid identity to the various Klotho and FGF amino acid sequences described herein. To determine the percent identity/homology of two amino acid sequences, the sequences are aligned for optimal comparison purposes (e.g., gaps can be introduced in the amino acid sequence of one protein for optimal alignment with the amino acid sequence of another protein). The amino acid residues at corresponding amino acid positions are then compared. When a position in one sequence is occupied by the same amino acid residue as the corresponding position in the other, then the molecules are identical at that position. The percent identity between the two sequences is a function of the number of identical positions shared by the sequences (i.e., % identity=# of identical positions/total # of positions multiplied by 100).

The amino acid sequences of molecules of the invention described herein have an amino acid sequence which is at least about 60%, 70%, 80%, 90%, 95%, 96%, 97%, 98%, 99% or more identical or homologous to an amino acid sequence described herein.

The nucleic acid sequences of molecules of the invention described herein have a nucleotide sequence which hybridizes to or is at least about 60%, 70%, 80%, 90%, 95%, 96%, 97%, 98%, 99% or more identical or homologous to a nucleotide sequence described herein.

Nucleic acid molecules appropriate for use in the fusion polypeptides of the invention may have a Klotho or FGF nucleotide sequence which hybridizes under stringent conditions to the complement of a nucleic acid molecule encoding Klotho or FGF, respectively. As used herein, the term "hybridizes under stringent conditions" is intended to describe conditions for hybridization and washing under which nucleotide sequences at least about 70%, 80%, 85%, 90% or more homologous to each other typically remain hybridized to each other. Such stringent conditions are known to those skilled in the art and can be found in Ausubel et al. Current Protocols in Molecular Biology, Wiley Interscience, New York (2001), 6.3.1-6.3.6. A specific, non-limiting example of stringent hybridization conditions are hybridization in 6× sodium chloride/sodium citrate (SSC) at about 45° C., followed by one or more washes in 0.2×SSC, 0.1% SDS at 50-65° C.

4.2. Klotho-FGF Fusion Polypeptides of the Invention

In some embodiments of the invention, a Klotho fusion polypeptide has a polypeptide chain having a first polypeptide sequence of a Klotho polypeptide or an active fragment thereof and a second polypeptide sequence encoding FGF or an active fragment thereof. In some embodiments, the fusion further comprises a modified Fc fragment having decreased affinity for Fc-gamma-receptor and/or increased serum half-life.

The invention includes fusion polypeptides which are at least about 95% or more homologous to an amino acid sequence presented in SEQ ID NO:19-28. The amino acid sequence of SEQ ID NO: 19 encodes a Klotho fusion polypeptide having a Klotho extracellular domain N-terminally linked to the FGF23 (R179Q) variant (SEQ ID NO: 36). The amino acid sequence of SEQ ID NO: 20 encodes a Klotho fusion polypeptide having an IgG signal peptide N-terminally linked to a Klotho extracellular domain lacking a signal peptide N-terminally linked to the FGF23 (R179Q) variant. The amino acid sequence of SEQ ID NO: 21 encodes a Klotho fusion polypeptide having a KL-D1 extracellular subdomain N-terminally linked to the FGF23 (R179Q) variant. The amino acid sequence of SEQ ID NO: 22 encodes a Klotho fusion polypeptide having a KL-D2 extracellular subdomain N-terminally linked to the FGF23 (R179Q) variant. The amino acid sequence of SEQ ID NO: 23 encodes a Klotho fusion polypeptide having two KL-D1 extracellular subdomains N-terminally linked to the FGF23 (R179Q) variant. The amino acid sequence of SEQ ID NO: 24 encodes a Klotho fusion polypeptide having two KL-D2 extracellular subdomains N-terminally linked to the FGF23 (R179Q) variant. The amino acid sequence of SEQ ID NO: 25 encodes a Klotho fusion polypeptide having the FGF23 (R179Q) variant N-terminally linked to a Klotho extracellular domain. The amino acid sequence of SEQ ID NO: 26 encodes a Klotho fusion polypeptide having the FGF23 (R179Q) variant N-terminally linked to a KL-D1 extracellular subdomain. The amino acid sequence of SEQ ID NO: 27 encodes a Klotho fusion polypeptide having the FGF23 (R179Q) variant N-terminally linked to a KL-D2 extracellular subdomain. The amino acid sequence of SEQ ID NO: 28 encodes a Klotho fusion polypeptide having the FGF23 (R179Q) variant N-terminally linked to two KL-D1 extracellular subdomains. The amino acid sequence of SEQ ID NO: 29 encodes a Klotho fusion polypeptide having the FGF23 (R179Q) variant N-terminally linked to two KL-D2 extracellular subdomains. In some embodiments, the fusion further comprises a modified Fc fragment having decreased affinity for Fc-gamma-receptor and/or increased serum half-life.

The Klotho fusion polypeptide of the invention may include an amino acid sequence which is at least about 95% identical to the amino acid sequence set forth in SEQ ID NO:7. The amino acid sequence of SEQ ID NO: 7 encodes a Klotho extracellular domain lacking a signal peptide. In some embodiments, the fusion further comprises a modified Fc fragment having decreased affinity for Fc-gamma-receptor and/or increased serum half-life.

The subject fusion proteins are described herein and can be made using methods known in the art. For example, the fusion polypeptides of the invention may be constructed as described in U.S. Pat. No. 6,194,177. The use of Klotho polypeptides is described in U.S. Pat. No. 6,579,850. The use of FGF nucleic acid molecules is described in U.S. Pat. No. 7,223,563.

In some embodiments, a nucleic acid molecule encoding the Klotho is cloned by PCR and ligated, in frame, with a nucleic acid molecule encoding FGF. In some embodiments, the fusion further comprises a modified Fc fragment having decreased affinity for Fc-gamma-receptor and/or increased serum half-life. The nucleic acid encoding the fusion polypeptide is operatively linked to a promoter to allow for expression. The nucleic acid molecule encoding the fusion polypeptide is subsequently transfected into a host cell for expression. The sequence of the final construct can be confirmed by sequencing.

When preparing the fusion proteins of the present invention, a nucleic acid molecule encoding an extracellular subdomain of Klotho will be fused in frame to the nucleic acid molecule encoding FGF and the (optional) nucleic acid encoding the modified Fc fragment. Expression of the resulting nucleic acid molecule results in the extracellular subdomain of Klotho being fused N-terminal in relation to the FGF polypeptide. Fusions are also possible in which the extracellular subdomain of Klotho is fused C-terminal in relation to the FGF polypeptide. Methods for making fusion proteins are well known in the art.

The fusion polypeptides of the invention have at least two polypeptides that are covalently linked, in which one polypeptide comes from one protein sequence or domain, e.g., Klotho, and the other polypeptide comes from another protein sequence or domain, e.g., FGF. In some embodiments, the fusion further comprises a modified Fc fragment having decreased affinity for Fc-gamma-receptor and/or increased serum half-life. In another embodiment, the invention comprises a FGF fused to a modified Fc fragment. Klotho and/or FGF and/or the (optional) modified Fc fragment, of the fusion polypeptides of the invention, can be joined by methods well known to those of skill in the art. These methods include both chemical and recombinant means.

Nucleic acids encoding the domains to be incorporated into the fusion polypeptides of the invention can be obtained using routine techniques in the field of recombinant genetics. Basic texts disclosing the general methods of use in this invention include Sambrook and Russell, Molecular Cloning, A Laboratory Manual (3rd ed. 2001); Kriegler, Gene Transfer and Expression: A Laboratory Manual (1990); and Current Protocols in Molecular Biology (Ausubel et al., eds., 1994-1999). In nucleic acids encoding a Klotho fusion polypeptide of the invention, the nucleic acid sequence encoding alpha-Klotho or beta-Klotho, represented by SEQ ID NO: 1 and SEQ ID NO: 3, respectively, may be used. In nucleic acids encoding a Klotho fusion polypeptide, the nucleic acid sequence encoding FGF19, FGF21, or FGF23, represented by SEQ ID NO: 30, SEQ ID NO: 32 and SEQ ID NO: 34, respectively, may be used. Nucleic acid sequences of molecules of the invention described herein comprise a nucleotide sequence which hybridizes to or is at least about 60%, 70%, 80%, 90%, 95%, 96%, 97%, 98%, 99% or more identical or homologous to SEQ ID NO: 1, SEQ ID NO:3, SEQ ID NO: 30, SEQ ID NO: 32, or SEQ ID NO: 34.

Nucleic acid sequences that encode the various components of the fusion [Klotho, and/or FGF peptide and/or the (optional) modified Fc fragment] can be obtained using any of a variety of methods. For example, the nucleic acid sequences encoding the polypeptides may be cloned from cDNA and genomic DNA libraries by hybridization with probes, or isolated using amplification techniques with oligonucleotide primers. More commonly, amplification techniques are used to amplify and isolate the Klotho and FGF sequences using a DNA or RNA template (see, e.g., Dieffenfach & Dveksler, PCR Primers: A Laboratory Manual (1995)). Alternatively, overlapping oligonucleotides can be produced synthetically and joined to produce one or more of the domains. Nucleic acids encoding Klotho or FGF can also be isolated from expression libraries using antibodies as probes.

According to the present invention, the various components of the fusion [Klotho, and/or, FGF and/or the (optional) modified Fc fragment] can be linked either directly or via a covalent linker, including amino acid linkers, such as a polyglycine linker, or another type of chemical linker, including, carbohydrate linkers, lipid linkers, fatty acid linkers, polyether linkers, such as PEG, etc. (See for example, Hermanson, Bioconjugate techniques (1996)). The polypeptides forming the fusion/fusion polypeptide are typically linked C-terminus to N-terminus, although they can also be linked C-terminus to C-terminus, N-terminus to N-terminus, or N-terminus to C-terminus. One or more polypeptide domains may be inserted at an internal location within a fusion polypeptide of the invention. The polypeptides of the fusion protein can be in any order. The fusion polypeptides may be produced by covalently linking a chain of amino acids from one protein sequence, e.g., an extracellular subdomain of Klotho, to a chain of amino acids from another protein sequence, e.g., FGF, by preparing a recombinant polynucleotide contiguously encoding the fusion protein. The different chains of amino acids in a fusion protein may be directly spliced together or may be indirectly spliced together via a chemical linking group or an amino acid linking group. The amino acid linking group can be about 200 amino acids or more in length, or generally 1 to 100 amino acids. In some embodiments, proline residues are incorporated into the linker to prevent the formation of significant secondary structural elements by the linker. Linkers can often be flexible amino acid subsequences that are synthesized as part of a recombinant fusion protein. Such flexible linkers are known to persons of skill in the art.

According to the present invention, the amino acid sequences of the fusion [an extracellular subdomain of Klotho and/or the FGF and/or the (optional) modified Fc fragment] may be linked via a peptide linker. Exemplary peptide linkers are well known in the art and described herein. For example, peptide linkers generally include several Gly and several Ser residues, such as: $(Gly_4\ Ser)_3$ (SEQ ID NO: 11), $Gly_4$ Ser polypeptide (SEQ ID NO: 12), Gly (SEQ ID NO: 13), Gly Gly (SEQ ID NO: 14), Gly Ser (SEQ ID NO: 15), $Gly_2$ Ser (SEQ ID NO: 16), Ala (SEQ ID NO: 17), and Ala Ala (SEQ ID NO: 18). Specifically, a peptide linker for use in a fusion protein of the invention may act as a flexible hinge.

The signal sequence of Klotho or FGF may be excluded prior to incorporation of Klotho into a fusion protein of the invention. The signal sequence for Klotho or FGF of the fusion protein may be included, e.g., the polypeptide represented by SEQ ID NO: 19. However, such sequences may also be omitted and replaced with the signal sequence of a different protein, e.g., the IgG signal sequence (SEQ ID NO: 9). Generally, the pharmaceutical compositions of the invention will contain the mature form of Klotho and FGF.

Generally, introns are excluded from either one or both the Klotho or the FGF moieties prior to incorporation into a fusion polypeptide.

The fusion polypeptides of the invention may include one or more polymers covalently attached to one or more reactive amino acid side chains. By way of example, not limitation, such polymers include polyethylene glycol (PEG), which can be attached to one or more free cysteine sulfhydryl residues, thereby blocking the formation of disulfide bonds and aggregation when the protein is exposed to oxidizing conditions. In addition, PEGylation of the fusion polypeptides of the invention is expected to provide such improved properties as increased half-life, solubility, and protease resistance. The fusion polypeptides of the invention may alternatively be modified by the covalent addition of polymers to free amino groups such as the lysine epsilon or the N-terminal amino group. Preferred cysteines and lysines for covalent modification will be those not involved in receptor binding, heparin binding, or in proper protein folding. It will be apparent to one skilled in the art that the methods for assaying the biochemical and/or biological activity of the fusion polypeptides may be employed in order to determine if modification of a particular amino acid residue affects the activity of the protein as desired. Other similar suitable modifications are contemplated and known in the art.

The invention is also directed to the expression of a fusion polypeptide that is at least about 95% or more homologous to an amino acid sequence presented in SEQ ID NO:19-28.

4.3. Expression of Fusion Polypeptides of the Invention

In order to express the fusion protein of the invention, DNA molecules obtained by any of the methods described herein or those that are known in the art, can be inserted into appropriate expression vectors by techniques well known in the art. For example, a double stranded cDNA can be cloned into a suitable vector by homopolymeric tailing or by restriction enzyme linking involving the use of synthetic DNA linkers or by blunt-ended ligation. DNA ligases are usually used to ligate the DNA molecules and undesirable joining can be avoided by treatment with alkaline phosphatase.

Therefore, the invention includes vectors (e.g., recombinant plasmids and bacteriophages) that include nucleic acid molecules (e.g., genes or recombinant nucleic acid molecules encoding genes) as described herein. The term "recombinant vector" includes a vector (e.g., plasmid, phage, phasmid, virus, cosmid, fosmid, or other purified nucleic acid vector) that has been altered, modified or engineered such that it contains greater, fewer or different nucleic acid sequences than those included in the native or natural nucleic acid molecule from which the recombinant vector was derived. For example, a recombinant vector may include a nucleotide sequence encoding a Klotho-FGF23 fusion operatively linked to regulatory sequences, e.g., promoter sequences, terminator sequences and/or artificial ribosome binding sites (RBSs), as defined herein. Recombinant vectors which allow for expression of the genes or nucleic acids included in them are referred to as "expression vectors."

For eukaryotic hosts, different transcriptional and translational regulatory sequences may be employed, depending on the nature of the host. They may be derived from viral sources, such as adenovirus, bovine papilloma virus, Simian virus or the like, where the regulatory signals are associated with a particular gene which has a high level of expression. Examples include, but are not limited to, the TK promoter of the Herpes virus, the SV40 early promoter, the yeast ga14 gene promoter, etc. Transcriptional initiation regulatory signals may be selected which allow for repression or activation, so that expression of the genes can be modulated.

In some of the molecules of the invention described herein, one or more DNA molecules having a nucleotide sequence encoding one or more polypeptide chains of a fusion polypeptide are operatively linked to one or more regulatory sequences, which are capable of integrating the desired DNA molecule into a host cell. Cells which have been stably transformed by the introduced DNA can be selected, for example, by introducing one or more markers which allow for selection of host cells which contain the expression vector. A selectable marker gene can either be linked directly to a nucleic acid sequence to be expressed, or be introduced into the same cell by co-transfection. Additional elements may also be needed for optimal synthesis of proteins described herein. It would be apparent to one of ordinary skill in the art which additional elements to use.

Factors of importance in selecting a particular plasmid or viral vector include, but are not limited to, the ease with which recipient cells that contain the vector are recognized and selected from those recipient cells which do not contain the vector; the number of copies of the vector which are desired in a particular host; and whether it is desirable to be able to "shuttle" the vector between host cells of different species.

Once the vector(s) is constructed to include a DNA sequence for expression, it may be introduced into an appropriate host cell by one or more of a variety of suitable methods that are known in the art, including but not limited to, for example, transformation, transfection, conjugation, protoplast fusion, electroporation, calcium phosphate-precipitation, direct microinjection, etc.

Host cells may either be prokaryotic or eukaryotic. Examples of eukaryotic host cells include, for example, mammalian cells, such as human, monkey, mouse, and Chinese hamster ovary (CHO) cells. Such cells facilitate post-translational modifications of proteins, including, for example, correct folding or glycosylation. Additionally, yeast cells can also be used to express fusion polypeptides of the invention. Like most mammalian cells, yeast cells also enable post-translational modifications of proteins, including, for example, glycosylation. A number of recombinant DNA strategies exist which utilize strong promoter sequences and high copy number plasmids that can be utilized for production of proteins in yeast. Yeast transcription and translation machinery can recognize leader sequences on cloned mammalian gene products, thereby enabling the secretion of peptides bearing leader sequences (i.e., pre-peptides). A particularly preferred method of high-yield production of the fusion polypeptides of the invention is through the use of dihydrofolate reductase (DHFR) amplification in DHFR-deficient CHO cells, by the use of successively increasing levels of methotrexate as described in U.S. Pat. No. 4,889,803. The polypeptide obtained may be in a glycosylated form.

After the introduction of one or more vector(s), host cells are usually grown in a selective medium, which selects for the growth of vector-containing cells. Purification of the recombinant proteins can be carried out by any of the methods known in the art or described herein, for example, any conventional procedures involving extraction, precipitation, chromatography and electrophoresis. A further purification procedure that may be used for purifying proteins is affinity chromatography using monoclonal antibodies which bind a target protein. Generally, crude preparations containing a recombinant protein are passed through a column on which a suitable monoclonal antibody is immobilized. The protein usually binds to the column via the specific antibody while the impurities pass through. After washing the column, the protein is eluted from the gel by changing pH or ionic strength, for example.

4.4. Assays for Assessing Fusion Polypeptide Activity

Assays described herein (See Example 2) and those known in the art can be used for detecting Klotho or FGF activity of the fusion polypeptides of the invention. Suitable activity assays include receptor binding assays, cellular proliferation assays and cell signaling assays. For example, a binding assay which may be used for determining whether a fusion polypeptide has Klotho or FGF activity includes, assaying the binding of a fusion polypeptide to an FGF receptor. FGF receptor binding assays include, but are not limited to, both competitive and non-competitive assay. For example, FGF receptor binding can be detected by contacting cells expressing an FGF receptor with a labeled FGF (for example, radio-active label) and increasing concentrations of an unlabeled Klotho-FGF fusion polypeptide. The two ligands that compete for binding to the same receptor are added to a reaction mixture containing the cell. The cells are subsequently washed and labeled FGF is measured. A decrease in the amount of the labeled FGF to its receptor in the presence of the unlabeled fusion polypeptide is indicative of binding of the Klotho-FGF fusion polypeptide to the receptor. Alternatively, the Klotho-FGF fusion polypeptide may be labeled and direct binding of the fusion polypeptide to the cell is detected.

Klotho or FGF activity can also be measured by determining whether the fusion polypeptide induces a cellular response. For example, in some embodiments, an assay for detecting the biological activity of a Klotho-FGF fusion polypeptide involves contacting cells which express an FGF receptor with a fusion polypeptide, assaying a cellular response such as, for example, cell proliferation or Egr-1 activation, myotube diameter in C2C12 cells, and comparing the cellular response in the presence and absence of the fusion polypeptide. An increase in the cellular response in the presence of the fusion polypeptide complex relative to the absence indicates that the fusion polypeptide has biological activity. Also, an increase in a downstream signaling event from the receptor can also be measured as indicia of biological activity (e.g., phosphorylation of FGFR, FRS2, ERK1/2, p70S6K etc.).

4.5 Pharmaceutical Compositions and Methods of Treatment

The invention also pertains to pharmaceutical compositions containing one or more fusion polypeptides of the invention and a pharmaceutically acceptable diluent or carrier. The pharmaceutical compositions can further include a pharmaceutically effective dose of heparin. Such pharmaceutical compositions may be included in a kit or container. Such kit or container may be packaged with instructions pertaining to the extended in vivo half-life or the in vitro shelf life of the fusion polypeptides. Optionally associated with such kit or container(s) can be a notice in the form prescribed by a governmental agency regulating the manufacture, use or sale of pharmaceuticals or biological products, which notice reflects approval by the agency of manufacture, use or sale for human administration. Such compositions may be used in methods of treating, preventing, or ameliorating a disease or a disease symptom (e.g., age-related condition or metabolic disorder) in a patient, preferably a mammal and most preferably a human, by administering the pharmaceutical composition to the patient.

In general, a therapeutically effective amount of a pharmaceutical composition of the invention is from about 0.0001 mg/kg to 0.001 mg/kg; 0.001 mg/kg to about 10 mg/kg body weight or from about 0.02 mg/kg to about 5 mg/kg body weight. Commonly, a therapeutically effective amount of a fusion polypeptide is from about 0.001 mg to about 0.01 mg, about 0.01 mg to about 100 mg, or from about 100 mg to about 1000 mg, for example. Preferably, a therapeutically effective amount of a fusion polypeptide is from about 0.001 mg/kg to 2 mg/kg.

The optimal pharmaceutical formulations for a fusion polypeptide can be determined by one or ordinary skilled in the art depending upon the route of administration and desired dosage. (See, for example, Remington's Pharmaceutical Sciences, 18th Ed. (1990), Mack Publishing Co., Easton, Pa., the entire disclosure of which is hereby incorporated by reference).

The fusion polypeptides of the invention may be administered as a pharmaceutical composition that may be in the form of a solid, liquid or gas (aerosol). Typical routes of administration may include, without limitation, oral, topical, parenteral, sublingual, rectal, vaginal, intradermal and intranasal. Parenteral administration includes subcutaneous injections, intravenous, intramuscular, intraperitoneal, intrapleural, intrasternal injection or infusion techniques. Preferably, the compositions are administered parenterally. More preferably, the compositions are administered intravenously. Pharmaceutical compositions of the invention can be formulated so as to allow a polypeptide of the invention to be bioavailable upon administration of the composition to a subject. Compositions can take the form of one or more dosage units, where, for example, a tablet can be a single dosage unit, and a container of a polypeptide of the invention in aerosol form can hold a plurality of dosage units.

Materials used in preparing the pharmaceutical compositions can be non-toxic in the amounts used. It will be evident to those of ordinary skill in the art that the optimal dosage of the active ingredient(s) in the pharmaceutical composition will depend on a variety of factors. Relevant factors include, without limitation, the type of subject (e.g., human), the overall health of the subject, the type of age-related condition or metabolic disorder the subject in need of treatment of, the use of the composition as part of a multi-drug regimen, the particular form of the polypeptide of the invention, the manner of administration, and the composition employed.

The pharmaceutically acceptable carrier or vehicle may be particulate, so that the compositions are, for example, in tablet or powder form. The carrier(s) can be liquid, with the compositions being, for example, an oral syrup or injectable liquid. In addition, the carrier(s) can be gaseous, so as to provide an aerosol composition useful in, e.g., inhalatory administration.

The term "carrier" refers to a diluent, adjuvant or excipient, with which a polypeptide of the invention is administered. Such pharmaceutical carriers can be liquids, such as water and oils, including those of petroleum, animal, vegetable or synthetic origin, such as peanut oil, soybean oil, mineral oil, sesame oil and the like. The carriers can be saline, gum acacia, gelatin, starch paste, talc, keratin, colloidal silica, urea, and the like. In addition, auxiliary, stabilizing, thickening, lubricating and coloring agents can be used. In one embodiment, when administered to a subject, the polypeptides of the invention and pharmaceutically acceptable carriers are sterile. Water is a preferred carrier when the polypeptide of the invention is administered intravenously. Saline solutions and aqueous dextrose and glycerol solutions can also be employed as liquid carriers, particularly for injectable solutions. Suitable pharmaceutical carriers also include excipients such as starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The present compositions, if desired, can also contain minor amounts of wetting or emulsifying agents, or pH buffering agents.

The composition may be intended for oral administration, and if so, the composition is preferably in solid or liquid form, where semi-solid, semi-liquid, suspension and gel forms are included within the forms considered herein as either solid or liquid.

As a solid composition for oral administration, the composition can be formulated into a powder, granule, compressed tablet, pill, capsule, chewing gum, wafer or the like form. Such a solid composition typically contains one or more inert diluents. In addition, one or more of the following can be present: binders such as ethyl cellulose, carboxymethylcellulose, microcrystalline cellulose, or gelatin; excipients such as starch, lactose or dextrins, disintegrating agents such as alginic acid, sodium alginate, Primogel, corn starch and the like; lubricants such as magnesium stearate or Sterotex; glidants such as colloidal silicon dioxide; sweetening agents such as sucrose or saccharin, a flavoring agent such as peppermint, methyl salicylate or orange flavoring, and a coloring agent.

When the pharmaceutical composition is in the form of a capsule, e.g., a gelatin capsule, it can contain, in addition to materials of the above type, a liquid carrier such as polyethylene glycol, cyclodextrin or a fatty oil.

The pharmaceutical composition can be in the form of a liquid, e.g., an elixir, syrup, solution, emulsion or suspension. The liquid can be useful for oral administration or for delivery by injection. When intended for oral administration, a composition can contain one or more of a sweetening agent, preservatives, dye/colorant and flavour enhancer. In a composition for administration by injection, one or more of a surfactant, preservative, wetting agent, dispersing agent, suspending agent, buffer, stabilizer and isotonic agent can also be included.

The liquid compositions of the invention, whether they are solutions, suspensions or other like form, can also include one or more of the following: sterile diluents such as water for injection, saline solution, preferably physiological saline, Ringer's solution, isotonic sodium chloride, fixed oils such as synthetic mono or digylcerides which can serve as the solvent or suspending medium, polyethylene glycols, glycerin, cyclodextrin, propylene glycol or other solvents; antibacterial agents such as benzyl alcohol or methyl paraben; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. A parenteral composition can be enclosed in an ampoule, a disposable syringe or a multiple-dose vial made of glass, plastic or other material. Physiological saline is a preferred adjuvant. An injectable composition is preferably sterile.

The pharmaceutical compositions contain an effective amount of a compound of the invention (e.g., fusion polypeptide) such that a suitable dosage will be obtained. The pharmaceutical compositions may contain the known effective amount of the compounds as currently prescribed for their respective disorders.

The route of administration of the polypeptide of the invention used in the prophylactic and/or therapeutic regimens which will be effective in the prevention, treatment, and/or management of a age-related condition or metabolic disorder can be based on the currently prescribed routes of administration for other therapeutics known in the art. The polypeptides of the invention can be administered by any convenient route, for example, by infusion or bolus injection, by absorption through epithelial or mucocutaneous linings (e.g., oral mucosa, rectal and intestinal mucosa, etc.). Administration can be systemic or local. Various delivery systems are known, e.g., microparticles, microcapsules, capsules, etc., and may be useful for administering a polypeptide of the invention. More than one polypeptides of the invention may be administered to a subject. Methods of administration may include, but are not limited to, oral administration and parenteral administration; parenteral administration including, but not limited to, intradermal, intramuscular, intraperitoneal, intravenous, subcutaneous, intranasal, epidural, sublingual, intranasal, intracerebral, intraventricular, intrathecal, intravaginal, transdermal, rectally, by inhalation, or topically to the ears, nose, eyes, or skin.

The polypeptides of the invention may be administered parenterally. Specifically, the polypeptides of the invention may be administered intravenously.

Pulmonary administration can also be employed, e.g., by use of an inhaler or nebulizer, and formulation with an aerosolizing agent, or via perfusion in a fluorocarbon or synthetic pulmonary surfactant. The polypeptides of the invention can also be formulated as a suppository, with traditional binders and carriers such as triglycerides.

The polypeptides of the invention can be delivered in a controlled release system. For example, a pump can be used (see Sefton, *CRC Crit. Ref Biomed. Eng.* 1987, 14, 201; Buchwald et al., Surgery 1980, 88: 507; Saudek et al., N. *Engl. J. Med.* 1989, 321: 574). Polymeric materials can also be used for controlled release of the polypeptides of the invention (see *Medical Applications of Controlled Release*, Langer and Wise (eds.), CRC Pres., Boca Raton, Fla., 1974; *Controlled Drug Bioavailability, Drug Product Design and Performance*, Smolen and Ball (eds.), Wiley, New York, 1984; Ranger and Peppas, *J. Macromol. Sci. Rev. Macromol. Chem.* 1983, 23, 61; see also Levy et al., *Science* 1985, 228, 190; During et al., *Ann. Neurol.*, 1989, 25, 351; Howard et al., *J. Neurosurg.*, 1989, 71, 105). Specifically, a controlled-release system can be placed in proximity of the target of the polypeptides of the invention, e.g., the brain, thus requiring only a fraction of the systemic dose (see, e.g., Goodson, in *Medical Applications of Controlled Release, supra*, vol. 2, 1984, pp. 115-138). Other controlled-release systems discussed in the review by Langer (*Science* 1990, 249, 1527-1533) can be used.

Polymeric materials used to achieve controlled or sustained release of the polypeptides of the invention are disclosed, e.g., in U.S. Pat. No. 5,679,377; U.S. Pat. No. 5,916,597; U.S. Pat. No. 5,912,015; U.S. Pat. No. 5,989,463; U.S. Pat. No. 5,128,326; PCT Publication No. WO 99/15154; and PCT Publication No. WO 99/20253. Examples of polymers used in sustained release formulations include, but are not limited to, poly(2-hydroxy ethyl methacrylate), poly(methyl methacrylate), poly(acrylic acid), poly(ethylene-co-vinyl acetate), poly(methacrylic acid), polyglycolides (PLG), polyanhydrides, poly(N-vinyl pyrrolidone), poly(vinyl alcohol), polyacrylamide, poly(ethylene glycol), polylactides (PLA), poly(lactide-co-glycolides) (PLGA), and polyorthoesters. Preferably, the polymer used in a sustained release formulation is inert, free of leachable impurities, stable on storage, sterile, and biodegradable.

In general, a therapeutically effective amount of a pharmaceutical composition of the invention is from about 0.0001 mg/kg to 0.001 mg/kg; 0.001 mg/kg to about 10 mg/kg body weight or from about 0.02 mg/kg to about 5 mg/kg body weight.

In other embodiments, the prophylactic and/or therapeutic regimen involves administering to a patient one or more doses of an effective amount of a polypeptide of the invention, wherein the dose of an effective amount achieves a plasma level of at least 0.01 μg/mL to at least 400 μg/mL of the polypeptide of the invention.

A prophylactic and/or therapeutic regimen may involve administering to a patient a plurality of doses of an effective amount of a polypeptide of the invention, wherein the plurality of doses maintains a plasma level of at least 0.01 μg/mL, to 400 μg/mL of the polypeptide of the invention. The prophylactic and/or therapeutic regimen may be administered for at least 1 day, 1 month, 2 months, 3 months, 4 months, 5 months, 6 months, 7 months, 8 months or 9 months.

The prophylactic and/or therapeutic regimen may involve administration of a polypeptide of the invention in combination with one or more additional therapeutics. The recommended dosages of the one or more therapeutics currently used for the prevention, treatment, and/or management of an age-related condition or metabolic disorder can be obtained from any reference in the art including, but not limited to, Hardman et al., eds., *Goodman & Gilman's The Pharmacological Basis Of Basis Of Therapeutics,* 10th ed., McGraw-Hill, New York, 2001; *Physician's Desk Reference* ($60^{th}$ ed., 2006), which is incorporated herein by reference in its entirety.

The invention includes methods of treating disorders wherein agonistic activity of Klotho protein and FGF are desirable. Examples of such methods of the invention include, but are not limited to age-related condition or metabolic disorders.

The invention includes methods for treating or preventing an age-related condition in an individual. An individual in need of treatment is administered a pharmacologically effective dose of a pharmaceutical composition containing a Klotho fusion polypeptide, having at least one extracellular subdomain of a Klotho protein and a fibroblast growth factor and an (optional) modified Fc fragment, so as to treat or prevent the age-related condition. In some embodiments, the Klotho fusion polypeptide is co-administered with a pharmacologically effective dose of heparin. Age-related conditions include sarcopenia, skin atrophy, muscle wasting, brain atrophy, atherosclerosis, arteriosclerosis, pulmonary emphysema, osteoporosis, osteoarthritis, immunologic incompetence, high blood pressure, dementia, Huntington's disease, Alzheimer's disease, cataracts, age-related macular degeneration, prostate cancer, stroke, diminished life expectancy, memory loss, wrinkles, impaired kidney function, and age-related hearing loss. In some embodiments, the Klotho fusion polypeptide contains at least one extracellular domain of an alpha Klotho protein. In a particular embodiment, a Klotho fusion protein containing at least one extracellular domain of alpha Klotho protein and fibroblast growth factor 23 is administered to an individual in need of treatment for muscle wasting.

The invention is also directed to a method for treating or preventing a metabolic disorder in an individual. An individual in need of treatment is administered a pharmacologically effective dose of a pharmaceutical composition containing a Klotho fusion polypeptide, having at least one extracellular subdomain of a Klotho protein and a fibroblast growth factor so as to treat the metabolic disorder, and an (optional) modified Fc fragment having decreased binding to FcRn and/or increased serum half-life and/or stability. In some embodiments, the Klotho fusion polypeptide is co-administered with a pharmacologically effective dose of heparin. The method may be used in the treatment or prevention of Type II Diabetes, Metabolic Syndrome, hyperglycemia, and obesity. In a particular embodiment, a Klotho fusion protein containing at least one extracellular domain of a beta-Klotho protein and fibroblast growth factor 21 is administered to an individual in need of treatment for a metabolic disorder.

The invention also provides methods for treating or preventing hyperphosphatemia or calcinosis in an individual. An individual in need of treatment is administered a pharmacologically effective dose of a pharmaceutical composition containing a Klotho fusion polypeptide, having at least one extracellular subdomain of a Klotho protein, a fibroblast growth factor and an (optional) modified Fc fragment so as to treat hyperphosphatemia or calcinosis. In some embodiments, the Klotho fusion polypeptide is co-administered with a pharmacologically effective dose of heparin. In a particular embodiment, a Klotho fusion protein containing at least one extracellular domain of an alpha Klotho protein and fibroblast growth factor 23 and an (optional) modified Fc fragment is administered to an individual in need of treatment for a hyperphosphatemia or calcinosis.

The invention is also directed to a method for treating or preventing chronic renal disease or chronic renal failure in an individual. An individual in need of treatment is administered a pharmacologically effective dose of a pharmaceutical composition containing a Klotho fusion polypeptide, having at least one extracellular subdomain of a Klotho protein, a fibroblast growth factor and an (optional) modified Fc fragment so as to treat chronic renal disease or chronic renal failure. In some embodiments, the Klotho fusion polypeptide is co-administered with a pharmacologically effective dose of heparin. In some embodiments, a Klotho fusion protein containing at least one extracellular domain of an alpha Klotho protein is administered to an individual in need of treatment for chronic renal disease or chronic renal failure.

The invention also includes methods for treating or preventing cancer in an individual. An individual in need of treatment is administered a pharmacologically effective dose of a pharmaceutical composition containing a Klotho fusion polypeptide, having at least one extracellular subdomain of a Klotho protein, a fibroblast growth factor and an (optional) modified Fc fragment so as to treat cancer. The method may be used in the treatment or prevention of breast cancer. In some embodiments, the Klotho fusion polypeptide is co-administered with a pharmacologically effective dose of heparin. In some embodiments, a Klotho fusion protein containing at least one extracellular domain of an alpha Klotho protein is administered to an individual in need of treatment for cancer.

In methods of treating disorders by administering a pharmaceutical composition containing a Klotho fusion polypeptide, the Klotho fusion polypeptide and an (optional) modified Fc fragment has at least one extracellular subdomain of a Klotho protein and a fibroblast growth factor. In a particular embodiment, the Klotho fusion protein contains at least one extracellular domain of a beta Klotho protein and fibroblast growth factor 21.

In another embodiment, the fusion comprises a FGF (e.g., FGF19, FGF21, FGF23 or FGF23 variant) and a modified Fc fragment with decreased binding to FcRn and/or increased serum stability. This type of fusion can be used in various diseases, as described above, or used to treat or prevent any FGF-related disease known in the art. The fusion can be administered to an individual in need thereof.

The fusion polypeptide compositions can be administered according to any method of administration known to those of skill in the art and described herein. Preferred methods of administration include subcutaneous or intravenous. Other effective modes of administration are described herein.

4.6. Methods of Treatment and Assays for Assessing Efficacy

Methods of the invention which provide administering the fusion polypeptides described herein to an individual can be used to treat a variety of disorders including an age-related disorder or a metabolic disorder. Without being limited by any particular theory, fusion polypeptides may be used to treat disorders in which there is dysregulation of Klotho or FGF. Exemplary disorders include metabolic disorders and age-related disorders. For example, both FGF23 or Klotho knock-out mice display a variety of similar phenotypes including, low physical activity, growth retardation, muscle wasting, skin atrophy, atherosclerosis, short life spans, etc. (See Razzaque and Lanske, *J. of Endrocrinology,* 194:1-10 (2007), which is herein incorporated by reference).

In particular, fusion polypeptides of the invention are particularly useful in the treatment of aging-related disorders, including muscle wasting. Without being bound to theory, the ability of Klotho and FGF23 to control mineral (e.g., phosphate and calcium) and vitamin D homeostasis may be the means by which these proteins modulate aging and muscle atrophy.

On the other hand, fusion polypeptides of the invention may be used for treating a metabolic disorder. For example, beta-Klotho and FGF19 have been shown to control bile acid homeostasis by regulating cholesterol 7-α-hydroxylase (CYP7A1). A non-limiting example of bile homeostasis disorder is cholestasis. The beta-Klotho and FGF21 have been shown to induce lipolysis in adipocytes and, therefore, reduced fat storage and increased glucose uptake. Non-limiting examples of lipolysis/fat storage disorders are obesity and associated metabolic and cardiovascular diseases.

Based at least in part on the finding that FGF23 is able to stimulate excretion of phosphate in the urine and thereby reduce phosphate levels in the serum, Klotho-FGF23 fusion polypeptides of the invention can be used for treating or preventing hyperphosphatemia or calcinosis in an individual. For example, it has been shown that a homozygous missense mutation in Klotho resulting in a deficiency in Klotho in a patient can cause severe tumoral calcinosis and artery calcification (Ichikawa et al., *J. Clin. Invest.* 117: 2684-2691 (2007), which is herein incorporated by reference). An individual is administered a pharmacologically effective dose of a pharmaceutical composition containing the Klotho fusion polypeptide, having at least one extracellular subdomain of a Klotho protein, a fibroblast growth factor and an (optional) modified Fc fragment so as to treat or prevent hyperphosphatemia or calcinosis. In particular, a Klotho fusion polypeptide containing at least one extracellular domain of an alpha Klotho protein, a fibroblast growth factor and an (optional) modified Fc fragment is useful for treating hyperphosphatemia or calcinosis.

Klotho fusion polypeptides of the invention can also be used for treating or preventing chronic renal disease or chronic renal failure in an individual. For example, it has been shown that Klotho expression is reduced in kidney of patients with chronic renal failure, compared to that in unaffected kidneys (Koh et al., *Biochem. Biophys. Res. Comm.* 280:1015-1020 (2001), which is herein incorporated by reference). An individual is administered a pharmacologically effective dose of a pharmaceutical composition containing the Klotho fusion polypeptide, having at least one extracellular subdomain of a Klotho protein, a fibroblast growth factor and an (optional) modified Fc fragment so as to treat or prevent chronic renal disease or chronic renal failure. In particular, a Klotho fusion polypeptide containing at least one extracellular domain of an alpha Klotho protein is useful for treating chronic renal disease or chronic renal failure.

Klotho fusion polypeptides of the invention can also be used for treating or preventing cancer in an individual. For example, it has been shown that Klotho expression is reduced in breast cancer tissue, compared to normal breast cancer tissue (Wolf et al., *Oncogene* (2008) advance online publication, which is herein incorporated by reference). An individual is administered a pharmacologically effective dose of a pharmaceutical composition containing the Klotho fusion polypeptide, having at least one extracellular subdomain of a Klotho protein, a fibroblast growth factor and an (optional) modified Fc fragment so as to treat or prevent cancer or breast cancer. In particular, a Klotho fusion protein containing at least one extracellular domain of an alpha Klotho protein is useful for treating cancer or breast cancer.

Methods for evaluating the efficacy and/or determining the effective dose of a Klotho fusion polypeptide of the invention on an age-related disorder or metabolic disorder include organismal based assays, e.g., using a mammal (e.g., a mouse, rat, primate, or some other non-human), or other animal (e.g., *Xenopus*, zebrafish, or an invertebrate such as a fly or nematode). The Klotho fusion polypeptide can be administered to the organism once or as a regimen (regular or irregular). A parameter of the organism is then evaluated, e.g., an age-associated parameter. Klotho fusion polypeptides that are of interest result in a change in the parameter relative to a reference, e.g., a parameter of a control organism. Other parameters (e.g., related to toxicity, clearance, and pharmacokinetics) can also be evaluated.

The Klotho fusion polypeptide of the invention may be evaluated using an animal that has a particular disorder, e.g., a disorder described herein, e.g., an age-related disorder, a metabolic disorder. These disorders can also provide a sensitized system in which the test polypeptide's effects on physiology can be observed. Exemplary disorders include: denervation, disuse atrophy; metabolic disorders (e.g., disorder of obese and/or diabetic animals such as db/db mouse and ob/ob mouse); cerebral, liver ischemia; cisplatin/taxol/vincristine models; various tissue (xenograph) transplants; transgenic bone models; pain syndromes (include inflammatory and neuropathic disorders); Paraquat, genotoxic, and oxidative stress models; and tumor I models.

For measuring an age-related disorder, the animal model can be an animal that has an altered phenotype when calorically restricted. For example, F344 rats provide a useful assay system for evaluating a Klotho fusion polypeptide. When calorically restricted, F344 rats have a 0 to 10% incidence of nephropathy. However, when fed ad libitum, they have a 60 to 100% incidence of nephropathy.

To evaluate a Klotho fusion polypeptide of the invention, it is administered to the animal (e.g., an F344 rat or other suitable animal) and a parameter of the animal is evaluated, e.g., after a period of time. The animal can be fed ad libitum or normally (e.g., not under caloric restriction, although some parameters can be evaluated under such conditions). Typically, a cohort of such animals is used for the assay. Generally, a test polypeptide can be indicated as favorably altering lifespan regulation in the animal if the test polypeptide affects the parameter in the direction of the phenotype of a similar animal subject to caloric restriction. Such test polypeptides may cause at least some of the lifespan regulatory effects of caloric restriction, e.g., a subset of such effects, without having to deprive the organism of caloric intake.

The parameter to be tested may be an age-associated or disease associated parameter, e.g., a symptom of the disorder associated with the animal model. For example, the test polypeptide can be administered to a SH Rat, and blood pressure is monitored. A test polypeptide that is favorably indicated can cause an amelioration of the symptom relative to a similar reference animal not treated with the polypeptide. Other parameters relevant to a disorder or to aging can include: antioxidant levels (e.g. antioxidant enzyme levels or activity), stress resistance (e.g., paraquat resistance), core body temperature, glucose levels, insulin levels, thyroid-stimulating hormone levels, prolactin levels, and leutinizing hormone levels.

To measure the effectiveness of the polypeptides of the invention for treating an age-related disorder, an animal having decreased Klotho expression may be used, e.g., mouse with a mutant Klotho; See Kuroo, et al. Nature, 390; 45 (1997) and U.S. Pub. No. 2003/0119910, both of which are herein incorporated by reference in their entirety. For example, the test polypeptide is administered to the mutant mouse and age-related parameters are monitored. A test polypeptide that is favorably indicated can cause an amelioration of the symptom relative to a similar reference animal not treated with the polypeptide. A parameter relevant to a metabolic disorder or to aging can be assessed by measurement of body weight, examination on the acquisition of reproductive ability, measurement of blood sugar level, observation of life span, observation of skin, observation of motor functions such as walking, and the like. The assessment can also be made by measurement of thymus weight, observation of the size of calcified nodules formed on the inner surface of thoracic cavity, and the like. Further, quantitative determination of mRNA for the Klotho gene or Klotho protein is also useful for the assessment.

Still other in vivo models and organismal assays include evaluating an animal for a metabolic parameter, e.g., a parameter relevant to an insulin disorder, type II diabetes. Exemplary metabolic parameters include: glucose concentration, insulin concentration, and insulin sensitivity.

Another exemplary system features tumors, e.g., in an animal model. The tumors can be spontaneous or induced. For example, the tumors can be developed from cells that have a variety of genetic constitutions, e.g., they can be p53+ or p53−. It is also possible to use organisms that an autoimmune disorder, e.g., an NZB mouse, which is predisposed to SLE. To evaluate features of bone disease, it is possible, for example, to use an animal that has an ovariectomy as a model, e.g., for osteoporosis. Similarly, for joint disease, the model can be based on adjuvant arthritis (e.g., mice can be immunized with cartilage proteoglycans, high mobility group proteins, streptococcal cell wall material, or collagens); for kidney disease, kd/kd mice can be used. Animal models of cognition, particularly learning and memory are also available. Animal models of diabetes and its complications are also available, e.g., the streptozotocin model. Canine models can be used, for example, for evaluating stroke and ischemia.

In assessing whether a test polypeptide is capable of altering life span regulation, a number of age-associated parameters or biomarkers can be monitored or evaluated. Exemplary age associated parameters include: (i) lifespan of the cell or the organism; (ii) presence or abundance of a gene transcript or gene product in the cell or organism that has a biological age dependent expression pattern; (iii) resistance of the cell or organism to stress; (iv) one so or more metabolic parameters of the cell or organism (exemplary parameters include circulating insulin levels, blood glucose levels; fat content; core body temperature and so forth); (v) proliferative capacity of the cell or a set of cells present in the organism; and (vi) physical appearance or behavior of the cell or organism.

The term "average lifespan" refers to the average of the age of death of a cohort of organisms. In some cases, the "average lifespan" is assessed using a cohort of genetically identical organisms under controlled environmental conditions. Deaths due to mishap are discarded. Where average lifespan cannot be determined (e.g., for humans) under controlled environmental conditions, reliable statistical information (e.g., from actuarial tables) for a sufficiently large population can be used as the average lifespan.

Characterization of molecular differences between two such organisms, e.g., one reference organism and one organism treated with a Klotho fusion polypeptide can reveal a difference in the physiological state of the organisms. The reference organism and the treated organism are typically the same chronological age. The term "chronological age" as used herein refers to time elapsed since a preselected event, such as conception, a defined embryological or fetal stage, or, more preferably, birth. A variety of criteria can be used to determine whether organisms are of the "same" chronological age for the comparative analysis. Typically, the degree of accuracy required is a function of the average lifespan of a wildtype organism. For example, for the nematode *C. elegans*, for which the laboratory wildtype strain N2 lives an to average of about 16 days under some controlled conditions, organisms of the same age may have lived for the same number of days. For mice, organism of the same age may have lived for the same number of weeks or months; for primates or humans, the same number of years (or within 2, 3, or 5 years); and so forth. Generally, organisms of the same chronological age may have lived for an amount of time within 15, 10, 5, 3, 2 or 1% of the average lifespan of a wildtype organism of that species. Preferably, the organisms are adult organisms, e.g., the organisms have lived for at least an amount of time in which the average wildtype organism has matured to an age at which it is competent to reproduce.

The organismal screening assay can be performed before the organisms exhibit overt physical features of aging. For example, the organisms may be adults that have lived only 10, 30, 40, 50, 60, or 70% of the average lifespan of a wildtype organism of the same species. Age-associated changes in metabolism, immune competence, and chromosomal structure have been reported. Any of these changes can be evaluated, either in a test subject (e.g., for an organism based assay), or for a patient (e.g., prior, during or after treatment with a therapeutic described herein.

A marker associated with caloric restriction can also be evaluated in a subject organism of a screening assay (or a treated subject). Although these markers may not be age-associated, they may be indicative of a physiological state that is altered when the Klotho pathway is modulated. The marker can be an mRNA or protein whose abundance changes in calorically restricted animals. WO01/12851 and U.S. Pat. No. 6,406,853 describe exemplary markers. Cellular models derived from cells of an animal described herein or analogous to an animal model described herein can be used for a cell-based assay.

Models for evaluating the effect of a test polypeptide on muscle atrophy include: 1) rat medial gastrocnemius muscle mass loss resulting from denervation, e.g., by severing the right sciatic nerve at mid-thigh; 2) rat medial gastrocnemius muscle mass loss resulting from immobilization, e.g., by fixed the right ankle joint at 90 degrees of flexion; 3) rat medial gastrocnemius muscle mass loss resulting from hind limb suspension; (see, e.g., U.S. 2003-0129686); 4) skeletal muscle atrophy resulting from treatment with the cachectic cytokine, interleukin-1 (IL-1) (R. N. Cooney, S. R. Kimball, T. C. Vary, *Shock* 7, 1-16 (1997)); and 5) skeletal muscle atrophy resulting from treatment with the glucocorticoid, dexamethasone (A. L. Goldberg, *J. Biol. Chem.* 244, 3223-9 (1969).)

Exemplary animal models for AMD include: laser-induced mouse model simulating exudative (wet) macular degeneration Bora et al., *Proc. Natl. Acad. Sci*. USA., 100:2679-84 (2003); a transgenic mouse expressing a mutated form of cathepsin D resulting in features associated with the "geographic atrophy" form of AMD (Rakoczy et al., *Am. J. Pathol.,* 161:1515-24 (2002)); and a transgenic mouse over expressing VEGF in the retinal pigment epithelium resulting in CNV. Schwesinger et al., *Am. J. Pathol.* 158:1161-72 (2001).

Exemplary animal models of Parkinson's disease include primates rendered Parkinsonian by treatment with the dopaminergic neurotoxin 1-methyl-4 phenyl 1,2,3,6-tetrahydropyridine (MPTP) (see, e.g., U.S. Patent Publication No. 20030055231 and Wichmann et al., *Ann. N.Y. Acad. Sci.,* 991:199-213 (2003); 6-hydroxydopamine-lesioned rats (e.g., Lab. Anim. Sci., 49:363-71 (1999)); and transgenic invertebrate models (e.g., Lakso et al., *J. Neurochem.* 86:165-72 (2003) and Link, *Mech. Ageing Dev.,* 122:1639-49 (2001)).

Exemplary molecular models of Type II diabetes include: a transgenic mouse having defective Nkx-2.2 or Nkx-6.1; (U.S. Pat. No. 6,127,598); Zucker Diabetic Fatty fa/fa (ZDF) rat. (U.S. Pat. No. 6,569,832); and Rhesus monkeys, which spontaneously develop obesity and subsequently frequently progress to overt type 2 diabetes (Hotta et al., *Diabetes,* 50:1126-33 (2001); and a transgenic mouse with a dominant-negative IGF-I receptor (KR-IGF-IR) having Type 2 diabetes-like insulin resistance.

Exemplary animal and cellular models for neuropathy include: vincristine induced sensory-motor neuropathy in mice (U.S. Pat. No. 5,420,112) or rabbits (Ogawa et al., *Neurotoxicology,* 21:501-11 (2000)); a streptozotocin (STZ)-diabetic rat for study of autonomic neuropathy (Schmidt et al., *Am. J. Pathol.,* 163:21-8 (2003)); and a progressive motor neuropathy (pmn) mouse (Martin et al., *Genomics,* 75:9-16 (2001)).

Exemplary animal models of hyperphosphatemia or tumoral calcinosis include Klotho knockout mice and FGF23 knockout mice (Yoshida et al., *Endocrinology* 143: 683-689 (2002)).

Exemplary animal models of chronic renal disease or chronic renal failure include COL4A3+/−mice (Beirowski et al., *J. Am. Soc. Nephroi.* 17:1986-1994 (2006)).

Exemplary animal models of cancer include the transplantation or implantation of cancer cells or tissue into nude mice, as is known in the art (Giovanella et al., *Adv. Cancer Res.* 44:69-120 (1985)). For example, animal models of breast cancer include nude mice transplanted or implanted with breast cancer cells or tissue (e.g., Yue et al., *Cancer Res.* 54:5092-5095 (1994); Glinsky et al., *Cancer Res.* 56:5319-5324 (1996); Visonneau *Am. J. Path.* 152:1299-1311 (1998)).

The compositions can be administered to a subject, e.g., an adult subject, particularly a healthy adult subject or a subject having an age-related disease. In the latter case, the method can include evaluating a subject, e.g., to characterize a symptom of an age-related disease or other disease marker, and thereby identifying a subject as having a neurodegenerative disease, e.g., Alzheimer's or an age-related disease or being pre-disposed to such a disease.

Skeletal Muscle Atrophy

Methods of the invention which provide administering the Klotho fusion polypeptide to an individual can be used to treat skeletal muscle atrophy. Muscle atrophy includes numerous neuromuscular, metabolic, immunological and neurological disorders and diseases as well as starvation, nutritional deficiency, metabolic stress, diabetes, aging, muscular dystrophy, or myopathy. Muscle atrophy occurs during the aging process. Muscle atrophy also results from reduced use or disuse of the muscle. Symptoms include a decline in skeletal muscle tissue mass. In human males, muscle mass declines by one-third between the ages of 50 and 80. Some molecular features of muscle atrophy include the upregulation of ubiquitin ligases, and the loss of myofibrillar proteins (Furuno et al., *J. Biol. Chem.,* 265:8550-8557, 1990). The breakdown of these proteins can be followed, e.g., by measuring 3-methyl-histidine production, which is a specific constituent of actin, and in certain muscles of myosin (Goodman, Biochem. J. 241:121-12, 1987 and Lowell, et al., Metabolism, 35:1121-112, 1986; Stein and Schluter, *Am. J. Physiol. Endocrinol. Metab.* 272: E688-E696, 1997). Release of creatine kinase (a cell damage marker) (Jackson, et al., Neurology, 41: 101 104, 1991) can also be indicative.

Non-Insulin-Dependent Diabetes

Methods of the invention which provide administering the Klotho fusion polypeptide to an individual can be used to treat Non-insulin-dependent Diabetes. Non-insulin-dependent Diabetes is also called "adult onset" diabetes and Type 2 diabetes. Type 2 diabetes also includes "non-obese type 2" and "obese type 2." Type II diabetes can be characterized by (1) reduced pancreatic-beta-islet-cell secretion of insulin such that less than necessary amounts of insulin are produced to keep blood glucose levels in balance and/or (2) "insulin resistance," wherein the body fails to respond normally to insulin. (U.S. Pat. No. 5,266,561 and U.S. Pat. No. 6,518,069). For example, glucose-stimulated insulin levels typically fail to rise above 4.0 nmol/L. (U.S. Pat. No. 5,266,561). Exemplary symptoms of Type II diabetes include: hyperglycemia while fasting (U.S. Pat. No. 5,266,561); fatigue; excessive thirst; frequent urination; blurred vision; and an increased rate of infections. Molecular indications of Type II diabetes include islet amyloid deposition in the pancreases.

Neuropathy

Neuropathy can include a central and/or peripheral nerve dysfunction caused by systemic disease, hereditary condition or toxic agent affecting motor, sensory, sensorimotor or autonomic nerves. (see, e.g., US Patent Application No. 20030013771). Symptoms can vary depending upon the cause of the nerve damage and the particular types of nerves affected. For example, symptoms of motor neuropathy include clumsiness in performing physical tasks or as muscular weakness, exhaustion after minor exertion, difficulty in standing or walking and attenuation or absence of a neuromuscular reflex. (U.S. Patent Application No. 20030013771) symptoms of autonomic neuropathy include constipation, cardiac irregularities and attenuation of the postural hypotensive reflex. (U.S. Patent Application No. 20030013771), symptoms of sensory neuropathy include pain and numbness; tingling in the hands, legs or feet; and extreme sensitivity to touch, and symptoms of retinopathy include blurred vision, sudden loss of vision, black spots, and flashing lights.

Alzheimer's Disease

Methods of the invention which provide administering the Klotho fusion polypeptide to an individual can be used to treat Alzheimer's Disease (AD) Alzheimer's Disease is a complex neurodegenerative disease that results in the irreversible loss of neurons. It provides merely one example of a neurodegenerative disease that is also an age-related condition. Clinical hallmarks of Alzheimer's Disease include progressive impairment in memory, judgment, orientation to physical surroundings, and language. Neuropathological hallmarks of AD include region-specific neuronal loss, amyloid plaques, and neurofibrillary tangles. Amyloid plaques are extracellular plaques containing the amyloid peptide (also known as Ap, or Ap42), which is a cleavage product of the, 8-amyloid precursor protein (also known as APP). Neurofibrillary tangles are insoluble intracellular aggregates composed of filaments of the abnormally hyperphosphorylated microtubule-associated protein, taut Amyloid plaques and neurofibrillary tangles may contribute to secondary events that lead to neuronal loss by apoptosis (Clark and Karlawish, *Ann. Intern. Med.* 138(5):400-410 (2003). For example, p-amyloid induces caspase-2-dependent apoptosis in cultured neurons (Troy et al. *J Neurosci.* 20(4):1386-1392). The deposition of plaques in viva may trigger apoptosis of proximal neurons in a similar manner.

A variety of criteria, including genetic, biochemical, physiological, and cognitive criteria, can be used to evaluate AD in a subject. Symptoms and diagnosis of AD are known to medical practitioners. Some exemplary symptoms and markers of AD are presented below. Information about these indications and other indications known to be associated with AD can be used as an "AD-related parameter." An AD related parameter can include qualitative or quantitative information. An example of quantitative information is a numerical value of one or more dimensions, e.g., a concentration of a protein or a tomographic map. Qualitative information can include an assessment, e.g., a physician's comments or a binary ("yes"/"no") and so forth. An AD-related parameter includes information that indicates that the subject is not diagnosed with AD or does not have a particular indication of AD, e.g., a cognitive test result that is not typical of AD or a genetic APOE polymorphism not associated with AD.

Progressive cognitive impairment is a hallmark of AD. This impairment can present as decline in memory, judgment, decision making, orientation to physical surroundings, and language (Nussbaum and Ellis, *New Eng J. Med.* 348(14):1356 35 1364 (2003)). Exclusion of other forms of dementia can assist in making a diagnosis of AD. Neuronal death leads to progressive cerebral atrophy in AD patients. Imaging techniques (e.g., magnetic resonance imaging, or computer assisted tomography) can be used to detect AD-associated lesions in the brain and/or brain atrophy.

AD patients may exhibit biochemical abnormalities that result from the pathology of the disease. For example, levels of tan protein in the cerebrospinal fluid is elevated in AD patients (Andreasen, N. et al. *Arch Neurol.* 58:349-350 (2001)).

Levels of amyloid beta 42 (A,B42) peptide can be reduced in CSF of AD patients. Levels of Ap42 can be increased in the plasma of AD patients (Ertekein-Taner, N., et al. *Science* 290:2303 2304 (2000)). Techniques to detect biochemical abnormalities in a sample from a subject include cellular, immunological, and other biological methods known in the art. For general guidance, see, e.g., techniques described in Sambrook & Russell, Molecular Cloning: A Laboratory Manual, 3r Edition, Cold Spring Harbor Laboratory, N.Y. (2001), Ausubel et al., Current Protocols in Molecular Biology (Greene Publishing Associates and Wiley Interscience, N.Y. (1989), (Harrow, E. and Lane, D. (1988) Antibodies: A Laboratory Manual, Cold Spring Harbor Laboratory Press, Cold Spring Harbor, N.Y.), and updated editions thereof.

For example, antibodies, other immunoglobulins, and other specific binding ligands can be used to detect a biomolecule, e.g., a protein or other antigen associated with AD. For example, one or more specific antibodies can be used to probe a sample. Various formats are possible, e.g., ELISAs, fluorescence-based assays, Western blots, and protein arrays. Methods of producing polypeptide arrays are described in the art, e.g., in De Wildt et al. (2000). *Nature Biotech.* 18, 989-994; Lucking et al. (1999). *Anal. Biochem.* 270, 103-111; Ge, H. (2000). *Nucleic Acids Res.* 28, e3, I-VII; MacBeath, G., and Schreiber, S. L. (2000). *Science* 289, 1760 to 1 763; and WO 99/5 1 773A1.

In one assay, a non-human animal model of AD (e.g., a mouse model) is used, e.g., to evaluate a polypeptide or a therapeutic regimen. For example, U.S. Pat. No. 6,509,515 describes one such model animal which is naturally able to be used with learning and memory tests. The animal expresses an amyloid precursor protein (APP) sequence at a level in brain tissues such that the animal develops a progressive necrologic disorder within a short period of time from birth, generally within a year from birth, preferably within 2 to 6 months, from birth. The APP protein sequence is introduced into the animal, or an ancestor of the animal, at an embryonic stage, preferably the one cell, or fertilized oocyte, stage, and generally not later than about the 8-cell stage. The zygote or embryo is then developed to term in a pseudo-pregnant as foster female. The amyloid precursor protein genes are introduced into an animal embryo so as to be chromosomally incorporated in a state which results in super endogenous expression of the amyloid precursor protein and the development of a progressive necrologic disease in the cortico-limbic areas of the brain, areas of the brain which are prominently affected in progressive necrologic disease states such as AD. The gliosis and clinical manifestations in affected transgenic animals model necrologic disease. The progressive aspects of the neurologic disease are characterized by diminished exploratory and/or locomotor behavior and diminished deoxyglucose uptake/utilization and hypertrophic gliosis in the cortico-limbic regions of the brain. Further, the changes that are seen are similar to those that are seen in some aging animals. Other animal models are also described in U.S. Pat. Nos. 5,387,742; 5,877,399; 6,358,752; and 6,187,992.

Parkinson's Disease

Methods of the invention which provide administering the Klotho fusion polypeptide to an individual can be used to treat Parkinson's Disease. Parkinson's disease includes neurodegeneration of dopaminergic neurons in the substantia nigra resulting in the degeneration of the nigrostriatal dopamine system that regulates motor function. This pathology, in turn, leads to motor dysfunctions. (see, e.g., and Lotharius et al., *Nat. Rev. Neurosci.,* 3:932-42 (2002)). Exemplary motor symptoms include: akinesia, stooped posture, gait difficulty, postural instability, catalepsy, muscle rigidity, and tremor. Exemplary non-motor symptoms include: depression, lack of motivation, passivity, dementia and gastrointestinal dysfunction (see, e.g., Fahn, *Ann. N.Y. Acad. Sci.,* 991:1-14 (2003) and Pfeiffer, *Lancet Neurol.,* 2:107-16 (2003)) Parkinson's has been observed in 0.5 to 1 percent of persons 65 to 69 years of age and 1 to 3 percent among persons 80 years of age and older. (see, e.g., Nussbaum et al., *N. Engl. J. Med.,* 348:1356-64 (2003)). Molecular markers of Parkinson's disease include reduction in aromatic L amino acid decarboxylase (AADC) (see, e.g., US App. No. 20020172664); and loss of dopamine content in the nigrostriatal neurons (see, e.g., Fahn, Ann. *N.Y. Acad. Sci.,* 991: 1-14 (2003) and Lotharius et al., Nat. Rev. Neurosci., 3:932-42 (2002)). In some familial cases, PD is linked to mutations in single genes encoding alpha-synuclein and parkin (an E3 ubiquitin ligase) proteins. (e.g., Riess et al., J. Neurol. 250 Suppl 1:I3 10 (2003) and Nussbaum et al., N. Engl. J. Med., 348:1356-64 (2003)). A missense mutation in a neuron-specific C-terminal ubiquitin hydrolase gene is also associated with Parkinson's. (e.g., Nussbaum et al., N. Engl. J. Med., 348:1356-64 (2003))

Huntington's Disease

Methods of the invention which provide administering the Klotho fusion polypeptide to an individual can be used to treat Huntington's Disease. Methods for evaluating the efficacy and/or determining the effective dose of a Klotho fusion polypeptide on Huntington's Disease include organismal based assays, e.g., using a mammal (e.g., a mouse, rat, primate, or some other non-human), or other animal (e.g., *Xenopus*, zebrafish, or an invertebrate such as a fly or nematode). A number of animal model system for Huntington's disease are available. See, e.g., Brouillet, Functional *Neurology* 15(4): 239-251 (2000); Ona et al. *Nature* 399: 263-267 (1999), Bates et al. *Hum Mol. Genet.* 6(10):1633-7 (1997); Hansson et al. *J. of Neurochemistry* 78: 694-703; and Rubinsztein, D. C., *Trends in Genetics*, Vol. 1S, No. 4, pp. 202-209 (a review on various animal and non-human models of HD).

An example of such an animal model is the transgenic mouse strain is the R6/2 line (Mangiarini et al. Cell 87: 493-506 (1996)). The R6/2 mice are transgenic Huntington's disease mice, which over-express exon 1 of the human HD gene (under the control of the endogenous promoter). The exon 1 of the R6/2 human HD gene has an expanded CAG/polyglutamine repeat lengths (150 CAG repeats on average). These mice develop a progressive, ultimately fatal neurological disease with many features of human Huntington's disease. Abnormal aggregates, constituted in part by the N terminal part of Huntingtin (encoded by HD exon 1), are observed in R6/2 mice, both 45 in the cytoplasm and nuclei of cells (Davies et al. *Cell* 90: 537-548 (1997)). For example, the human Huntingtin protein in the transgenic animal is encoded by a gene that includes at least 55 CAG repeats and more preferably about 150 CAG repeats. These transgenic animals can develop a Huntington's disease-like phenotype.

These transgenic mice are characterized by reduced weight gain, reduced lifespan and motor impairment characterized by abnormal gait, resting tremor, hindlimb clasping and hyperactivity from 8 to 10 weeks after birth (for example the R6/2 strain; see Mangiarini et al. *Cell* 87: 493-506 (1996)). The phenotype worsens progressively toward hypokinesia. The brains of these transgenic mice also demonstrate neurochemical and histological abnormalities, such as changes in neurotransmitter receptors (glutamate, dopaminergic), decreased concentration of N-acetylaspartate (a marker of neuronal integrity) and reduced striatum and brain size. Accordingly, evaluating can include assessing parameters related to neurotransmitter levels, neurotransmitter receptor levels, brain size and striatum size. In addition, abnormal aggregates containing the transgenic part of or full-length human Huntingtin protein are present in the brain tissue of these animals (e.g., the R6/2 transgenic mouse strain). See, e.g., Mangiarini et al. *Cell* 87: 493-506 (1996), Davies et al. *Cell* 90: 537-548 (1997), Brouillet, Functional Neurology 15(4): 239-251 (2000) and Cha et al. *Proc. Natl. Acad. Sci*. USA 95: 6480-6485 (1998).

To test the effect of the test polypeptide or known polypeptide described in the application in an animal model, different concentrations of test polypeptide are administered to the transgenic animal, for example by injecting the test polypeptide into circulation of the animal. A Huntington's disease-like symptom may be evaluated in the animal. The progression of the Huntington's disease-like symptoms, e.g., as described above for the mouse model, is then monitored to determine whether treatment with the test polypeptide results in reduction or delay of symptoms. In another assay, disaggregation of the Huntingtin protein aggregates in these animals is monitored. The animal can then be sacrificed and brain slices are obtained. The brain slices are then analyzed for the presence of aggregates containing the transgenic human Huntingtin protein, a portion thereof, or a fusion protein comprising human Huntingtin protein, or a portion thereof. This analysis can includes, for example, staining the slices of brain tissue with anti-Huntingtin antibody and adding a secondary antibody conjugated with FITC which recognizes the anti-Huntington's antibody (e.g., the anti-Huntingtin antibody is mouse anti-human antibody and the secondary antibody is specific for human antibody) and visualizing the protein aggregates by fluorescent microscopy.

A variety of methods are available to evaluate and/or monitor Huntington's disease. A variety of clinical symptoms and indicia for the disease are known. Huntington's disease causes a movement disorder, psychiatric difficulties and cognitive changes. The degree, age of onset, and manifestation of these symptoms can vary. The movement disorder can include quick, random, dance-like movements called chorea.

Exemplary motor evaluations include: ocular pursuit, saccade initiation, saccade velocity, dysarthria, tongue protrusion, finger tap ability, pronate/supinate, a lo fist-hand-palm sequence, rigidity of arms, bradykinesia, maximal dystonia (trunk, upper and lower extremities), maximal chorea (e.g., trunk, face, upper and lower extremities), gait, tandem walking, and retropulsion. An exemplary treatment can cause a change in the Total Motor Score 4 (TMS-4), a subscale of the UHDRS, e.g., over a one-year period.

Cancer

Methods of the invention which provide administering the Klotho fusion polypeptide to an individual can be used to treat cacner. Cancer includes any disease that is caused by or results in inappropriately high levels of cell division, inappropriately low levels of apoptosis, or both. Examples of cancers include, without limitation, leukemias (e.g., acute leukemia, acute lymphocytic leukemia, acute myelocytic leukemia, acute myeloblastic leukemia, acute promyelocytic leukemia, acute myelomonocytic leukemia, acute monocytic leukemia, acute erythroleukemia, chronic leukemia, chronic myelocytic leukemia, chronic lymphocytic leukemia), polycythemia vera, lymphoma (Hodgkin's disease, non-Hodgkin's disease), Waldenstrom's macroglobulinemia, heavy chain disease, and solid tumors such as sarcomas and carcinomas (e.g., fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, nile duct carcinoma, choriocarcinoma, seminoma, embryonal carcinoma, Wilm's tumor, cervical cancer, uterine cancer, testicular cancer, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodenroglioma, schwannoma, meningioma, melanoma, neuroblastoma, and retinoblastoma). Lymphoproliferative disorders are also considered to be proliferative diseases.

All patents, patent applications, and published references cited herein are hereby incorporated by reference in their entirety. While this invention has been particularly shown and described with references to embodiments thereof, it will be understood by those skilled in the art that various changes in form and details may be made therein without departing from the scope of the invention encompassed by the appended claims.

5. EXAMPLES

Example 1

Expression and Purification of Klotho Fusion Polypeptides

Expression of the Klotho Fusion Polypeptide

The polypeptides of the invention were made by transiently transfecting HEK293T cells with an expression vector encoding a Klotho fusion polypeptide having the extracellular domain of alpha Klotho and the FGF23 (R179Q) variant. Conditioned media containing expressed polypeptides were generated by transient transfection of the respective expression plasmids for Klotho, FGF23, and the Klotho-FGF23 (R179Q) fusion protein. The transfections were performed in 6-well plates using Lipofectamine 2000 (Invitrogen, Cat #11668-019). Five hours after transfection, the transfection mix was replaced with 3 ml DMEM plus 1% FBS. Conditioned media were collected 72 hours after the addition of 3 ml DMEM plus 1% FBS. Samples of conditioned medium from various transiently transfected HEK293T cells were separated by SDS-polyacrylamide gel electrophoresis (SDS-PAGE) and analyzed by Western blot (FIG. 2A) or stained with Coomassie blue (FIG. 2B).

SDS-polyacrylamide gel electrophoresis was performed on various samples (lane 1, Control; lane 2, FGF23; lane 3, sKlotho; lanes 4-6, sKlotho-FGF23). Coomassie blue staining revealed the expression of a high, >180 kDa band (FIG. 2B, indicated by arrow on the right) that was not present in lanes 1-3, which contained samples that had not been transfected with the vector encoding the Klotho fusion polypeptide. The quality of the Klotho fusion polypeptide secreted into the media was evaluated by Western blot (FIG. 2A). An anti-FGF23 rat monoclonal IgG2A (R&D Systems, Cat#MAB26291) was used as the primary antibody to detect the Klotho fusion polypeptides by Western blot. The Western blot confirmed that the additional bands observed in the Coomassie stained gels were Klotho fusion polypeptides. The Western blot confirmed that the Klotho fusion polypeptides had the expected molecular weight for the Klotho fusion polypeptide. This analysis shows the expression of the Klotho-FGF23 (R179Q) fusion protein.

Purification of the Klotho Fusion Polypeptide

The polypeptides of the invention were purified from conditioned media from a culture of HEK293T cells transiently transfected with an expression vector encoding a Klotho fusion polypeptide having the extracellular domain of alpha Klotho and the FGF23 R179Q variant. To generate conditioned medium, an expression vector encoding sKlotho-FGF23-6×His ( "6×His" disclosed as SEQ ID No: 54)was transfected (500 μg DNA in 18 ml of OptiMEM 1 (GIBCO, Cat#11058) mixed with 18 ml of 2 μg/ml polyethlinimine (PEI) into HEK293 cells grown in suspension in expression medium (464 ml of HEK293T cells at $10^6$ cells/ml in Freestype 293 expression medium (GIBCO, Cat #12338)). After transfection, the culture was allowed to grow (120 hours; 37° C. in a 5% $CO_2$ incubator; shaking at 125 rpm). At the end of incubation, conditioned medium was harvested by centrifugation (1000 rpm for five minutes). The conditioned medium was then applied to a nickel-agarose column. The sKlotho-FGF23-6×His ("6×His " disclosed as SEQ ID No: 54) bound tightly to the column and was eluted with 50 mM imidazole. The resulting purified material was then dialyzed in PBS to remove imidazole. A sample of the purified sKlotho-FGF23-6×His ("6×His" disclosed as SEQ ID No: 54) was separated by SDS-PAGE (lane 1, purified sKlotho-FGF23-6×His ("6×His" disclosed as SEQ ID No: 54); lane 2, molecular weight marker) and analyzed by staining with Coomassie blue (FIG. 2C). The stained SDS-PAGE gel confirmed that the purified sKlotho-FGF23-6×His ("6×His" disclosed as SEQ ID No: 54) had the expected molecular weight. The inability to detect bands corresponding to proteins other than full-length sKlotho-FGF23-6×His ("6×His" disclosed as SEQ ID No: 54) in the lane loaded with the purified material also showed that the sKlotho-FGF23-6×His ("6×His" disclosed as SEQ ID No: 54) was purified.

Example 2

In vitro Assay Assessing the Activity of the Klotho Fusion Polypeptide

Egr-1-Luciferase

The biological activity of the expressed alpha Klotho fusion polypeptide was tested in Egr-1-luciferase reporter assays. Binding of the Klotho fusion polypeptide to the FGF23 receptor resulted in the downstream activation of Egr-1 and the expression of a luciferase reporter regulated by the Egr-1 promoter. The Egr-1-luciferase reporter gene was constructed based on that reported by Urakawa et al. (Nature, 2006, Vol 444, 770-774). HEK293T cells seeded in 48-well poly-D-lysine plate were transfected with the Egr-1-luciferase reporter gene together with a transfection normalization reporter gene (*Renilla luciferase*). Five hours after transfection of the Egr-1 luciferase reporter gene, the transfection mix was replaced with 3 ml DMEM plus 1% FBS. Conditioned media were collected 72 hours after the addition of 3 ml DMEM plus 1% FBS. Five hours later, the transfection mix was replaced with a sample to be tested for activity. In initial experiments, 50% conditioned medium (alone or containing Klotho, FGF23, Klotho and FGF23, and the Klotho-FGF23(R179Q) fusion protein) and 50% DMEM with 1% FBS in the presence or absence of 20 μg/ml heparin (Sigma, Cat#H8537; dissolved in DMEM as 2 mg/ml stock) were tested in the Egr-1-luciferase reporter assays (FIG. 3). Further experiments used defined quantities of the purified polypeptides (FIGS. 4A and 4B). Cells were lysed 20 hours later in passive lysis buffer (Promega, Cat #E194A) and luciferase activities were determined using Dual-Glo Luciferase Assay System (Promega, Cat#E2940).

In initial experiments, Klotho fusion polypeptide activity was demonstrated in unfractionated conditioned medium. Using the Egr-1-luciferase reporter gene (FIG. 3) these experiments quantified the fold changes in the expression of the luciferase reporter. Conditioned medium containing a combination of FGF23 and the extracellular domain of Klotho protein activated Egr-1-luciferase, but conditioned medium containing only FGF23 or conditioned medium containing only the extracellular domain of Klotho, did not activate Egr-1-luciferase. Conditioned medium containing the fusion protein sKlotho-FGF23(R179Q) activated the Egr-1-luciferase reporter gene in contrast to conditioned media containing either FGF23 or Klotho alone. In these experiments, conditioned medium containing the fusion protein sKlotho-FGF23(R179Q) activated the Egr-1-luciferase reporter gene significantly better than conditioned medium containing a combination of FGF23 and Klotho. In the presence of heparin, the inductions by conditioned medium containing the fusion protein sKlotho-FGF23 (R179Q) and the conditioned medium containing a combination of FGF23 and Klotho were significantly enhanced. Table 1 lists the relative expression of various FGF-Klotho fusion polypeptides in conditioned medium and the relative activity of the unfractionated conditioned medium corresponding to the various FGF-Klotho fusion polypeptides in Egr-1-luciferase reporter assays.

TABLE 1

Expression and Activities of sKlotho-FGF23 fusion variants

| | sKlotho-FGF23 fusion constructs | Expression | Activity in Egr-1-luc reporter gene |
|---|---|---|---|
| 1 | sKlotho-FGF23 | good | yes |
| 2 | IgG sp-sKlotho-FGF23 | good | yes |
| 3 | sKL-D1-FGF23 | good | no |
| 4 | sKL-D2-FGF23 | no | n.a. |
| 5 | s(KL-D1)2-FGF23 | good | no |
| 6 | sKL-D1/D2-FGF23 | no | n.a. |
| 7 | ssKlotho(ΔN-26)-FGF23 | poor | no* |
| 8 | sKLD1-D2(Δ692-965)-FGF23 | poor | no* |
| 9 | sKL-D1-D2(Δ507-798)-FGF23 | poor | no* |
| 10 | FGF23-sKlotho | poor | no* |

*lack of activity may be the result of low expression

Egr-1-luciferase reporter assays were also performed using defined quantities of proteins purified from the conditioned medium, using the purification procedure as described in Example 1. Consistent with previous results using unfractionated conditioned medium containing the expressed polypeptides, treatment with a combination of purified FGF23 and sKlotho resulted in luciferase reporter activity, but treatment with purified FGF23 alone did not (FIG. 5A). The luciferase reporter activity from the combination of purified FGF23 and sKlotho was further dependent on the dose of purified sKlotho, and the effect could be enhanced by the presence of heparin (20 μg/ml). An effect of the sKlotho-FGF23-6×His ("6×His" disclosed as SEQ ID No: 54)fusion polypeptide on luciferase activity could be detected at concentrations as low as about 1.21 nM (1.2 fold change) and at least up to about 19.3 nM (2.4 fold change) in Egr-1-luciferase reporter assays (FIG. 5B). The activity of the sKlotho-FGF23-6×His ("6×His" disclosed as SEQ ID No: 54) fusion polypeptide on luciferase activity was significantly enhanced in the presence of heparin (20 μg/ml). In the presence of heparin, the effect of the sKlotho-FGF23-6×His ("6×His" disclosed as SEQ ID No: 54) fusion polypeptide on luciferase activity could be detected at a concentration as low as about 0.6 nM (2.0 fold change). The result showed that purified sKlotho-FGF23-6×His ("6×His" disclosed as SEQ ID No: 54) dose-dependently induced the EGR-1-luc reporter gene, and that treatment with sKlotho-FGF23-6×His ("6×His" disclosed as SEQ ID No: 54).

Example 3

In vitro Assay Assessing the Effect of the Klotho Fusion Polypeptide on Muscle Cells The biological effect of the expressed Klotho fusion polypeptide was tested on C2C12 myoblasts. Treatment of C2C12 myoblasts with IGF-1, FGF2, or sKlotho-FGF23 resulted in myotube growth and phosphorylation of signaling proteins. C2C12 myoblasts were seeded at a density of 40,000 cells/well in 6-well poly-D-lysine and fibronectin coated plates in growth medium (3 parts DMEM and 1 part F12), 10% FBS, 1% Glut; 1% P/S; 1% Linolic acid; 0.1% ITS: [insulin (10 mg/ml), transferrin (5.5 mg/ml), and selenium (5 ng/ml)]. After myoblasts reached confluence (3 days), medium was changed into differentiation medium (DMED with 2% horse serum; 1% Glut; 1% P/S).

For the myotube diameter experiments, three days after confluent media was changed into differentiation medium, cells were treated with IGF-1 (10 nM), FGF2 (20 ng/ml) or sKlotho-FGF23 (20 nM) in the absence or presence of dexamethasone (100 μM) for 24 hours in differentiation medium. At the end of treatment, cells were fixed with glutaraldehyde (5% in PBS) and multiple fluorescent images were collected. Myotube diameter was measured using the Pipeline Pilot program to determine hypertrophy or atrophy.

For the signaling protein phosphorylation, experiments, three days after confluent media was changed into differentiation medium, cells were starved for four hours with DMEM without FBS and then treated with IGF-1 (10 nM), FGF2 (20 ng/ml) or sKlotho-FGF23 (20 nM) in the absence or presence of Rapamycin (40 nM) for 30 min. Cells were lysed in RIPA buffer in the presence of protease and phosphatase inhibitors. Western blot analysis was carried out and membranes were probed with different antibodies as indicated in the figure and developed on X-ray films, which were scanned.

The results of this study showed that sKlotho-FGF23 resulted in an increase in myotube diameter compared to the control and induced C2C12 myotube hypertrophy similar to results for IGF-1 and FGF2 (FIG. 4A). In addition, treatment with sKlotho-FGF23, IGF-1, and FGF2 could partially reverse myotube atrophy induced by dexamethasone, based on measurements of myotube diameter. No difference was observed between sKlotho-FGF23 and FGF2 on myotube morphology (measured by thickness of the myotubes) in the absence or presence of dexamethasone. The trophic effects of sKlotho-FGF23, IGF-1, and FGF2 were statistically significant.

Consistent with the effects on C2C12 myotubes, sKlotho-FGF23 fusion protein signaling led to the phosphorylation of p70S6K and ERK, but not AKT or FoxO, in C2C12 myotubes (FIG. 4B). The effect of sKlotho-FGF23 on signaling was similar to that of FGF2, but was distinct from that of IGF-1. The extent of ERK phosphorylation by sKlotho-FGF23 was observed to be less than that of IGF-1 or FGF2. The phosphorylation of p70S6K by sKlotho-FGF23 was rapamycin sensitive. In the experiments involving C2C12 cells, heparin was not required to activate signaling. These results show that a sKlotho-FGF23 fusion polypeptide activated signaling in C2C12 myotubes.

Example 4

Fusion Polypeptides Comprising sKlotho, FGF23 and FcLALA

Various fusion polypeptides are constructed using sKlotho, FGF23, and a modified Fc fragment of an antibody. These modified Fc molecules have altered (decreased) binding to FcRn and thus increased serum half-life. They also have modified bioavailability and alterered transport to mucosal surfaces and other targets in the body. In this example, the FGF23 and sKlotho are fused to FcLALA, which is described in U.S. Pat. No. 7,217,798 and Hessell et al. 2007 Nature 449:101-104, Intervening between the various components of these fusion polypeptides are linkers, as described in Lode et al. 1998 Proc. Natl. Acad. Sci. USA 95: 2475-2480. These fusions are inserted into constructs, e.g., pcDNA3.1 (Invitrogen, Carlsbad, Calif.), and expressed in HEK293 cells.

A. sKlotho-FGF23-FcLALA v1

A fusion is constructed which comprises: sKlotho, a linker, FGF23, another linker, and FcLALA. This embodiment, designated sKlotho-FGF23-FcLALA v1, is presented in SEQ ID NOs: 46 and 47, below.

The nucleotide sequence of sKlotho-FGF23-FcLALA v1 (wherein initiation ATG as 1) is presented as SEQ ID NO: 46.

The amino acid sequence of sKlotho-FGF23-FcLALA v1 is presented below as SEQ ID NO: 47.

In this sequence, the various components of the fusion are as follows:

sKlotho: 1-982; Linked: 983-1001; FGF23: 1002-1228; Linker 2; 1229-1233; FcLALA: 1234-1459.

B. sKlotho-FGF23-FcLALA v2

A fusion is constructed which comprises: sKlotho, a linker, FGF23, another linker, and FcLALA. This embodiment is designated sKlotho-FGF23-FcLALA v2 and presented as SEQ ID NOs: 48 and 49, below.

The nucleotide sequence of sKlotho-FGF23-FcLALA v2 (wherein initiation ATG as 1) is presented as SEQ ID NO: 48.

The amino acid sequence of sKlotho-FGF23-FcLALA v2 is presented below as SEQ ID NO: 49.

In this sequence, the various components of the fusion are as follows:

sKlotho: (aa or amino acids) 1-982; Linker 1: 983-1001; FGF23: 1002-1228; Linker 2; 1229-1233; FcLALA: 1234-1450.

Other fusion polypeptides can be constructed by combining in various combinations the FGF, Klotho, modified Fc fragments, and (optionally) linker sequences, and variants and derivatives thereof, as described herein or known in the art.

Example 5

Fusion Polypeptides Comprising FGF23 and FcLALA

Various fusion polypeptides are constructed using FGF23, and a modified Fc fragment of an antibody, as described in U.S. Pat. No. 7,217,798. These modified Fc molecules have altered (decreased) binding to FcRn and thus increased serum half-life. They also have modified bioavailability and altered transport to mucosal surfaces and other targets in the body. In this example, FGF23 is fused to FcLALA, Intervening between the various components of these fusion polypeptides are linkers, as described in Lode et al. 1998 Proc. Natl. Acad. Sci. USA 95: 2475-2480. These fusions are inserted constructs, e.g., pcDNA3.1 (Invitrogen, Carlsbad, Calif.), and expressed in HEK293 cells.

C. FGF23-FcLALA v1

A fusion is constructed which comprises: FGF23, a linker, and FcLALA. This construct is designated FGF23-FcLALA v1 and presented below as SEQ ID NOs: 50 and 51.

The nucleotide sequence of FGF23-FcLALA v1 (wherein initiation ATG as 1) is presented below as SEQ ID NO: 50.

The amino acid sequence of FGF23 (R179Q)-FcLALAv1 is presented below as SEQ ID NO: 51.

In this sequence, the various components of the fusion are as follows:

FGF23: (aa) 1-251; Linker: 252-256; FcLALA: 257-482.

D. FGF23-FcLALA v2

A fusion is constructed which comprises: FGF23-FcLALA v2, which comprises FGF23 and FcLALA.

The nucleotide sequence of FGF23-FcLALA v2 (wherein initiation ATG as 1) is presented below as SEQ ID NO: 52.

The amino acid sequence of FGF23 (R179Q)-FcLALAv2 is presented below as SEQ ID NO: 53.

In this sequence, the various components of the fusion are as follows:

FGF23: 1-251; Linker: 252-256; FcLALA: 257-473.

Other fusion polypeptides can be constructed by combining in various combinations the FGF sequences, modified Fc fragments, and (optionally) linkers, and variants and derivatives thereof, as described herein or known in the art.

What is claimed is:

1. A fusion polypeptide comprising, in order from N-terminus to C-terminus, a polypeptide comprising the sequence of amino acids 34 to 982 of SEQ ID NO: 19; one or more linkers; and a polypeptide comprising the sequence of amino acids 1000 to 1228 of SEQ ID NO: 19, wherein the fusion polypeptide is capable of activating Egr-1.

2. The fusion polypeptide of claim 1, further comprising a signal peptide.

3. A pharmaceutical composition comprising the fusion polypeptide of claim 1 and a pharmaceutically acceptable carrier.

4. The fusion polypeptide of claim 1, wherein the one or more linkers comprise one or more polypeptide linkers.

5. A nucleic acid comprising a sequence that encodes a fusion polypeptide comprising, in order from N-terminus to C-terminus, a polypeptide comprising the sequence of amino acids 34 to 982 of SEQ ID NO: 19; one or more linkers; and a polypeptide comprising the sequence of amino acids 1000 to 1228 of SEQ ID NO: 19, wherein the fusion polypeptide is capable of activating Egr-1.

6. A host cell containing the nucleic acid of claim 5.

7. A vector comprising the nucleic acid of claim 5.

8. A fusion polypeptide comprising, in order from N-terminus to C-terminus, a polypeptide consisting of the sequence of amino acids 34 to 982 of SEQ ID NO: 19; one or more linkers; and a polypeptide consisting of the sequence of amino acids 1000 to 1228 of SEQ ID NO: 19, wherein the fusion polypeptide is capable of activating Egr-1.

9. The fusion polypeptide of claim 8, wherein the one or more linkers comprise one or more polypeptide linkers.

10. The fusion polypeptide of claim 8, further comprising a signal peptide.

11. A pharmaceutical composition comprising the fusion polypeptide of claim 8 and a pharmaceutically acceptable carrier.

* * * * *

SEQUENCE LISTING

```
<160> NUMBER OF SEQ ID NOS: 54

<210> SEQ ID NO 1
<211> LENGTH: 5003
<212> TYPE: DNA
<213> ORGANISM: Homo sapiens

<400> SEQUENCE: 1

cgcgcagcat gcccgccagc gccccgccgc gccgcccgcg gccgccgccg ccgtcgctgt     60

cgctgctgct ggtgctgctg ggcctgggcg gccgccgcct gcgtgcggag ccgggcgacg    120

gcgcgcagac ctgggcccgt ttctcgcggc ctcctgcccc cgaggccgcg ggcctcttcc    180

agggcacctt ccccgacggc ttcctctggg ccgtgggcag cgccgcctac cagaccgagg    240

gcggctggca gcagcacggc aagggtgcgt ccatctggga tacgttcacc caccaccccc    300

tggcaccccc gggagactcc cggaacgcca gtctgccgtt gggcgccccg tcgccgctgc    360

agcccgccac cggggacgta gccagcgaca gctacaacaa cgtcttccgc gacacggagg    420

cgctgcgcga gctcggggtc actcactacc gcttctccat ctcgtgggcg cgagtgctcc    480

ccaatggcag cgcgggcgtc cccaaccgcg aggggctgcg ctactaccgg cgcctgctgg    540

agcggctgcg ggagctgggc gtgcagcccg tggtcaccct gtaccactgg gacctgcccc    600

agcgcctgca ggacgcctac ggcggctggg ccaaccgcgc cctggccgac cacttcaggg    660

attacgcgga gctctgcttc cgccacttcg gcggtcaggt caagtactgg atcaccatcg    720

acaaccccta cgtggtggcc tggcacggct acgccaccgg gcgcctggcc cccggcatcc    780

ggggcagccc gcggctcggg tacctggtgg cgcacaacct cctcctggct catgccaaag    840

tctggcatct ctacaatact tctttccgtc ccactcaggg aggtcaggtg tccattgccc    900

taagctctca ctggatcaat cctcgaagaa tgaccgacca cagcatcaaa gaatgtcaaa    960

aatctctgga ctttgtacta ggttggtttg ccaaacccgt atttattgat ggtgactatc   1020
```

```
ccgagagcat gaagaataac ctttcatcta ttctgcctga ttttactgaa tctgagaaaa   1080
agttcatcaa aggaactgct gacttttttg ctctttgctt tggacccacc ttgagttttc   1140
aacttttgga ccctcacatg aagttccgcc aattggaatc tcccaacctg aggcaactgc   1200
tttcctggat tgaccttgaa tttaaccatc ctcaaatatt tattgtggaa aatggctggt   1260
ttgtctcagg gaccaccaag agagatgatg ccaaatatat gtattacctc aaaaagttca   1320
tcatggaaac cttaaaagcc atcaagctgg atggggtgga tgtcatcggg tataccgcat   1380
ggtccctcat ggatggtttc gagtggcaca gaggttacag catcaggcgt ggactcttct   1440
atgttgactt tctaagccag gacaagatgt tgttgccaaa gtcttcagcc ttgttctacc   1500
aaaagctgat agagaaaaat ggcttccctc ctttacctga aaatcagccc ctagaaggga   1560
catttccctg tgactttgct tggggagttg ttgacaacta cattcaagta gataccactc   1620
tgtctcagtt taccgacctg aatgtttacc tgtgggatgt ccaccacagt aaaaggctta   1680
ttaaagtgga tggggttgtg accaagaaga ggaaatccta ctgtgttgac tttgctgcca   1740
tccagcccca gatcgcttta ctccaggaaa tgcacgttac acattttcgc ttctccctgg   1800
actgggccct gattctccct ctgggtaacc agtcccaggt gaaccacacc atcctgcagt   1860
actatcgctg catggccagc gagcttgtcc gtgtcaacat caccccagtg gtggccctgt   1920
ggcagcctat ggccccgaac caaggactgc cgcgcctcct ggccaggcag ggcgcctggg   1980
agaaccccta cactgccctg gcctttgcag agtatgcccg actgtgcttt caagagctcg   2040
gccatcacgt caagctttgg ataacgatga atgagccgta tacaaggaat atgacataca   2100
gtgctggcca caaccttctg aaggcccatg ccctggcttg gcatgtgtac aatgaaaagt   2160
ttaggcatgc tcagaatggg aaaatatcca tagccttgca ggctgattgg atagaacctg   2220
cctgcccttt ctcccaaaag gacaaagagg tggccgagag agttttggaa tttgacattg   2280
gctggctggc tgagcccatt ttcggctctg gagattatcc atgggtgatg agggactggc   2340
tgaaccaaag aaacaatttt cttcttcctt atttcactga agatgaaaaa aagctaatcc   2400
agggtacctt tgacttttg gctttaagcc attataccac catccttgta gactcagaaa   2460
aagaagatcc aataaaatac aatgattacc tagaagtgca agaaatgacc gacatcacgt   2520
ggctcaactc ccccagtcag gtggcggtag tgccctgggg gttgcgcaaa gtgctgaact   2580
ggctgaagtt caagtacgga gacctcccca tgtacataat atccaacgga atcgatgacg   2640
ggctgcatgc tgaggacgac cagctgaggg tgtattatat gcagaattac ataaacgaag   2700
ctctcaaagc ccacatactg gatggtatca atctttgcgg atactttgct tattcgttta   2760
acgaccgcac agctccgagg tttggcctct atcgttatgc tgcagatcag tttgagccca   2820
aggcatccat gaaacattac aggaaaatta ttgacagcaa tggtttcccg ggcccagaaa   2880
ctctggaaag attttgtcca gaagaattca ccgtgtgtac tgagtgcagt ttttttcaca   2940
cccgaaagtc tttactggct ttcatagctt ttctattttt tgcttctatt atttctctct   3000
cccttatatt ttactactcg aagaaaggca gaagaagtta caaatagttc tgaacatttt   3060
tctattcatt cattttgaaa taattatgca gacacatcag ctgttaacca tttgcacctc   3120
taagtgttgt gaaactgtaa atttcataca tttgacttct agaaaacatt tttgtggctt   3180
atgacagagg ttttgaaatg ggcataggtg atcgtaaaat attgaataat gcgaatagtg   3240
cctgaatttg ttctcttttt gggtgattaa aaaactgaca ggcactataa tttctgtaac   3300
acactaacaa aagcatgaaa aataggaacc acaccaatgc aacatttgtg cagaaatttg   3360
```

```
aatgacaaga ttaggaatat tttcttctgc acccacttct aaatttaatg tttttctgga   3420

agtagtaatt gcaagagttc gaatagaaag ttatgtacca agtaaccatt tctcagctgc   3480

cataataatg cctagtggct tcccctctgt caaatctagt ttcctatgga aaagaagatg   3540

gcagatacag gagagacgac agagggtcct aggctggaat gttcctttcg aaagcaatgc   3600

ttctatcaaa tactagtatt aatttatgta tctggttaat gacatacttg gagagcaaat   3660

tatggaaatg tgtattttat atgatttttg aggtcctgtc taaaccctgt gtccctgagg   3720

gatctgtctc actggcatct tgttgagggc cttgcacata ggaaactttt gataagtatc   3780

tgcggaaaaa caaacatgaa tcctgtgata ttgggctctt caggaagcat aaagcaattg   3840

tgaaatacag tataccgcag tggctctagg tggaggaaag gaggaaaaag tgcttattat   3900

gtgcaacatt atgattaatc tgattataca ccatttttga gcagatcttg gaatgaatga   3960

catgaccttt ccctagagaa taaggatgaa ataatcactc attctatgaa cagtgacact   4020

actttctatt ctttagctgt actgtaattt ctttgagttg atagttttac aaattcttaa   4080

taggttcaaa agcaatctgg tctgaataac actggatttg tttctgtgat ctctgaggtc   4140

tattttatgt ttttgctgct acttctgtgg aagtagcttt gaactagttt tactttgaac   4200

tttcacgctg aaacatgcta gtgatatcta gaaagggcta attaggtctc atcctttaat   4260

gccccttaaa taagtcttgc tgattttcag acagggaagt ctctctatta cactggagct   4320

gttttataga taagtcaata ttgtatcagg caagataaac caatgtcata acaggcattg   4380

ccaacctcac tgacacaggg tcatagtgta taataatata ctgtactata taatatatca   4440

tctttagagg tatgattttt tcatgaaaga taagcttttg gtaatattca ttttaaagtg   4500

gacttattaa aattggatgc tagagaatca agtttatttt atgtatatat ttttctgatt   4560

ataagagtaa tatatgttca ttgtaaaaat ttttaaaaca cagaaactat atgcaaagaa   4620

aaaataaaaa ttatctataa tctcagaacc cagaaatagc cactattaac atttcctacg   4680

tattttattt tacatagatc atattgtata tagttagtat ctttattaat ttttattatg   4740

aaactttcct ttgtcattat tagtcttcaa aagcatgatt tttaatagtt gttgagtatt   4800

ccaccacagg aatgtatcac aacttaaccg ttcccgtttg ttagactagt ttcttattaa   4860

tgttgatgaa tgttgtttaa aaataatttt gttgctacat ttactttaat ttccttgact   4920

gtaaagagaa gtaattttgc tccttgataa agtattatat taataataaa tctgcctgca   4980

actttttgcc ttctttcata atc                                          5003
```

```
<210> SEQ ID NO 2
<211> LENGTH: 1012
<212> TYPE: PRT
<213> ORGANISM: Homo sapiens

<400> SEQUENCE: 2

Met Pro Ala Ser Ala Pro Pro Arg Arg Pro Arg Pro Pro Pro Pro Ser
1               5                   10                  15

Leu Ser Leu Leu Leu Val Leu Leu Gly Leu Gly Gly Arg Arg Leu Arg
            20                  25                  30

Ala Glu Pro Gly Asp Gly Ala Gln Thr Trp Ala Arg Phe Ser Arg Pro
        35                  40                  45

Pro Ala Pro Glu Ala Ala Gly Leu Phe Gln Gly Thr Phe Pro Asp Gly
    50                  55                  60

Phe Leu Trp Ala Val Gly Ser Ala Ala Tyr Gln Thr Glu Gly Gly Trp
65                  70                  75                  80
```

```
Gln Gln His Gly Lys Gly Ala Ser Ile Trp Asp Thr Phe Thr His His
                85                  90                  95

Pro Leu Ala Pro Pro Gly Asp Ser Arg Asn Ala Ser Leu Pro Leu Gly
            100                 105                 110

Ala Pro Ser Pro Leu Gln Pro Ala Thr Gly Asp Val Ala Ser Asp Ser
        115                 120                 125

Tyr Asn Asn Val Phe Arg Asp Thr Glu Ala Leu Arg Glu Leu Gly Val
    130                 135                 140

Thr His Tyr Arg Phe Ser Ile Ser Trp Ala Arg Val Leu Pro Asn Gly
145                 150                 155                 160

Ser Ala Gly Val Pro Asn Arg Glu Gly Leu Arg Tyr Tyr Arg Arg Leu
                165                 170                 175

Leu Glu Arg Leu Arg Glu Leu Gly Val Gln Pro Val Val Thr Leu Tyr
            180                 185                 190

His Trp Asp Leu Pro Gln Arg Leu Gln Asp Ala Tyr Gly Gly Trp Ala
        195                 200                 205

Asn Arg Ala Leu Ala Asp His Phe Arg Asp Tyr Ala Glu Leu Cys Phe
    210                 215                 220

Arg His Phe Gly Gly Gln Val Lys Tyr Trp Ile Thr Ile Asp Asn Pro
225                 230                 235                 240

Tyr Val Val Ala Trp His Gly Tyr Ala Thr Gly Arg Leu Ala Pro Gly
                245                 250                 255

Ile Arg Gly Ser Pro Arg Leu Gly Tyr Leu Val Ala His Asn Leu Leu
            260                 265                 270

Leu Ala His Ala Lys Val Trp His Leu Tyr Asn Thr Ser Phe Arg Pro
        275                 280                 285

Thr Gln Gly Gly Gln Val Ser Ile Ala Leu Ser Ser His Trp Ile Asn
    290                 295                 300

Pro Arg Arg Met Thr Asp His Ser Ile Lys Glu Cys Gln Lys Ser Leu
305                 310                 315                 320

Asp Phe Val Leu Gly Trp Phe Ala Lys Pro Val Phe Ile Asp Gly Asp
                325                 330                 335

Tyr Pro Glu Ser Met Lys Asn Asn Leu Ser Ser Ile Leu Pro Asp Phe
            340                 345                 350

Thr Glu Ser Glu Lys Lys Phe Ile Lys Gly Thr Ala Asp Phe Phe Ala
        355                 360                 365

Leu Cys Phe Gly Pro Thr Leu Ser Phe Gln Leu Leu Asp Pro His Met
    370                 375                 380

Lys Phe Arg Gln Leu Glu Ser Pro Asn Leu Arg Gln Leu Leu Ser Trp
385                 390                 395                 400

Ile Asp Leu Glu Phe Asn His Pro Gln Ile Phe Ile Val Glu Asn Gly
                405                 410                 415

Trp Phe Val Ser Gly Thr Thr Lys Arg Asp Asp Ala Lys Tyr Met Tyr
            420                 425                 430

Tyr Leu Lys Lys Phe Ile Met Glu Thr Leu Lys Ala Ile Lys Leu Asp
        435                 440                 445

Gly Val Asp Val Ile Gly Tyr Thr Ala Trp Ser Leu Met Asp Gly Phe
    450                 455                 460

Glu Trp His Arg Gly Tyr Ser Ile Arg Arg Gly Leu Phe Tyr Val Asp
465                 470                 475                 480

Phe Leu Ser Gln Asp Lys Met Leu Leu Pro Lys Ser Ser Ala Leu Phe
                485                 490                 495

Tyr Gln Lys Leu Ile Glu Lys Asn Gly Phe Pro Pro Leu Pro Glu Asn
```

```
            500                 505                 510

Gln Pro Leu Glu Gly Thr Phe Pro Cys Asp Phe Ala Trp Gly Val Val
        515                 520                 525

Asp Asn Tyr Ile Gln Val Asp Thr Thr Leu Ser Gln Phe Thr Asp Leu
    530                 535                 540

Asn Val Tyr Leu Trp Asp Val His His Ser Lys Arg Leu Ile Lys Val
545                 550                 555                 560

Asp Gly Val Val Thr Lys Lys Arg Lys Ser Tyr Cys Val Asp Phe Ala
                565                 570                 575

Ala Ile Gln Pro Gln Ile Ala Leu Leu Gln Glu Met His Val Thr His
            580                 585                 590

Phe Arg Phe Ser Leu Asp Trp Ala Leu Ile Leu Pro Leu Gly Asn Gln
        595                 600                 605

Ser Gln Val Asn His Thr Ile Leu Gln Tyr Tyr Arg Cys Met Ala Ser
    610                 615                 620

Glu Leu Val Arg Val Asn Ile Thr Pro Val Val Ala Leu Trp Gln Pro
625                 630                 635                 640

Met Ala Pro Asn Gln Gly Leu Pro Arg Leu Leu Ala Arg Gln Gly Ala
                645                 650                 655

Trp Glu Asn Pro Tyr Thr Ala Leu Ala Phe Ala Glu Tyr Ala Arg Leu
            660                 665                 670

Cys Phe Gln Glu Leu Gly His His Val Lys Leu Trp Ile Thr Met Asn
        675                 680                 685

Glu Pro Tyr Thr Arg Asn Met Thr Tyr Ser Ala Gly His Asn Leu Leu
    690                 695                 700

Lys Ala His Ala Leu Ala Trp His Val Tyr Asn Glu Lys Phe Arg His
705                 710                 715                 720

Ala Gln Asn Gly Lys Ile Ser Ile Ala Leu Gln Ala Asp Trp Ile Glu
                725                 730                 735

Pro Ala Cys Pro Phe Ser Gln Lys Asp Lys Glu Val Ala Glu Arg Val
            740                 745                 750

Leu Glu Phe Asp Ile Gly Trp Leu Ala Glu Pro Ile Phe Gly Ser Gly
        755                 760                 765

Asp Tyr Pro Trp Val Met Arg Asp Trp Leu Asn Gln Arg Asn Asn Phe
    770                 775                 780

Leu Leu Pro Tyr Phe Thr Glu Asp Glu Lys Lys Leu Ile Gln Gly Thr
785                 790                 795                 800

Phe Asp Phe Leu Ala Leu Ser His Tyr Thr Thr Ile Leu Val Asp Ser
                805                 810                 815

Glu Lys Glu Asp Pro Ile Lys Tyr Asn Asp Tyr Leu Glu Val Gln Glu
            820                 825                 830

Met Thr Asp Ile Thr Trp Leu Asn Ser Pro Ser Gln Val Ala Val Val
        835                 840                 845

Pro Trp Gly Leu Arg Lys Val Leu Asn Trp Leu Lys Phe Lys Tyr Gly
    850                 855                 860

Asp Leu Pro Met Tyr Ile Ile Ser Asn Gly Ile Asp Asp Gly Leu His
865                 870                 875                 880

Ala Glu Asp Asp Gln Leu Arg Val Tyr Tyr Met Gln Asn Tyr Ile Asn
                885                 890                 895

Glu Ala Leu Lys Ala His Ile Leu Asp Gly Ile Asn Leu Cys Gly Tyr
            900                 905                 910

Phe Ala Tyr Ser Phe Asn Asp Arg Thr Ala Pro Arg Phe Gly Leu Tyr
        915                 920                 925
```

```
Arg Tyr Ala Ala Asp Gln Phe Glu Pro Lys Ala Ser Met Lys His Tyr
    930                 935                 940

Arg Lys Ile Ile Asp Ser Asn Gly Phe Pro Gly Pro Glu Thr Leu Glu
945                 950                 955                 960

Arg Phe Cys Pro Glu Glu Phe Thr Val Cys Thr Glu Cys Ser Phe Phe
                965                 970                 975

His Thr Arg Lys Ser Leu Leu Ala Phe Ile Ala Phe Leu Phe Phe Ala
            980                 985                 990

Ser Ile Ile Ser Leu Ser Leu Ile  Phe Tyr Tyr Ser Lys  Lys Gly Arg
        995                 1000                1005

Arg Ser  Tyr Lys
    1010
```

<210> SEQ ID NO 3
<211> LENGTH: 3279
<212> TYPE: DNA
<213> ORGANISM: Homo sapiens

<400> SEQUENCE: 3

```
atcctcagtc tcccagttca agctaatcat tgacagagct ttacaatcac aagcttttac     60

tgaagctttg ataagacagt ccagcagttg gtggcaaatg aagccaggct gtgcggcagg    120

atctccaggg aatgaatgga ttttcttcag cactgatgaa ataaccacac gctataggaa    180

tacaatgtcc aacgggggat tgcaaagatc tgtcatcctg tcagcactta ttctgctacg    240

agctgttact ggattctctg gagatggaag agctatatgg tctaaaaatc ctaattttac    300

tccggtaaat gaaagtcagc tgtttctcta tgacactttc cctaaaaact tttctgggg    360

tattgggact ggagcattgc aagtggaagg gagttggaag aaggatggaa aaggaccttc    420

tatatgggat catttcatcc acacacacct taaaaatgtc agcagcacga atggttccag    480

tgacagttat atttttctgg aaaaagactt atcagccctg gattttatag gagtttcttt    540

ttatcaattt tcaatttcct ggccaaggct ttccccgat ggaatagtaa cagttgccaa    600

cgcaaaaggt ctgcagtact acagtactct tctggacgct ctagtgctta gaaacattga    660

acctatagtt actttatacc actgggattt gcctttggca ctacaagaaa aatatggggg    720

gtggaaaaat gataccataa tagatatctt caatgactat gccacatact gtttccagat    780

gtttggggac cgtgtcaaat attggattac aattcacaac ccatatctag tggcttggca    840

tgggtatggg acaggtatgc atgcccctgg agagaaggga aatttagcag ctgtctacac    900

tgtgggacac aacttgatca aggctcactc gaaagtttgg cataactaca acacacattt    960

ccgcccacat cagaagggtt ggttatcgat cacgttggga tctcattgga tcgagccaaa   1020

ccggtcggaa aacacgatgg atatattcaa atgtcaacaa tccatggttt ctgtgcttgg   1080

atggtttgcc aaccctatcc atggggatgg cgactatcca gaggggatga gaaagaagtt   1140

gttctccgtt ctacccattt tctctgaagc agagaagcat gagatgagag gcacagctga   1200

tttctttgcc ttttcttttg gacccaacaa cttcaagccc ctaaacacca tggctaaaat   1260

gggacaaaat gtttcactta atttaagaga agcgctgaac tggattaaac tggaatacaa   1320

caaccctcga atcttgattg ctgagaatgg ctggttcaca gacagtcgtg tgaaaacaga   1380

agacaccacg gccatctaca tgatgaagaa tttcctcagc caggtgcttc aagcaataag   1440

gttagatgaa atacgagtgt ttggttatac tgcctggtct ctcctggatg gctttgaatg   1500

gcaggatgct tacaccatcc gccgaggatt attttatgtg gattttaaca gtaaacagaa   1560
```

```
agagcggaaa cctaagtctt cagcacacta ctacaaacag atcatacgag aaaatggttt   1620

ttctttaaaa gagtccacgc cagatgtgca gggccagttt ccctgtgact tctcctgggg   1680

tgtcactgaa tctgttctta agcccgagtc tgtggcttcg tccccacagt tcagcgatcc   1740

tcatctgtac gtgtggaacg ccactggcaa cagactgttg caccgagtgg aaggggtgag   1800

gctgaaaaca cgacccgctc aatgcacaga ttttgtaaac atcaaaaaac aacttgagat   1860

gttggcaaga atgaaagtca cccactaccg gtttgctctg gattgggcct cggtccttcc   1920

cactggcaac ctgtccgcgg tgaaccgaca ggccctgagg tactacaggt gcgtggtcag   1980

tgaggggctg aagcttggca tctccgcgat ggtcaccctg tattatccga cccacgccca   2040

cctaggcctc cccgagcctc tgttgcatgc cgacgggtgg ctgaacccat cgacggccga   2100

ggccttccag gcctacgctg ggctgtgctt ccaggagctg gggg acctgg tgaagctctg   2160

gatcaccatc aacgagccta accggctaag tgacatctac aaccgctctg gcaacgacac   2220

ctacggggcg gcgcacaacc tgctggtggc ccacgccctg gcctggcgcc tctacgaccg   2280

gcagttcagg ccctcacagc gcggggccgt gtcgctgtcg ctgcacgcgg actgggcgga   2340

acccgccaac ccctatgctg actcgcactg gagggcggcc gagcgcttcc tgcagttcga   2400

gatcgcctgg ttcgccgagc cgctcttcaa gaccggggac taccccgcgg ccatgaggga   2460

atacattgcc tccaagcacc gacgggggct ttccagctcg gccctgccgc gcctcaccga   2520

ggccgaaagg aggctgctca agggcacggt cgacttctgc gcgctcaacc acttcaccac   2580

taggttcgtg atgcacgagc agctggccgg cagccgctac gactcggaca gggacatcca   2640

gtttctgcag gacatcaccc gcctgagctc ccccacgcgc ctggctgtga ttccctgggg   2700

ggtgcgcaag ctgctgcggt gggtccggag gaactacggc gacatggaca tttacatcac   2760

cgccagtggc atcgacgacc aggctctgga ggatgaccgg ctccggaagt actacctagg   2820

gaagtacctt caggaggtgc tgaaagcata cctgattgat aaagtcagaa tcaaaggcta   2880

ttatgcattc aaactggctg aagagaaatc taaacccaga tttggattct tcacatctga   2940

ttttaaagct aaatcctcaa tacaatttta caacaaagtg atcagcagca ggggcttccc   3000

ttttgagaac agtagttcta gatgcagtca gacccaagaa aatacagagt gcactgtctg   3060

cttattcctt gtgcagaaga aaccactgat attcctgggt tgttgcttct tctccaccct   3120

ggttctactc ttatcaattg ccatttttca aaggcagaag agaagaaagt tttggaaagc   3180

aaaaaactta caacacatac cattaaagaa aggcaagaga gttgttagct aaactgatct   3240

gtctgcatga tagacagttt aaaaattcat cccagttcc                          3279
```

```
<210> SEQ ID NO 4
<211> LENGTH: 1044
<212> TYPE: PRT
<213> ORGANISM: Homo sapiens

<400> SEQUENCE: 4

Met Lys Pro Gly Cys Ala Ala Gly Ser Pro Gly Asn Glu Trp Ile Phe
1               5                   10                  15

Phe Ser Thr Asp Glu Ile Thr Thr Arg Tyr Arg Asn Thr Met Ser Asn
            20                  25                  30

Gly Gly Leu Gln Arg Ser Val Ile Leu Ser Ala Leu Ile Leu Leu Arg
        35                  40                  45

Ala Val Thr Gly Phe Ser Gly Asp Gly Arg Ala Ile Trp Ser Lys Asn
    50                  55                  60

Pro Asn Phe Thr Pro Val Asn Glu Ser Gln Leu Phe Leu Tyr Asp Thr
```

-continued

```
65                  70                  75                  80

Phe Pro Lys Asn Phe Phe Trp Gly Ile Gly Thr Gly Ala Leu Gln Val
                85                  90                  95

Glu Gly Ser Trp Lys Lys Asp Gly Lys Gly Pro Ser Ile Trp Asp His
            100                 105                 110

Phe Ile His Thr His Leu Lys Asn Val Ser Ser Thr Asn Gly Ser Ser
        115                 120                 125

Asp Ser Tyr Ile Phe Leu Glu Lys Asp Leu Ser Ala Leu Asp Phe Ile
    130                 135                 140

Gly Val Ser Phe Tyr Gln Phe Ser Ile Ser Trp Pro Arg Leu Phe Pro
145                 150                 155                 160

Asp Gly Ile Val Thr Val Ala Asn Ala Lys Gly Leu Gln Tyr Tyr Ser
                165                 170                 175

Thr Leu Leu Asp Ala Leu Val Leu Arg Asn Ile Glu Pro Ile Val Thr
            180                 185                 190

Leu Tyr His Trp Asp Leu Pro Leu Ala Leu Gln Glu Lys Tyr Gly Gly
        195                 200                 205

Trp Lys Asn Asp Thr Ile Ile Asp Ile Phe Asn Asp Tyr Ala Thr Tyr
    210                 215                 220

Cys Phe Gln Met Phe Gly Asp Arg Val Lys Tyr Trp Ile Thr Ile His
225                 230                 235                 240

Asn Pro Tyr Leu Val Ala Trp His Gly Tyr Gly Thr Gly Met His Ala
                245                 250                 255

Pro Gly Glu Lys Gly Asn Leu Ala Ala Val Tyr Thr Val Gly His Asn
            260                 265                 270

Leu Ile Lys Ala His Ser Lys Val Trp His Asn Tyr Asn Thr His Phe
        275                 280                 285

Arg Pro His Gln Lys Gly Trp Leu Ser Ile Thr Leu Gly Ser His Trp
    290                 295                 300

Ile Glu Pro Asn Arg Ser Glu Asn Thr Met Asp Ile Phe Lys Cys Gln
305                 310                 315                 320

Gln Ser Met Val Ser Val Leu Gly Trp Phe Ala Asn Pro Ile His Gly
                325                 330                 335

Asp Gly Asp Tyr Pro Glu Gly Met Arg Lys Lys Leu Phe Ser Val Leu
            340                 345                 350

Pro Ile Phe Ser Glu Ala Glu Lys His Glu Met Arg Gly Thr Ala Asp
        355                 360                 365

Phe Phe Ala Phe Ser Phe Gly Pro Asn Asn Phe Lys Pro Leu Asn Thr
    370                 375                 380

Met Ala Lys Met Gly Gln Asn Val Ser Leu Asn Leu Arg Glu Ala Leu
385                 390                 395                 400

Asn Trp Ile Lys Leu Glu Tyr Asn Asn Pro Arg Ile Leu Ile Ala Glu
                405                 410                 415

Asn Gly Trp Phe Thr Asp Ser Arg Val Lys Thr Glu Asp Thr Thr Ala
            420                 425                 430

Ile Tyr Met Met Lys Asn Phe Leu Ser Gln Val Leu Gln Ala Ile Arg
        435                 440                 445

Leu Asp Glu Ile Arg Val Phe Gly Tyr Thr Ala Trp Ser Leu Leu Asp
    450                 455                 460

Gly Phe Glu Trp Gln Asp Ala Tyr Thr Ile Arg Arg Gly Leu Phe Tyr
465                 470                 475                 480

Val Asp Phe Asn Ser Lys Gln Lys Glu Arg Lys Pro Lys Ser Ser Ala
                485                 490                 495
```

-continued

```
His Tyr Tyr Lys Gln Ile Ile Arg Glu Asn Gly Phe Ser Leu Lys Glu
            500                 505                 510

Ser Thr Pro Asp Val Gln Gly Gln Phe Pro Cys Asp Phe Ser Trp Gly
        515                 520                 525

Val Thr Glu Ser Val Leu Lys Pro Glu Ser Val Ala Ser Ser Pro Gln
    530                 535                 540

Phe Ser Asp Pro His Leu Tyr Val Trp Asn Ala Thr Gly Asn Arg Leu
545                 550                 555                 560

Leu His Arg Val Glu Gly Val Arg Leu Lys Thr Arg Pro Ala Gln Cys
                565                 570                 575

Thr Asp Phe Val Asn Ile Lys Lys Gln Leu Glu Met Leu Ala Arg Met
            580                 585                 590

Lys Val Thr His Tyr Arg Phe Ala Leu Asp Trp Ala Ser Val Leu Pro
        595                 600                 605

Thr Gly Asn Leu Ser Ala Val Asn Arg Gln Ala Leu Arg Tyr Tyr Arg
    610                 615                 620

Cys Val Val Ser Glu Gly Leu Lys Leu Gly Ile Ser Ala Met Val Thr
625                 630                 635                 640

Leu Tyr Tyr Pro Thr His Ala His Leu Gly Leu Pro Glu Pro Leu Leu
                645                 650                 655

His Ala Asp Gly Trp Leu Asn Pro Ser Thr Ala Glu Ala Phe Gln Ala
            660                 665                 670

Tyr Ala Gly Leu Cys Phe Gln Glu Leu Gly Asp Leu Val Lys Leu Trp
        675                 680                 685

Ile Thr Ile Asn Glu Pro Asn Arg Leu Ser Asp Ile Tyr Asn Arg Ser
    690                 695                 700

Gly Asn Asp Thr Tyr Gly Ala Ala His Asn Leu Leu Val Ala His Ala
705                 710                 715                 720

Leu Ala Trp Arg Leu Tyr Asp Arg Gln Phe Arg Pro Ser Gln Arg Gly
                725                 730                 735

Ala Val Ser Leu Ser Leu His Ala Asp Trp Ala Glu Pro Ala Asn Pro
            740                 745                 750

Tyr Ala Asp Ser His Trp Arg Ala Ala Glu Arg Phe Leu Gln Phe Glu
        755                 760                 765

Ile Ala Trp Phe Ala Glu Pro Leu Phe Lys Thr Gly Asp Tyr Pro Ala
    770                 775                 780

Ala Met Arg Glu Tyr Ile Ala Ser Lys His Arg Arg Gly Leu Ser Ser
785                 790                 795                 800

Ser Ala Leu Pro Arg Leu Thr Glu Ala Glu Arg Arg Leu Leu Lys Gly
                805                 810                 815

Thr Val Asp Phe Cys Ala Leu Asn His Phe Thr Thr Arg Phe Val Met
            820                 825                 830

His Glu Gln Leu Ala Gly Ser Arg Tyr Asp Ser Asp Arg Asp Ile Gln
        835                 840                 845

Phe Leu Gln Asp Ile Thr Arg Leu Ser Ser Pro Thr Arg Leu Ala Val
    850                 855                 860

Ile Pro Trp Gly Val Arg Lys Leu Leu Arg Trp Val Arg Arg Asn Tyr
865                 870                 875                 880

Gly Asp Met Asp Ile Tyr Ile Thr Ala Ser Gly Ile Asp Asp Gln Ala
                885                 890                 895

Leu Glu Asp Asp Arg Leu Arg Lys Tyr Tyr Leu Gly Lys Tyr Leu Gln
            900                 905                 910
```

```
Glu Val Leu Lys Ala Tyr Leu Ile Asp Lys Val Arg Ile Lys Gly Tyr
        915                 920                 925

Tyr Ala Phe Lys Leu Ala Glu Glu Lys Ser Lys Pro Arg Phe Gly Phe
    930                 935                 940

Phe Thr Ser Asp Phe Lys Ala Lys Ser Ser Ile Gln Phe Tyr Asn Lys
945                 950                 955                 960

Val Ile Ser Ser Arg Gly Phe Pro Phe Glu Asn Ser Ser Ser Arg Cys
                965                 970                 975

Ser Gln Thr Gln Glu Asn Thr Glu Cys Thr Val Cys Leu Phe Leu Val
            980                 985                 990

Gln Lys Lys Pro Leu Ile Phe Leu  Gly Cys Cys Phe Phe  Ser Thr Leu
        995                 1000                1005

Val Leu  Leu Leu Ser Ile Ala  Ile Phe Gln Arg Gln  Lys Arg Arg
    1010                1015                1020

Lys Phe  Trp Lys Ala Lys Asn  Leu Gln His Ile Pro  Leu Lys Lys
    1025                1030                1035

Gly Lys  Arg Val Val Ser
    1040


<210> SEQ ID NO 5
<211> LENGTH: 449
<212> TYPE: PRT
<213> ORGANISM: Homo sapiens

<400> SEQUENCE: 5

Gln Gly Thr Phe Pro Asp Gly Phe Leu Trp Ala Val Gly Ser Ala Ala
1               5                   10                  15

Tyr Gln Thr Glu Gly Gly Trp Gln Gln His Gly Lys Gly Ala Ser Ile
            20                  25                  30

Trp Asp Thr Phe Thr His His Pro Leu Ala Pro Pro Gly Asp Ser Arg
        35                  40                  45

Asn Ala Ser Leu Pro Leu Gly Ala Pro Ser Pro Leu Gln Pro Ala Thr
    50                  55                  60

Gly Asp Val Ala Ser Asp Ser Tyr Asn Asn Val Phe Arg Asp Thr Glu
65                  70                  75                  80

Ala Leu Arg Glu Leu Gly Val Thr His Tyr Arg Phe Ser Ile Ser Trp
                85                  90                  95

Ala Arg Val Leu Pro Asn Gly Ser Ala Gly Val Pro Asn Arg Glu Gly
            100                 105                 110

Leu Arg Tyr Tyr Arg Arg Leu Leu Glu Arg Leu Arg Glu Leu Gly Val
        115                 120                 125

Gln Pro Val Val Thr Leu Tyr His Trp Asp Leu Pro Gln Arg Leu Gln
    130                 135                 140

Asp Ala Tyr Gly Gly Trp Ala Asn Arg Ala Leu Ala Asp His Phe Arg
145                 150                 155                 160

Asp Tyr Ala Glu Leu Cys Phe Arg His Phe Gly Gly Gln Val Lys Tyr
                165                 170                 175

Trp Ile Thr Ile Asp Asn Pro Tyr Val Val Ala Trp His Gly Tyr Ala
            180                 185                 190

Thr Gly Arg Leu Ala Pro Gly Ile Arg Gly Ser Pro Arg Leu Gly Tyr
        195                 200                 205

Leu Val Ala His Asn Leu Leu Leu Ala His Ala Lys Val Trp His Leu
    210                 215                 220

Tyr Asn Thr Ser Phe Arg Pro Thr Gln Gly Gly Gln Val Ser Ile Ala
225                 230                 235                 240
```

```
Leu Ser Ser His Trp Ile Asn Pro Arg Arg Met Thr Asp His Ser Ile
                245                 250                 255

Lys Glu Cys Gln Lys Ser Leu Asp Phe Val Leu Gly Trp Phe Ala Lys
            260                 265                 270

Pro Val Phe Ile Asp Gly Asp Tyr Pro Glu Ser Met Lys Asn Asn Leu
        275                 280                 285

Ser Ser Ile Leu Pro Asp Phe Thr Glu Ser Glu Lys Lys Phe Ile Lys
    290                 295                 300

Gly Thr Ala Asp Phe Phe Ala Leu Cys Phe Gly Pro Thr Leu Ser Phe
305                 310                 315                 320

Gln Leu Leu Asp Pro His Met Lys Phe Arg Gln Leu Glu Ser Pro Asn
                325                 330                 335

Leu Arg Gln Leu Leu Ser Trp Ile Asp Leu Glu Phe Asn His Pro Gln
            340                 345                 350

Ile Phe Ile Val Glu Asn Gly Trp Phe Val Ser Gly Thr Thr Lys Arg
        355                 360                 365

Asp Asp Ala Lys Tyr Met Tyr Tyr Leu Lys Lys Phe Ile Met Glu Thr
    370                 375                 380

Leu Lys Ala Ile Lys Leu Asp Gly Val Asp Val Ile Gly Tyr Thr Ala
385                 390                 395                 400

Trp Ser Leu Met Asp Gly Phe Glu Trp His Arg Gly Tyr Ser Ile Arg
                405                 410                 415

Arg Gly Leu Phe Tyr Val Asp Phe Leu Ser Gln Asp Lys Met Leu Leu
            420                 425                 430

Pro Lys Ser Ser Ala Leu Phe Tyr Gln Lys Leu Ile Glu Lys Asn Gly
        435                 440                 445

Phe


<210> SEQ ID NO 6
<211> LENGTH: 437
<212> TYPE: PRT
<213> ORGANISM: Homo sapiens

<400> SEQUENCE: 6

Gly Thr Phe Pro Cys Asp Phe Ala Trp Gly Val Val Asp Asn Tyr Ile
1               5                   10                  15

Gln Val Asp Thr Thr Leu Ser Gln Phe Thr Asp Leu Asn Val Tyr Leu
            20                  25                  30

Trp Asp Val His His Ser Lys Arg Leu Ile Lys Val Asp Gly Val Val
        35                  40                  45

Thr Lys Lys Arg Lys Ser Tyr Cys Val Asp Phe Ala Ala Ile Gln Pro
    50                  55                  60

Gln Ile Ala Leu Leu Gln Glu Met His Val Thr His Phe Arg Phe Ser
65                  70                  75                  80

Leu Asp Trp Ala Leu Ile Leu Pro Leu Gly Asn Gln Ser Gln Val Asn
                85                  90                  95

His Thr Ile Leu Gln Tyr Tyr Arg Cys Met Ala Ser Glu Leu Val Arg
            100                 105                 110

Val Asn Ile Thr Pro Val Val Ala Leu Trp Gln Pro Met Ala Pro Asn
        115                 120                 125

Gln Gly Leu Pro Arg Leu Leu Ala Arg Gln Gly Ala Trp Glu Asn Pro
    130                 135                 140

Tyr Thr Ala Leu Ala Phe Ala Glu Tyr Ala Arg Leu Cys Phe Gln Glu
145                 150                 155                 160
```

```
Leu Gly His His Val Lys Leu Trp Ile Thr Met Asn Glu Pro Tyr Thr
                165                 170                 175

Arg Asn Met Thr Tyr Ser Ala Gly His Asn Leu Leu Lys Ala His Ala
            180                 185                 190

Leu Ala Trp His Val Tyr Asn Glu Lys Phe Arg His Ala Gln Asn Gly
        195                 200                 205

Lys Ile Ser Ile Ala Leu Gln Ala Asp Trp Ile Glu Pro Ala Cys Pro
    210                 215                 220

Phe Ser Gln Lys Asp Lys Glu Val Ala Glu Arg Val Leu Glu Phe Asp
225                 230                 235                 240

Ile Gly Trp Leu Ala Glu Pro Ile Phe Gly Ser Gly Asp Tyr Pro Trp
                245                 250                 255

Val Met Arg Asp Trp Leu Asn Gln Arg Asn Asn Phe Leu Leu Pro Tyr
            260                 265                 270

Phe Thr Glu Asp Glu Lys Lys Leu Ile Gln Gly Thr Phe Asp Phe Leu
        275                 280                 285

Ala Leu Ser His Tyr Thr Thr Ile Leu Val Asp Ser Glu Lys Glu Asp
    290                 295                 300

Pro Ile Lys Tyr Asn Asp Tyr Leu Glu Val Gln Glu Met Thr Asp Ile
305                 310                 315                 320

Thr Trp Leu Asn Ser Pro Ser Gln Val Ala Val Val Pro Trp Gly Leu
                325                 330                 335

Arg Lys Val Leu Asn Trp Leu Lys Phe Lys Tyr Gly Asp Leu Pro Met
            340                 345                 350

Tyr Ile Ile Ser Asn Gly Ile Asp Asp Gly Leu His Ala Glu Asp Asp
        355                 360                 365

Gln Leu Arg Val Tyr Tyr Met Gln Asn Tyr Ile Asn Glu Ala Leu Lys
    370                 375                 380

Ala His Ile Leu Asp Gly Ile Asn Leu Cys Gly Tyr Phe Ala Tyr Ser
385                 390                 395                 400

Phe Asn Asp Arg Thr Ala Pro Arg Phe Gly Leu Tyr Arg Tyr Ala Ala
                405                 410                 415

Asp Gln Phe Glu Pro Lys Ala Ser Met Lys His Tyr Arg Lys Ile Ile
            420                 425                 430

Asp Ser Asn Gly Phe
        435


<210> SEQ ID NO 7
<211> LENGTH: 949
<212> TYPE: PRT
<213> ORGANISM: Homo sapiens

<400> SEQUENCE: 7

Glu Pro Gly Asp Gly Ala Gln Thr Trp Ala Arg Phe Ser Arg Pro Pro
1               5                   10                  15

Ala Pro Glu Ala Ala Gly Leu Phe Gln Gly Thr Phe Pro Asp Gly Phe
            20                  25                  30

Leu Trp Ala Val Gly Ser Ala Ala Tyr Gln Thr Glu Gly Gly Trp Gln
        35                  40                  45

Gln His Gly Lys Gly Ala Ser Ile Trp Asp Thr Phe Thr His His Pro
    50                  55                  60

Leu Ala Pro Pro Gly Asp Ser Arg Asn Ala Ser Leu Pro Leu Gly Ala
65                  70                  75                  80

Pro Ser Pro Leu Gln Pro Ala Thr Gly Asp Val Ala Ser Asp Ser Tyr
```

```
                85                  90                  95

Asn Asn Val Phe Arg Asp Thr Glu Ala Leu Arg Glu Leu Gly Val Thr
            100                 105                 110

His Tyr Arg Phe Ser Ile Ser Trp Ala Arg Val Leu Pro Asn Gly Ser
        115                 120                 125

Ala Gly Val Pro Asn Arg Glu Gly Leu Arg Tyr Tyr Arg Arg Leu Leu
    130                 135                 140

Glu Arg Leu Arg Glu Leu Gly Val Gln Pro Val Val Thr Leu Tyr His
145                 150                 155                 160

Trp Asp Leu Pro Gln Arg Leu Gln Asp Ala Tyr Gly Gly Trp Ala Asn
                165                 170                 175

Arg Ala Leu Ala Asp His Phe Arg Asp Tyr Ala Glu Leu Cys Phe Arg
            180                 185                 190

His Phe Gly Gly Gln Val Lys Tyr Trp Ile Thr Ile Asp Asn Pro Tyr
        195                 200                 205

Val Val Ala Trp His Gly Tyr Ala Thr Gly Arg Leu Ala Pro Gly Ile
    210                 215                 220

Arg Gly Ser Pro Arg Leu Gly Tyr Leu Val Ala His Asn Leu Leu Leu
225                 230                 235                 240

Ala His Ala Lys Val Trp His Leu Tyr Asn Thr Ser Phe Arg Pro Thr
                245                 250                 255

Gln Gly Gly Gln Val Ser Ile Ala Leu Ser Ser His Trp Ile Asn Pro
            260                 265                 270

Arg Arg Met Thr Asp His Ser Ile Lys Glu Cys Gln Lys Ser Leu Asp
        275                 280                 285

Phe Val Leu Gly Trp Phe Ala Lys Pro Val Phe Ile Asp Gly Asp Tyr
    290                 295                 300

Pro Glu Ser Met Lys Asn Asn Leu Ser Ser Ile Leu Pro Asp Phe Thr
305                 310                 315                 320

Glu Ser Glu Lys Lys Phe Ile Lys Gly Thr Ala Asp Phe Phe Ala Leu
                325                 330                 335

Cys Phe Gly Pro Thr Leu Ser Phe Gln Leu Leu Asp Pro His Met Lys
            340                 345                 350

Phe Arg Gln Leu Glu Ser Pro Asn Leu Arg Gln Leu Leu Ser Trp Ile
        355                 360                 365

Asp Leu Glu Phe Asn His Pro Gln Ile Phe Ile Val Glu Asn Gly Trp
    370                 375                 380

Phe Val Ser Gly Thr Thr Lys Arg Asp Asp Ala Lys Tyr Met Tyr Tyr
385                 390                 395                 400

Leu Lys Lys Phe Ile Met Glu Thr Leu Lys Ala Ile Lys Leu Asp Gly
                405                 410                 415

Val Asp Val Ile Gly Tyr Thr Ala Trp Ser Leu Met Asp Gly Phe Glu
            420                 425                 430

Trp His Arg Gly Tyr Ser Ile Arg Arg Gly Leu Phe Tyr Val Asp Phe
        435                 440                 445

Leu Ser Gln Asp Lys Met Leu Leu Pro Lys Ser Ser Ala Leu Phe Tyr
    450                 455                 460

Gln Lys Leu Ile Glu Lys Asn Gly Phe Pro Pro Leu Pro Glu Asn Gln
465                 470                 475                 480

Pro Leu Glu Gly Thr Phe Pro Cys Asp Phe Ala Trp Gly Val Val Asp
                485                 490                 495

Asn Tyr Ile Gln Val Asp Thr Thr Leu Ser Gln Phe Thr Asp Leu Asn
            500                 505                 510
```

```
Val Tyr Leu Trp Asp Val His His Ser Lys Arg Leu Ile Lys Val Asp
        515                 520                 525

Gly Val Val Thr Lys Lys Arg Lys Ser Tyr Cys Val Asp Phe Ala Ala
    530                 535                 540

Ile Gln Pro Gln Ile Ala Leu Leu Gln Glu Met His Val Thr His Phe
545                 550                 555                 560

Arg Phe Ser Leu Asp Trp Ala Leu Ile Leu Pro Leu Gly Asn Gln Ser
                565                 570                 575

Gln Val Asn His Thr Ile Leu Gln Tyr Tyr Arg Cys Met Ala Ser Glu
            580                 585                 590

Leu Val Arg Val Asn Ile Thr Pro Val Val Ala Leu Trp Gln Pro Met
        595                 600                 605

Ala Pro Asn Gln Gly Leu Pro Arg Leu Leu Ala Arg Gln Gly Ala Trp
    610                 615                 620

Glu Asn Pro Tyr Thr Ala Leu Ala Phe Ala Glu Tyr Ala Arg Leu Cys
625                 630                 635                 640

Phe Gln Glu Leu Gly His His Val Lys Leu Trp Ile Thr Met Asn Glu
                645                 650                 655

Pro Tyr Thr Arg Asn Met Thr Tyr Ser Ala Gly His Asn Leu Leu Lys
            660                 665                 670

Ala His Ala Leu Ala Trp His Val Tyr Asn Glu Lys Phe Arg His Ala
        675                 680                 685

Gln Asn Gly Lys Ile Ser Ile Ala Leu Gln Ala Asp Trp Ile Glu Pro
    690                 695                 700

Ala Cys Pro Phe Ser Gln Lys Asp Lys Glu Val Ala Glu Arg Val Leu
705                 710                 715                 720

Glu Phe Asp Ile Gly Trp Leu Ala Glu Pro Ile Phe Gly Ser Gly Asp
                725                 730                 735

Tyr Pro Trp Val Met Arg Asp Trp Leu Asn Gln Arg Asn Asn Phe Leu
            740                 745                 750

Leu Pro Tyr Phe Thr Glu Asp Glu Lys Lys Leu Ile Gln Gly Thr Phe
        755                 760                 765

Asp Phe Leu Ala Leu Ser His Tyr Thr Thr Ile Leu Val Asp Ser Glu
    770                 775                 780

Lys Glu Asp Pro Ile Lys Tyr Asn Asp Tyr Leu Glu Val Gln Glu Met
785                 790                 795                 800

Thr Asp Ile Thr Trp Leu Asn Ser Pro Ser Gln Val Ala Val Val Pro
                805                 810                 815

Trp Gly Leu Arg Lys Val Leu Asn Trp Leu Lys Phe Lys Tyr Gly Asp
            820                 825                 830

Leu Pro Met Tyr Ile Ile Ser Asn Gly Ile Asp Asp Gly Leu His Ala
        835                 840                 845

Glu Asp Asp Gln Leu Arg Val Tyr Tyr Met Gln Asn Tyr Ile Asn Glu
    850                 855                 860

Ala Leu Lys Ala His Ile Leu Asp Gly Ile Asn Leu Cys Gly Tyr Phe
865                 870                 875                 880

Ala Tyr Ser Phe Asn Asp Arg Thr Ala Pro Arg Phe Gly Leu Tyr Arg
                885                 890                 895

Tyr Ala Ala Asp Gln Phe Glu Pro Lys Ala Ser Met Lys His Tyr Arg
            900                 905                 910

Lys Ile Ile Asp Ser Asn Gly Phe Pro Gly Pro Glu Thr Leu Glu Arg
        915                 920                 925
```

```
Phe Cys Pro Glu Glu Phe Thr Val Cys Thr Glu Cys Ser Phe Phe His
    930                 935                 940

Thr Arg Lys Ser Leu
945


<210> SEQ ID NO 8
<211> LENGTH: 33
<212> TYPE: PRT
<213> ORGANISM: Homo sapiens

<400> SEQUENCE: 8

Met Pro Ala Ser Ala Pro Pro Arg Arg Pro Arg Pro Pro Pro Pro Ser
1               5                   10                  15

Leu Ser Leu Leu Leu Val Leu Leu Gly Leu Gly Gly Arg Arg Leu Arg
            20                  25                  30

Ala


<210> SEQ ID NO 9
<211> LENGTH: 25
<212> TYPE: PRT
<213> ORGANISM: Homo sapiens

<400> SEQUENCE: 9

Met Ser Val Leu Thr Gln Val Leu Ala Leu Leu Leu Leu Trp Leu Thr
1               5                   10                  15

Gly Thr Arg Cys Arg Arg Leu Arg Ala
            20                  25


<210> SEQ ID NO 10
<211> LENGTH: 45
<212> TYPE: DNA
<213> ORGANISM: Artificial Sequence
<220> FEATURE:
<223> OTHER INFORMATION: Description of Artificial Sequence: Synthetic
      linker oligonucleotide

<400> SEQUENCE: 10

ggaggtggag gttcaggagg tggaggttca ggaggtggag gttca                      45


<210> SEQ ID NO 11
<211> LENGTH: 15
<212> TYPE: PRT
<213> ORGANISM: Artificial Sequence
<220> FEATURE:
<223> OTHER INFORMATION: Description of Artificial Sequence: Synthetic
      linker peptide

<400> SEQUENCE: 11

Gly Gly Gly Gly Ser Gly Gly Gly Gly Ser Gly Gly Gly Gly Ser
1               5                   10                  15


<210> SEQ ID NO 12
<211> LENGTH: 5
<212> TYPE: PRT
<213> ORGANISM: Artificial Sequence
<220> FEATURE:
<223> OTHER INFORMATION: Description of Artificial Sequence: Synthetic
      linker peptide

<400> SEQUENCE: 12

Gly Gly Gly Gly Ser
1               5


<210> SEQ ID NO 13
```

<211> LENGTH: 1
<212> TYPE: PRT
<213> ORGANISM: Artificial Sequence
<220> FEATURE:
<223> OTHER INFORMATION: Description of Artificial Sequence: Synthetic
      linker residue

<400> SEQUENCE: 13

Gly
1

<210> SEQ ID NO 14
<211> LENGTH: 2
<212> TYPE: PRT
<213> ORGANISM: Artificial Sequence
<220> FEATURE:
<223> OTHER INFORMATION: Description of Artificial Sequence: Synthetic
      linker peptide

<400> SEQUENCE: 14

Gly Gly
1

<210> SEQ ID NO 15
<211> LENGTH: 2
<212> TYPE: PRT
<213> ORGANISM: Artificial Sequence
<220> FEATURE:
<223> OTHER INFORMATION: Description of Artificial Sequence: Synthetic
      linker peptide

<400> SEQUENCE: 15

Gly Ser
1

<210> SEQ ID NO 16
<211> LENGTH: 3
<212> TYPE: PRT
<213> ORGANISM: Artificial Sequence
<220> FEATURE:
<223> OTHER INFORMATION: Description of Artificial Sequence: Synthetic
      linker peptide

<400> SEQUENCE: 16

Gly Gly Ser
1

<210> SEQ ID NO 17
<211> LENGTH: 1
<212> TYPE: PRT
<213> ORGANISM: Artificial Sequence
<220> FEATURE:
<223> OTHER INFORMATION: Description of Artificial Sequence: Synthetic
      linker residue

<400> SEQUENCE: 17

Ala
1

<210> SEQ ID NO 18
<211> LENGTH: 2
<212> TYPE: PRT
<213> ORGANISM: Artificial Sequence
<220> FEATURE:
<223> OTHER INFORMATION: Description of Artificial Sequence: Synthetic
      linker peptide

<400> SEQUENCE: 18

```
Ala Ala
1


<210> SEQ ID NO 19
<211> LENGTH: 1228
<212> TYPE: PRT
<213> ORGANISM: Artificial Sequence
<220> FEATURE:
<223> OTHER INFORMATION: Description of Artificial Sequence: Synthetic
      fusion polypeptide

<400> SEQUENCE: 19

Met Pro Ala Ser Ala Pro Pro Arg Arg Pro Arg Pro Pro Pro Pro Ser
1               5                   10                  15

Leu Ser Leu Leu Leu Val Leu Leu Gly Leu Gly Gly Arg Arg Leu Arg
            20                  25                  30

Ala Glu Pro Gly Asp Gly Ala Gln Thr Trp Ala Arg Phe Ser Arg Pro
        35                  40                  45

Pro Ala Pro Glu Ala Ala Gly Leu Phe Gln Gly Thr Phe Pro Asp Gly
    50                  55                  60

Phe Leu Trp Ala Val Gly Ser Ala Ala Tyr Gln Thr Glu Gly Gly Trp
65                  70                  75                  80

Gln Gln His Gly Lys Gly Ala Ser Ile Trp Asp Thr Phe Thr His His
                85                  90                  95

Pro Leu Ala Pro Pro Gly Asp Ser Arg Asn Ala Ser Leu Pro Leu Gly
            100                 105                 110

Ala Pro Ser Pro Leu Gln Pro Ala Thr Gly Asp Val Ala Ser Asp Ser
        115                 120                 125

Tyr Asn Asn Val Phe Arg Asp Thr Glu Ala Leu Arg Glu Leu Gly Val
    130                 135                 140

Thr His Tyr Arg Phe Ser Ile Ser Trp Ala Arg Val Leu Pro Asn Gly
145                 150                 155                 160

Ser Ala Gly Val Pro Asn Arg Glu Gly Leu Arg Tyr Tyr Arg Arg Leu
                165                 170                 175

Leu Glu Arg Leu Arg Glu Leu Gly Val Gln Pro Val Val Thr Leu Tyr
            180                 185                 190

His Trp Asp Leu Pro Gln Arg Leu Gln Asp Ala Tyr Gly Gly Trp Ala
        195                 200                 205

Asn Arg Ala Leu Ala Asp His Phe Arg Asp Tyr Ala Glu Leu Cys Phe
    210                 215                 220

Arg His Phe Gly Gly Gln Val Lys Tyr Trp Ile Thr Ile Asp Asn Pro
225                 230                 235                 240

Tyr Val Val Ala Trp His Gly Tyr Ala Thr Gly Arg Leu Ala Pro Gly
                245                 250                 255

Ile Arg Gly Ser Pro Arg Leu Gly Tyr Leu Val Ala His Asn Leu Leu
            260                 265                 270

Leu Ala His Ala Lys Val Trp His Leu Tyr Asn Thr Ser Phe Arg Pro
        275                 280                 285

Thr Gln Gly Gly Gln Val Ser Ile Ala Leu Ser Ser His Trp Ile Asn
    290                 295                 300

Pro Arg Arg Met Thr Asp His Ser Ile Lys Glu Cys Gln Lys Ser Leu
305                 310                 315                 320

Asp Phe Val Leu Gly Trp Phe Ala Lys Pro Val Phe Ile Asp Gly Asp
                325                 330                 335

Tyr Pro Glu Ser Met Lys Asn Asn Leu Ser Ser Ile Leu Pro Asp Phe
            340                 345                 350
```

```
Thr Glu Ser Glu Lys Lys Phe Ile Lys Gly Thr Ala Asp Phe Phe Ala
        355                 360                 365

Leu Cys Phe Gly Pro Thr Leu Ser Phe Gln Leu Leu Asp Pro His Met
    370                 375                 380

Lys Phe Arg Gln Leu Glu Ser Pro Asn Leu Arg Gln Leu Leu Ser Trp
385                 390                 395                 400

Ile Asp Leu Glu Phe Asn His Pro Gln Ile Phe Ile Val Glu Asn Gly
                405                 410                 415

Trp Phe Val Ser Gly Thr Thr Lys Arg Asp Asp Ala Lys Tyr Met Tyr
            420                 425                 430

Tyr Leu Lys Lys Phe Ile Met Glu Thr Leu Lys Ala Ile Lys Leu Asp
        435                 440                 445

Gly Val Asp Val Ile Gly Tyr Thr Ala Trp Ser Leu Met Asp Gly Phe
    450                 455                 460

Glu Trp His Arg Gly Tyr Ser Ile Arg Arg Gly Leu Phe Tyr Val Asp
465                 470                 475                 480

Phe Leu Ser Gln Asp Lys Met Leu Leu Pro Lys Ser Ser Ala Leu Phe
                485                 490                 495

Tyr Gln Lys Leu Ile Glu Lys Asn Gly Phe Pro Pro Leu Pro Glu Asn
            500                 505                 510

Gln Pro Leu Glu Gly Thr Phe Pro Cys Asp Phe Ala Trp Gly Val Val
        515                 520                 525

Asp Asn Tyr Ile Gln Val Asp Thr Thr Leu Ser Gln Phe Thr Asp Leu
    530                 535                 540

Asn Val Tyr Leu Trp Asp Val His His Ser Lys Arg Leu Ile Lys Val
545                 550                 555                 560

Asp Gly Val Val Thr Lys Lys Arg Lys Ser Tyr Cys Val Asp Phe Ala
                565                 570                 575

Ala Ile Gln Pro Gln Ile Ala Leu Leu Gln Glu Met His Val Thr His
            580                 585                 590

Phe Arg Phe Ser Leu Asp Trp Ala Leu Ile Leu Pro Leu Gly Asn Gln
        595                 600                 605

Ser Gln Val Asn His Thr Ile Leu Gln Tyr Tyr Arg Cys Met Ala Ser
    610                 615                 620

Glu Leu Val Arg Val Asn Ile Thr Pro Val Val Ala Leu Trp Gln Pro
625                 630                 635                 640

Met Ala Pro Asn Gln Gly Leu Pro Arg Leu Leu Ala Arg Gln Gly Ala
                645                 650                 655

Trp Glu Asn Pro Tyr Thr Ala Leu Ala Phe Ala Glu Tyr Ala Arg Leu
            660                 665                 670

Cys Phe Gln Glu Leu Gly His His Val Lys Leu Trp Ile Thr Met Asn
        675                 680                 685

Glu Pro Tyr Thr Arg Asn Met Thr Tyr Ser Ala Gly His Asn Leu Leu
    690                 695                 700

Lys Ala His Ala Leu Ala Trp His Val Tyr Asn Glu Lys Phe Arg His
705                 710                 715                 720

Ala Gln Asn Gly Lys Ile Ser Ile Ala Leu Gln Ala Asp Trp Ile Glu
                725                 730                 735

Pro Ala Cys Pro Phe Ser Gln Lys Asp Lys Glu Val Ala Glu Arg Val
            740                 745                 750

Leu Glu Phe Asp Ile Gly Trp Leu Ala Glu Pro Ile Phe Gly Ser Gly
        755                 760                 765
```

```
Asp Tyr Pro Trp Val Met Arg Asp Trp Leu Asn Gln Arg Asn Asn Phe
    770                 775                 780

Leu Leu Pro Tyr Phe Thr Glu Asp Glu Lys Lys Leu Ile Gln Gly Thr
785                 790                 795                 800

Phe Asp Phe Leu Ala Leu Ser His Tyr Thr Thr Ile Leu Val Asp Ser
                805                 810                 815

Glu Lys Glu Asp Pro Ile Lys Tyr Asn Asp Tyr Leu Glu Val Gln Glu
            820                 825                 830

Met Thr Asp Ile Thr Trp Leu Asn Ser Pro Ser Gln Val Ala Val Val
        835                 840                 845

Pro Trp Gly Leu Arg Lys Val Leu Asn Trp Leu Lys Phe Lys Tyr Gly
    850                 855                 860

Asp Leu Pro Met Tyr Ile Ile Ser Asn Gly Ile Asp Asp Gly Leu His
865                 870                 875                 880

Ala Glu Asp Asp Gln Leu Arg Val Tyr Tyr Met Gln Asn Tyr Ile Asn
                885                 890                 895

Glu Ala Leu Lys Ala His Ile Leu Asp Gly Ile Asn Leu Cys Gly Tyr
            900                 905                 910

Phe Ala Tyr Ser Phe Asn Asp Arg Thr Ala Pro Arg Phe Gly Leu Tyr
        915                 920                 925

Arg Tyr Ala Ala Asp Gln Phe Glu Pro Lys Ala Ser Met Lys His Tyr
    930                 935                 940

Arg Lys Ile Ile Asp Ser Asn Gly Phe Pro Gly Pro Glu Thr Leu Glu
945                 950                 955                 960

Arg Phe Cys Pro Glu Glu Phe Thr Val Cys Thr Glu Cys Ser Phe Phe
                965                 970                 975

His Thr Arg Lys Ser Leu Gly Ser Gly Gly Gly Gly Ser Gly Gly Gly
            980                 985                 990

Gly Ser Gly Gly Gly Gly Ser Leu  Lys Tyr Pro Asn Ala  Ser Pro Leu
        995                 1000                1005

Leu Gly  Ser Ser Trp Gly Gly  Leu Ile His Leu Tyr  Thr Ala Thr
    1010                1015                1020

Ala Arg  Asn Ser Tyr His Leu  Gln Ile His Lys Asn  Gly His Val
    1025                1030                1035

Asp Gly  Ala Pro His Gln Thr  Ile Tyr Ser Ala Leu  Met Ile Arg
    1040                1045                1050

Ser Glu  Asp Ala Gly Phe Val  Val Ile Thr Gly Val  Met Ser Arg
    1055                1060                1065

Arg Tyr  Leu Cys Met Asp Phe  Arg Gly Asn Ile Phe  Gly Ser His
    1070                1075                1080

Tyr Phe  Asp Pro Glu Asn Cys  Arg Phe Gln His Gln  Thr Leu Glu
    1085                1090                1095

Asn Gly  Tyr Asp Val Tyr His  Ser Pro Gln Tyr His  Phe Leu Val
    1100                1105                1110

Ser Leu  Gly Arg Ala Lys Arg  Ala Phe Leu Pro Gly  Met Asn Pro
    1115                1120                1125

Pro Pro  Tyr Ser Gln Phe Leu  Ser Arg Arg Asn Glu  Ile Pro Leu
    1130                1135                1140

Ile His  Phe Asn Thr Pro Ile  Pro Arg Arg His Thr  Gln Ser Ala
    1145                1150                1155

Glu Asp  Asp Ser Glu Arg Asp  Pro Leu Asn Val Leu  Lys Pro Arg
    1160                1165                1170

Ala Arg  Met Thr Pro Ala Pro  Ala Ser Cys Ser Gln  Glu Leu Pro
```

```
    1175                1180                1185

Ser Ala  Glu Asp Asn Ser Pro  Met Ala Ser Asp Pro  Leu Gly Val
    1190                1195                1200

Val Arg  Gly Gly Arg Val Asn  Thr His Ala Gly Gly  Thr Gly Pro
    1205                1210                1215

Glu Gly  Cys Arg Pro Phe Ala  Lys Phe Ile
    1220                1225


<210> SEQ ID NO 20
<211> LENGTH: 1220
<212> TYPE: PRT
<213> ORGANISM: Artificial Sequence
<220> FEATURE:
<223> OTHER INFORMATION: Description of Artificial Sequence: Synthetic
      fusion polypeptide

<400> SEQUENCE: 20

Met Ser Val Leu Thr Gln Val Leu Ala Leu Leu Leu Leu Trp Leu Thr
1               5                   10                  15

Gly Leu Gly Gly Arg Arg Leu Arg Ala Glu Pro Gly Asp Gly Ala Gln
            20                  25                  30

Thr Trp Ala Arg Phe Ser Arg Pro Pro Ala Pro Glu Ala Ala Gly Leu
        35                  40                  45

Phe Gln Gly Thr Phe Pro Asp Gly Phe Leu Trp Ala Val Gly Ser Ala
    50                  55                  60

Ala Tyr Gln Thr Glu Gly Gly Trp Gln Gln His Gly Lys Gly Ala Ser
65                  70                  75                  80

Ile Trp Asp Thr Phe Thr His His Pro Leu Ala Pro Pro Gly Asp Ser
                85                  90                  95

Arg Asn Ala Ser Leu Pro Leu Gly Ala Pro Ser Pro Leu Gln Pro Ala
            100                 105                 110

Thr Gly Asp Val Ala Ser Asp Ser Tyr Asn Asn Val Phe Arg Asp Thr
        115                 120                 125

Glu Ala Leu Arg Glu Leu Gly Val Thr His Tyr Arg Phe Ser Ile Ser
    130                 135                 140

Trp Ala Arg Val Leu Pro Asn Gly Ser Ala Gly Val Pro Asn Arg Glu
145                 150                 155                 160

Gly Leu Arg Tyr Tyr Arg Arg Leu Leu Glu Arg Leu Arg Glu Leu Gly
                165                 170                 175

Val Gln Pro Val Val Thr Leu Tyr His Trp Asp Leu Pro Gln Arg Leu
            180                 185                 190

Gln Asp Ala Tyr Gly Gly Trp Ala Asn Arg Ala Leu Ala Asp His Phe
        195                 200                 205

Arg Asp Tyr Ala Glu Leu Cys Phe Arg His Phe Gly Gly Gln Val Lys
    210                 215                 220

Tyr Trp Ile Thr Ile Asp Asn Pro Tyr Val Val Ala Trp His Gly Tyr
225                 230                 235                 240

Ala Thr Gly Arg Leu Ala Pro Gly Ile Arg Gly Ser Pro Arg Leu Gly
                245                 250                 255

Tyr Leu Val Ala His Asn Leu Leu Leu Ala His Ala Lys Val Trp His
            260                 265                 270

Leu Tyr Asn Thr Ser Phe Arg Pro Thr Gln Gly Gly Gln Val Ser Ile
        275                 280                 285

Ala Leu Ser Ser His Trp Ile Asn Pro Arg Arg Met Thr Asp His Ser
    290                 295                 300
```

```
Ile Lys Glu Cys Gln Lys Ser Leu Asp Phe Val Leu Gly Trp Phe Ala
305                 310                 315                 320

Lys Pro Val Phe Ile Asp Gly Asp Tyr Pro Glu Ser Met Lys Asn Asn
                325                 330                 335

Leu Ser Ser Ile Leu Pro Asp Phe Thr Glu Ser Glu Lys Lys Phe Ile
            340                 345                 350

Lys Gly Thr Ala Asp Phe Phe Ala Leu Cys Phe Gly Pro Thr Leu Ser
        355                 360                 365

Phe Gln Leu Leu Asp Pro His Met Lys Phe Arg Gln Leu Glu Ser Pro
    370                 375                 380

Asn Leu Arg Gln Leu Leu Ser Trp Ile Asp Leu Glu Phe Asn His Pro
385                 390                 395                 400

Gln Ile Phe Ile Val Glu Asn Gly Trp Phe Val Ser Gly Thr Thr Lys
                405                 410                 415

Arg Asp Asp Ala Lys Tyr Met Tyr Tyr Leu Lys Lys Phe Ile Met Glu
            420                 425                 430

Thr Leu Lys Ala Ile Lys Leu Asp Gly Val Asp Val Ile Gly Tyr Thr
        435                 440                 445

Ala Trp Ser Leu Met Asp Gly Phe Glu Trp His Arg Gly Tyr Ser Ile
    450                 455                 460

Arg Arg Gly Leu Phe Tyr Val Asp Phe Leu Ser Gln Asp Lys Met Leu
465                 470                 475                 480

Leu Pro Lys Ser Ser Ala Leu Phe Tyr Gln Lys Leu Ile Glu Lys Asn
                485                 490                 495

Gly Phe Pro Pro Leu Pro Glu Asn Gln Pro Leu Glu Gly Thr Phe Pro
            500                 505                 510

Cys Asp Phe Ala Trp Gly Val Val Asp Asn Tyr Ile Gln Val Asp Thr
        515                 520                 525

Thr Leu Ser Gln Phe Thr Asp Leu Asn Val Tyr Leu Trp Asp Val His
    530                 535                 540

His Ser Lys Arg Leu Ile Lys Val Asp Gly Val Val Thr Lys Lys Arg
545                 550                 555                 560

Lys Ser Tyr Cys Val Asp Phe Ala Ala Ile Gln Pro Gln Ile Ala Leu
                565                 570                 575

Leu Gln Glu Met His Val Thr His Phe Arg Phe Ser Leu Asp Trp Ala
            580                 585                 590

Leu Ile Leu Pro Leu Gly Asn Gln Ser Gln Val Asn His Thr Ile Leu
        595                 600                 605

Gln Tyr Tyr Arg Cys Met Ala Ser Glu Leu Val Arg Val Asn Ile Thr
    610                 615                 620

Pro Val Val Ala Leu Trp Gln Pro Met Ala Pro Asn Gln Gly Leu Pro
625                 630                 635                 640

Arg Leu Leu Ala Arg Gln Gly Ala Trp Glu Asn Pro Tyr Thr Ala Leu
                645                 650                 655

Ala Phe Ala Glu Tyr Ala Arg Leu Cys Phe Gln Glu Leu Gly His His
            660                 665                 670

Val Lys Leu Trp Ile Thr Met Asn Glu Pro Tyr Thr Arg Asn Met Thr
        675                 680                 685

Tyr Ser Ala Gly His Asn Leu Leu Lys Ala His Ala Leu Ala Trp His
    690                 695                 700

Val Tyr Asn Glu Lys Phe Arg His Ala Gln Asn Gly Lys Ile Ser Ile
705                 710                 715                 720

Ala Leu Gln Ala Asp Trp Ile Glu Pro Ala Cys Pro Phe Ser Gln Lys
```

-continued

```
                725                 730                 735

Asp Lys Glu Val Ala Glu Arg Val Leu Glu Phe Asp Ile Gly Trp Leu
            740                 745                 750

Ala Glu Pro Ile Phe Gly Ser Gly Asp Tyr Pro Trp Val Met Arg Asp
        755                 760                 765

Trp Leu Asn Gln Arg Asn Asn Phe Leu Leu Pro Tyr Phe Thr Glu Asp
    770                 775                 780

Glu Lys Lys Leu Ile Gln Gly Thr Phe Asp Phe Leu Ala Leu Ser His
785                 790                 795                 800

Tyr Thr Thr Ile Leu Val Asp Ser Glu Lys Glu Asp Pro Ile Lys Tyr
                805                 810                 815

Asn Asp Tyr Leu Glu Val Gln Glu Met Thr Asp Ile Thr Trp Leu Asn
            820                 825                 830

Ser Pro Ser Gln Val Ala Val Val Pro Trp Gly Leu Arg Lys Val Leu
        835                 840                 845

Asn Trp Leu Lys Phe Lys Tyr Gly Asp Leu Pro Met Tyr Ile Ile Ser
    850                 855                 860

Asn Gly Ile Asp Asp Gly Leu His Ala Glu Asp Asp Gln Leu Arg Val
865                 870                 875                 880

Tyr Tyr Met Gln Asn Tyr Ile Asn Glu Ala Leu Lys Ala His Ile Leu
                885                 890                 895

Asp Gly Ile Asn Leu Cys Gly Tyr Phe Ala Tyr Ser Phe Asn Asp Arg
            900                 905                 910

Thr Ala Pro Arg Phe Gly Leu Tyr Arg Tyr Ala Ala Asp Gln Phe Glu
        915                 920                 925

Pro Lys Ala Ser Met Lys His Tyr Arg Lys Ile Ile Asp Ser Asn Gly
    930                 935                 940

Phe Pro Gly Pro Glu Thr Leu Glu Arg Phe Cys Pro Glu Glu Phe Thr
945                 950                 955                 960

Val Cys Thr Glu Cys Ser Phe Phe His Thr Arg Lys Ser Leu Gly Ser
                965                 970                 975

Gly Gly Gly Gly Ser Gly Gly Gly Gly Ser Gly Gly Gly Gly Ser Leu
            980                 985                 990

Lys Tyr Pro Asn Ala Ser Pro Leu  Leu Gly Ser Ser Trp  Gly Gly Leu
        995                 1000                1005

Ile His  Leu Tyr Thr Ala Thr  Ala Arg Asn Ser Tyr  His Leu Gln
    1010                1015                1020

Ile His  Lys Asn Gly His Val  Asp Gly Ala Pro His  Gln Thr Ile
    1025                1030                1035

Tyr Ser  Ala Leu Met Ile Arg  Ser Glu Asp Ala Gly  Phe Val Val
    1040                1045                1050

Ile Thr  Gly Val Met Ser Arg  Arg Tyr Leu Cys Met  Asp Phe Arg
    1055                1060                1065

Gly Asn  Ile Phe Gly Ser His  Tyr Phe Asp Pro Glu  Asn Cys Arg
    1070                1075                1080

Phe Gln  His Gln Thr Leu Glu  Asn Gly Tyr Asp Val  Tyr His Ser
    1085                1090                1095

Pro Gln  Tyr His Phe Leu Val  Ser Leu Gly Arg Ala  Lys Arg Ala
    1100                1105                1110

Phe Leu  Pro Gly Met Asn Pro  Pro Pro Tyr Ser Gln  Phe Leu Ser
    1115                1120                1125

Arg Arg  Asn Glu Ile Pro Leu  Ile His Phe Asn Thr  Pro Ile Pro
    1130                1135                1140
```

```
Arg Arg  His Thr Gln Ser Ala  Glu Asp Asp Ser Glu  Arg Asp Pro
    1145                 1150                 1155

Leu Asn  Val Leu Lys Pro Arg  Ala Arg Met Thr Pro  Ala Pro Ala
    1160                 1165                 1170

Ser Cys  Ser Gln Glu Leu Pro  Ser Ala Glu Asp Asn  Ser Pro Met
    1175                 1180                 1185

Ala Ser  Asp Pro Leu Gly Val  Val Arg Gly Gly Arg  Val Asn Thr
    1190                 1195                 1200

His Ala  Gly Gly Thr Gly Pro  Glu Gly Cys Arg Pro  Phe Ala Lys
    1205                 1210                 1215

Phe Ile
    1220


<210> SEQ ID NO 21
<211> LENGTH: 762
<212> TYPE: PRT
<213> ORGANISM: Artificial Sequence
<220> FEATURE:
<223> OTHER INFORMATION: Description of Artificial Sequence: Synthetic
      fusion polypeptide

<400> SEQUENCE: 21

Met Pro Ala Ser Ala Pro Pro Arg Arg Pro Arg Pro Pro Pro Pro Ser
1               5                   10                  15

Leu Ser Leu Leu Leu Val Leu Leu Gly Leu Gly Gly Arg Arg Leu Arg
            20                  25                  30

Ala Glu Pro Gly Asp Gly Ala Gln Thr Trp Ala Arg Phe Ser Arg Pro
        35                  40                  45

Pro Ala Pro Glu Ala Ala Gly Leu Phe Gln Gly Thr Phe Pro Asp Gly
    50                  55                  60

Phe Leu Trp Ala Val Gly Ser Ala Ala Tyr Gln Thr Glu Gly Gly Trp
65                  70                  75                  80

Gln Gln His Gly Lys Gly Ala Ser Ile Trp Asp Thr Phe Thr His His
                85                  90                  95

Pro Leu Ala Pro Pro Gly Asp Ser Arg Asn Ala Ser Leu Pro Leu Gly
            100                 105                 110

Ala Pro Ser Pro Leu Gln Pro Ala Thr Gly Asp Val Ala Ser Asp Ser
        115                 120                 125

Tyr Asn Asn Val Phe Arg Asp Thr Glu Ala Leu Arg Glu Leu Gly Val
    130                 135                 140

Thr His Tyr Arg Phe Ser Ile Ser Trp Ala Arg Val Leu Pro Asn Gly
145                 150                 155                 160

Ser Ala Gly Val Pro Asn Arg Glu Gly Leu Arg Tyr Tyr Arg Arg Leu
                165                 170                 175

Leu Glu Arg Leu Arg Glu Leu Gly Val Gln Pro Val Val Thr Leu Tyr
            180                 185                 190

His Trp Asp Leu Pro Gln Arg Leu Gln Asp Ala Tyr Gly Gly Trp Ala
        195                 200                 205

Asn Arg Ala Leu Ala Asp His Phe Arg Asp Tyr Ala Glu Leu Cys Phe
    210                 215                 220

Arg His Phe Gly Gly Gln Val Lys Tyr Trp Ile Thr Ile Asp Asn Pro
225                 230                 235                 240

Tyr Val Val Ala Trp His Gly Tyr Ala Thr Gly Arg Leu Ala Pro Gly
                245                 250                 255

Ile Arg Gly Ser Pro Arg Leu Gly Tyr Leu Val Ala His Asn Leu Leu
```

```
            260                 265                 270

Leu Ala His Ala Lys Val Trp His Leu Tyr Asn Thr Ser Phe Arg Pro
        275                 280                 285

Thr Gln Gly Gly Gln Val Ser Ile Ala Leu Ser Ser His Trp Ile Asn
    290                 295                 300

Pro Arg Arg Met Thr Asp His Ser Ile Lys Glu Cys Gln Lys Ser Leu
305                 310                 315                 320

Asp Phe Val Leu Gly Trp Phe Ala Lys Pro Val Phe Ile Asp Gly Asp
                325                 330                 335

Tyr Pro Glu Ser Met Lys Asn Asn Leu Ser Ser Ile Leu Pro Asp Phe
            340                 345                 350

Thr Glu Ser Glu Lys Lys Phe Ile Lys Gly Thr Ala Asp Phe Phe Ala
        355                 360                 365

Leu Cys Phe Gly Pro Thr Leu Ser Phe Gln Leu Leu Asp Pro His Met
    370                 375                 380

Lys Phe Arg Gln Leu Glu Ser Pro Asn Leu Arg Gln Leu Leu Ser Trp
385                 390                 395                 400

Ile Asp Leu Glu Phe Asn His Pro Gln Ile Phe Ile Val Glu Asn Gly
                405                 410                 415

Trp Phe Val Ser Gly Thr Thr Lys Arg Asp Asp Ala Lys Tyr Met Tyr
            420                 425                 430

Tyr Leu Lys Lys Phe Ile Met Glu Thr Leu Lys Ala Ile Lys Leu Asp
        435                 440                 445

Gly Val Asp Val Ile Gly Tyr Thr Ala Trp Ser Leu Met Asp Gly Phe
    450                 455                 460

Glu Trp His Arg Gly Tyr Ser Ile Arg Arg Gly Leu Phe Tyr Val Asp
465                 470                 475                 480

Phe Leu Ser Gln Asp Lys Met Leu Leu Pro Lys Ser Ser Ala Leu Phe
                485                 490                 495

Tyr Gln Lys Leu Ile Glu Lys Asn Gly Phe Pro Pro Leu Pro Glu Asn
            500                 505                 510

Gln Pro Leu Glu Gly Ser Gly Gly Gly Gly Ser Gly Gly Gly Gly Ser
        515                 520                 525

Gly Gly Gly Gly Ser Leu Lys Tyr Pro Asn Ala Ser Pro Leu Leu Gly
    530                 535                 540

Ser Ser Trp Gly Gly Leu Ile His Leu Tyr Thr Ala Thr Ala Arg Asn
545                 550                 555                 560

Ser Tyr His Leu Gln Ile His Lys Asn Gly His Val Asp Gly Ala Pro
                565                 570                 575

His Gln Thr Ile Tyr Ser Ala Leu Met Ile Arg Ser Glu Asp Ala Gly
            580                 585                 590

Phe Val Val Ile Thr Gly Val Met Ser Arg Arg Tyr Leu Cys Met Asp
        595                 600                 605

Phe Arg Gly Asn Ile Phe Gly Ser His Tyr Phe Asp Pro Glu Asn Cys
    610                 615                 620

Arg Phe Gln His Gln Thr Leu Glu Asn Gly Tyr Asp Val Tyr His Ser
625                 630                 635                 640

Pro Gln Tyr His Phe Leu Val Ser Leu Gly Arg Ala Lys Arg Ala Phe
                645                 650                 655

Leu Pro Gly Met Asn Pro Pro Pro Tyr Ser Gln Phe Leu Ser Arg Arg
            660                 665                 670

Asn Glu Ile Pro Leu Ile His Phe Asn Thr Pro Ile Pro Arg Arg His
        675                 680                 685
```

```
Thr Gln Ser Ala Glu Asp Asp Ser Glu Arg Asp Pro Leu Asn Val Leu
    690                 695                 700

Lys Pro Arg Ala Arg Met Thr Pro Ala Pro Ala Ser Cys Ser Gln Glu
705                 710                 715                 720

Leu Pro Ser Ala Glu Asp Asn Ser Pro Met Ala Ser Asp Pro Leu Gly
                725                 730                 735

Val Val Arg Gly Gly Arg Val Asn Thr His Ala Gly Gly Thr Gly Pro
            740                 745                 750

Glu Gly Cys Arg Pro Phe Ala Lys Phe Ile
        755                 760


<210> SEQ ID NO 22
<211> LENGTH: 752
<212> TYPE: PRT
<213> ORGANISM: Artificial Sequence
<220> FEATURE:
<223> OTHER INFORMATION: Description of Artificial Sequence: Synthetic
      fusion polypeptide

<400> SEQUENCE: 22

Met Pro Ala Ser Ala Pro Pro Arg Arg Pro Arg Pro Pro Pro Pro Ser
1               5                   10                  15

Leu Ser Leu Leu Leu Val Leu Leu Gly Leu Gly Gly Arg Arg Leu Pro
            20                  25                  30

Leu Pro Glu Asn Gln Pro Leu Glu Gly Thr Phe Pro Cys Asp Phe Ala
        35                  40                  45

Trp Gly Val Val Asp Asn Tyr Ile Gln Val Asp Thr Thr Leu Ser Gln
    50                  55                  60

Phe Thr Asp Leu Asn Val Tyr Leu Trp Asp Val His His Ser Lys Arg
65                  70                  75                  80

Leu Ile Lys Val Asp Gly Val Val Thr Lys Lys Arg Lys Ser Tyr Cys
                85                  90                  95

Val Asp Phe Ala Ala Ile Gln Pro Gln Ile Ala Leu Leu Gln Glu Met
            100                 105                 110

His Val Thr His Phe Arg Phe Ser Leu Asp Trp Ala Leu Ile Leu Pro
        115                 120                 125

Leu Gly Asn Gln Ser Gln Val Asn His Thr Ile Leu Gln Tyr Tyr Arg
    130                 135                 140

Cys Met Ala Ser Glu Leu Val Arg Val Asn Ile Thr Pro Val Val Ala
145                 150                 155                 160

Leu Trp Gln Pro Met Ala Pro Asn Gln Gly Leu Pro Arg Leu Leu Ala
                165                 170                 175

Arg Gln Gly Ala Trp Glu Asn Pro Tyr Thr Ala Leu Ala Phe Ala Glu
            180                 185                 190

Tyr Ala Arg Leu Cys Phe Gln Glu Leu Gly His His Val Lys Leu Trp
        195                 200                 205

Ile Thr Met Asn Glu Pro Tyr Thr Arg Asn Met Thr Tyr Ser Ala Gly
    210                 215                 220

His Asn Leu Leu Lys Ala His Ala Leu Ala Trp His Val Tyr Asn Glu
225                 230                 235                 240

Lys Phe Arg His Ala Gln Asn Gly Lys Ile Ser Ile Ala Leu Gln Ala
                245                 250                 255

Asp Trp Ile Glu Pro Ala Cys Pro Phe Ser Gln Lys Asp Lys Glu Val
            260                 265                 270

Ala Glu Arg Val Leu Glu Phe Asp Ile Gly Trp Leu Ala Glu Pro Ile
```

```
        275                 280                 285

Phe Gly Ser Gly Asp Tyr Pro Trp Val Met Arg Asp Trp Leu Asn Gln
    290                 295                 300

Arg Asn Asn Phe Leu Leu Pro Tyr Phe Thr Glu Asp Glu Lys Lys Leu
305                 310                 315                 320

Ile Gln Gly Thr Phe Asp Phe Leu Ala Leu Ser His Tyr Thr Thr Ile
                325                 330                 335

Leu Val Asp Ser Glu Lys Glu Asp Pro Ile Lys Tyr Asn Asp Tyr Leu
            340                 345                 350

Glu Val Gln Glu Met Thr Asp Ile Thr Trp Leu Asn Ser Pro Ser Gln
        355                 360                 365

Val Ala Val Val Pro Trp Gly Leu Arg Lys Val Leu Asn Trp Leu Lys
    370                 375                 380

Phe Lys Tyr Gly Asp Leu Pro Met Tyr Ile Ile Ser Asn Gly Ile Asp
385                 390                 395                 400

Asp Gly Leu His Ala Glu Asp Asp Gln Leu Arg Val Tyr Tyr Met Gln
                405                 410                 415

Asn Tyr Ile Asn Glu Ala Leu Lys Ala His Ile Leu Asp Gly Ile Asn
            420                 425                 430

Leu Cys Gly Tyr Phe Ala Tyr Ser Phe Asn Asp Arg Thr Ala Pro Arg
        435                 440                 445

Phe Gly Leu Tyr Arg Tyr Ala Ala Asp Gln Phe Glu Pro Lys Ala Ser
    450                 455                 460

Met Lys His Tyr Arg Lys Ile Ile Asp Ser Asn Gly Phe Pro Gly Pro
465                 470                 475                 480

Glu Thr Leu Glu Arg Phe Cys Pro Glu Glu Phe Thr Val Cys Thr Glu
                485                 490                 495

Cys Ser Phe Phe His Thr Arg Lys Ser Leu Gly Ser Gly Gly Gly Gly
            500                 505                 510

Ser Gly Gly Gly Gly Ser Gly Gly Gly Gly Ser Leu Lys Tyr Pro Asn
        515                 520                 525

Ala Ser Pro Leu Leu Gly Ser Ser Trp Gly Gly Leu Ile His Leu Tyr
    530                 535                 540

Thr Ala Thr Ala Arg Asn Ser Tyr His Leu Gln Ile His Lys Asn Gly
545                 550                 555                 560

His Val Asp Gly Ala Pro His Gln Thr Ile Tyr Ser Ala Leu Met Ile
                565                 570                 575

Arg Ser Glu Asp Ala Gly Phe Val Val Ile Thr Gly Val Met Ser Arg
            580                 585                 590

Arg Tyr Leu Cys Met Asp Phe Arg Gly Asn Ile Phe Gly Ser His Tyr
        595                 600                 605

Phe Asp Pro Glu Asn Cys Arg Phe Gln His Gln Thr Leu Glu Asn Gly
    610                 615                 620

Tyr Asp Val Tyr His Ser Pro Gln Tyr His Phe Leu Val Ser Leu Gly
625                 630                 635                 640

Arg Ala Lys Arg Ala Phe Leu Pro Gly Met Asn Pro Pro Pro Tyr Ser
                645                 650                 655

Gln Phe Leu Ser Arg Arg Asn Glu Ile Pro Leu Ile His Phe Asn Thr
            660                 665                 670

Pro Ile Pro Arg Arg His Thr Gln Ser Ala Glu Asp Asp Ser Glu Arg
        675                 680                 685

Asp Pro Leu Asn Val Leu Lys Pro Arg Ala Arg Met Thr Pro Ala Pro
    690                 695                 700
```

```
Ala Ser Cys Ser Gln Glu Leu Pro Ser Ala Glu Asp Asn Ser Pro Met
705                 710                 715                 720

Ala Ser Asp Pro Leu Gly Val Val Arg Gly Gly Arg Val Asn Thr His
                725                 730                 735

Ala Gly Gly Thr Gly Pro Glu Gly Cys Arg Pro Phe Ala Lys Phe Ile
            740                 745                 750


<210> SEQ ID NO 23
<211> LENGTH: 1215
<212> TYPE: PRT
<213> ORGANISM: Artificial Sequence
<220> FEATURE:
<223> OTHER INFORMATION: Description of Artificial Sequence: Synthetic
      fusion polypeptide

<400> SEQUENCE: 23

Met Pro Ala Ser Ala Pro Pro Arg Arg Pro Arg Pro Pro Pro Pro Ser
1               5                   10                  15

Leu Ser Leu Leu Leu Val Leu Leu Gly Leu Gly Gly Arg Arg Leu Arg
            20                  25                  30

Ala Glu Pro Gly Asp Gly Ala Gln Thr Trp Ala Arg Phe Ser Arg Pro
        35                  40                  45

Pro Ala Pro Glu Ala Ala Gly Leu Phe Gln Gly Thr Phe Pro Asp Gly
    50                  55                  60

Phe Leu Trp Ala Val Gly Ser Ala Ala Tyr Gln Thr Glu Gly Gly Trp
65                  70                  75                  80

Gln Gln His Gly Lys Gly Ala Ser Ile Trp Asp Thr Phe Thr His His
                85                  90                  95

Pro Leu Ala Pro Pro Gly Asp Ser Arg Asn Ala Ser Leu Pro Leu Gly
            100                 105                 110

Ala Pro Ser Pro Leu Gln Pro Ala Thr Gly Asp Val Ala Ser Asp Ser
        115                 120                 125

Tyr Asn Asn Val Phe Arg Asp Thr Glu Ala Leu Arg Glu Leu Gly Val
    130                 135                 140

Thr His Tyr Arg Phe Ser Ile Ser Trp Ala Arg Val Leu Pro Asn Gly
145                 150                 155                 160

Ser Ala Gly Val Pro Asn Arg Glu Gly Leu Arg Tyr Tyr Arg Arg Leu
                165                 170                 175

Leu Glu Arg Leu Arg Glu Leu Gly Val Gln Pro Val Val Thr Leu Tyr
            180                 185                 190

His Trp Asp Leu Pro Gln Arg Leu Gln Asp Ala Tyr Gly Gly Trp Ala
        195                 200                 205

Asn Arg Ala Leu Ala Asp His Phe Arg Asp Tyr Ala Glu Leu Cys Phe
    210                 215                 220

Arg His Phe Gly Gly Gln Val Lys Tyr Trp Ile Thr Ile Asp Asn Pro
225                 230                 235                 240

Tyr Val Val Ala Trp His Gly Tyr Ala Thr Gly Arg Leu Ala Pro Gly
                245                 250                 255

Ile Arg Gly Ser Pro Arg Leu Gly Tyr Leu Val Ala His Asn Leu Leu
            260                 265                 270

Leu Ala His Ala Lys Val Trp His Leu Tyr Asn Thr Ser Phe Arg Pro
        275                 280                 285

Thr Gln Gly Gly Gln Val Ser Ile Ala Leu Ser Ser His Trp Ile Asn
    290                 295                 300

Pro Arg Arg Met Thr Asp His Ser Ile Lys Glu Cys Gln Lys Ser Leu
```

-continued

```
305                 310                 315                 320

Asp Phe Val Leu Gly Trp Phe Ala Lys Pro Val Phe Ile Asp Gly Asp
                325                 330                 335

Tyr Pro Glu Ser Met Lys Asn Asn Leu Ser Ser Ile Leu Pro Asp Phe
            340                 345                 350

Thr Glu Ser Glu Lys Lys Phe Ile Lys Gly Thr Ala Asp Phe Phe Ala
        355                 360                 365

Leu Cys Phe Gly Pro Thr Leu Ser Phe Gln Leu Leu Asp Pro His Met
    370                 375                 380

Lys Phe Arg Gln Leu Glu Ser Pro Asn Leu Arg Gln Leu Leu Ser Trp
385                 390                 395                 400

Ile Asp Leu Glu Phe Asn His Pro Gln Ile Phe Ile Val Glu Asn Gly
                405                 410                 415

Trp Phe Val Ser Gly Thr Thr Lys Arg Asp Asp Ala Lys Tyr Met Tyr
            420                 425                 430

Tyr Leu Lys Lys Phe Ile Met Glu Thr Leu Lys Ala Ile Lys Leu Asp
        435                 440                 445

Gly Val Asp Val Ile Gly Tyr Thr Ala Trp Ser Leu Met Asp Gly Phe
    450                 455                 460

Glu Trp His Arg Gly Tyr Ser Ile Arg Arg Gly Leu Phe Tyr Val Asp
465                 470                 475                 480

Phe Leu Ser Gln Asp Lys Met Leu Leu Pro Lys Ser Ser Ala Leu Phe
                485                 490                 495

Tyr Gln Lys Leu Ile Glu Lys Asn Gly Phe Pro Pro Leu Pro Glu Asn
            500                 505                 510

Gln Pro Leu Glu Gly Ser Gly Thr Phe Pro Asp Gly Phe Leu Trp Ala
        515                 520                 525

Val Gly Ser Ala Ala Tyr Gln Thr Glu Gly Gly Trp Gln Gln His Gly
    530                 535                 540

Lys Gly Ala Ser Ile Trp Asp Thr Phe Thr His His Pro Leu Ala Pro
545                 550                 555                 560

Pro Gly Asp Ser Arg Asn Ala Ser Leu Pro Leu Gly Ala Pro Ser Pro
                565                 570                 575

Leu Gln Pro Ala Thr Gly Asp Val Ala Ser Asp Ser Tyr Asn Asn Val
            580                 585                 590

Phe Arg Asp Thr Glu Ala Leu Arg Glu Leu Gly Val Thr His Tyr Arg
        595                 600                 605

Phe Ser Ile Ser Trp Ala Arg Val Leu Pro Asn Gly Ser Ala Gly Val
    610                 615                 620

Pro Asn Arg Glu Gly Leu Arg Tyr Tyr Arg Arg Leu Leu Glu Arg Leu
625                 630                 635                 640

Arg Glu Leu Gly Val Gln Pro Val Val Thr Leu Tyr His Trp Asp Leu
                645                 650                 655

Pro Gln Arg Leu Gln Asp Ala Tyr Gly Gly Trp Ala Asn Arg Ala Leu
            660                 665                 670

Ala Asp His Phe Arg Asp Tyr Ala Glu Leu Cys Phe Arg His Phe Gly
        675                 680                 685

Gly Gln Val Lys Tyr Trp Ile Thr Ile Asp Asn Pro Tyr Val Val Ala
    690                 695                 700

Trp His Gly Tyr Ala Thr Gly Arg Leu Ala Pro Gly Ile Arg Gly Ser
705                 710                 715                 720

Pro Arg Leu Gly Tyr Leu Val Ala His Asn Leu Leu Leu Ala His Ala
                725                 730                 735
```

```
Lys Val Trp His Leu Tyr Asn Thr Ser Phe Arg Pro Thr Gln Gly Gly
            740                 745                 750

Gln Val Ser Ile Ala Leu Ser Ser His Trp Ile Asn Pro Arg Arg Met
        755                 760                 765

Thr Asp His Ser Ile Lys Glu Cys Gln Lys Ser Leu Asp Phe Val Leu
    770                 775                 780

Gly Trp Phe Ala Lys Pro Val Phe Ile Asp Gly Asp Tyr Pro Glu Ser
785                 790                 795                 800

Met Lys Asn Asn Leu Ser Ser Ile Leu Pro Asp Phe Thr Glu Ser Glu
                805                 810                 815

Lys Lys Phe Ile Lys Gly Thr Ala Asp Phe Phe Ala Leu Cys Phe Gly
            820                 825                 830

Pro Thr Leu Ser Phe Gln Leu Leu Asp Pro His Met Lys Phe Arg Gln
        835                 840                 845

Leu Glu Ser Pro Asn Leu Arg Gln Leu Leu Ser Trp Ile Asp Leu Glu
    850                 855                 860

Phe Asn His Pro Gln Ile Phe Ile Val Glu Asn Gly Trp Phe Val Ser
865                 870                 875                 880

Gly Thr Thr Lys Arg Asp Asp Ala Lys Tyr Met Tyr Tyr Leu Lys Lys
                885                 890                 895

Phe Ile Met Glu Thr Leu Lys Ala Ile Lys Leu Asp Gly Val Asp Val
            900                 905                 910

Ile Gly Tyr Thr Ala Trp Ser Leu Met Asp Gly Phe Glu Trp His Arg
        915                 920                 925

Gly Tyr Ser Ile Arg Arg Gly Leu Phe Tyr Val Asp Phe Leu Ser Gln
    930                 935                 940

Asp Lys Met Leu Leu Pro Lys Ser Ser Ala Leu Phe Tyr Gln Lys Leu
945                 950                 955                 960

Ile Glu Lys Asn Gly Phe Pro Glu Phe Gly Ser Gly Gly Gly Gly Ser
                965                 970                 975

Gly Gly Gly Gly Ser Gly Gly Gly Gly Ser Leu Lys Tyr Pro Asn Ala
            980                 985                 990

Ser Pro Leu Leu Gly Ser Ser Trp  Gly Gly Leu Ile His  Leu Tyr Thr
        995                 1000                1005

Ala Thr  Ala Arg Asn Ser Tyr  His Leu Gln Ile His  Lys Asn Gly
    1010                1015                1020

His Val  Asp Gly Ala Pro His  Gln Thr Ile Tyr Ser  Ala Leu Met
    1025                1030                1035

Ile Arg  Ser Glu Asp Ala Gly  Phe Val Val Ile Thr  Gly Val Met
    1040                1045                1050

Ser Arg  Arg Tyr Leu Cys Met  Asp Phe Arg Gly Asn  Ile Phe Gly
    1055                1060                1065

Ser His  Tyr Phe Asp Pro Glu  Asn Cys Arg Phe Gln  His Gln Thr
    1070                1075                1080

Leu Glu  Asn Gly Tyr Asp Val  Tyr His Ser Pro Gln  Tyr His Phe
    1085                1090                1095

Leu Val  Ser Leu Gly Arg Ala  Lys Arg Ala Phe Leu  Pro Gly Met
    1100                1105                1110

Asn Pro  Pro Pro Tyr Ser Gln  Phe Leu Ser Arg Arg  Asn Glu Ile
    1115                1120                1125

Pro Leu  Ile His Phe Asn Thr  Pro Ile Pro Arg Arg  His Thr Gln
    1130                1135                1140
```

```
Ser Ala  Glu Asp Asp Ser Glu  Arg Asp Pro Leu Asn  Val Leu Lys
    1145                 1150                 1155

Pro Arg  Ala Arg Met Thr Pro  Ala Pro Ala Ser Cys  Ser Gln Glu
    1160                 1165                 1170

Leu Pro  Ser Ala Glu Asp Asn  Ser Pro Met Ala Ser  Asp Pro Leu
    1175                 1180                 1185

Gly Val  Val Arg Gly Gly Arg  Val Asn Thr His Ala  Gly Gly Thr
    1190                 1195                 1200

Gly Pro  Glu Gly Cys Arg Pro  Phe Ala Lys Phe Ile
    1205                 1210                 1215


<210> SEQ ID NO 24
<211> LENGTH: 1189
<212> TYPE: PRT
<213> ORGANISM: Artificial Sequence
<220> FEATURE:
<223> OTHER INFORMATION: Description of Artificial Sequence: Synthetic
      fusion polypeptide

<400> SEQUENCE: 24

Met Pro Ala Ser Ala Pro Pro Arg Arg Pro Arg Pro Pro Pro Pro Ser
1               5                   10                  15

Leu Ser Leu Leu Leu Val Leu Leu Gly Leu Gly Gly Arg Arg Leu Pro
            20                  25                  30

Leu Pro Glu Asn Gln Pro Leu Glu Gly Thr Phe Pro Cys Asp Phe Ala
        35                  40                  45

Trp Gly Val Val Asp Asn Tyr Ile Gln Val Asp Thr Thr Leu Ser Gln
    50                  55                  60

Phe Thr Asp Leu Asn Val Tyr Leu Trp Asp Val His His Ser Lys Arg
65                  70                  75                  80

Leu Ile Lys Val Asp Gly Val Val Thr Lys Lys Arg Lys Ser Tyr Cys
                85                  90                  95

Val Asp Phe Ala Ala Ile Gln Pro Gln Ile Ala Leu Leu Gln Glu Met
            100                 105                 110

His Val Thr His Phe Arg Phe Ser Leu Asp Trp Ala Leu Ile Leu Pro
        115                 120                 125

Leu Gly Asn Gln Ser Gln Val Asn His Thr Ile Leu Gln Tyr Tyr Arg
    130                 135                 140

Cys Met Ala Ser Glu Leu Val Arg Val Asn Ile Thr Pro Val Val Ala
145                 150                 155                 160

Leu Trp Gln Pro Met Ala Pro Asn Gln Gly Leu Pro Arg Leu Leu Ala
                165                 170                 175

Arg Gln Gly Ala Trp Glu Asn Pro Tyr Thr Ala Leu Ala Phe Ala Glu
            180                 185                 190

Tyr Ala Arg Leu Cys Phe Gln Glu Leu Gly His His Val Lys Leu Trp
        195                 200                 205

Ile Thr Met Asn Glu Pro Tyr Thr Arg Asn Met Thr Tyr Ser Ala Gly
    210                 215                 220

His Asn Leu Leu Lys Ala His Ala Leu Ala Trp His Val Tyr Asn Glu
225                 230                 235                 240

Lys Phe Arg His Ala Gln Asn Gly Lys Ile Ser Ile Ala Leu Gln Ala
                245                 250                 255

Asp Trp Ile Glu Pro Ala Cys Pro Phe Ser Gln Lys Asp Lys Glu Val
            260                 265                 270

Ala Glu Arg Val Leu Glu Phe Asp Ile Gly Trp Leu Ala Glu Pro Ile
        275                 280                 285
```

```
Phe Gly Ser Gly Asp Tyr Pro Trp Val Met Arg Asp Trp Leu Asn Gln
    290                 295                 300

Arg Asn Asn Phe Leu Leu Pro Tyr Phe Thr Glu Asp Glu Lys Lys Leu
305                 310                 315                 320

Ile Gln Gly Thr Phe Asp Phe Leu Ala Leu Ser His Tyr Thr Thr Ile
                325                 330                 335

Leu Val Asp Ser Glu Lys Glu Asp Pro Ile Lys Tyr Asn Asp Tyr Leu
            340                 345                 350

Glu Val Gln Glu Met Thr Asp Ile Thr Trp Leu Asn Ser Pro Ser Gln
        355                 360                 365

Val Ala Val Val Pro Trp Gly Leu Arg Lys Val Leu Asn Trp Leu Lys
    370                 375                 380

Phe Lys Tyr Gly Asp Leu Pro Met Tyr Ile Ile Ser Asn Gly Ile Asp
385                 390                 395                 400

Asp Gly Leu His Ala Glu Asp Asp Gln Leu Arg Val Tyr Tyr Met Gln
                405                 410                 415

Asn Tyr Ile Asn Glu Ala Leu Lys Ala His Ile Leu Asp Gly Ile Asn
            420                 425                 430

Leu Cys Gly Tyr Phe Ala Tyr Ser Phe Asn Asp Arg Thr Ala Pro Arg
        435                 440                 445

Phe Gly Leu Tyr Arg Tyr Ala Ala Asp Gln Phe Glu Pro Lys Ala Ser
    450                 455                 460

Met Lys His Tyr Arg Lys Ile Ile Asp Ser Asn Gly Phe Pro Gly Pro
465                 470                 475                 480

Glu Thr Leu Glu Arg Phe Cys Pro Glu Glu Phe Thr Val Cys Thr Glu
                485                 490                 495

Cys Ser Phe Phe His Thr Arg Lys Ser Leu Gly Thr Phe Pro Cys Asp
            500                 505                 510

Phe Ala Trp Gly Val Val Asp Asn Tyr Ile Gln Val Asp Thr Thr Leu
        515                 520                 525

Ser Gln Phe Thr Asp Leu Asn Val Tyr Leu Trp Asp Val His His Ser
    530                 535                 540

Lys Arg Leu Ile Lys Val Asp Gly Val Val Thr Lys Lys Arg Lys Ser
545                 550                 555                 560

Tyr Cys Val Asp Phe Ala Ala Ile Gln Pro Gln Ile Ala Leu Leu Gln
                565                 570                 575

Glu Met His Val Thr His Phe Arg Phe Ser Leu Asp Trp Ala Leu Ile
            580                 585                 590

Leu Pro Leu Gly Asn Gln Ser Gln Val Asn His Thr Ile Leu Gln Tyr
        595                 600                 605

Tyr Arg Cys Met Ala Ser Glu Leu Val Arg Val Asn Ile Thr Pro Val
    610                 615                 620

Val Ala Leu Trp Gln Pro Met Ala Pro Asn Gln Gly Leu Pro Arg Leu
625                 630                 635                 640

Leu Ala Arg Gln Gly Ala Trp Glu Asn Pro Tyr Thr Ala Leu Ala Phe
                645                 650                 655

Ala Glu Tyr Ala Arg Leu Cys Phe Gln Glu Leu Gly His His Val Lys
            660                 665                 670

Leu Trp Ile Thr Met Asn Glu Pro Tyr Thr Arg Asn Met Thr Tyr Ser
        675                 680                 685

Ala Gly His Asn Leu Leu Lys Ala His Ala Leu Ala Trp His Val Tyr
    690                 695                 700
```

```
Asn Glu Lys Phe Arg His Ala Gln Asn Gly Lys Ile Ser Ile Ala Leu
705                 710                 715                 720

Gln Ala Asp Trp Ile Glu Pro Ala Cys Pro Phe Ser Gln Lys Asp Lys
                725                 730                 735

Glu Val Ala Glu Arg Val Leu Glu Phe Asp Ile Gly Trp Leu Ala Glu
            740                 745                 750

Pro Ile Phe Gly Ser Gly Asp Tyr Pro Trp Val Met Arg Asp Trp Leu
        755                 760                 765

Asn Gln Arg Asn Asn Phe Leu Leu Pro Tyr Phe Thr Glu Asp Glu Lys
    770                 775                 780

Lys Leu Ile Gln Gly Thr Phe Asp Phe Leu Ala Leu Ser His Tyr Thr
785                 790                 795                 800

Thr Ile Leu Val Asp Ser Glu Lys Glu Asp Pro Ile Lys Tyr Asn Asp
                805                 810                 815

Tyr Leu Glu Val Gln Glu Met Thr Asp Ile Thr Trp Leu Asn Ser Pro
            820                 825                 830

Ser Gln Val Ala Val Val Pro Trp Gly Leu Arg Lys Val Leu Asn Trp
        835                 840                 845

Leu Lys Phe Lys Tyr Gly Asp Leu Pro Met Tyr Ile Ile Ser Asn Gly
    850                 855                 860

Ile Asp Asp Gly Leu His Ala Glu Asp Asp Gln Leu Arg Val Tyr Tyr
865                 870                 875                 880

Met Gln Asn Tyr Ile Asn Glu Ala Leu Lys Ala His Ile Leu Asp Gly
                885                 890                 895

Ile Asn Leu Cys Gly Tyr Phe Ala Tyr Ser Phe Asn Asp Arg Thr Ala
            900                 905                 910

Pro Arg Phe Gly Leu Tyr Arg Tyr Ala Ala Asp Gln Phe Glu Pro Lys
        915                 920                 925

Ala Ser Met Lys His Tyr Arg Lys Ile Ile Asp Ser Asn Gly Phe Gly
    930                 935                 940

Ser Gly Gly Gly Gly Ser Gly Gly Gly Gly Ser Gly Gly Gly Gly Ser
945                 950                 955                 960

Leu Lys Tyr Pro Asn Ala Ser Pro Leu Leu Gly Ser Ser Trp Gly Gly
                965                 970                 975

Leu Ile His Leu Tyr Thr Ala Thr Ala Arg Asn Ser Tyr His Leu Gln
            980                 985                 990

Ile His Lys Asn Gly His Val Asp  Gly Ala Pro His Gln  Thr Ile Tyr
        995                 1000                1005

Ser Ala  Leu Met Ile Arg Ser  Glu Asp Ala Gly Phe  Val Val Ile
    1010                1015                1020

Thr Gly  Val Met Ser Arg Arg  Tyr Leu Cys Met Asp  Phe Arg Gly
    1025                1030                1035

Asn Ile  Phe Gly Ser His Tyr  Phe Asp Pro Glu Asn  Cys Arg Phe
    1040                1045                1050

Gln His  Gln Thr Leu Glu Asn  Gly Tyr Asp Val Tyr  His Ser Pro
    1055                1060                1065

Gln Tyr  His Phe Leu Val Ser  Leu Gly Arg Ala Lys  Arg Ala Phe
    1070                1075                1080

Leu Pro  Gly Met Asn Pro Pro  Pro Tyr Ser Gln Phe  Leu Ser Arg
    1085                1090                1095

Arg Asn  Glu Ile Pro Leu Ile  His Phe Asn Thr Pro  Ile Pro Arg
    1100                1105                1110

Arg His  Thr Gln Ser Ala Glu  Asp Asp Ser Glu Arg  Asp Pro Leu
```

```
    1115                1120                1125

Asn Val  Leu Lys Pro Arg Ala  Arg Met Thr Pro Ala  Pro Ala Ser
    1130                1135                1140

Cys Ser  Gln Glu Leu Pro Ser  Ala Glu Asp Asn Ser  Pro Met Ala
    1145                1150                1155

Ser Asp  Pro Leu Gly Val Val  Arg Gly Gly Arg Val  Asn Thr His
    1160                1165                1170

Ala Gly  Gly Thr Gly Pro Glu  Gly Cys Arg Pro Phe  Ala Lys Phe
    1175                1180                1185

Ile


<210> SEQ ID NO 25
<211> LENGTH: 1219
<212> TYPE: PRT
<213> ORGANISM: Artificial Sequence
<220> FEATURE:
<223> OTHER INFORMATION: Description of Artificial Sequence: Synthetic
      fusion polypeptide

<400> SEQUENCE: 25

Met Leu Gly Ala Arg Leu Arg Leu Trp Val Cys Ala Leu Cys Ser Val
1               5                   10                  15

Cys Ser Met Ser Val Leu Arg Ala Tyr Pro Asn Ala Ser Pro Leu Leu
            20                  25                  30

Gly Ser Ser Trp Gly Gly Leu Ile His Leu Tyr Thr Ala Thr Ala Arg
        35                  40                  45

Asn Ser Tyr His Leu Gln Ile His Lys Asn Gly His Val Asp Gly Ala
    50                  55                  60

Pro His Gln Thr Ile Tyr Ser Ala Leu Met Ile Arg Ser Glu Asp Ala
65                  70                  75                  80

Gly Phe Val Val Ile Thr Gly Val Met Ser Arg Arg Tyr Leu Cys Met
                85                  90                  95

Asp Phe Arg Gly Asn Ile Phe Gly Ser His Tyr Phe Asp Pro Glu Asn
            100                 105                 110

Cys Arg Phe Gln His Gln Thr Leu Glu Asn Gly Tyr Asp Val Tyr His
        115                 120                 125

Ser Pro Gln Tyr His Phe Leu Val Ser Leu Gly Arg Ala Lys Arg Ala
    130                 135                 140

Phe Leu Pro Gly Met Asn Pro Pro Pro Tyr Ser Gln Phe Leu Ser Arg
145                 150                 155                 160

Arg Asn Glu Ile Pro Leu Ile His Phe Asn Thr Pro Ile Pro Arg Arg
                165                 170                 175

His Thr Gln Ser Ala Glu Asp Asp Ser Glu Arg Asp Pro Leu Asn Val
            180                 185                 190

Leu Lys Pro Arg Ala Arg Met Thr Pro Ala Pro Ala Ser Cys Ser Gln
        195                 200                 205

Glu Leu Pro Ser Ala Glu Asp Asn Ser Pro Met Ala Ser Asp Pro Leu
    210                 215                 220

Gly Val Val Arg Gly Gly Arg Val Asn Thr His Ala Gly Gly Thr Gly
225                 230                 235                 240

Pro Glu Gly Cys Arg Pro Phe Ala Lys Phe Ile Gly Ser Gly Gly Gly
                245                 250                 255

Gly Ser Gly Gly Gly Gly Ser Gly Gly Gly Gly Ser Leu Lys Glu Pro
            260                 265                 270

Gly Asp Gly Ala Gln Thr Trp Ala Arg Phe Ser Arg Pro Pro Ala Pro
```

```
        275                 280                 285

Glu Ala Ala Gly Leu Phe Gln Gly Thr Phe Pro Asp Gly Phe Leu Trp
    290                 295                 300

Ala Val Gly Ser Ala Ala Tyr Gln Thr Glu Gly Gly Trp Gln Gln His
305                 310                 315                 320

Gly Lys Gly Ala Ser Ile Trp Asp Thr Phe Thr His His Pro Leu Ala
                325                 330                 335

Pro Pro Gly Asp Ser Arg Asn Ala Ser Leu Pro Leu Gly Ala Pro Ser
            340                 345                 350

Pro Leu Gln Pro Ala Thr Gly Asp Val Ala Ser Asp Ser Tyr Asn Asn
        355                 360                 365

Val Phe Arg Asp Thr Glu Ala Leu Arg Glu Leu Gly Val Thr His Tyr
    370                 375                 380

Arg Phe Ser Ile Ser Trp Ala Arg Val Leu Pro Asn Gly Ser Ala Gly
385                 390                 395                 400

Val Pro Asn Arg Glu Gly Leu Arg Tyr Tyr Arg Arg Leu Leu Glu Arg
                405                 410                 415

Leu Arg Glu Leu Gly Val Gln Pro Val Val Thr Leu Tyr His Trp Asp
            420                 425                 430

Leu Pro Gln Arg Leu Gln Asp Ala Tyr Gly Gly Trp Ala Asn Arg Ala
        435                 440                 445

Leu Ala Asp His Phe Arg Asp Tyr Ala Glu Leu Cys Phe Arg His Phe
    450                 455                 460

Gly Gly Gln Val Lys Tyr Trp Ile Thr Ile Asp Asn Pro Tyr Val Val
465                 470                 475                 480

Ala Trp His Gly Tyr Ala Thr Gly Arg Leu Ala Pro Gly Ile Arg Gly
                485                 490                 495

Ser Pro Arg Leu Gly Tyr Leu Val Ala His Asn Leu Leu Leu Ala His
            500                 505                 510

Ala Lys Val Trp His Leu Tyr Asn Thr Ser Phe Arg Pro Thr Gln Gly
        515                 520                 525

Gly Gln Val Ser Ile Ala Leu Ser Ser His Trp Ile Asn Pro Arg Arg
    530                 535                 540

Met Thr Asp His Ser Ile Lys Glu Cys Gln Lys Ser Leu Asp Phe Val
545                 550                 555                 560

Leu Gly Trp Phe Ala Lys Pro Val Phe Ile Asp Gly Asp Tyr Pro Glu
                565                 570                 575

Ser Met Lys Asn Asn Leu Ser Ser Ile Leu Pro Asp Phe Thr Glu Ser
            580                 585                 590

Glu Lys Lys Phe Ile Lys Gly Thr Ala Asp Phe Phe Ala Leu Cys Phe
        595                 600                 605

Gly Pro Thr Leu Ser Phe Gln Leu Leu Asp Pro His Met Lys Phe Arg
    610                 615                 620

Gln Leu Glu Ser Pro Asn Leu Arg Gln Leu Leu Ser Trp Ile Asp Leu
625                 630                 635                 640

Glu Phe Asn His Pro Gln Ile Phe Ile Val Glu Asn Gly Trp Phe Val
                645                 650                 655

Ser Gly Thr Thr Lys Arg Asp Asp Ala Lys Tyr Met Tyr Tyr Leu Lys
            660                 665                 670

Lys Phe Ile Met Glu Thr Leu Lys Ala Ile Lys Leu Asp Gly Val Asp
        675                 680                 685

Val Ile Gly Tyr Thr Ala Trp Ser Leu Met Asp Gly Phe Glu Trp His
    690                 695                 700
```

```
Arg Gly Tyr Ser Ile Arg Arg Gly Leu Phe Tyr Val Asp Phe Leu Ser
705                 710                 715                 720

Gln Asp Lys Met Leu Leu Pro Lys Ser Ser Ala Leu Phe Tyr Gln Lys
                725                 730                 735

Leu Ile Glu Lys Asn Gly Phe Pro Pro Leu Pro Glu Asn Gln Pro Leu
            740                 745                 750

Glu Gly Thr Phe Pro Cys Asp Phe Ala Trp Gly Val Val Asp Asn Tyr
        755                 760                 765

Ile Gln Val Asp Thr Thr Leu Ser Gln Phe Thr Asp Leu Asn Val Tyr
    770                 775                 780

Leu Trp Asp Val His His Ser Lys Arg Leu Ile Lys Val Asp Gly Val
785                 790                 795                 800

Val Thr Lys Lys Arg Lys Ser Tyr Cys Val Asp Phe Ala Ala Ile Gln
                805                 810                 815

Pro Gln Ile Ala Leu Leu Gln Glu Met His Val Thr His Phe Arg Phe
            820                 825                 830

Ser Leu Asp Trp Ala Leu Ile Leu Pro Leu Gly Asn Gln Ser Gln Val
        835                 840                 845

Asn His Thr Ile Leu Gln Tyr Tyr Arg Cys Met Ala Ser Glu Leu Val
    850                 855                 860

Arg Val Asn Ile Thr Pro Val Val Ala Leu Trp Gln Pro Met Ala Pro
865                 870                 875                 880

Asn Gln Gly Leu Pro Arg Leu Leu Ala Arg Gln Gly Ala Trp Glu Asn
                885                 890                 895

Pro Tyr Thr Ala Leu Ala Phe Ala Glu Tyr Ala Arg Leu Cys Phe Gln
            900                 905                 910

Glu Leu Gly His His Val Lys Leu Trp Ile Thr Met Asn Glu Pro Tyr
        915                 920                 925

Thr Arg Asn Met Thr Tyr Ser Ala Gly His Asn Leu Leu Lys Ala His
    930                 935                 940

Ala Leu Ala Trp His Val Tyr Asn Glu Lys Phe Arg His Ala Gln Asn
945                 950                 955                 960

Gly Lys Ile Ser Ile Ala Leu Gln Ala Asp Trp Ile Glu Pro Ala Cys
                965                 970                 975

Pro Phe Ser Gln Lys Asp Lys Glu Val Ala Glu Arg Val Leu Glu Phe
            980                 985                 990

Asp Ile Gly Trp Leu Ala Glu Pro  Ile Phe Gly Ser Gly  Asp Tyr Pro
        995                 1000                1005

Trp Val  Met Arg Asp Trp Leu  Asn Gln Arg Asn Asn  Phe Leu Leu
    1010                 1015                1020

Pro Tyr  Phe Thr Glu Asp Glu  Lys Lys Leu Ile Gln  Gly Thr Phe
    1025                 1030                1035

Asp Phe  Leu Ala Leu Ser His  Tyr Thr Thr Ile Leu  Val Asp Ser
    1040                 1045                1050

Glu Lys  Glu Asp Pro Ile Lys  Tyr Asn Asp Tyr Leu  Glu Val Gln
    1055                 1060                1065

Glu Met  Thr Asp Ile Thr Trp  Leu Asn Ser Pro Ser  Gln Val Ala
    1070                 1075                1080

Val Val  Pro Trp Gly Leu Arg  Lys Val Leu Asn Trp  Leu Lys Phe
    1085                 1090                1095

Lys Tyr  Gly Asp Leu Pro Met  Tyr Ile Ile Ser Asn  Gly Ile Asp
    1100                 1105                1110
```

```
Asp Gly  Leu His Ala Glu Asp  Asp Gln Leu Arg Val  Tyr Tyr Met
    1115                 1120                 1125

Gln Asn  Tyr Ile Asn Glu Ala  Leu Lys Ala His Ile  Leu Asp Gly
    1130                 1135                 1140

Ile Asn  Leu Cys Gly Tyr Phe  Ala Tyr Ser Phe Asn  Asp Arg Thr
    1145                 1150                 1155

Ala Pro  Arg Phe Gly Leu Tyr  Arg Tyr Ala Ala Asp  Gln Phe Glu
    1160                 1165                 1170

Pro Lys  Ala Ser Met Lys His  Tyr Arg Lys Ile Ile  Asp Ser Asn
    1175                 1180                 1185

Gly Phe  Pro Gly Pro Glu Thr  Leu Glu Arg Phe Cys  Pro Glu Glu
    1190                 1195                 1200

Phe Thr  Val Cys Thr Glu Cys  Ser Phe Phe His Thr  Arg Lys Ser
    1205                 1210                 1215

Leu
```

<210> SEQ ID NO 26
<211> LENGTH: 700
<212> TYPE: PRT
<213> ORGANISM: Artificial Sequence
<220> FEATURE:
<223> OTHER INFORMATION: Description of Artificial Sequence: Synthetic fusion polypeptide

<400> SEQUENCE: 26

```
Met Leu Gly Ala Arg Leu Arg Leu Trp Val Cys Ala Leu Cys Ser Val
1               5                   10                  15

Cys Ser Met Ser Val Leu Arg Ala Tyr Pro Asn Ala Ser Pro Leu Leu
            20                  25                  30

Gly Ser Ser Trp Gly Gly Leu Ile His Leu Tyr Thr Ala Thr Ala Arg
        35                  40                  45

Asn Ser Tyr His Leu Gln Ile His Lys Asn Gly His Val Asp Gly Ala
    50                  55                  60

Pro His Gln Thr Ile Tyr Ser Ala Leu Met Ile Arg Ser Glu Asp Ala
65                  70                  75                  80

Gly Phe Val Val Ile Thr Gly Val Met Ser Arg Arg Tyr Leu Cys Met
                85                  90                  95

Asp Phe Arg Gly Asn Ile Phe Gly Ser His Tyr Phe Asp Pro Glu Asn
            100                 105                 110

Cys Arg Phe Gln His Gln Thr Leu Glu Asn Gly Tyr Asp Val Tyr His
        115                 120                 125

Ser Pro Gln Tyr His Phe Leu Val Ser Leu Gly Arg Ala Lys Arg Ala
    130                 135                 140

Phe Leu Pro Gly Met Asn Pro Pro Pro Tyr Ser Gln Phe Leu Ser Arg
145                 150                 155                 160

Arg Asn Glu Ile Pro Leu Ile His Phe Asn Thr Pro Ile Pro Arg Arg
                165                 170                 175

His Thr Gln Ser Ala Glu Asp Asp Ser Glu Arg Asp Pro Leu Asn Val
            180                 185                 190

Leu Lys Pro Arg Ala Arg Met Thr Pro Ala Pro Ala Ser Cys Ser Gln
        195                 200                 205

Glu Leu Pro Ser Ala Glu Asp Asn Ser Pro Met Ala Ser Asp Pro Leu
    210                 215                 220

Gly Val Val Arg Gly Gly Arg Val Asn Thr His Ala Gly Gly Thr Gly
225                 230                 235                 240
```

```
Pro Glu Gly Cys Arg Pro Phe Ala Lys Phe Ile Gln Gly Thr Phe Pro
                245                 250                 255

Asp Gly Phe Leu Trp Ala Val Gly Ser Ala Ala Tyr Gln Thr Glu Gly
            260                 265                 270

Gly Trp Gln Gln His Gly Lys Gly Ala Ser Ile Trp Asp Thr Phe Thr
        275                 280                 285

His His Pro Leu Ala Pro Pro Gly Asp Ser Arg Asn Ala Ser Leu Pro
    290                 295                 300

Leu Gly Ala Pro Ser Pro Leu Gln Pro Ala Thr Gly Asp Val Ala Ser
305                 310                 315                 320

Asp Ser Tyr Asn Asn Val Phe Arg Asp Thr Glu Ala Leu Arg Glu Leu
                325                 330                 335

Gly Val Thr His Tyr Arg Phe Ser Ile Ser Trp Ala Arg Val Leu Pro
            340                 345                 350

Asn Gly Ser Ala Gly Val Pro Asn Arg Glu Gly Leu Arg Tyr Tyr Arg
        355                 360                 365

Arg Leu Leu Glu Arg Leu Arg Glu Leu Gly Val Gln Pro Val Val Thr
    370                 375                 380

Leu Tyr His Trp Asp Leu Pro Gln Arg Leu Gln Asp Ala Tyr Gly Gly
385                 390                 395                 400

Trp Ala Asn Arg Ala Leu Ala Asp His Phe Arg Asp Tyr Ala Glu Leu
                405                 410                 415

Cys Phe Arg His Phe Gly Gly Gln Val Lys Tyr Trp Ile Thr Ile Asp
            420                 425                 430

Asn Pro Tyr Val Val Ala Trp His Gly Tyr Ala Thr Gly Arg Leu Ala
        435                 440                 445

Pro Gly Ile Arg Gly Ser Pro Arg Leu Gly Tyr Leu Val Ala His Asn
    450                 455                 460

Leu Leu Leu Ala His Ala Lys Val Trp His Leu Tyr Asn Thr Ser Phe
465                 470                 475                 480

Arg Pro Thr Gln Gly Gly Gln Val Ser Ile Ala Leu Ser Ser His Trp
                485                 490                 495

Ile Asn Pro Arg Arg Met Thr Asp His Ser Ile Lys Glu Cys Gln Lys
            500                 505                 510

Ser Leu Asp Phe Val Leu Gly Trp Phe Ala Lys Pro Val Phe Ile Asp
        515                 520                 525

Gly Asp Tyr Pro Glu Ser Met Lys Asn Asn Leu Ser Ser Ile Leu Pro
    530                 535                 540

Asp Phe Thr Glu Ser Glu Lys Lys Phe Ile Lys Gly Thr Ala Asp Phe
545                 550                 555                 560

Phe Ala Leu Cys Phe Gly Pro Thr Leu Ser Phe Gln Leu Leu Asp Pro
                565                 570                 575

His Met Lys Phe Arg Gln Leu Glu Ser Pro Asn Leu Arg Gln Leu Leu
            580                 585                 590

Ser Trp Ile Asp Leu Glu Phe Asn His Pro Gln Ile Phe Ile Val Glu
        595                 600                 605

Asn Gly Trp Phe Val Ser Gly Thr Thr Lys Arg Asp Asp Ala Lys Tyr
    610                 615                 620

Met Tyr Tyr Leu Lys Lys Phe Ile Met Glu Thr Leu Lys Ala Ile Lys
625                 630                 635                 640

Leu Asp Gly Val Asp Val Ile Gly Tyr Thr Ala Trp Ser Leu Met Asp
                645                 650                 655

Gly Phe Glu Trp His Arg Gly Tyr Ser Ile Arg Arg Gly Leu Phe Tyr
```

```
            660                 665                 670

Val Asp Phe Leu Ser Gln Asp Lys Met Leu Leu Pro Lys Ser Ser Ala
        675                 680                 685

Leu Phe Tyr Gln Lys Leu Ile Glu Lys Asn Gly Phe
    690                 695                 700


<210> SEQ ID NO 27
<211> LENGTH: 688
<212> TYPE: PRT
<213> ORGANISM: Artificial Sequence
<220> FEATURE:
<223> OTHER INFORMATION: Description of Artificial Sequence: Synthetic
      fusion polypeptide

<400> SEQUENCE: 27

Met Leu Gly Ala Arg Leu Arg Leu Trp Val Cys Ala Leu Cys Ser Val
1               5                   10                  15

Cys Ser Met Ser Val Leu Arg Ala Tyr Pro Asn Ala Ser Pro Leu Leu
            20                  25                  30

Gly Ser Ser Trp Gly Gly Leu Ile His Leu Tyr Thr Ala Thr Ala Arg
        35                  40                  45

Asn Ser Tyr His Leu Gln Ile His Lys Asn Gly His Val Asp Gly Ala
    50                  55                  60

Pro His Gln Thr Ile Tyr Ser Ala Leu Met Ile Arg Ser Glu Asp Ala
65                  70                  75                  80

Gly Phe Val Val Ile Thr Gly Val Met Ser Arg Arg Tyr Leu Cys Met
                85                  90                  95

Asp Phe Arg Gly Asn Ile Phe Gly Ser His Tyr Phe Asp Pro Glu Asn
            100                 105                 110

Cys Arg Phe Gln His Gln Thr Leu Glu Asn Gly Tyr Asp Val Tyr His
        115                 120                 125

Ser Pro Gln Tyr His Phe Leu Val Ser Leu Gly Arg Ala Lys Arg Ala
    130                 135                 140

Phe Leu Pro Gly Met Asn Pro Pro Pro Tyr Ser Gln Phe Leu Ser Arg
145                 150                 155                 160

Arg Asn Glu Ile Pro Leu Ile His Phe Asn Thr Pro Ile Pro Arg Arg
                165                 170                 175

His Thr Gln Ser Ala Glu Asp Asp Ser Glu Arg Asp Pro Leu Asn Val
            180                 185                 190

Leu Lys Pro Arg Ala Arg Met Thr Pro Ala Pro Ala Ser Cys Ser Gln
        195                 200                 205

Glu Leu Pro Ser Ala Glu Asp Asn Ser Pro Met Ala Ser Asp Pro Leu
    210                 215                 220

Gly Val Val Arg Gly Gly Arg Val Asn Thr His Ala Gly Gly Thr Gly
225                 230                 235                 240

Pro Glu Gly Cys Arg Pro Phe Ala Lys Phe Ile Gly Thr Phe Pro Cys
                245                 250                 255

Asp Phe Ala Trp Gly Val Val Asp Asn Tyr Ile Gln Val Asp Thr Thr
            260                 265                 270

Leu Ser Gln Phe Thr Asp Leu Asn Val Tyr Leu Trp Asp Val His His
        275                 280                 285

Ser Lys Arg Leu Ile Lys Val Asp Gly Val Val Thr Lys Lys Arg Lys
    290                 295                 300

Ser Tyr Cys Val Asp Phe Ala Ala Ile Gln Pro Gln Ile Ala Leu Leu
305                 310                 315                 320
```

```
Gln Glu Met His Val Thr His Phe Arg Phe Ser Leu Asp Trp Ala Leu
                325                 330                 335

Ile Leu Pro Leu Gly Asn Gln Ser Gln Val Asn His Thr Ile Leu Gln
            340                 345                 350

Tyr Tyr Arg Cys Met Ala Ser Glu Leu Val Arg Val Asn Ile Thr Pro
        355                 360                 365

Val Val Ala Leu Trp Gln Pro Met Ala Pro Asn Gln Gly Leu Pro Arg
    370                 375                 380

Leu Leu Ala Arg Gln Gly Ala Trp Glu Asn Pro Tyr Thr Ala Leu Ala
385                 390                 395                 400

Phe Ala Glu Tyr Ala Arg Leu Cys Phe Gln Glu Leu Gly His His Val
                405                 410                 415

Lys Leu Trp Ile Thr Met Asn Glu Pro Tyr Thr Arg Asn Met Thr Tyr
            420                 425                 430

Ser Ala Gly His Asn Leu Leu Lys Ala His Ala Leu Ala Trp His Val
        435                 440                 445

Tyr Asn Glu Lys Phe Arg His Ala Gln Asn Gly Lys Ile Ser Ile Ala
    450                 455                 460

Leu Gln Ala Asp Trp Ile Glu Pro Ala Cys Pro Phe Ser Gln Lys Asp
465                 470                 475                 480

Lys Glu Val Ala Glu Arg Val Leu Glu Phe Asp Ile Gly Trp Leu Ala
                485                 490                 495

Glu Pro Ile Phe Gly Ser Gly Asp Tyr Pro Trp Val Met Arg Asp Trp
            500                 505                 510

Leu Asn Gln Arg Asn Asn Phe Leu Leu Pro Tyr Phe Thr Glu Asp Glu
        515                 520                 525

Lys Lys Leu Ile Gln Gly Thr Phe Asp Phe Leu Ala Leu Ser His Tyr
    530                 535                 540

Thr Thr Ile Leu Val Asp Ser Glu Lys Glu Asp Pro Ile Lys Tyr Asn
545                 550                 555                 560

Asp Tyr Leu Glu Val Gln Glu Met Thr Asp Ile Thr Trp Leu Asn Ser
                565                 570                 575

Pro Ser Gln Val Ala Val Val Pro Trp Gly Leu Arg Lys Val Leu Asn
            580                 585                 590

Trp Leu Lys Phe Lys Tyr Gly Asp Leu Pro Met Tyr Ile Ile Ser Asn
        595                 600                 605

Gly Ile Asp Asp Gly Leu His Ala Glu Asp Asp Gln Leu Arg Val Tyr
    610                 615                 620

Tyr Met Gln Asn Tyr Ile Asn Glu Ala Leu Lys Ala His Ile Leu Asp
625                 630                 635                 640

Gly Ile Asn Leu Cys Gly Tyr Phe Ala Tyr Ser Phe Asn Asp Arg Thr
                645                 650                 655

Ala Pro Arg Phe Gly Leu Tyr Arg Tyr Ala Ala Asp Gln Phe Glu Pro
            660                 665                 670

Lys Ala Ser Met Lys His Tyr Arg Lys Ile Ile Asp Ser Asn Gly Phe
        675                 680                 685
```

<210> SEQ ID NO 28
<211> LENGTH: 1149
<212> TYPE: PRT
<213> ORGANISM: Artificial Sequence
<220> FEATURE:
<223> OTHER INFORMATION: Description of Artificial Sequence: Synthetic fusion polypeptide

<400> SEQUENCE: 28

```
Met Leu Gly Ala Arg Leu Arg Leu Trp Val Cys Ala Leu Cys Ser Val
1               5                   10                  15

Cys Ser Met Ser Val Leu Arg Ala Tyr Pro Asn Ala Ser Pro Leu Leu
            20                  25                  30

Gly Ser Ser Trp Gly Gly Leu Ile His Leu Tyr Thr Ala Thr Ala Arg
        35                  40                  45

Asn Ser Tyr His Leu Gln Ile His Lys Asn Gly His Val Asp Gly Ala
    50                  55                  60

Pro His Gln Thr Ile Tyr Ser Ala Leu Met Ile Arg Ser Glu Asp Ala
65                  70                  75                  80

Gly Phe Val Val Ile Thr Gly Val Met Ser Arg Arg Tyr Leu Cys Met
                85                  90                  95

Asp Phe Arg Gly Asn Ile Phe Gly Ser His Tyr Phe Asp Pro Glu Asn
            100                 105                 110

Cys Arg Phe Gln His Gln Thr Leu Glu Asn Gly Tyr Asp Val Tyr His
        115                 120                 125

Ser Pro Gln Tyr His Phe Leu Val Ser Leu Gly Arg Ala Lys Arg Ala
    130                 135                 140

Phe Leu Pro Gly Met Asn Pro Pro Pro Tyr Ser Gln Phe Leu Ser Arg
145                 150                 155                 160

Arg Asn Glu Ile Pro Leu Ile His Phe Asn Thr Pro Ile Pro Arg Arg
                165                 170                 175

His Thr Gln Ser Ala Glu Asp Asp Ser Glu Arg Asp Pro Leu Asn Val
            180                 185                 190

Leu Lys Pro Arg Ala Arg Met Thr Pro Ala Pro Ala Ser Cys Ser Gln
        195                 200                 205

Glu Leu Pro Ser Ala Glu Asp Asn Ser Pro Met Ala Ser Asp Pro Leu
    210                 215                 220

Gly Val Val Arg Gly Gly Arg Val Asn Thr His Ala Gly Gly Thr Gly
225                 230                 235                 240

Pro Glu Gly Cys Arg Pro Phe Ala Lys Phe Ile Gln Gly Thr Phe Pro
                245                 250                 255

Asp Gly Phe Leu Trp Ala Val Gly Ser Ala Ala Tyr Gln Thr Glu Gly
            260                 265                 270

Gly Trp Gln Gln His Gly Lys Gly Ala Ser Ile Trp Asp Thr Phe Thr
        275                 280                 285

His His Pro Leu Ala Pro Pro Gly Asp Ser Arg Asn Ala Ser Leu Pro
    290                 295                 300

Leu Gly Ala Pro Ser Pro Leu Gln Pro Ala Thr Gly Asp Val Ala Ser
305                 310                 315                 320

Asp Ser Tyr Asn Asn Val Phe Arg Asp Thr Glu Ala Leu Arg Glu Leu
                325                 330                 335

Gly Val Thr His Tyr Arg Phe Ser Ile Ser Trp Ala Arg Val Leu Pro
            340                 345                 350

Asn Gly Ser Ala Gly Val Pro Asn Arg Glu Gly Leu Arg Tyr Tyr Arg
        355                 360                 365

Arg Leu Leu Glu Arg Leu Arg Glu Leu Gly Val Gln Pro Val Val Thr
    370                 375                 380

Leu Tyr His Trp Asp Leu Pro Gln Arg Leu Gln Asp Ala Tyr Gly Gly
385                 390                 395                 400

Trp Ala Asn Arg Ala Leu Ala Asp His Phe Arg Asp Tyr Ala Glu Leu
                405                 410                 415
```

```
Cys Phe Arg His Phe Gly Gly Gln Val Lys Tyr Trp Ile Thr Ile Asp
            420                 425                 430

Asn Pro Tyr Val Val Ala Trp His Gly Tyr Ala Thr Gly Arg Leu Ala
        435                 440                 445

Pro Gly Ile Arg Gly Ser Pro Arg Leu Gly Tyr Leu Val Ala His Asn
    450                 455                 460

Leu Leu Leu Ala His Ala Lys Val Trp His Leu Tyr Asn Thr Ser Phe
465                 470                 475                 480

Arg Pro Thr Gln Gly Gly Gln Val Ser Ile Ala Leu Ser Ser His Trp
                485                 490                 495

Ile Asn Pro Arg Arg Met Thr Asp His Ser Ile Lys Glu Cys Gln Lys
            500                 505                 510

Ser Leu Asp Phe Val Leu Gly Trp Phe Ala Lys Pro Val Phe Ile Asp
        515                 520                 525

Gly Asp Tyr Pro Glu Ser Met Lys Asn Asn Leu Ser Ser Ile Leu Pro
    530                 535                 540

Asp Phe Thr Glu Ser Glu Lys Lys Phe Ile Lys Gly Thr Ala Asp Phe
545                 550                 555                 560

Phe Ala Leu Cys Phe Gly Pro Thr Leu Ser Phe Gln Leu Leu Asp Pro
                565                 570                 575

His Met Lys Phe Arg Gln Leu Glu Ser Pro Asn Leu Arg Gln Leu Leu
            580                 585                 590

Ser Trp Ile Asp Leu Glu Phe Asn His Pro Gln Ile Phe Ile Val Glu
        595                 600                 605

Asn Gly Trp Phe Val Ser Gly Thr Thr Lys Arg Asp Asp Ala Lys Tyr
    610                 615                 620

Met Tyr Tyr Leu Lys Lys Phe Ile Met Glu Thr Leu Lys Ala Ile Lys
625                 630                 635                 640

Leu Asp Gly Val Asp Val Ile Gly Tyr Thr Ala Trp Ser Leu Met Asp
                645                 650                 655

Gly Phe Glu Trp His Arg Gly Tyr Ser Ile Arg Arg Gly Leu Phe Tyr
            660                 665                 670

Val Asp Phe Leu Ser Gln Asp Lys Met Leu Leu Pro Lys Ser Ser Ala
        675                 680                 685

Leu Phe Tyr Gln Lys Leu Ile Glu Lys Asn Gly Phe Gln Gly Thr Phe
    690                 695                 700

Pro Asp Gly Phe Leu Trp Ala Val Gly Ser Ala Ala Tyr Gln Thr Glu
705                 710                 715                 720

Gly Gly Trp Gln Gln His Gly Lys Gly Ala Ser Ile Trp Asp Thr Phe
                725                 730                 735

Thr His His Pro Leu Ala Pro Pro Gly Asp Ser Arg Asn Ala Ser Leu
            740                 745                 750

Pro Leu Gly Ala Pro Ser Pro Leu Gln Pro Ala Thr Gly Asp Val Ala
        755                 760                 765

Ser Asp Ser Tyr Asn Asn Val Phe Arg Asp Thr Glu Ala Leu Arg Glu
    770                 775                 780

Leu Gly Val Thr His Tyr Arg Phe Ser Ile Ser Trp Ala Arg Val Leu
785                 790                 795                 800

Pro Asn Gly Ser Ala Gly Val Pro Asn Arg Glu Gly Leu Arg Tyr Tyr
                805                 810                 815

Arg Arg Leu Leu Glu Arg Leu Arg Glu Leu Gly Val Gln Pro Val Val
            820                 825                 830

Thr Leu Tyr His Trp Asp Leu Pro Gln Arg Leu Gln Asp Ala Tyr Gly
```

```
        835                 840                 845

Gly Trp Ala Asn Arg Ala Leu Ala Asp His Phe Arg Asp Tyr Ala Glu
    850                 855                 860

Leu Cys Phe Arg His Phe Gly Gly Gln Val Lys Tyr Trp Ile Thr Ile
865                 870                 875                 880

Asp Asn Pro Tyr Val Val Ala Trp His Gly Tyr Ala Thr Gly Arg Leu
                885                 890                 895

Ala Pro Gly Ile Arg Gly Ser Pro Arg Leu Gly Tyr Leu Val Ala His
            900                 905                 910

Asn Leu Leu Leu Ala His Ala Lys Val Trp His Leu Tyr Asn Thr Ser
        915                 920                 925

Phe Arg Pro Thr Gln Gly Gly Gln Val Ser Ile Ala Leu Ser Ser His
    930                 935                 940

Trp Ile Asn Pro Arg Arg Met Thr Asp His Ser Ile Lys Glu Cys Gln
945                 950                 955                 960

Lys Ser Leu Asp Phe Val Leu Gly Trp Phe Ala Lys Pro Val Phe Ile
                965                 970                 975

Asp Gly Asp Tyr Pro Glu Ser Met Lys Asn Asn Leu Ser Ser Ile Leu
            980                 985                 990

Pro Asp Phe Thr Glu Ser Glu Lys  Lys Phe Ile Lys Gly  Thr Ala Asp
        995                 1000                1005

Phe Phe  Ala Leu Cys Phe Gly  Pro Thr Leu Ser Phe  Gln Leu Leu
    1010                1015                1020

Asp Pro  His Met Lys Phe Arg  Gln Leu Glu Ser Pro  Asn Leu Arg
    1025                1030                1035

Gln Leu  Leu Ser Trp Ile Asp  Leu Glu Phe Asn His  Pro Gln Ile
    1040                1045                1050

Phe Ile  Val Glu Asn Gly Trp  Phe Val Ser Gly Thr  Thr Lys Arg
    1055                1060                1065

Asp Asp  Ala Lys Tyr Met Tyr  Tyr Leu Lys Lys Phe  Ile Met Glu
    1070                1075                1080

Thr Leu  Lys Ala Ile Lys Leu  Asp Gly Val Asp Val  Ile Gly Tyr
    1085                1090                1095

Thr Ala  Trp Ser Leu Met Asp  Gly Phe Glu Trp His  Arg Gly Tyr
    1100                1105                1110

Ser Ile  Arg Arg Gly Leu Phe  Tyr Val Asp Phe Leu  Ser Gln Asp
    1115                1120                1125

Lys Met  Leu Leu Pro Lys Ser  Ser Ala Leu Phe Tyr  Gln Lys Leu
    1130                1135                1140

Ile Glu  Lys Asn Gly Phe
    1145


<210> SEQ ID NO 29
<211> LENGTH: 1125
<212> TYPE: PRT
<213> ORGANISM: Artificial Sequence
<220> FEATURE:
<223> OTHER INFORMATION: Description of Artificial Sequence: Synthetic
      fusion polypeptide

<400> SEQUENCE: 29

Met Leu Gly Ala Arg Leu Arg Leu Trp Val Cys Ala Leu Cys Ser Val
1               5                   10                  15

Cys Ser Met Ser Val Leu Arg Ala Tyr Pro Asn Ala Ser Pro Leu Leu
            20                  25                  30
```

```
Gly Ser Ser Trp Gly Gly Leu Ile His Leu Tyr Thr Ala Thr Ala Arg
        35                  40                  45

Asn Ser Tyr His Leu Gln Ile His Lys Asn Gly His Val Asp Gly Ala
    50                  55                  60

Pro His Gln Thr Ile Tyr Ser Ala Leu Met Ile Arg Ser Glu Asp Ala
65                  70                  75                  80

Gly Phe Val Val Ile Thr Gly Val Met Ser Arg Arg Tyr Leu Cys Met
                85                  90                  95

Asp Phe Arg Gly Asn Ile Phe Gly Ser His Tyr Phe Asp Pro Glu Asn
            100                 105                 110

Cys Arg Phe Gln His Gln Thr Leu Glu Asn Gly Tyr Asp Val Tyr His
        115                 120                 125

Ser Pro Gln Tyr His Phe Leu Val Ser Leu Gly Arg Ala Lys Arg Ala
    130                 135                 140

Phe Leu Pro Gly Met Asn Pro Pro Pro Tyr Ser Gln Phe Leu Ser Arg
145                 150                 155                 160

Arg Asn Glu Ile Pro Leu Ile His Phe Asn Thr Pro Ile Pro Arg Arg
                165                 170                 175

His Thr Gln Ser Ala Glu Asp Asp Ser Glu Arg Asp Pro Leu Asn Val
            180                 185                 190

Leu Lys Pro Arg Ala Arg Met Thr Pro Ala Pro Ala Ser Cys Ser Gln
        195                 200                 205

Glu Leu Pro Ser Ala Glu Asp Asn Ser Pro Met Ala Ser Asp Pro Leu
    210                 215                 220

Gly Val Val Arg Gly Gly Arg Val Asn Thr His Ala Gly Gly Thr Gly
225                 230                 235                 240

Pro Glu Gly Cys Arg Pro Phe Ala Lys Phe Ile Gly Thr Phe Pro Cys
                245                 250                 255

Asp Phe Ala Trp Gly Val Val Asp Asn Tyr Ile Gln Val Asp Thr Thr
            260                 265                 270

Leu Ser Gln Phe Thr Asp Leu Asn Val Tyr Leu Trp Asp Val His His
        275                 280                 285

Ser Lys Arg Leu Ile Lys Val Asp Gly Val Val Thr Lys Lys Arg Lys
    290                 295                 300

Ser Tyr Cys Val Asp Phe Ala Ala Ile Gln Pro Gln Ile Ala Leu Leu
305                 310                 315                 320

Gln Glu Met His Val Thr His Phe Arg Phe Ser Leu Asp Trp Ala Leu
                325                 330                 335

Ile Leu Pro Leu Gly Asn Gln Ser Gln Val Asn His Thr Ile Leu Gln
            340                 345                 350

Tyr Tyr Arg Cys Met Ala Ser Glu Leu Val Arg Val Asn Ile Thr Pro
        355                 360                 365

Val Val Ala Leu Trp Gln Pro Met Ala Pro Asn Gln Gly Leu Pro Arg
    370                 375                 380

Leu Leu Ala Arg Gln Gly Ala Trp Glu Asn Pro Tyr Thr Ala Leu Ala
385                 390                 395                 400

Phe Ala Glu Tyr Ala Arg Leu Cys Phe Gln Glu Leu Gly His His Val
                405                 410                 415

Lys Leu Trp Ile Thr Met Asn Glu Pro Tyr Thr Arg Asn Met Thr Tyr
            420                 425                 430

Ser Ala Gly His Asn Leu Leu Lys Ala His Ala Leu Ala Trp His Val
        435                 440                 445

Tyr Asn Glu Lys Phe Arg His Ala Gln Asn Gly Lys Ile Ser Ile Ala
```

```
    450                 455                 460

Leu Gln Ala Asp Trp Ile Glu Pro Ala Cys Pro Phe Ser Gln Lys Asp
465                 470                 475                 480

Lys Glu Val Ala Glu Arg Val Leu Glu Phe Asp Ile Gly Trp Leu Ala
                485                 490                 495

Glu Pro Ile Phe Gly Ser Gly Asp Tyr Pro Trp Val Met Arg Asp Trp
            500                 505                 510

Leu Asn Gln Arg Asn Asn Phe Leu Leu Pro Tyr Phe Thr Glu Asp Glu
        515                 520                 525

Lys Lys Leu Ile Gln Gly Thr Phe Asp Phe Leu Ala Leu Ser His Tyr
    530                 535                 540

Thr Thr Ile Leu Val Asp Ser Glu Lys Glu Asp Pro Ile Lys Tyr Asn
545                 550                 555                 560

Asp Tyr Leu Glu Val Gln Glu Met Thr Asp Ile Thr Trp Leu Asn Ser
                565                 570                 575

Pro Ser Gln Val Ala Val Val Pro Trp Gly Leu Arg Lys Val Leu Asn
            580                 585                 590

Trp Leu Lys Phe Lys Tyr Gly Asp Leu Pro Met Tyr Ile Ile Ser Asn
        595                 600                 605

Gly Ile Asp Asp Gly Leu His Ala Glu Asp Asp Gln Leu Arg Val Tyr
    610                 615                 620

Tyr Met Gln Asn Tyr Ile Asn Glu Ala Leu Lys Ala His Ile Leu Asp
625                 630                 635                 640

Gly Ile Asn Leu Cys Gly Tyr Phe Ala Tyr Ser Phe Asn Asp Arg Thr
                645                 650                 655

Ala Pro Arg Phe Gly Leu Tyr Arg Tyr Ala Ala Asp Gln Phe Glu Pro
            660                 665                 670

Lys Ala Ser Met Lys His Tyr Arg Lys Ile Ile Asp Ser Asn Gly Phe
        675                 680                 685

Gly Thr Phe Pro Cys Asp Phe Ala Trp Gly Val Val Asp Asn Tyr Ile
    690                 695                 700

Gln Val Asp Thr Thr Leu Ser Gln Phe Thr Asp Leu Asn Val Tyr Leu
705                 710                 715                 720

Trp Asp Val His His Ser Lys Arg Leu Ile Lys Val Asp Gly Val Val
                725                 730                 735

Thr Lys Lys Arg Lys Ser Tyr Cys Val Asp Phe Ala Ala Ile Gln Pro
            740                 745                 750

Gln Ile Ala Leu Leu Gln Glu Met His Val Thr His Phe Arg Phe Ser
        755                 760                 765

Leu Asp Trp Ala Leu Ile Leu Pro Leu Gly Asn Gln Ser Gln Val Asn
    770                 775                 780

His Thr Ile Leu Gln Tyr Tyr Arg Cys Met Ala Ser Glu Leu Val Arg
785                 790                 795                 800

Val Asn Ile Thr Pro Val Val Ala Leu Trp Gln Pro Met Ala Pro Asn
                805                 810                 815

Gln Gly Leu Pro Arg Leu Leu Ala Arg Gln Gly Ala Trp Glu Asn Pro
            820                 825                 830

Tyr Thr Ala Leu Ala Phe Ala Glu Tyr Ala Arg Leu Cys Phe Gln Glu
        835                 840                 845

Leu Gly His His Val Lys Leu Trp Ile Thr Met Asn Glu Pro Tyr Thr
    850                 855                 860

Arg Asn Met Thr Tyr Ser Ala Gly His Asn Leu Leu Lys Ala His Ala
865                 870                 875                 880
```

```
Leu Ala Trp His Val Tyr Asn Glu Lys Phe Arg His Ala Gln Asn Gly
                885                 890                 895

Lys Ile Ser Ile Ala Leu Gln Ala Asp Trp Ile Glu Pro Ala Cys Pro
            900                 905                 910

Phe Ser Gln Lys Asp Lys Glu Val Ala Glu Arg Val Leu Glu Phe Asp
        915                 920                 925

Ile Gly Trp Leu Ala Glu Pro Ile Phe Gly Ser Gly Asp Tyr Pro Trp
    930                 935                 940

Val Met Arg Asp Trp Leu Asn Gln Arg Asn Asn Phe Leu Leu Pro Tyr
945                 950                 955                 960

Phe Thr Glu Asp Glu Lys Lys Leu Ile Gln Gly Thr Phe Asp Phe Leu
                965                 970                 975

Ala Leu Ser His Tyr Thr Thr Ile Leu Val Asp Ser Glu Lys Glu Asp
            980                 985                 990

Pro Ile Lys Tyr Asn Asp Tyr Leu  Glu Val Gln Glu Met  Thr Asp Ile
        995                 1000                1005

Thr Trp  Leu Asn Ser Pro Ser  Gln Val Ala Val Val  Pro Trp Gly
    1010                 1015                 1020

Leu Arg  Lys Val Leu Asn Trp  Leu Lys Phe Lys Tyr  Gly Asp Leu
    1025                 1030                 1035

Pro Met  Tyr Ile Ile Ser Asn  Gly Ile Asp Asp Gly  Leu His Ala
    1040                 1045                 1050

Glu Asp  Asp Gln Leu Arg Val  Tyr Tyr Met Gln Asn  Tyr Ile Asn
    1055                 1060                 1065

Glu Ala  Leu Lys Ala His Ile  Leu Asp Gly Ile Asn  Leu Cys Gly
    1070                 1075                 1080

Tyr Phe  Ala Tyr Ser Phe Asn  Asp Arg Thr Ala Pro  Arg Phe Gly
    1085                 1090                 1095

Leu Tyr  Arg Tyr Ala Ala Asp  Gln Phe Glu Pro Lys  Ala Ser Met
    1100                 1105                 1110

Lys His  Tyr Arg Lys Ile Ile  Asp Ser Asn Gly Phe
    1115                 1120                 1125
```

<210> SEQ ID NO 30
<211> LENGTH: 2157
<212> TYPE: DNA
<213> ORGANISM: Homo sapiens

<400> SEQUENCE: 30

```
gctcccagcc aagaacctcg gggccgctgc gcggtgggga ggagttcccc gaaacccggc     60

cgctaagcga ggcctcctcc tcccgcagat ccgaacggcc tgggcggggt caccccggct    120

gggacaagaa gccgccgcct gcctgcccgg gcccggggag ggggctgggg ctggggccgg    180

aggcggggtg tgagtgggtg tgtgcggggg gcggaggctt gatgcaatcc cgataagaaa    240

tgctcgggtg tcttgggcac ctacccgtgg ggcccgtaag gcgctactat ataaggctgc    300

cggcccggag ccgccgcgcc gtcagagcag gagcgctgcg tccaggatct agggccacga    360

ccatcccaac ccggcactca cagccccgca gcgcatcccg gtcgccgccc agcctcccgc    420

acccccatcg ccggagctgc gccgagagcc ccagggaggt gccatgcgga gcgggtgtgt    480

ggtggtccac gtatggatcc tggccggcct ctggctggcc gtggccgggc gccccctcgc    540

cttctcggac gcggggcccc acgtgcacta cggctggggc gaccccatcc gcctgcggca    600

cctgtacacc tccggccccc acgggctctc cagctgcttc ctgcgcatcc gtgccgacgg    660
```

-continued

```
cgtcgtggac tgcgcgcggg gccagagcgc gcacagtttg ctggagatca aggcagtcgc     720

tctgcggacc gtggccatca agggcgtgca cagcgtgcgg tacctctgca tgggcgccga     780

cggcaagatg caggggctgc ttcagtactc ggaggaagac tgtgctttcg aggaggagat     840

ccgcccagat ggctacaatg tgtaccgatc cgagaagcac cgcctcccgg tctccctgag     900

cagtgccaaa cagcggcagc tgtacaagaa cagaggcttt cttccactct ctcatttcct     960

gcccatgctg cccatggtcc cagaggagcc tgaggacctc aggggccact tggaatctga    1020

catgttctct tcgcccctgg agaccgacag catggaccca tttgggcttg tcaccggact    1080

ggaggccgtg aggagtccca gctttgagaa gtaactgaga ccatgcccgg gcctcttcac    1140

tgctgccagg ggctgtggta cctgcagcgt gggggacgtg cttctacaag aacagtcctg    1200

agtccacgtt ctgtttagct ttaggaagaa acatctagaa gttgtacata ttcagagttt    1260

tccattggca gtgccagttt ctagccaata gacttgtctg atcataacat tgtaagcctg    1320

tagcttgccc agctgctgcc tgggccccca ttctgctccc tcgaggttgc tggacaagct    1380

gctgcactgt ctcagttctg cttgaatacc tccatcgatg gggaactcac ttcctttgga    1440

aaaattctta tgtcaagctg aaattctcta atttttctc atcacttccc caggagcagc    1500

cagaagacag gcagtagttt taatttcagg aacaggtgat ccactctgta aaacagcagg    1560

taaatttcac tcaaccccat gtgggaattg atctatatct ctacttccag ggaccatttg    1620

cccttcccaa atccctccag gccagaactg actggagcag gcatggccca ccaggcttca    1680

ggagtagggg aagcctggag ccccactcca gccctgggac aacttgagaa ttcccccctga    1740

ggccagttct gtcatggatg ctgtcctgag aataacttgc tgtcccggtg tcacctgctt    1800

ccatctccca gcccaccagc cctctgccca cctcacatgc ctccccatgg attggggcct    1860

cccaggcccc ccaccttatg tcaacctgca cttcttgttc aaaaatcagg aaaagaaaag    1920

atttgaagac cccaagtctt gtcaataact tgctgtgtgg aagcagcggg ggaagaccta    1980

gaaccctttc cccagcactt ggttttccaa catgatattt atgagtaatt tattttgata    2040

tgtacatctc ttattttctt acattattta tgcccccaaa ttatatttat gtatgtaagt    2100

gaggtttgtt ttgtatatta aaatggagtt tgtttgtaaa aaaaaaaaaa aaaaaaa       2157
```

```
<210> SEQ ID NO 31
<211> LENGTH: 216
<212> TYPE: PRT
<213> ORGANISM: Homo sapiens

<400> SEQUENCE: 31

Met Arg Ser Gly Cys Val Val Val His Val Trp Ile Leu Ala Gly Leu
1               5                   10                  15

Trp Leu Ala Val Ala Gly Arg Pro Leu Ala Phe Ser Asp Ala Gly Pro
            20                  25                  30

His Val His Tyr Gly Trp Gly Asp Pro Ile Arg Leu Arg His Leu Tyr
        35                  40                  45

Thr Ser Gly Pro His Gly Leu Ser Ser Cys Phe Leu Arg Ile Arg Ala
    50                  55                  60

Asp Gly Val Val Asp Cys Ala Arg Gly Gln Ser Ala His Ser Leu Leu
65                  70                  75                  80

Glu Ile Lys Ala Val Ala Leu Arg Thr Val Ala Ile Lys Gly Val His
                85                  90                  95

Ser Val Arg Tyr Leu Cys Met Gly Ala Asp Gly Lys Met Gln Gly Leu
            100                 105                 110
```

```
Leu Gln Tyr Ser Glu Glu Asp Cys Ala Phe Glu Glu Glu Ile Arg Pro
        115                 120                 125

Asp Gly Tyr Asn Val Tyr Arg Ser Glu Lys His Arg Leu Pro Val Ser
    130                 135                 140

Leu Ser Ser Ala Lys Gln Arg Gln Leu Tyr Lys Asn Arg Gly Phe Leu
145                 150                 155                 160

Pro Leu Ser His Phe Leu Pro Met Leu Pro Met Val Pro Glu Glu Pro
                165                 170                 175

Glu Asp Leu Arg Gly His Leu Glu Ser Asp Met Phe Ser Ser Pro Leu
            180                 185                 190

Glu Thr Asp Ser Met Asp Pro Phe Gly Leu Val Thr Gly Leu Glu Ala
        195                 200                 205

Val Arg Ser Pro Ser Phe Glu Lys
    210                 215


<210> SEQ ID NO 32
<211> LENGTH: 940
<212> TYPE: DNA
<213> ORGANISM: Homo sapiens

<400> SEQUENCE: 32

ctgtcagctg aggatccagc cgaaagagga gccaggcact caggccacct gagtctactc      60

acctggacaa ctggaatctg gcaccaattc taaaccactc agcttctccg agctcacacc     120

ccggagatca cctgaggacc cgagccattg atggactcgg acgagaccgg gttcgagcac     180

tcaggactgt gggtttctgt gctggctggt cttctgctgg gagcctgcca ggcacacccc     240

atccctgact ccagtcctct cctgcaattc gggggccaag tccggcagcg gtacctctac     300

acagatgatg cccagcagac agaagcccac ctggagatca gggaggatgg gacggtgggg     360

ggcgctgctg accagagccc cgaaagtctc ctgcagctga aagccttgaa gccgggagtt     420

attcaaatct tgggagtcaa gacatccagg ttcctgtgcc agcggccaga tggggccctg     480

tatggatcgc tccactttga ccctgaggcc tgcagcttcc gggagctgct tcttgaggac     540

ggatacaatg tttaccagtc cgaagcccac ggcctcccgc tgcacctgcc agggaacaag     600

tccccacacc gggaccctgc accccgagga ccagctcgct tcctgccact accaggcctg     660

ccccccgcac tcccggagcc acccggaatc ctggcccccc agccccccga tgtgggctcc     720

tcggaccctc tgagcatggt gggaccttcc cagggccgaa gccccagcta cgcttcctga     780

agccagaggc tgtttactat gacatctcct ctttatttat taggttattt atcttattta     840

ttttttattt tttcttactt gagataataa agagttccag aggagaaaaa aaaaaaaaaa     900

aaaaaaaaaa aaaaaaaaaa aaaaaaaaaa aaaaaaaaaa                           940


<210> SEQ ID NO 33
<211> LENGTH: 209
<212> TYPE: PRT
<213> ORGANISM: Homo sapiens

<400> SEQUENCE: 33

Met Asp Ser Asp Glu Thr Gly Phe Glu His Ser Gly Leu Trp Val Ser
1               5                   10                  15

Val Leu Ala Gly Leu Leu Leu Gly Ala Cys Gln Ala His Pro Ile Pro
            20                  25                  30

Asp Ser Ser Pro Leu Leu Gln Phe Gly Gly Gln Val Arg Gln Arg Tyr
        35                  40                  45

Leu Tyr Thr Asp Asp Ala Gln Gln Thr Glu Ala His Leu Glu Ile Arg
```

```
    50                  55                  60

Glu Asp Gly Thr Val Gly Gly Ala Ala Asp Gln Ser Pro Glu Ser Leu
65                  70                  75                  80

Leu Gln Leu Lys Ala Leu Lys Pro Gly Val Ile Gln Ile Leu Gly Val
                85                  90                  95

Lys Thr Ser Arg Phe Leu Cys Gln Arg Pro Asp Gly Ala Leu Tyr Gly
            100                 105                 110

Ser Leu His Phe Asp Pro Glu Ala Cys Ser Phe Arg Glu Leu Leu Leu
        115                 120                 125

Glu Asp Gly Tyr Asn Val Tyr Gln Ser Glu Ala His Gly Leu Pro Leu
    130                 135                 140

His Leu Pro Gly Asn Lys Ser Pro His Arg Asp Pro Ala Pro Arg Gly
145                 150                 155                 160

Pro Ala Arg Phe Leu Pro Leu Pro Gly Leu Pro Pro Ala Leu Pro Glu
                165                 170                 175

Pro Pro Gly Ile Leu Ala Pro Gln Pro Pro Asp Val Gly Ser Ser Asp
            180                 185                 190

Pro Leu Ser Met Val Gly Pro Ser Gln Gly Arg Ser Pro Ser Tyr Ala
        195                 200                 205

Ser


<210> SEQ ID NO 34
<211> LENGTH: 3018
<212> TYPE: DNA
<213> ORGANISM: Homo sapiens

<400> SEQUENCE: 34

cggcaaaaag gagggaatcc agtctaggat cctcacacca gctacttgca agggagaagg     60

aaaaggccag taaggcctgg gccaggagag tcccgacagg agtgtcaggt ttcaatctca    120

gcaccagcca ctcagagcag ggcacgatgt tgggggcccg cctcaggctc tgggtctgtg    180

ccttgtgcag cgtctgcagc atgagcgtcc tcagagccta tcccaatgcc tccccactgc    240

tcggctccag ctggggtggc ctgatccacc tgtacacagc cacagccagg aacagctacc    300

acctgcagat ccacaagaat ggccatgtgg atggcgcacc ccatcagacc atctacagtg    360

ccctgatgat cagatcagag gatgctggct ttgtggtgat tacaggtgtg atgagcagaa    420

gatacctctg catggatttc agaggcaaca tttttggatc acactatttc gacccggaga    480

actgcaggtt ccaacaccag acgctggaaa acgggtacga cgtctaccac tctcctcagt    540

atcacttcct ggtcagtctg ggccgggcga agagagcctt cctgccaggc atgaacccac    600

ccccgtactc ccagttcctg tcccggagga acgagatccc cctaattcac ttcaacaccc    660

ccataccacg gcggcacacc cggagcgccg aggacgactc ggagcgggac cccctgaacg    720

tgctgaagcc ccgggcccgg atgaccccgg ccccggcctc ctgttcacag gagctcccga    780

gcgccgagga caacagcccg atggccagtg acccattagg ggtggtcagg ggcggtcgag    840

tgaacacgca cgctggggga acgggcccgg aaggctgccg ccccttcgcc aagttcatct    900

agggtcgctg gaagggcacc ctctttaacc catccctcag caaacgcagc tcttcccaag    960

gaccaggtcc cttgacgttc cgaggatggg aaaggtgaca ggggcatgta tggaatttgc   1020

tgcttctctg gggtcccttc cacaggaggt cctgtgagaa ccaacctttg aggcccaagt   1080

catggggttt caccgccttc ctcactccat atagaacacc tttcccaata ggaaacccca   1140

acaggtaaac tagaaatttc cccttcatga aggtagagag aaggggtctc tcccaacata   1200
```

```
tttctcttcc ttgtgcctct cctctttatc acttttaagc ataaaaaaaa aaaaaaaaaa   1260

aaaaaaaaaa aaaagcagtg ggttcctgag ctcaagactt tgaaggtgta gggaagagga   1320

aatcggagat cccagaagct tctccactgc cctatgcatt tatgttagat gccccgatcc   1380

cactggcatt tgagtgtgca aaccttgaca ttaacagctg aatggggcaa gttgatgaaa   1440

acactacttt caagccttcg ttcttccttg agcatctctg ggaagagct gtcaaaagac   1500

tggtggtagg ctggtgaaaa cttgacagct agacttgatg cttgctgaaa tgaggcagga   1560

atcataatag aaaactcagc ctccctacag ggtgagcacc ttctgtctcg ctgtctccct   1620

ctgtgcagcc acagccagag ggcccagaat ggccccactc tgttcccaag cagttcatga   1680

tacagcctca ccttttggcc ccatctctgg tttttgaaaa tttggtctaa ggaataaata   1740

gcttttacac tggctcacga aaatctgccc tgctagaatt tgcttttcaa aatggaaata   1800

aattccaact ctcctaagag gcatttaatt aaggctctac ttccaggttg agtaggaatc   1860

cattctgaac aaactacaaa aatgtgactg ggaagggggc tttgagagac tgggactgct   1920

ctgggttagg ttttctgtgg actgaaaaat cgtgtccttt tctctaaatg aagtggcatc   1980

aaggactcag gggaaagaa atcaggggac atgttataga agttatgaaa agacaaccac   2040

atggtcaggc tcttgtctgt ggtctctagg gctctgcagc agcagtggct cttcgattag   2100

ttaaaactct cctaggctga cacatctggg tctcaatccc cttggaaatt cttggtgcat   2160

taaatgaagc cttaccccat tactgcggtt cttcctgtaa gggggctcca ttttcctccc   2220

tctctttaaa tgaccaccta aaggacagta tattaacaag caaagtcgat tcaacaacag   2280

cttcttccca gtcacttttt tttttctcac tgccatcaca tactaacctt atactttgat   2340

ctattctttt tggttatgag agaaatgttg ggcaactgtt tttacctgat ggttttaagc   2400

tgaacttgaa ggactggttc ctattctgaa acagtaaaac tatgtataat agtatatagc   2460

catgcatggc aaatatttta atatttctgt tttcatttcc tgttggaaat attatcctgc   2520

ataatagcta ttggaggctc ctcagtgaaa gatcccaaaa ggattttggt ggaaaactag   2580

ttgtaatctc acaaactcaa cactaccatc aggggtttc tttatggcaa agccaaaata   2640

gctcctacaa tttcttatat ccctcgtcat gtggcagtat ttatttattt atttggaagt   2700

ttgcctatcc ttctatattt atagatattt ataaaaatgt aaccccttt tcctttcttc   2760

tgtttaaaat aaaaataaaa tttatctcag cttctgttag cttatcctct ttgtagtact   2820

acttaaaagc atgtcggaat ataagaataa aaaggattat gggaggggaa cattagggaa   2880

atccagagaa ggcaaaattg aaaaaaagat tttagaattt taaaatttc aaagatttct   2940

tccattcata aggagactca atgattttaa ttgatctaga cagaattatt taagttttat   3000

caatattgga tttctggt                                                 3018
```

```
<210> SEQ ID NO 35
<211> LENGTH: 251
<212> TYPE: PRT
<213> ORGANISM: Homo sapiens

<400> SEQUENCE: 35

Met Leu Gly Ala Arg Leu Arg Leu Trp Val Cys Ala Leu Cys Ser Val
1               5                   10                  15

Cys Ser Met Ser Val Leu Arg Ala Tyr Pro Asn Ala Ser Pro Leu Leu
            20                  25                  30

Gly Ser Ser Trp Gly Gly Leu Ile His Leu Tyr Thr Ala Thr Ala Arg
        35                  40                  45
```

```
Asn Ser Tyr His Leu Gln Ile His Lys Asn Gly His Val Asp Gly Ala
    50                  55                  60

Pro His Gln Thr Ile Tyr Ser Ala Leu Met Ile Arg Ser Glu Asp Ala
65                  70                  75                  80

Gly Phe Val Val Ile Thr Gly Val Met Ser Arg Arg Tyr Leu Cys Met
                85                  90                  95

Asp Phe Arg Gly Asn Ile Phe Gly Ser His Tyr Phe Asp Pro Glu Asn
            100                 105                 110

Cys Arg Phe Gln His Gln Thr Leu Glu Asn Gly Tyr Asp Val Tyr His
        115                 120                 125

Ser Pro Gln Tyr His Phe Leu Val Ser Leu Gly Arg Ala Lys Arg Ala
    130                 135                 140

Phe Leu Pro Gly Met Asn Pro Pro Pro Tyr Ser Gln Phe Leu Ser Arg
145                 150                 155                 160

Arg Asn Glu Ile Pro Leu Ile His Phe Asn Thr Pro Ile Pro Arg Arg
                165                 170                 175

His Thr Arg Ser Ala Glu Asp Asp Ser Glu Arg Asp Pro Leu Asn Val
            180                 185                 190

Leu Lys Pro Arg Ala Arg Met Thr Pro Ala Pro Ala Ser Cys Ser Gln
        195                 200                 205

Glu Leu Pro Ser Ala Glu Asp Asn Ser Pro Met Ala Ser Asp Pro Leu
    210                 215                 220

Gly Val Val Arg Gly Gly Arg Val Asn Thr His Ala Gly Gly Thr Gly
225                 230                 235                 240

Pro Glu Gly Cys Arg Pro Phe Ala Lys Phe Ile
                245                 250


<210> SEQ ID NO 36
<211> LENGTH: 251
<212> TYPE: PRT
<213> ORGANISM: Artificial Sequence
<220> FEATURE:
<223> OTHER INFORMATION: Description of Artificial Sequence: Synthetic
      fusion polypeptide

<400> SEQUENCE: 36

Met Leu Gly Ala Arg Leu Arg Leu Trp Val Cys Ala Leu Cys Ser Val
1               5                   10                  15

Cys Ser Met Ser Val Leu Arg Ala Tyr Pro Asn Ala Ser Pro Leu Leu
            20                  25                  30

Gly Ser Ser Trp Gly Gly Leu Ile His Leu Tyr Thr Ala Thr Ala Arg
        35                  40                  45

Asn Ser Tyr His Leu Gln Ile His Lys Asn Gly His Val Asp Gly Ala
    50                  55                  60

Pro His Gln Thr Ile Tyr Ser Ala Leu Met Ile Arg Ser Glu Asp Ala
65                  70                  75                  80

Gly Phe Val Val Ile Thr Gly Val Met Ser Arg Arg Tyr Leu Cys Met
                85                  90                  95

Asp Phe Arg Gly Asn Ile Phe Gly Ser His Tyr Phe Asp Pro Glu Asn
            100                 105                 110

Cys Arg Phe Gln His Gln Thr Leu Glu Asn Gly Tyr Asp Val Tyr His
        115                 120                 125

Ser Pro Gln Tyr His Phe Leu Val Ser Leu Gly Arg Ala Lys Arg Ala
    130                 135                 140

Phe Leu Pro Gly Met Asn Pro Pro Pro Tyr Ser Gln Phe Leu Ser Arg
145                 150                 155                 160
```

```
Arg Asn Glu Ile Pro Leu Ile His Phe Asn Thr Pro Ile Pro Arg Arg
                165                 170                 175

His Thr Gln Ser Ala Glu Asp Asp Ser Glu Arg Asp Pro Leu Asn Val
            180                 185                 190

Leu Lys Pro Arg Ala Arg Met Thr Pro Ala Pro Ala Ser Cys Ser Gln
        195                 200                 205

Glu Leu Pro Ser Ala Glu Asp Asn Ser Pro Met Ala Ser Asp Pro Leu
    210                 215                 220

Gly Val Val Arg Gly Gly Arg Val Asn Thr His Ala Gly Gly Thr Gly
225                 230                 235                 240

Pro Glu Gly Cys Arg Pro Phe Ala Lys Phe Ile
                245                 250


<210> SEQ ID NO 37
<211> LENGTH: 431
<212> TYPE: PRT
<213> ORGANISM: Homo sapiens

<400> SEQUENCE: 37

Tyr Asp Thr Phe Pro Lys Asn Phe Phe Trp Gly Ile Gly Thr Gly Ala
1               5                   10                  15

Leu Gln Val Glu Gly Ser Trp Lys Lys Asp Gly Lys Gly Pro Ser Ile
            20                  25                  30

Trp Asp His Phe Ile His Thr His Leu Lys Asn Val Ser Ser Thr Asn
        35                  40                  45

Gly Ser Ser Asp Ser Tyr Ile Phe Leu Glu Lys Asp Leu Ser Ala Leu
    50                  55                  60

Asp Phe Ile Gly Val Ser Phe Tyr Gln Phe Ser Ile Ser Trp Pro Arg
65                  70                  75                  80

Leu Phe Pro Asp Gly Ile Val Thr Val Ala Asn Ala Lys Gly Leu Gln
                85                  90                  95

Tyr Tyr Ser Thr Leu Leu Asp Ala Leu Val Leu Arg Asn Ile Glu Pro
            100                 105                 110

Ile Val Thr Leu Tyr His Trp Asp Leu Pro Leu Ala Leu Gln Glu Lys
        115                 120                 125

Tyr Gly Gly Trp Lys Asn Asp Thr Ile Ile Asp Ile Phe Asn Asp Tyr
    130                 135                 140

Ala Thr Tyr Cys Phe Gln Met Phe Gly Asp Arg Val Lys Tyr Trp Ile
145                 150                 155                 160

Thr Ile His Asn Pro Tyr Leu Val Ala Trp His Gly Tyr Gly Thr Gly
                165                 170                 175

Met His Ala Pro Gly Glu Lys Gly Asn Leu Ala Ala Val Tyr Thr Val
            180                 185                 190

Gly His Asn Leu Ile Lys Ala His Ser Lys Val Trp His Asn Tyr Asn
        195                 200                 205

Thr His Phe Arg Pro His Gln Lys Gly Trp Leu Ser Ile Thr Leu Gly
    210                 215                 220

Ser His Trp Ile Glu Pro Asn Arg Ser Glu Asn Thr Met Asp Ile Phe
225                 230                 235                 240

Lys Cys Gln Gln Ser Met Val Ser Val Leu Gly Trp Phe Ala Asn Pro
                245                 250                 255

Ile His Gly Asp Gly Asp Tyr Pro Glu Gly Met Arg Lys Lys Leu Phe
            260                 265                 270

Ser Val Leu Pro Ile Phe Ser Glu Ala Glu Lys His Glu Met Arg Gly
```

```
        275                 280                 285

Thr Ala Asp Phe Phe Ala Phe Ser Phe Gly Pro Asn Asn Phe Lys Pro
    290                 295                 300

Leu Asn Thr Met Ala Lys Met Gly Gln Asn Val Ser Leu Asn Leu Arg
305                 310                 315                 320

Glu Ala Leu Asn Trp Ile Lys Leu Glu Tyr Asn Asn Pro Arg Ile Leu
                325                 330                 335

Ile Ala Glu Asn Gly Trp Phe Thr Asp Ser Arg Val Lys Thr Glu Asp
            340                 345                 350

Thr Thr Ala Ile Tyr Met Met Lys Asn Phe Leu Ser Gln Val Leu Gln
        355                 360                 365

Ala Ile Arg Leu Asp Glu Ile Arg Val Phe Gly Tyr Thr Ala Trp Ser
    370                 375                 380

Leu Leu Asp Gly Phe Glu Trp Gln Asp Ala Tyr Thr Ile Arg Arg Gly
385                 390                 395                 400

Leu Phe Tyr Val Asp Phe Asn Ser Lys Gln Lys Glu Arg Lys Pro Lys
                405                 410                 415

Ser Ser Ala His Tyr Tyr Lys Gln Ile Ile Arg Glu Asn Gly Phe
            420                 425                 430


<210> SEQ ID NO 38
<211> LENGTH: 397
<212> TYPE: PRT
<213> ORGANISM: Homo sapiens

<400> SEQUENCE: 38

Thr Arg Pro Ala Gln Cys Thr Asp Phe Val Asn Ile Lys Lys Gln Leu
1               5                   10                  15

Glu Met Leu Ala Arg Met Lys Val Thr His Tyr Arg Phe Ala Leu Asp
            20                  25                  30

Trp Ala Ser Val Leu Pro Thr Gly Asn Leu Ser Ala Val Asn Arg Gln
        35                  40                  45

Ala Leu Arg Tyr Tyr Arg Cys Val Val Ser Glu Gly Leu Lys Leu Gly
    50                  55                  60

Ile Ser Ala Met Val Thr Leu Tyr Tyr Pro Thr His Ala His Leu Gly
65                  70                  75                  80

Leu Pro Glu Pro Leu Leu His Ala Asp Gly Trp Leu Asn Pro Ser Thr
                85                  90                  95

Ala Glu Ala Phe Gln Ala Tyr Ala Gly Leu Cys Phe Gln Glu Leu Gly
            100                 105                 110

Asp Leu Val Lys Leu Trp Ile Thr Ile Asn Glu Pro Asn Arg Leu Ser
        115                 120                 125

Asp Ile Tyr Asn Arg Ser Gly Asn Asp Thr Tyr Gly Ala Ala His Asn
    130                 135                 140

Leu Leu Val Ala His Ala Leu Ala Trp Arg Leu Tyr Asp Arg Gln Phe
145                 150                 155                 160

Arg Pro Ser Gln Arg Gly Ala Val Ser Leu Ser Leu His Ala Asp Trp
                165                 170                 175

Ala Glu Pro Ala Asn Pro Tyr Ala Asp Ser His Trp Arg Ala Ala Glu
            180                 185                 190

Arg Phe Leu Gln Phe Glu Ile Ala Trp Phe Ala Glu Pro Leu Phe Lys
        195                 200                 205

Thr Gly Asp Tyr Pro Ala Ala Met Arg Glu Tyr Ile Ala Ser Lys His
    210                 215                 220
```

```
Arg Arg Gly Leu Ser Ser Ser Ala Leu Pro Arg Leu Thr Glu Ala Glu
225                 230                 235                 240

Arg Arg Leu Leu Lys Gly Thr Val Asp Phe Cys Ala Leu Asn His Phe
                245                 250                 255

Thr Thr Arg Phe Val Met His Glu Gln Leu Ala Gly Ser Arg Tyr Asp
            260                 265                 270

Ser Asp Arg Asp Ile Gln Phe Leu Gln Asp Ile Thr Arg Leu Ser Ser
        275                 280                 285

Pro Thr Arg Leu Ala Val Ile Pro Trp Gly Val Arg Lys Leu Leu Arg
    290                 295                 300

Trp Val Arg Arg Asn Tyr Gly Asp Met Asp Ile Tyr Ile Thr Ala Ser
305                 310                 315                 320

Gly Ile Asp Asp Gln Ala Leu Glu Asp Asp Arg Leu Arg Lys Tyr Tyr
                325                 330                 335

Leu Gly Lys Tyr Leu Gln Glu Val Leu Lys Ala Tyr Leu Ile Asp Lys
            340                 345                 350

Val Arg Ile Lys Gly Tyr Tyr Ala Phe Lys Leu Ala Glu Glu Lys Ser
        355                 360                 365

Lys Pro Arg Phe Gly Phe Phe Thr Ser Asp Phe Lys Ala Lys Ser Ser
    370                 375                 380

Ile Gln Phe Tyr Asn Lys Val Ile Ser Ser Arg Gly Phe
385                 390                 395


<210> SEQ ID NO 39
<211> LENGTH: 946
<212> TYPE: PRT
<213> ORGANISM: Homo sapiens

<400> SEQUENCE: 39

Gly Phe Ser Gly Asp Gly Arg Ala Ile Trp Ser Lys Asn Pro Asn Phe
1               5                   10                  15

Thr Pro Val Asn Glu Ser Gln Leu Phe Leu Tyr Asp Thr Phe Pro Lys
            20                  25                  30

Asn Phe Phe Trp Gly Ile Gly Thr Gly Ala Leu Gln Val Glu Gly Ser
        35                  40                  45

Trp Lys Lys Asp Gly Lys Gly Pro Ser Ile Trp Asp His Phe Ile His
    50                  55                  60

Thr His Leu Lys Asn Val Ser Ser Thr Asn Gly Ser Ser Asp Ser Tyr
65                  70                  75                  80

Ile Phe Leu Glu Lys Asp Leu Ser Ala Leu Asp Phe Ile Gly Val Ser
                85                  90                  95

Phe Tyr Gln Phe Ser Ile Ser Trp Pro Arg Leu Phe Pro Asp Gly Ile
            100                 105                 110

Val Thr Val Ala Asn Ala Lys Gly Leu Gln Tyr Tyr Ser Thr Leu Leu
        115                 120                 125

Asp Ala Leu Val Leu Arg Asn Ile Glu Pro Ile Val Thr Leu Tyr His
    130                 135                 140

Trp Asp Leu Pro Leu Ala Leu Gln Glu Lys Tyr Gly Gly Trp Lys Asn
145                 150                 155                 160

Asp Thr Ile Ile Asp Ile Phe Asn Asp Tyr Ala Thr Tyr Cys Phe Gln
                165                 170                 175

Met Phe Gly Asp Arg Val Lys Tyr Trp Ile Thr Ile His Asn Pro Tyr
            180                 185                 190

Leu Val Ala Trp His Gly Tyr Gly Thr Gly Met His Ala Pro Gly Glu
        195                 200                 205
```

```
Lys Gly Asn Leu Ala Ala Val Tyr Thr Val Gly His Asn Leu Ile Lys
    210                 215                 220

Ala His Ser Lys Val Trp His Asn Tyr Asn Thr His Phe Arg Pro His
225                 230                 235                 240

Gln Lys Gly Trp Leu Ser Ile Thr Leu Gly Ser His Trp Ile Glu Pro
                245                 250                 255

Asn Arg Ser Glu Asn Thr Met Asp Ile Phe Lys Cys Gln Gln Ser Met
            260                 265                 270

Val Ser Val Leu Gly Trp Phe Ala Asn Pro Ile His Gly Asp Gly Asp
        275                 280                 285

Tyr Pro Glu Gly Met Arg Lys Lys Leu Phe Ser Val Leu Pro Ile Phe
    290                 295                 300

Ser Glu Ala Glu Lys His Glu Met Arg Gly Thr Ala Asp Phe Phe Ala
305                 310                 315                 320

Phe Ser Phe Gly Pro Asn Asn Phe Lys Pro Leu Asn Thr Met Ala Lys
                325                 330                 335

Met Gly Gln Asn Val Ser Leu Asn Leu Arg Glu Ala Leu Asn Trp Ile
            340                 345                 350

Lys Leu Glu Tyr Asn Asn Pro Arg Ile Leu Ile Ala Glu Asn Gly Trp
        355                 360                 365

Phe Thr Asp Ser Arg Val Lys Thr Glu Asp Thr Thr Ala Ile Tyr Met
    370                 375                 380

Met Lys Asn Phe Leu Ser Gln Val Leu Gln Ala Ile Arg Leu Asp Glu
385                 390                 395                 400

Ile Arg Val Phe Gly Tyr Thr Ala Trp Ser Leu Leu Asp Gly Phe Glu
                405                 410                 415

Trp Gln Asp Ala Tyr Thr Ile Arg Arg Gly Leu Phe Tyr Val Asp Phe
            420                 425                 430

Asn Ser Lys Gln Lys Glu Arg Lys Pro Lys Ser Ser Ala His Tyr Tyr
        435                 440                 445

Lys Gln Ile Ile Arg Glu Asn Gly Phe Ser Leu Lys Glu Ser Thr Pro
    450                 455                 460

Asp Val Gln Gly Gln Phe Pro Cys Asp Phe Ser Trp Gly Val Thr Glu
465                 470                 475                 480

Ser Val Leu Lys Pro Glu Ser Val Ala Ser Ser Pro Gln Phe Ser Asp
                485                 490                 495

Pro His Leu Tyr Val Trp Asn Ala Thr Gly Asn Arg Leu Leu His Arg
            500                 505                 510

Val Glu Gly Val Arg Leu Lys Thr Arg Pro Ala Gln Cys Thr Asp Phe
        515                 520                 525

Val Asn Ile Lys Lys Gln Leu Glu Met Leu Ala Arg Met Lys Val Thr
    530                 535                 540

His Tyr Arg Phe Ala Leu Asp Trp Ala Ser Val Leu Pro Thr Gly Asn
545                 550                 555                 560

Leu Ser Ala Val Asn Arg Gln Ala Leu Arg Tyr Tyr Arg Cys Val Val
                565                 570                 575

Ser Glu Gly Leu Lys Leu Gly Ile Ser Ala Met Val Thr Leu Tyr Tyr
            580                 585                 590

Pro Thr His Ala His Leu Gly Leu Pro Glu Pro Leu Leu His Ala Asp
        595                 600                 605

Gly Trp Leu Asn Pro Ser Thr Ala Glu Ala Phe Gln Ala Tyr Ala Gly
    610                 615                 620
```

```
Leu Cys Phe Gln Glu Leu Gly Asp Leu Val Lys Leu Trp Ile Thr Ile
625                 630                 635                 640

Asn Glu Pro Asn Arg Leu Ser Asp Ile Tyr Asn Arg Ser Gly Asn Asp
                645                 650                 655

Thr Tyr Gly Ala Ala His Asn Leu Leu Val Ala His Ala Leu Ala Trp
            660                 665                 670

Arg Leu Tyr Asp Arg Gln Phe Arg Pro Ser Gln Arg Gly Ala Val Ser
        675                 680                 685

Leu Ser Leu His Ala Asp Trp Ala Glu Pro Ala Asn Pro Tyr Ala Asp
    690                 695                 700

Ser His Trp Arg Ala Ala Glu Arg Phe Leu Gln Phe Glu Ile Ala Trp
705                 710                 715                 720

Phe Ala Glu Pro Leu Phe Lys Thr Gly Asp Tyr Pro Ala Ala Met Arg
                725                 730                 735

Glu Tyr Ile Ala Ser Lys His Arg Arg Gly Leu Ser Ser Ser Ala Leu
            740                 745                 750

Pro Arg Leu Thr Glu Ala Glu Arg Arg Leu Leu Lys Gly Thr Val Asp
        755                 760                 765

Phe Cys Ala Leu Asn His Phe Thr Thr Arg Phe Val Met His Glu Gln
    770                 775                 780

Leu Ala Gly Ser Arg Tyr Asp Ser Asp Arg Asp Ile Gln Phe Leu Gln
785                 790                 795                 800

Asp Ile Thr Arg Leu Ser Ser Pro Thr Arg Leu Ala Val Ile Pro Trp
                805                 810                 815

Gly Val Arg Lys Leu Leu Arg Trp Val Arg Arg Asn Tyr Gly Asp Met
            820                 825                 830

Asp Ile Tyr Ile Thr Ala Ser Gly Ile Asp Asp Gln Ala Leu Glu Asp
        835                 840                 845

Asp Arg Leu Arg Lys Tyr Tyr Leu Gly Lys Tyr Leu Gln Glu Val Leu
    850                 855                 860

Lys Ala Tyr Leu Ile Asp Lys Val Arg Ile Lys Gly Tyr Tyr Ala Phe
865                 870                 875                 880

Lys Leu Ala Glu Glu Lys Ser Lys Pro Arg Phe Gly Phe Phe Thr Ser
                885                 890                 895

Asp Phe Lys Ala Lys Ser Ser Ile Gln Phe Tyr Asn Lys Val Ile Ser
            900                 905                 910

Ser Arg Gly Phe Pro Phe Glu Asn Ser Ser Ser Arg Cys Ser Gln Thr
        915                 920                 925

Gln Glu Asn Thr Glu Cys Thr Val Cys Leu Phe Leu Val Gln Lys Lys
    930                 935                 940

Pro Leu
945
```

<210> SEQ ID NO 40
<211> LENGTH: 1195
<212> TYPE: PRT
<213> ORGANISM: Artificial Sequence
<220> FEATURE:
<223> OTHER INFORMATION: Description of Artificial Sequence: Synthetic fusion polypeptide

<400> SEQUENCE: 40

```
Glu Pro Gly Asp Gly Ala Gln Thr Trp Ala Arg Phe Ser Arg Pro Pro
1               5                   10                  15

Ala Pro Glu Ala Ala Gly Leu Phe Gln Gly Thr Phe Pro Asp Gly Phe
            20                  25                  30
```

```
Leu Trp Ala Val Gly Ser Ala Ala Tyr Gln Thr Glu Gly Gly Trp Gln
        35                  40                  45

Gln His Gly Lys Gly Ala Ser Ile Trp Asp Thr Phe Thr His His Pro
    50                  55                  60

Leu Ala Pro Pro Gly Asp Ser Arg Asn Ala Ser Leu Pro Leu Gly Ala
65                  70                  75                  80

Pro Ser Pro Leu Gln Pro Ala Thr Gly Asp Val Ala Ser Asp Ser Tyr
                85                  90                  95

Asn Asn Val Phe Arg Asp Thr Glu Ala Leu Arg Glu Leu Gly Val Thr
            100                 105                 110

His Tyr Arg Phe Ser Ile Ser Trp Ala Arg Val Leu Pro Asn Gly Ser
        115                 120                 125

Ala Gly Val Pro Asn Arg Glu Gly Leu Arg Tyr Tyr Arg Arg Leu Leu
    130                 135                 140

Glu Arg Leu Arg Glu Leu Gly Val Gln Pro Val Val Thr Leu Tyr His
145                 150                 155                 160

Trp Asp Leu Pro Gln Arg Leu Gln Asp Ala Tyr Gly Gly Trp Ala Asn
                165                 170                 175

Arg Ala Leu Ala Asp His Phe Arg Asp Tyr Ala Glu Leu Cys Phe Arg
            180                 185                 190

His Phe Gly Gly Gln Val Lys Tyr Trp Ile Thr Ile Asp Asn Pro Tyr
        195                 200                 205

Val Val Ala Trp His Gly Tyr Ala Thr Gly Arg Leu Ala Pro Gly Ile
    210                 215                 220

Arg Gly Ser Pro Arg Leu Gly Tyr Leu Val Ala His Asn Leu Leu Leu
225                 230                 235                 240

Ala His Ala Lys Val Trp His Leu Tyr Asn Thr Ser Phe Arg Pro Thr
                245                 250                 255

Gln Gly Gly Gln Val Ser Ile Ala Leu Ser Ser His Trp Ile Asn Pro
            260                 265                 270

Arg Arg Met Thr Asp His Ser Ile Lys Glu Cys Gln Lys Ser Leu Asp
        275                 280                 285

Phe Val Leu Gly Trp Phe Ala Lys Pro Val Phe Ile Asp Gly Asp Tyr
    290                 295                 300

Pro Glu Ser Met Lys Asn Asn Leu Ser Ser Ile Leu Pro Asp Phe Thr
305                 310                 315                 320

Glu Ser Glu Lys Lys Phe Ile Lys Gly Thr Ala Asp Phe Phe Ala Leu
                325                 330                 335

Cys Phe Gly Pro Thr Leu Ser Phe Gln Leu Leu Asp Pro His Met Lys
            340                 345                 350

Phe Arg Gln Leu Glu Ser Pro Asn Leu Arg Gln Leu Leu Ser Trp Ile
        355                 360                 365

Asp Leu Glu Phe Asn His Pro Gln Ile Phe Ile Val Glu Asn Gly Trp
    370                 375                 380

Phe Val Ser Gly Thr Thr Lys Arg Asp Asp Ala Lys Tyr Met Tyr Tyr
385                 390                 395                 400

Leu Lys Lys Phe Ile Met Glu Thr Leu Lys Ala Ile Lys Leu Asp Gly
                405                 410                 415

Val Asp Val Ile Gly Tyr Thr Ala Trp Ser Leu Met Asp Gly Phe Glu
            420                 425                 430

Trp His Arg Gly Tyr Ser Ile Arg Arg Gly Leu Phe Tyr Val Asp Phe
        435                 440                 445
```

```
Leu Ser Gln Asp Lys Met Leu Leu Pro Lys Ser Ser Ala Leu Phe Tyr
    450                 455                 460

Gln Lys Leu Ile Glu Lys Asn Gly Phe Pro Pro Leu Pro Glu Asn Gln
465                 470                 475                 480

Pro Leu Glu Gly Thr Phe Pro Cys Asp Phe Ala Trp Gly Val Val Asp
                485                 490                 495

Asn Tyr Ile Gln Val Asp Thr Thr Leu Ser Gln Phe Thr Asp Leu Asn
            500                 505                 510

Val Tyr Leu Trp Asp Val His His Ser Lys Arg Leu Ile Lys Val Asp
        515                 520                 525

Gly Val Val Thr Lys Lys Arg Lys Ser Tyr Cys Val Asp Phe Ala Ala
    530                 535                 540

Ile Gln Pro Gln Ile Ala Leu Leu Gln Glu Met His Val Thr His Phe
545                 550                 555                 560

Arg Phe Ser Leu Asp Trp Ala Leu Ile Leu Pro Leu Gly Asn Gln Ser
                565                 570                 575

Gln Val Asn His Thr Ile Leu Gln Tyr Tyr Arg Cys Met Ala Ser Glu
            580                 585                 590

Leu Val Arg Val Asn Ile Thr Pro Val Val Ala Leu Trp Gln Pro Met
        595                 600                 605

Ala Pro Asn Gln Gly Leu Pro Arg Leu Leu Ala Arg Gln Gly Ala Trp
    610                 615                 620

Glu Asn Pro Tyr Thr Ala Leu Ala Phe Ala Glu Tyr Ala Arg Leu Cys
625                 630                 635                 640

Phe Gln Glu Leu Gly His His Val Lys Leu Trp Ile Thr Met Asn Glu
                645                 650                 655

Pro Tyr Thr Arg Asn Met Thr Tyr Ser Ala Gly His Asn Leu Leu Lys
            660                 665                 670

Ala His Ala Leu Ala Trp His Val Tyr Asn Glu Lys Phe Arg His Ala
        675                 680                 685

Gln Asn Gly Lys Ile Ser Ile Ala Leu Gln Ala Asp Trp Ile Glu Pro
    690                 695                 700

Ala Cys Pro Phe Ser Gln Lys Asp Lys Glu Val Ala Glu Arg Val Leu
705                 710                 715                 720

Glu Phe Asp Ile Gly Trp Leu Ala Glu Pro Ile Phe Gly Ser Gly Asp
                725                 730                 735

Tyr Pro Trp Val Met Arg Asp Trp Leu Asn Gln Arg Asn Asn Phe Leu
            740                 745                 750

Leu Pro Tyr Phe Thr Glu Asp Glu Lys Lys Leu Ile Gln Gly Thr Phe
        755                 760                 765

Asp Phe Leu Ala Leu Ser His Tyr Thr Thr Ile Leu Val Asp Ser Glu
    770                 775                 780

Lys Glu Asp Pro Ile Lys Tyr Asn Asp Tyr Leu Glu Val Gln Glu Met
785                 790                 795                 800

Thr Asp Ile Thr Trp Leu Asn Ser Pro Ser Gln Val Ala Val Val Pro
                805                 810                 815

Trp Gly Leu Arg Lys Val Leu Asn Trp Leu Lys Phe Lys Tyr Gly Asp
            820                 825                 830

Leu Pro Met Tyr Ile Ile Ser Asn Gly Ile Asp Asp Gly Leu His Ala
        835                 840                 845

Glu Asp Asp Gln Leu Arg Val Tyr Tyr Met Gln Asn Tyr Ile Asn Glu
    850                 855                 860

Ala Leu Lys Ala His Ile Leu Asp Gly Ile Asn Leu Cys Gly Tyr Phe
```

```
865                 870                 875                 880

Ala Tyr Ser Phe Asn Asp Arg Thr Ala Pro Arg Phe Gly Leu Tyr Arg
                885                 890                 895

Tyr Ala Ala Asp Gln Phe Glu Pro Lys Ala Ser Met Lys His Tyr Arg
            900                 905                 910

Lys Ile Ile Asp Ser Asn Gly Phe Pro Gly Pro Glu Thr Leu Glu Arg
        915                 920                 925

Phe Cys Pro Glu Glu Phe Thr Val Cys Thr Glu Cys Ser Phe Phe His
    930                 935                 940

Thr Arg Lys Ser Leu Gly Ser Gly Gly Gly Gly Ser Gly Gly Gly Gly
945                 950                 955                 960

Ser Gly Gly Gly Gly Ser Leu Lys Tyr Pro Asn Ala Ser Pro Leu Leu
                965                 970                 975

Gly Ser Ser Trp Gly Gly Leu Ile His Leu Tyr Thr Ala Thr Ala Arg
            980                 985                 990

Asn Ser Tyr His Leu Gln Ile His  Lys Asn Gly His Val  Asp Gly Ala
        995                 1000                1005

Pro His  Gln Thr Ile Tyr Ser  Ala Leu Met Ile Arg  Ser Glu Asp
    1010                1015                1020

Ala Gly  Phe Val Val Ile Thr  Gly Val Met Ser Arg  Arg Tyr Leu
    1025                1030                1035

Cys Met  Asp Phe Arg Gly Asn  Ile Phe Gly Ser His  Tyr Phe Asp
    1040                1045                1050

Pro Glu  Asn Cys Arg Phe Gln  His Gln Thr Leu Glu  Asn Gly Tyr
    1055                1060                1065

Asp Val  Tyr His Ser Pro Gln  Tyr His Phe Leu Val  Ser Leu Gly
    1070                1075                1080

Arg Ala  Lys Arg Ala Phe Leu  Pro Gly Met Asn Pro  Pro Pro Tyr
    1085                1090                1095

Ser Gln  Phe Leu Ser Arg Arg  Asn Glu Ile Pro Leu  Ile His Phe
    1100                1105                1110

Asn Thr  Pro Ile Pro Arg Arg  His Thr Arg Ser Ala  Glu Asp Asp
    1115                1120                1125

Ser Glu  Arg Asp Pro Leu Asn  Val Leu Lys Pro Arg  Ala Arg Met
    1130                1135                1140

Thr Pro  Ala Pro Ala Ser Cys  Ser Gln Glu Leu Pro  Ser Ala Glu
    1145                1150                1155

Asp Asn  Ser Pro Met Ala Ser  Asp Pro Leu Gly Val  Val Arg Gly
    1160                1165                1170

Gly Arg  Val Asn Thr His Ala  Gly Gly Thr Gly Pro  Glu Gly Cys
    1175                1180                1185

Arg Pro  Phe Ala Lys Phe Ile
    1190                1195


<210> SEQ ID NO 41
<211> LENGTH: 1195
<212> TYPE: PRT
<213> ORGANISM: Artificial Sequence
<220> FEATURE:
<223> OTHER INFORMATION: Description of Artificial Sequence: Synthetic
      fusion polypeptide

<400> SEQUENCE: 41

Glu Pro Gly Asp Gly Ala Gln Thr Trp Ala Arg Phe Ser Arg Pro Pro
1               5                   10                  15
```

```
Ala Pro Glu Ala Ala Gly Leu Phe Gln Gly Thr Phe Pro Asp Gly Phe
            20                  25                  30

Leu Trp Ala Val Gly Ser Ala Ala Tyr Gln Thr Glu Gly Gly Trp Gln
        35                  40                  45

Gln His Gly Lys Gly Ala Ser Ile Trp Asp Thr Phe Thr His His Pro
    50                  55                  60

Leu Ala Pro Pro Gly Asp Ser Arg Asn Ala Ser Leu Pro Leu Gly Ala
65                  70                  75                  80

Pro Ser Pro Leu Gln Pro Ala Thr Gly Asp Val Ala Ser Asp Ser Tyr
                85                  90                  95

Asn Asn Val Phe Arg Asp Thr Glu Ala Leu Arg Glu Leu Gly Val Thr
            100                 105                 110

His Tyr Arg Phe Ser Ile Ser Trp Ala Arg Val Leu Pro Asn Gly Ser
        115                 120                 125

Ala Gly Val Pro Asn Arg Glu Gly Leu Arg Tyr Tyr Arg Arg Leu Leu
    130                 135                 140

Glu Arg Leu Arg Glu Leu Gly Val Gln Pro Val Val Thr Leu Tyr His
145                 150                 155                 160

Trp Asp Leu Pro Gln Arg Leu Gln Asp Ala Tyr Gly Gly Trp Ala Asn
                165                 170                 175

Arg Ala Leu Ala Asp His Phe Arg Asp Tyr Ala Glu Leu Cys Phe Arg
            180                 185                 190

His Phe Gly Gly Gln Val Lys Tyr Trp Ile Thr Ile Asp Asn Pro Tyr
        195                 200                 205

Val Val Ala Trp His Gly Tyr Ala Thr Gly Arg Leu Ala Pro Gly Ile
    210                 215                 220

Arg Gly Ser Pro Arg Leu Gly Tyr Leu Val Ala His Asn Leu Leu Leu
225                 230                 235                 240

Ala His Ala Lys Val Trp His Leu Tyr Asn Thr Ser Phe Arg Pro Thr
                245                 250                 255

Gln Gly Gly Gln Val Ser Ile Ala Leu Ser Ser His Trp Ile Asn Pro
            260                 265                 270

Arg Arg Met Thr Asp His Ser Ile Lys Glu Cys Gln Lys Ser Leu Asp
        275                 280                 285

Phe Val Leu Gly Trp Phe Ala Lys Pro Val Phe Ile Asp Gly Asp Tyr
    290                 295                 300

Pro Glu Ser Met Lys Asn Asn Leu Ser Ser Ile Leu Pro Asp Phe Thr
305                 310                 315                 320

Glu Ser Glu Lys Lys Phe Ile Lys Gly Thr Ala Asp Phe Phe Ala Leu
                325                 330                 335

Cys Phe Gly Pro Thr Leu Ser Phe Gln Leu Leu Asp Pro His Met Lys
            340                 345                 350

Phe Arg Gln Leu Glu Ser Pro Asn Leu Arg Gln Leu Leu Ser Trp Ile
        355                 360                 365

Asp Leu Glu Phe Asn His Pro Gln Ile Phe Ile Val Glu Asn Gly Trp
    370                 375                 380

Phe Val Ser Gly Thr Thr Lys Arg Asp Asp Ala Lys Tyr Met Tyr Tyr
385                 390                 395                 400

Leu Lys Lys Phe Ile Met Glu Thr Leu Lys Ala Ile Lys Leu Asp Gly
                405                 410                 415

Val Asp Val Ile Gly Tyr Thr Ala Trp Ser Leu Met Asp Gly Phe Glu
            420                 425                 430

Trp His Arg Gly Tyr Ser Ile Arg Arg Gly Leu Phe Tyr Val Asp Phe
```

```
        435                 440                 445

Leu Ser Gln Asp Lys Met Leu Leu Pro Lys Ser Ser Ala Leu Phe Tyr
    450                 455                 460

Gln Lys Leu Ile Glu Lys Asn Gly Phe Pro Pro Leu Pro Glu Asn Gln
465                 470                 475                 480

Pro Leu Glu Gly Thr Phe Pro Cys Asp Phe Ala Trp Gly Val Val Asp
                485                 490                 495

Asn Tyr Ile Gln Val Asp Thr Thr Leu Ser Gln Phe Thr Asp Leu Asn
            500                 505                 510

Val Tyr Leu Trp Asp Val His His Ser Lys Arg Leu Ile Lys Val Asp
        515                 520                 525

Gly Val Val Thr Lys Lys Arg Lys Ser Tyr Cys Val Asp Phe Ala Ala
    530                 535                 540

Ile Gln Pro Gln Ile Ala Leu Leu Gln Glu Met His Val Thr His Phe
545                 550                 555                 560

Arg Phe Ser Leu Asp Trp Ala Leu Ile Leu Pro Leu Gly Asn Gln Ser
                565                 570                 575

Gln Val Asn His Thr Ile Leu Gln Tyr Tyr Arg Cys Met Ala Ser Glu
            580                 585                 590

Leu Val Arg Val Asn Ile Thr Pro Val Val Ala Leu Trp Gln Pro Met
        595                 600                 605

Ala Pro Asn Gln Gly Leu Pro Arg Leu Leu Ala Arg Gln Gly Ala Trp
    610                 615                 620

Glu Asn Pro Tyr Thr Ala Leu Ala Phe Ala Glu Tyr Ala Arg Leu Cys
625                 630                 635                 640

Phe Gln Glu Leu Gly His His Val Lys Leu Trp Ile Thr Met Asn Glu
                645                 650                 655

Pro Tyr Thr Arg Asn Met Thr Tyr Ser Ala Gly His Asn Leu Leu Lys
            660                 665                 670

Ala His Ala Leu Ala Trp His Val Tyr Asn Glu Lys Phe Arg His Ala
        675                 680                 685

Gln Asn Gly Lys Ile Ser Ile Ala Leu Gln Ala Asp Trp Ile Glu Pro
    690                 695                 700

Ala Cys Pro Phe Ser Gln Lys Asp Lys Glu Val Ala Glu Arg Val Leu
705                 710                 715                 720

Glu Phe Asp Ile Gly Trp Leu Ala Glu Pro Ile Phe Gly Ser Gly Asp
                725                 730                 735

Tyr Pro Trp Val Met Arg Asp Trp Leu Asn Gln Arg Asn Asn Phe Leu
            740                 745                 750

Leu Pro Tyr Phe Thr Glu Asp Glu Lys Lys Leu Ile Gln Gly Thr Phe
        755                 760                 765

Asp Phe Leu Ala Leu Ser His Tyr Thr Thr Ile Leu Val Asp Ser Glu
    770                 775                 780

Lys Glu Asp Pro Ile Lys Tyr Asn Asp Tyr Leu Glu Val Gln Glu Met
785                 790                 795                 800

Thr Asp Ile Thr Trp Leu Asn Ser Pro Ser Gln Val Ala Val Val Pro
                805                 810                 815

Trp Gly Leu Arg Lys Val Leu Asn Trp Leu Lys Phe Lys Tyr Gly Asp
            820                 825                 830

Leu Pro Met Tyr Ile Ile Ser Asn Gly Ile Asp Asp Gly Leu His Ala
        835                 840                 845

Glu Asp Asp Gln Leu Arg Val Tyr Tyr Met Gln Asn Tyr Ile Asn Glu
    850                 855                 860
```

```
Ala Leu Lys Ala His Ile Leu Asp Gly Ile Asn Leu Cys Gly Tyr Phe
865                 870                 875                 880

Ala Tyr Ser Phe Asn Asp Arg Thr Ala Pro Arg Phe Gly Leu Tyr Arg
                885                 890                 895

Tyr Ala Ala Asp Gln Phe Glu Pro Lys Ala Ser Met Lys His Tyr Arg
            900                 905                 910

Lys Ile Ile Asp Ser Asn Gly Phe Pro Gly Pro Glu Thr Leu Glu Arg
        915                 920                 925

Phe Cys Pro Glu Glu Phe Thr Val Cys Thr Glu Cys Ser Phe Phe His
    930                 935                 940

Thr Arg Lys Ser Leu Gly Ser Gly Gly Gly Gly Ser Gly Gly Gly Gly
945                 950                 955                 960

Ser Gly Gly Gly Gly Ser Leu Lys Tyr Pro Asn Ala Ser Pro Leu Leu
                965                 970                 975

Gly Ser Ser Trp Gly Gly Leu Ile His Leu Tyr Thr Ala Thr Ala Arg
            980                 985                 990

Asn Ser Tyr His Leu Gln Ile His  Lys Asn Gly His Val  Asp Gly Ala
        995                 1000                1005

Pro His  Gln Thr Ile Tyr Ser  Ala Leu Met Ile Arg  Ser Glu Asp
    1010                1015                1020

Ala Gly  Phe Val Val Ile Thr  Gly Val Met Ser Arg  Arg Tyr Leu
    1025                1030                1035

Cys Met  Asp Phe Arg Gly Asn  Ile Phe Gly Ser His  Tyr Phe Asp
    1040                1045                1050

Pro Glu  Asn Cys Arg Phe Gln  His Gln Thr Leu Glu  Asn Gly Tyr
    1055                1060                1065

Asp Val  Tyr His Ser Pro Gln  Tyr His Phe Leu Val  Ser Leu Gly
    1070                1075                1080

Arg Ala  Lys Arg Ala Phe Leu  Pro Gly Met Asn Pro  Pro Pro Tyr
    1085                1090                1095

Ser Gln  Phe Leu Ser Arg Arg  Asn Glu Ile Pro Leu  Ile His Phe
    1100                1105                1110

Asn Thr  Pro Ile Pro Arg Arg  His Thr Gln Ser Ala  Glu Asp Asp
    1115                1120                1125

Ser Glu  Arg Asp Pro Leu Asn  Val Leu Lys Pro Arg  Ala Arg Met
    1130                1135                1140

Thr Pro  Ala Pro Ala Ser Cys  Ser Gln Glu Leu Pro  Ser Ala Glu
    1145                1150                1155

Asp Asn  Ser Pro Met Ala Ser  Asp Pro Leu Gly Val  Val Arg Gly
    1160                1165                1170

Gly Arg  Val Asn Thr His Ala  Gly Gly Thr Gly Pro  Glu Gly Cys
    1175                1180                1185

Arg Pro  Phe Ala Lys Phe Ile
    1190                1195


<210> SEQ ID NO 42
<211> LENGTH: 227
<212> TYPE: PRT
<213> ORGANISM: Artificial Sequence
<220> FEATURE:
<223> OTHER INFORMATION: Description of Artificial Sequence: Synthetic
      fusion polypeptide

<400> SEQUENCE: 42

Tyr Pro Asn Ala Ser Pro Leu Leu Gly Ser Ser Trp Gly Gly Leu Ile
```

```
1               5                   10                  15

His Leu Tyr Thr Ala Thr Ala Arg Asn Ser Tyr His Leu Gln Ile His
            20                  25                  30

Lys Asn Gly His Val Asp Gly Ala Pro His Gln Thr Ile Tyr Ser Ala
        35                  40                  45

Leu Met Ile Arg Ser Glu Asp Ala Gly Phe Val Val Ile Thr Gly Val
    50                  55                  60

Met Ser Arg Arg Tyr Leu Cys Met Asp Phe Arg Gly Asn Ile Phe Gly
65                  70                  75                  80

Ser His Tyr Phe Asp Pro Glu Asn Cys Arg Phe Gln His Gln Thr Leu
                85                  90                  95

Glu Asn Gly Tyr Asp Val Tyr His Ser Pro Gln Tyr His Phe Leu Val
            100                 105                 110

Ser Leu Gly Arg Ala Lys Arg Ala Phe Leu Pro Gly Met Asn Pro Pro
        115                 120                 125

Pro Tyr Ser Gln Phe Leu Ser Arg Arg Asn Glu Ile Pro Leu Ile His
    130                 135                 140

Phe Asn Thr Pro Ile Pro Arg Arg His Thr Arg Ser Ala Glu Asp Asp
145                 150                 155                 160

Ser Glu Arg Asp Pro Leu Asn Val Leu Lys Pro Arg Ala Arg Met Thr
                165                 170                 175

Pro Ala Pro Ala Ser Cys Ser Gln Glu Leu Pro Ser Ala Glu Asp Asn
            180                 185                 190

Ser Pro Met Ala Ser Asp Pro Leu Gly Val Val Arg Gly Gly Arg Val
        195                 200                 205

Asn Thr His Ala Gly Gly Thr Gly Pro Glu Gly Cys Arg Pro Phe Ala
    210                 215                 220

Lys Phe Ile
225


<210> SEQ ID NO 43
<211> LENGTH: 227
<212> TYPE: PRT
<213> ORGANISM: Artificial Sequence
<220> FEATURE:
<223> OTHER INFORMATION: Description of Artificial Sequence: Synthetic
      fusion polypeptide

<400> SEQUENCE: 43

Tyr Pro Asn Ala Ser Pro Leu Leu Gly Ser Ser Trp Gly Gly Leu Ile
1               5                   10                  15

His Leu Tyr Thr Ala Thr Ala Arg Asn Ser Tyr His Leu Gln Ile His
            20                  25                  30

Lys Asn Gly His Val Asp Gly Ala Pro His Gln Thr Ile Tyr Ser Ala
        35                  40                  45

Leu Met Ile Arg Ser Glu Asp Ala Gly Phe Val Val Ile Thr Gly Val
    50                  55                  60

Met Ser Arg Arg Tyr Leu Cys Met Asp Phe Arg Gly Asn Ile Phe Gly
65                  70                  75                  80

Ser His Tyr Phe Asp Pro Glu Asn Cys Arg Phe Gln His Gln Thr Leu
                85                  90                  95

Glu Asn Gly Tyr Asp Val Tyr His Ser Pro Gln Tyr His Phe Leu Val
            100                 105                 110

Ser Leu Gly Arg Ala Lys Arg Ala Phe Leu Pro Gly Met Asn Pro Pro
        115                 120                 125
```

```
Pro Tyr Ser Gln Phe Leu Ser Arg Arg Asn Glu Ile Pro Leu Ile His
    130                 135                 140

Phe Asn Thr Pro Ile Pro Arg Arg His Thr Gln Ser Ala Glu Asp Asp
145                 150                 155                 160

Ser Glu Arg Asp Pro Leu Asn Val Leu Lys Pro Arg Ala Arg Met Thr
                165                 170                 175

Pro Ala Pro Ala Ser Cys Ser Gln Glu Leu Pro Ser Ala Glu Asp Asn
            180                 185                 190

Ser Pro Met Ala Ser Asp Pro Leu Gly Val Val Arg Gly Gly Arg Val
        195                 200                 205

Asn Thr His Ala Gly Gly Thr Gly Pro Glu Gly Cys Arg Pro Phe Ala
    210                 215                 220

Lys Phe Ile
225


<210> SEQ ID NO 44
<211> LENGTH: 982
<212> TYPE: PRT
<213> ORGANISM: Artificial Sequence
<220> FEATURE:
<223> OTHER INFORMATION: Description of Artificial Sequence: Synthetic
      fusion polypeptide

<400> SEQUENCE: 44

Met Pro Ala Ser Ala Pro Pro Arg Arg Pro Arg Pro Pro Pro Pro Ser
1               5                   10                  15

Leu Ser Leu Leu Leu Val Leu Leu Gly Leu Gly Gly Arg Arg Leu Arg
            20                  25                  30

Ala Glu Pro Gly Asp Gly Ala Gln Thr Trp Ala Arg Phe Ser Arg Pro
        35                  40                  45

Pro Ala Pro Glu Ala Ala Gly Leu Phe Gln Gly Thr Phe Pro Asp Gly
    50                  55                  60

Phe Leu Trp Ala Val Gly Ser Ala Ala Tyr Gln Thr Glu Gly Gly Trp
65                  70                  75                  80

Gln Gln His Gly Lys Gly Ala Ser Ile Trp Asp Thr Phe Thr His His
                85                  90                  95

Pro Leu Ala Pro Pro Gly Asp Ser Arg Asn Ala Ser Leu Pro Leu Gly
            100                 105                 110

Ala Pro Ser Pro Leu Gln Pro Ala Thr Gly Asp Val Ala Ser Asp Ser
        115                 120                 125

Tyr Asn Asn Val Phe Arg Asp Thr Glu Ala Leu Arg Glu Leu Gly Val
    130                 135                 140

Thr His Tyr Arg Phe Ser Ile Ser Trp Ala Arg Val Leu Pro Asn Gly
145                 150                 155                 160

Ser Ala Gly Val Pro Asn Arg Glu Gly Leu Arg Tyr Tyr Arg Arg Leu
                165                 170                 175

Leu Glu Arg Leu Arg Glu Leu Gly Val Gln Pro Val Val Thr Leu Tyr
            180                 185                 190

His Trp Asp Leu Pro Gln Arg Leu Gln Asp Ala Tyr Gly Gly Trp Ala
        195                 200                 205

Asn Arg Ala Leu Ala Asp His Phe Arg Asp Tyr Ala Glu Leu Cys Phe
    210                 215                 220

Arg His Phe Gly Gly Gln Val Lys Tyr Trp Ile Thr Ile Asp Asn Pro
225                 230                 235                 240

Tyr Val Val Ala Trp His Gly Tyr Ala Thr Gly Arg Leu Ala Pro Gly
                245                 250                 255
```

-continued

```
Ile Arg Gly Ser Pro Arg Leu Gly Tyr Leu Val Ala His Asn Leu Leu
            260                 265                 270

Leu Ala His Ala Lys Val Trp His Leu Tyr Asn Thr Ser Phe Arg Pro
        275                 280                 285

Thr Gln Gly Gly Gln Val Ser Ile Ala Leu Ser Ser His Trp Ile Asn
    290                 295                 300

Pro Arg Arg Met Thr Asp His Ser Ile Lys Glu Cys Gln Lys Ser Leu
305                 310                 315                 320

Asp Phe Val Leu Gly Trp Phe Ala Lys Pro Val Phe Ile Asp Gly Asp
                325                 330                 335

Tyr Pro Glu Ser Met Lys Asn Asn Leu Ser Ser Ile Leu Pro Asp Phe
            340                 345                 350

Thr Glu Ser Glu Lys Lys Phe Ile Lys Gly Thr Ala Asp Phe Phe Ala
        355                 360                 365

Leu Cys Phe Gly Pro Thr Leu Ser Phe Gln Leu Leu Asp Pro His Met
    370                 375                 380

Lys Phe Arg Gln Leu Glu Ser Pro Asn Leu Arg Gln Leu Leu Ser Trp
385                 390                 395                 400

Ile Asp Leu Glu Phe Asn His Pro Gln Ile Phe Ile Val Glu Asn Gly
                405                 410                 415

Trp Phe Val Ser Gly Thr Thr Lys Arg Asp Asp Ala Lys Tyr Met Tyr
            420                 425                 430

Tyr Leu Lys Lys Phe Ile Met Glu Thr Leu Lys Ala Ile Lys Leu Asp
        435                 440                 445

Gly Val Asp Val Ile Gly Tyr Thr Ala Trp Ser Leu Met Asp Gly Phe
    450                 455                 460

Glu Trp His Arg Gly Tyr Ser Ile Arg Arg Gly Leu Phe Tyr Val Asp
465                 470                 475                 480

Phe Leu Ser Gln Asp Lys Met Leu Leu Pro Lys Ser Ser Ala Leu Phe
                485                 490                 495

Tyr Gln Lys Leu Ile Glu Lys Asn Gly Phe Pro Pro Leu Pro Glu Asn
            500                 505                 510

Gln Pro Leu Glu Gly Thr Phe Pro Cys Asp Phe Ala Trp Gly Val Val
        515                 520                 525

Asp Asn Tyr Ile Gln Val Asp Thr Thr Leu Ser Gln Phe Thr Asp Leu
    530                 535                 540

Asn Val Tyr Leu Trp Asp Val His His Ser Lys Arg Leu Ile Lys Val
545                 550                 555                 560

Asp Gly Val Val Thr Lys Lys Arg Lys Ser Tyr Cys Val Asp Phe Ala
                565                 570                 575

Ala Ile Gln Pro Gln Ile Ala Leu Leu Gln Glu Met His Val Thr His
            580                 585                 590

Phe Arg Phe Ser Leu Asp Trp Ala Leu Ile Leu Pro Leu Gly Asn Gln
        595                 600                 605

Ser Gln Val Asn His Thr Ile Leu Gln Tyr Tyr Arg Cys Met Ala Ser
    610                 615                 620

Glu Leu Val Arg Val Asn Ile Thr Pro Val Val Ala Leu Trp Gln Pro
625                 630                 635                 640

Met Ala Pro Asn Gln Gly Leu Pro Arg Leu Leu Ala Arg Gln Gly Ala
                645                 650                 655

Trp Glu Asn Pro Tyr Thr Ala Leu Ala Phe Ala Glu Tyr Ala Arg Leu
            660                 665                 670
```

```
Cys Phe Gln Glu Leu Gly His His Val Lys Leu Trp Ile Thr Met Asn
        675                 680                 685

Glu Pro Tyr Thr Arg Asn Met Thr Tyr Ser Ala Gly His Asn Leu Leu
    690                 695                 700

Lys Ala His Ala Leu Ala Trp His Val Tyr Asn Glu Lys Phe Arg His
705                 710                 715                 720

Ala Gln Asn Gly Lys Ile Ser Ile Ala Leu Gln Ala Asp Trp Ile Glu
                725                 730                 735

Pro Ala Cys Pro Phe Ser Gln Lys Asp Lys Glu Val Ala Glu Arg Val
            740                 745                 750

Leu Glu Phe Asp Ile Gly Trp Leu Ala Glu Pro Ile Phe Gly Ser Gly
        755                 760                 765

Asp Tyr Pro Trp Val Met Arg Asp Trp Leu Asn Gln Arg Asn Asn Phe
    770                 775                 780

Leu Leu Pro Tyr Phe Thr Glu Asp Glu Lys Lys Leu Ile Gln Gly Thr
785                 790                 795                 800

Phe Asp Phe Leu Ala Leu Ser His Tyr Thr Thr Ile Leu Val Asp Ser
                805                 810                 815

Glu Lys Glu Asp Pro Ile Lys Tyr Asn Asp Tyr Leu Glu Val Gln Glu
            820                 825                 830

Met Thr Asp Ile Thr Trp Leu Asn Ser Pro Ser Gln Val Ala Val Val
        835                 840                 845

Pro Trp Gly Leu Arg Lys Val Leu Asn Trp Leu Lys Phe Lys Tyr Gly
    850                 855                 860

Asp Leu Pro Met Tyr Ile Ile Ser Asn Gly Ile Asp Asp Gly Leu His
865                 870                 875                 880

Ala Glu Asp Asp Gln Leu Arg Val Tyr Tyr Met Gln Asn Tyr Ile Asn
                885                 890                 895

Glu Ala Leu Lys Ala His Ile Leu Asp Gly Ile Asn Leu Cys Gly Tyr
            900                 905                 910

Phe Ala Tyr Ser Phe Asn Asp Arg Thr Ala Pro Arg Phe Gly Leu Tyr
        915                 920                 925

Arg Tyr Ala Ala Asp Gln Phe Glu Pro Lys Ala Ser Met Lys His Tyr
    930                 935                 940

Arg Lys Ile Ile Asp Ser Asn Gly Phe Pro Gly Pro Glu Thr Leu Glu
945                 950                 955                 960

Arg Phe Cys Pro Glu Glu Phe Thr Val Cys Thr Glu Cys Ser Phe Phe
                965                 970                 975

His Thr Arg Lys Ser Leu
            980


<210> SEQ ID NO 45
<211> LENGTH: 974
<212> TYPE: PRT
<213> ORGANISM: Artificial Sequence
<220> FEATURE:
<223> OTHER INFORMATION: Description of Artificial Sequence: Synthetic
      fusion polypeptide

<400> SEQUENCE: 45

Met Ser Val Leu Thr Gln Val Leu Ala Leu Leu Leu Leu Trp Leu Thr
1               5                   10                  15

Gly Leu Gly Gly Arg Arg Leu Arg Ala Glu Pro Gly Asp Gly Ala Gln
            20                  25                  30

Thr Trp Ala Arg Phe Ser Arg Pro Pro Ala Pro Glu Ala Ala Gly Leu
        35                  40                  45
```

```
Phe Gln Gly Thr Phe Pro Asp Gly Phe Leu Trp Ala Val Gly Ser Ala
    50                  55                  60

Ala Tyr Gln Thr Glu Gly Gly Trp Gln Gln His Gly Lys Gly Ala Ser
65                  70                  75                  80

Ile Trp Asp Thr Phe Thr His His Pro Leu Ala Pro Pro Gly Asp Ser
                85                  90                  95

Arg Asn Ala Ser Leu Pro Leu Gly Ala Pro Ser Pro Leu Gln Pro Ala
            100                 105                 110

Thr Gly Asp Val Ala Ser Asp Ser Tyr Asn Asn Val Phe Arg Asp Thr
        115                 120                 125

Glu Ala Leu Arg Glu Leu Gly Val Thr His Tyr Arg Phe Ser Ile Ser
    130                 135                 140

Trp Ala Arg Val Leu Pro Asn Gly Ser Ala Gly Val Pro Asn Arg Glu
145                 150                 155                 160

Gly Leu Arg Tyr Tyr Arg Arg Leu Leu Glu Arg Leu Arg Glu Leu Gly
                165                 170                 175

Val Gln Pro Val Val Thr Leu Tyr His Trp Asp Leu Pro Gln Arg Leu
            180                 185                 190

Gln Asp Ala Tyr Gly Gly Trp Ala Asn Arg Ala Leu Ala Asp His Phe
        195                 200                 205

Arg Asp Tyr Ala Glu Leu Cys Phe Arg His Phe Gly Gly Gln Val Lys
    210                 215                 220

Tyr Trp Ile Thr Ile Asp Asn Pro Tyr Val Val Ala Trp His Gly Tyr
225                 230                 235                 240

Ala Thr Gly Arg Leu Ala Pro Gly Ile Arg Gly Ser Pro Arg Leu Gly
                245                 250                 255

Tyr Leu Val Ala His Asn Leu Leu Leu Ala His Ala Lys Val Trp His
            260                 265                 270

Leu Tyr Asn Thr Ser Phe Arg Pro Thr Gln Gly Gly Gln Val Ser Ile
        275                 280                 285

Ala Leu Ser Ser His Trp Ile Asn Pro Arg Arg Met Thr Asp His Ser
    290                 295                 300

Ile Lys Glu Cys Gln Lys Ser Leu Asp Phe Val Leu Gly Trp Phe Ala
305                 310                 315                 320

Lys Pro Val Phe Ile Asp Gly Asp Tyr Pro Glu Ser Met Lys Asn Asn
                325                 330                 335

Leu Ser Ser Ile Leu Pro Asp Phe Thr Glu Ser Glu Lys Lys Phe Ile
            340                 345                 350

Lys Gly Thr Ala Asp Phe Phe Ala Leu Cys Phe Gly Pro Thr Leu Ser
        355                 360                 365

Phe Gln Leu Leu Asp Pro His Met Lys Phe Arg Gln Leu Glu Ser Pro
    370                 375                 380

Asn Leu Arg Gln Leu Leu Ser Trp Ile Asp Leu Glu Phe Asn His Pro
385                 390                 395                 400

Gln Ile Phe Ile Val Glu Asn Gly Trp Phe Val Ser Gly Thr Thr Lys
                405                 410                 415

Arg Asp Asp Ala Lys Tyr Met Tyr Tyr Leu Lys Lys Phe Ile Met Glu
            420                 425                 430

Thr Leu Lys Ala Ile Lys Leu Asp Gly Val Asp Val Ile Gly Tyr Thr
        435                 440                 445

Ala Trp Ser Leu Met Asp Gly Phe Glu Trp His Arg Gly Tyr Ser Ile
    450                 455                 460
```

```
Arg Arg Gly Leu Phe Tyr Val Asp Phe Leu Ser Gln Asp Lys Met Leu
465                 470                 475                 480

Leu Pro Lys Ser Ser Ala Leu Phe Tyr Gln Lys Leu Ile Glu Lys Asn
                485                 490                 495

Gly Phe Pro Pro Leu Pro Glu Asn Gln Pro Leu Glu Gly Thr Phe Pro
            500                 505                 510

Cys Asp Phe Ala Trp Gly Val Val Asp Asn Tyr Ile Gln Val Asp Thr
        515                 520                 525

Thr Leu Ser Gln Phe Thr Asp Leu Asn Val Tyr Leu Trp Asp Val His
    530                 535                 540

His Ser Lys Arg Leu Ile Lys Val Asp Gly Val Val Thr Lys Lys Arg
545                 550                 555                 560

Lys Ser Tyr Cys Val Asp Phe Ala Ala Ile Gln Pro Gln Ile Ala Leu
                565                 570                 575

Leu Gln Glu Met His Val Thr His Phe Arg Phe Ser Leu Asp Trp Ala
            580                 585                 590

Leu Ile Leu Pro Leu Gly Asn Gln Ser Gln Val Asn His Thr Ile Leu
        595                 600                 605

Gln Tyr Tyr Arg Cys Met Ala Ser Glu Leu Val Arg Val Asn Ile Thr
    610                 615                 620

Pro Val Val Ala Leu Trp Gln Pro Met Ala Pro Asn Gln Gly Leu Pro
625                 630                 635                 640

Arg Leu Leu Ala Arg Gln Gly Ala Trp Glu Asn Pro Tyr Thr Ala Leu
                645                 650                 655

Ala Phe Ala Glu Tyr Ala Arg Leu Cys Phe Gln Glu Leu Gly His His
            660                 665                 670

Val Lys Leu Trp Ile Thr Met Asn Glu Pro Tyr Thr Arg Asn Met Thr
        675                 680                 685

Tyr Ser Ala Gly His Asn Leu Leu Lys Ala His Ala Leu Ala Trp His
    690                 695                 700

Val Tyr Asn Glu Lys Phe Arg His Ala Gln Asn Gly Lys Ile Ser Ile
705                 710                 715                 720

Ala Leu Gln Ala Asp Trp Ile Glu Pro Ala Cys Pro Phe Ser Gln Lys
                725                 730                 735

Asp Lys Glu Val Ala Glu Arg Val Leu Glu Phe Asp Ile Gly Trp Leu
            740                 745                 750

Ala Glu Pro Ile Phe Gly Ser Gly Asp Tyr Pro Trp Val Met Arg Asp
        755                 760                 765

Trp Leu Asn Gln Arg Asn Asn Phe Leu Leu Pro Tyr Phe Thr Glu Asp
    770                 775                 780

Glu Lys Lys Leu Ile Gln Gly Thr Phe Asp Phe Leu Ala Leu Ser His
785                 790                 795                 800

Tyr Thr Thr Ile Leu Val Asp Ser Glu Lys Glu Asp Pro Ile Lys Tyr
                805                 810                 815

Asn Asp Tyr Leu Glu Val Gln Glu Met Thr Asp Ile Thr Trp Leu Asn
            820                 825                 830

Ser Pro Ser Gln Val Ala Val Val Pro Trp Gly Leu Arg Lys Val Leu
        835                 840                 845

Asn Trp Leu Lys Phe Lys Tyr Gly Asp Leu Pro Met Tyr Ile Ile Ser
    850                 855                 860

Asn Gly Ile Asp Asp Gly Leu His Ala Glu Asp Asp Gln Leu Arg Val
865                 870                 875                 880

Tyr Tyr Met Gln Asn Tyr Ile Asn Glu Ala Leu Lys Ala His Ile Leu
```

```
                885                 890                 895

Asp Gly Ile Asn Leu Cys Gly Tyr Phe Ala Tyr Ser Phe Asn Asp Arg
            900                 905                 910

Thr Ala Pro Arg Phe Gly Leu Tyr Arg Tyr Ala Ala Asp Gln Phe Glu
        915                 920                 925

Pro Lys Ala Ser Met Lys His Tyr Arg Lys Ile Ile Asp Ser Asn Gly
    930                 935                 940

Phe Pro Gly Pro Glu Thr Leu Glu Arg Phe Cys Pro Glu Glu Phe Thr
945                 950                 955                 960

Val Cys Thr Glu Cys Ser Phe Phe His Thr Arg Lys Ser Leu
                965                 970


<210> SEQ ID NO 46
<211> LENGTH: 4380
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 46

atgcccgcca gcgccccgcc gcgccgcccg cggccgccgc cgccgtcgct gtcgctgctg     60

ctggtgctgc tgggcctggg cggccgccgc ctgcgtgcgg agccgggcga cggcgcgcag    120

acctgggccc gtttctcgcg gcctcctgcc cccgaggccg cgggcctctt ccagggcacc    180

ttccccgacg gcttcctctg ggccgtgggc agcgccgcct accagaccga gggcggctgg    240

cagcagcacg gcaagggtgc gtccatctgg gatacgttca cccaccaccc cctggcaccc    300

ccgggagact cccggaacgc cagtctgccg ttgggcgccc cgtcgccgct gcagcccgcc    360

accggggacg tagccagcga cagctacaac aacgtcttcc gcgacacgga ggcgctgcgc    420

gagctcgggg tcactcacta ccgcttctcc atctcgtggg cgcgagtgct ccccaatggc    480

agcgcgggcg tccccaaccg cgaggggctg cgctactacc ggcgcctgct ggagcggctg    540

cgggagctgg gcgtgcagcc cgtggtcacc ctgtaccact gggacctgcc ccagcgcctg    600

caggacgcct acggcggctg ggccaaccgc gccctggccg accacttcag ggattacgcg    660

gagctctgct tccgccactt cggcggtcag gtcaagtact ggatcaccat cgacaacccc    720

tacgtggtgg cctggcacgg ctacgccacc gggcgcctgg cccccggcat ccggggcagc    780

ccgcggctcg ggtacctggt ggcgcacaac ctcctcctgg ctcatgccaa agtctggcat    840

ctctacaata cttctttccg tcccactcag ggaggtcagg tgtccattgc cctaagctct    900

cactggatca atcctcgaag aatgaccgac cacagcatca aagaatgtca aaaatctctg    960

gactttgtac taggttggtt tgccaaaccc gtatttattg atggtgacta tcccgagagc   1020

atgaagaata acctttcatc tattctgcct gattttactg aatctgagaa aaagttcatc   1080

aaaggaactg ctgacttttt tgctctttgc tttggaccca ccttgagttt tcaacttttg   1140

gaccctcaca tgaagttccg ccaattggaa tctcccaacc tgaggcaact gctttcctgg   1200

attgaccttg aatttaacca tcctcaaata tttattgtgg aaaatggctg gtttgtctca   1260

gggaccacca agagagatga tgccaaatat atgtattacc tcaaaaagtt catcatggaa   1320

accttaaaag ccatcaagct ggatggggtg gatgtcatcg ggtataccgc atggtccctc   1380

atggatggtt tcgagtggca cagaggttac agcatcaggc gtggactctt ctatgttgac   1440

tttctaagcc aggacaagat gttgttgcca aagtcttcag ccttgttcta ccaaaagctg   1500

atagagaaaa atggcttccc tcctttacct gaaaatcagc ccctagaagg gacatttccc   1560
```

```
tgtgactttg cttggggagt tgttgacaac tacattcaag tagataccac tctgtctcag   1620
tttaccgacc tgaatgttta cctgtgggat gtccaccaca gtaaaaggct tattaaagtg   1680
gatggggttg tgaccaagaa gaggaaatcc tactgtgttg actttgctgc catccagccc   1740
cagatcgctt tactccagga aatgcacgtt acacattttc gcttctccct ggactgggcc   1800
ctgattctcc ctctgggtaa ccagtcccag gtgaaccaca ccatcctgca gtactatcgc   1860
tgcatggcca gcgagcttgt ccgtgtcaac atcaccccag tggtggccct gtggcagcct   1920
atggccccga accaaggact gccgcgcctc ctggccaggc agggcgcctg ggagaacccc   1980
tacactgccc tggcctttgc agagtatgcc cgactgtgct ttcaagagct cggccatcac   2040
gtcaagcttt ggataacgat gaatgagccg tatacaagga atatgacata cagtgctggc   2100
cacaaccttc tgaaggccca tgccctggct tggcatgtgt acaatgaaaa gtttaggcat   2160
gctcagaatg ggaaaatatc catagccttg caggctgatt ggatagaacc tgcctgccct   2220
ttctcccaaa aggacaaaga ggtggccgag agagttttgg aatttgacat tggctggctg   2280
gctgagccca ttttcggctc tggagattat ccatgggtga tgagggactg gctgaaccaa   2340
agaaacaatt ttcttcttcc ttatttcact gaagatgaaa aaaagctaat ccagggtacc   2400
tttgactttt tggctttaag ccattatacc accatccttg tagactcaga aaaagaagat   2460
ccaataaaat acaatgatta cctagaagtg caagaaatga ccgacatcac gtggctcaac   2520
tcccccagtc aggtggcggt agtgccctgg gggttgcgca aagtgctgaa ctggctgaag   2580
ttcaagtacg gagacctccc catgtacata atatccaacg gaatcgatga cgggctgcat   2640
gctgaggacg accagctgag ggtgtattat atgcagaatt acataaacga agctctcaaa   2700
gcccacatac tggatggtat caatctttgc ggatactttg cttattcgtt taacgaccgc   2760
acagctccga ggtttggcct ctatcgttat gctgcagatc agtttgagcc caaggcatcc   2820
atgaaacatt acaggaaaat tattgacagc aatggtttcc cgggcccaga aactctggaa   2880
agattttgtc cagaagaatt caccgtgtgt actgagtgca gtttttttca cacccgaaag   2940
tctttaggat ccggaggtgg aggttcagga ggtggaggtt caggaggtgg aggttcactt   3000
aagtatccca atgcctcccc actgctcggc tccagctggg gtggcctgat ccacctgtac   3060
acagccacag ccaggaacag ctaccacctg cagatccaca agaatggcca tgtggatggc   3120
gcaccccatc agaccatcta cagtgccctg atgatcagat cagaggatgc tggctttgtg   3180
gtgattacag gtgtgatgag cagaagatac ctctgcatgg atttcagagg caacattttt   3240
ggatcacact atttcgaccc ggagaactgc aggttccaac accagacgct ggaaaacggg   3300
tacgacgtct accactctcc tcagtatcac ttcctggtca gtctgggccg ggcgaagaga   3360
gccttcctgc caggcatgaa cccacccccg tactcccagt tcctgtcccg gaggaacgag   3420
atcccccctaa ttcacttcaa cacccccata ccacggcggc acacccagag cgccgaggac   3480
gactcggagc gggacccccct gaacgtgctg aagccccggg cccggatgac cccggccccg   3540
gcctcctgtt cacaggagct cccgagcgcc gaggacaaca gcccgatggc cagtgaccca   3600
ttaggggtgg tcaggggcgg tcgagtgaac acgcacgctg gggaacggg cccggaaggc   3660
tgccgcccct tcgccaagtt catcggaggt ggaggttcaa aaacccacac gtgtcctcct   3720
tgtcctgccc cagaagcagc aggtggtcca tcagtttttc ttttccctcc caaacccaag   3780
gatacgctga tgatctctcg cacgcctgag gtgacatgcg tcgtagtaga cgtgagccac   3840
gaagatcccg aggtgaagtt caattggtat gtggacggag tagaagtgca taacgcgaaa   3900
```

```
actaagccgc gcgaggaaca atataacagt acttacaggg tggtatccgt gctcacagtc   3960

ctgcaccagg actggctgaa cggtaaggaa tacaagtgca aagtaagcaa caaggcactt   4020

cccgcgccta ttgagaaaac aatctccaag gcgaagggac aaccaagaga acctcaggtt   4080

tacactctcc cgccttccag ggaagagatg accaaaaatc aagtttccct gacttgcctc   4140

gtcaaaggat tctacccttc cgacattgct gttgaatggg aaagcaatgg acaaccagag   4200

aacaactaca agacaacacc cccggtgctg gatagtgacg gatctttctt tctctactca   4260

aagctgaccg tggataagtc caggtggcag cagggaaacg tgttttcctg ctctgtcatg   4320

catgaagcgc tgcataatca ctatacccag aagtctctga gcttgagccc aggcaagtaa   4380
```

```
<210> SEQ ID NO 47
<211> LENGTH: 1459
<212> TYPE: PRT
<213> ORGANISM: Artificial Sequence
<220> FEATURE:
<223> OTHER INFORMATION: Description of Artificial Sequence: Synthetic
      fusion polypeptide derived from human

<400> SEQUENCE: 47

Met Pro Ala Ser Ala Pro Pro Arg Arg Pro Arg Pro Pro Pro Pro Ser
1               5                   10                  15

Leu Ser Leu Leu Leu Val Leu Leu Gly Leu Gly Gly Arg Arg Leu Arg
            20                  25                  30

Ala Glu Pro Gly Asp Gly Ala Gln Thr Trp Ala Arg Phe Ser Arg Pro
        35                  40                  45

Pro Ala Pro Glu Ala Ala Gly Leu Phe Gln Gly Thr Phe Pro Asp Gly
    50                  55                  60

Phe Leu Trp Ala Val Gly Ser Ala Ala Tyr Gln Thr Glu Gly Gly Trp
65                  70                  75                  80

Gln Gln His Gly Lys Gly Ala Ser Ile Trp Asp Thr Phe Thr His His
                85                  90                  95

Pro Leu Ala Pro Pro Gly Asp Ser Arg Asn Ala Ser Leu Pro Leu Gly
            100                 105                 110

Ala Pro Ser Pro Leu Gln Pro Ala Thr Gly Asp Val Ala Ser Asp Ser
        115                 120                 125

Tyr Asn Asn Val Phe Arg Asp Thr Glu Ala Leu Arg Glu Leu Gly Val
    130                 135                 140

Thr His Tyr Arg Phe Ser Ile Ser Trp Ala Arg Val Leu Pro Asn Gly
145                 150                 155                 160

Ser Ala Gly Val Pro Asn Arg Glu Gly Leu Arg Tyr Tyr Arg Arg Leu
                165                 170                 175

Leu Glu Arg Leu Arg Glu Leu Gly Val Gln Pro Val Val Thr Leu Tyr
            180                 185                 190

His Trp Asp Leu Pro Gln Arg Leu Gln Asp Ala Tyr Gly Gly Trp Ala
        195                 200                 205

Asn Arg Ala Leu Ala Asp His Phe Arg Asp Tyr Ala Glu Leu Cys Phe
    210                 215                 220

Arg His Phe Gly Gly Gln Val Lys Tyr Trp Ile Thr Ile Asp Asn Pro
225                 230                 235                 240

Tyr Val Val Ala Trp His Gly Tyr Ala Thr Gly Arg Leu Ala Pro Gly
                245                 250                 255

Ile Arg Gly Ser Pro Arg Leu Gly Tyr Leu Val Ala His Asn Leu Leu
            260                 265                 270

Leu Ala His Ala Lys Val Trp His Leu Tyr Asn Thr Ser Phe Arg Pro
```

```
        275                 280                 285

Thr Gln Gly Gly Gln Val Ser Ile Ala Leu Ser Ser His Trp Ile Asn
    290                 295                 300

Pro Arg Arg Met Thr Asp His Ser Ile Lys Glu Cys Gln Lys Ser Leu
305                 310                 315                 320

Asp Phe Val Leu Gly Trp Phe Ala Lys Pro Val Phe Ile Asp Gly Asp
                325                 330                 335

Tyr Pro Glu Ser Met Lys Asn Asn Leu Ser Ser Ile Leu Pro Asp Phe
            340                 345                 350

Thr Glu Ser Glu Lys Lys Phe Ile Lys Gly Thr Ala Asp Phe Phe Ala
        355                 360                 365

Leu Cys Phe Gly Pro Thr Leu Ser Phe Gln Leu Leu Asp Pro His Met
    370                 375                 380

Lys Phe Arg Gln Leu Glu Ser Pro Asn Leu Arg Gln Leu Leu Ser Trp
385                 390                 395                 400

Ile Asp Leu Glu Phe Asn His Pro Gln Ile Phe Ile Val Glu Asn Gly
                405                 410                 415

Trp Phe Val Ser Gly Thr Thr Lys Arg Asp Asp Ala Lys Tyr Met Tyr
            420                 425                 430

Tyr Leu Lys Lys Phe Ile Met Glu Thr Leu Lys Ala Ile Lys Leu Asp
        435                 440                 445

Gly Val Asp Val Ile Gly Tyr Thr Ala Trp Ser Leu Met Asp Gly Phe
    450                 455                 460

Glu Trp His Arg Gly Tyr Ser Ile Arg Arg Gly Leu Phe Tyr Val Asp
465                 470                 475                 480

Phe Leu Ser Gln Asp Lys Met Leu Leu Pro Lys Ser Ser Ala Leu Phe
                485                 490                 495

Tyr Gln Lys Leu Ile Glu Lys Asn Gly Phe Pro Pro Leu Pro Glu Asn
            500                 505                 510

Gln Pro Leu Glu Gly Thr Phe Pro Cys Asp Phe Ala Trp Gly Val Val
        515                 520                 525

Asp Asn Tyr Ile Gln Val Asp Thr Thr Leu Ser Gln Phe Thr Asp Leu
    530                 535                 540

Asn Val Tyr Leu Trp Asp Val His His Ser Lys Arg Leu Ile Lys Val
545                 550                 555                 560

Asp Gly Val Val Thr Lys Lys Arg Lys Ser Tyr Cys Val Asp Phe Ala
                565                 570                 575

Ala Ile Gln Pro Gln Ile Ala Leu Leu Gln Glu Met His Val Thr His
            580                 585                 590

Phe Arg Phe Ser Leu Asp Trp Ala Leu Ile Leu Pro Leu Gly Asn Gln
        595                 600                 605

Ser Gln Val Asn His Thr Ile Leu Gln Tyr Tyr Arg Cys Met Ala Ser
    610                 615                 620

Glu Leu Val Arg Val Asn Ile Thr Pro Val Val Ala Leu Trp Gln Pro
625                 630                 635                 640

Met Ala Pro Asn Gln Gly Leu Pro Arg Leu Leu Ala Arg Gln Gly Ala
                645                 650                 655

Trp Glu Asn Pro Tyr Thr Ala Leu Ala Phe Ala Glu Tyr Ala Arg Leu
            660                 665                 670

Cys Phe Gln Glu Leu Gly His His Val Lys Leu Trp Ile Thr Met Asn
        675                 680                 685

Glu Pro Tyr Thr Arg Asn Met Thr Tyr Ser Ala Gly His Asn Leu Leu
    690                 695                 700
```

```
Lys Ala His Ala Leu Ala Trp His Val Tyr Asn Glu Lys Phe Arg His
705                 710                 715                 720

Ala Gln Asn Gly Lys Ile Ser Ile Ala Leu Gln Ala Asp Trp Ile Glu
                725                 730                 735

Pro Ala Cys Pro Phe Ser Gln Lys Asp Lys Glu Val Ala Glu Arg Val
            740                 745                 750

Leu Glu Phe Asp Ile Gly Trp Leu Ala Glu Pro Ile Phe Gly Ser Gly
        755                 760                 765

Asp Tyr Pro Trp Val Met Arg Asp Trp Leu Asn Gln Arg Asn Asn Phe
    770                 775                 780

Leu Leu Pro Tyr Phe Thr Glu Asp Glu Lys Lys Leu Ile Gln Gly Thr
785                 790                 795                 800

Phe Asp Phe Leu Ala Leu Ser His Tyr Thr Thr Ile Leu Val Asp Ser
                805                 810                 815

Glu Lys Glu Asp Pro Ile Lys Tyr Asn Asp Tyr Leu Glu Val Gln Glu
            820                 825                 830

Met Thr Asp Ile Thr Trp Leu Asn Ser Pro Ser Gln Val Ala Val Val
        835                 840                 845

Pro Trp Gly Leu Arg Lys Val Leu Asn Trp Leu Lys Phe Lys Tyr Gly
    850                 855                 860

Asp Leu Pro Met Tyr Ile Ile Ser Asn Gly Ile Asp Asp Gly Leu His
865                 870                 875                 880

Ala Glu Asp Asp Gln Leu Arg Val Tyr Tyr Met Gln Asn Tyr Ile Asn
                885                 890                 895

Glu Ala Leu Lys Ala His Ile Leu Asp Gly Ile Asn Leu Cys Gly Tyr
            900                 905                 910

Phe Ala Tyr Ser Phe Asn Asp Arg Thr Ala Pro Arg Phe Gly Leu Tyr
        915                 920                 925

Arg Tyr Ala Ala Asp Gln Phe Glu Pro Lys Ala Ser Met Lys His Tyr
    930                 935                 940

Arg Lys Ile Ile Asp Ser Asn Gly Phe Pro Gly Pro Glu Thr Leu Glu
945                 950                 955                 960

Arg Phe Cys Pro Glu Glu Phe Thr Val Cys Thr Glu Cys Ser Phe Phe
                965                 970                 975

His Thr Arg Lys Ser Leu Gly Ser Gly Gly Gly Gly Ser Gly Gly Gly
            980                 985                 990

Gly Ser Gly Gly Gly Gly Ser Leu  Lys Tyr Pro Asn Ala  Ser Pro Leu
        995                 1000                1005

Leu Gly  Ser Ser Trp Gly Gly  Leu Ile His Leu Tyr  Thr Ala Thr
    1010                1015                1020

Ala Arg  Asn Ser Tyr His Leu  Gln Ile His Lys Asn  Gly His Val
    1025                1030                1035

Asp Gly  Ala Pro His Gln Thr  Ile Tyr Ser Ala Leu  Met Ile Arg
    1040                1045                1050

Ser Glu  Asp Ala Gly Phe Val  Val Ile Thr Gly Val  Met Ser Arg
    1055                1060                1065

Arg Tyr  Leu Cys Met Asp Phe  Arg Gly Asn Ile Phe  Gly Ser His
    1070                1075                1080

Tyr Phe  Asp Pro Glu Asn Cys  Arg Phe Gln His Gln  Thr Leu Glu
    1085                1090                1095

Asn Gly  Tyr Asp Val Tyr His  Ser Pro Gln Tyr His  Phe Leu Val
    1100                1105                1110
```

```
Ser Leu  Gly Arg Ala Lys Arg  Ala Phe Leu Pro Gly  Met Asn Pro
    1115                 1120                 1125

Pro Pro  Tyr Ser Gln Phe Leu  Ser Arg Arg Asn Glu  Ile Pro Leu
    1130                 1135                 1140

Ile His  Phe Asn Thr Pro Ile  Pro Arg Arg His Thr  Gln Ser Ala
    1145                 1150                 1155

Glu Asp  Asp Ser Glu Arg Asp  Pro Leu Asn Val Leu  Lys Pro Arg
    1160                 1165                 1170

Ala Arg  Met Thr Pro Ala Pro  Ala Ser Cys Ser Gln  Glu Leu Pro
    1175                 1180                 1185

Ser Ala  Glu Asp Asn Ser Pro  Met Ala Ser Asp Pro  Leu Gly Val
    1190                 1195                 1200

Val Arg  Gly Gly Arg Val Asn  Thr His Ala Gly Gly  Thr Gly Pro
    1205                 1210                 1215

Glu Gly  Cys Arg Pro Phe Ala  Lys Phe Ile Gly Gly  Gly Gly Ser
    1220                 1225                 1230

Lys Thr  His Thr Cys Pro Pro  Cys Pro Ala Pro Glu  Ala Ala Gly
    1235                 1240                 1245

Gly Pro  Ser Val Phe Leu Phe  Pro Pro Lys Pro Lys  Asp Thr Leu
    1250                 1255                 1260

Met Ile  Ser Arg Thr Pro Glu  Val Thr Cys Val Val  Val Asp Val
    1265                 1270                 1275

Ser His  Glu Asp Pro Glu Val  Lys Phe Asn Trp Tyr  Val Asp Gly
    1280                 1285                 1290

Val Glu  Val His Asn Ala Lys  Thr Lys Pro Arg Glu  Glu Gln Tyr
    1295                 1300                 1305

Asn Ser  Thr Tyr Arg Val Val  Ser Val Leu Thr Val  Leu His Gln
    1310                 1315                 1320

Asp Trp  Leu Asn Gly Lys Glu  Tyr Lys Cys Lys Val  Ser Asn Lys
    1325                 1330                 1335

Ala Leu  Pro Ala Pro Ile Glu  Lys Thr Ile Ser Lys  Ala Lys Gly
    1340                 1345                 1350

Gln Pro  Arg Glu Pro Gln Val  Tyr Thr Leu Pro Pro  Ser Arg Glu
    1355                 1360                 1365

Glu Met  Thr Lys Asn Gln Val  Ser Leu Thr Cys Leu  Val Lys Gly
    1370                 1375                 1380

Phe Tyr  Pro Ser Asp Ile Ala  Val Glu Trp Glu Ser  Asn Gly Gln
    1385                 1390                 1395

Pro Glu  Asn Asn Tyr Lys Thr  Thr Pro Pro Val Leu  Asp Ser Asp
    1400                 1405                 1410

Gly Ser  Phe Phe Leu Tyr Ser  Lys Leu Thr Val Asp  Lys Ser Arg
    1415                 1420                 1425

Trp Gln  Gln Gly Asn Val Phe  Ser Cys Ser Val Met  His Glu Ala
    1430                 1435                 1440

Leu His  Asn His Tyr Thr Gln  Lys Ser Leu Ser Leu  Ser Pro Gly
    1445                 1450                 1455

Lys
```

<210> SEQ ID NO 48
<211> LENGTH: 4353
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 48

```
atgcccgcca gcgccccgcc gcgccgcccg cggccgccgc cgccgtcgct gtcgctgctg     60
ctggtgctgc tgggcctggg cggccgccgc ctgcgtgcgg agccgggcga cggcgcgcag    120
acctgggccc gtttctcgcg gcctcctgcc cccgaggccg cgggcctctt ccagggcacc    180
ttccccgacg gcttcctctg ggccgtgggc agcgccgcct accagaccga gggcggctgg    240
cagcagcacg gcaagggtgc gtccatctgg gatacgttca cccaccaccc cctggcaccc    300
ccgggagact cccggaacgc cagtctgccg ttgggcgccc cgtcgccgct gcagcccgcc    360
accggggacg tagccagcga cagctacaac aacgtcttcc gcgacacgga ggcgctgcgc    420
gagctcgggg tcactcacta ccgcttctcc atctcgtggg cgcgagtgct ccccaatggc    480
agcgcgggcg tccccaaccg cgaggggctg cgctactacc ggcgcctgct ggagcggctg    540
cgggagctgg gcgtgcagcc cgtggtcacc ctgtaccact gggacctgcc ccagcgcctg    600
caggacgcct acggcggctg ggccaaccgc gccctggccg accacttcag ggattacgcg    660
gagctctgct tccgccactt cggcggtcag gtcaagtact ggatcaccat cgacaacccc    720
tacgtggtgg cctggcacgg ctacgccacc gggcgcctgg cccccggcat ccggggcagc    780
ccgcggctcg ggtacctggt ggcgcacaac ctcctcctgg ctcatgccaa agtctggcat    840
ctctacaata cttctttccg tcccactcag ggaggtcagg tgtccattgc cctaagctct    900
cactggatca atcctcgaag aatgaccgac cacagcatca aagaatgtca aaaatctctg    960
gactttgtac taggttggtt tgccaaaccc gtatttattg atggtgacta tcccgagagc   1020
atgaagaata acctttcatc tattctgcct gattttactg aatctgagaa aaagttcatc   1080
aaaggaactg ctgacttttt tgctctttgc tttggaccca ccttgagttt tcaacttttg   1140
gaccctcaca tgaagttccg ccaattggaa tctcccaacc tgaggcaact gctttcctgg   1200
attgaccttg aatttaacca tcctcaaata tttattgtgg aaaatggctg gtttgtctca   1260
gggaccacca agagagatga tgccaaatat atgtattacc tcaaaaagtt catcatggaa   1320
accttaaaag ccatcaagct ggatggggtg gatgtcatcg ggtataccgc atggtccctc   1380
atggatggtt tcgagtggca cagaggttac agcatcaggc gtggactctt ctatgttgac   1440
tttctaagcc aggacaagat gttgttgcca aagtcttcag ccttgttcta ccaaaagctg   1500
atagagaaaa atggcttccc tcctttacct gaaaatcagc ccctagaagg gacatttccc   1560
tgtgactttg cttggggagt tgttgacaac tacattcaag tagataccac tctgtctcag   1620
tttaccgacc tgaatgttta cctgtgggat gtccaccaca gtaaaaggct tattaaagtg   1680
gatggggttg tgaccaagaa gaggaaatcc tactgtgttg actttgctgc catccagccc   1740
cagatcgctt tactccagga aatgcacgtt acacattttc gcttctccct ggactgggcc   1800
ctgattctcc ctctgggtaa ccagtcccag gtgaaccaca ccatcctgca gtactatcgc   1860
tgcatggcca gcgagcttgt ccgtgtcaac atcaccccag tggtggccct gtggcagcct   1920
atggccccga accaaggact gccgcgcctc ctggccaggc agggcgcctg ggagaacccc   1980
tacactgccc tggcctttgc agagtatgcc cgactgtgct ttcaagagct cggccatcac   2040
gtcaagcttt ggataacgat gaatgagccg tatacaagga atatgacata cagtgctggc   2100
cacaaccttc tgaaggccca tgccctggct tggcatgtgt acaatgaaaa gtttaggcat   2160
gctcagaatg ggaaaatatc catagccttg caggctgatt ggatagaacc tgcctgccct   2220
ttctcccaaa aggacaaaga ggtggccgag agagttttgg aatttgacat tggctggctg   2280
```

```
gctgagccca ttttcggctc tggagattat ccatgggtga tgagggactg gctgaaccaa   2340

agaaacaatt ttcttcttcc ttatttcact gaagatgaaa aaaagctaat ccagggtacc   2400

tttgactttt tggctttaag ccattatacc accatccttg tagactcaga aaaagaagat   2460

ccaataaaat acaatgatta cctagaagtg caagaaatga ccgacatcac gtggctcaac   2520

tcccccagtc aggtggcggt agtgccctgg gggttgcgca aagtgctgaa ctggctgaag   2580

ttcaagtacg gagacctccc catgtacata atatccaacg gaatcgatga cgggctgcat   2640

gctgaggacg accagctgag ggtgtattat atgcagaatt acataaacga agctctcaaa   2700

gcccacatac tggatggtat caatctttgc ggatactttg cttattcgtt taacgaccgc   2760

acagctccga ggtttggcct ctatcgttat gctgcagatc agtttgagcc caaggcatcc   2820

atgaaacatt acaggaaaat tattgacagc aatggtttcc cgggcccaga aactctggaa   2880

agattttgtc cagaagaatt caccgtgtgt actgagtgca gtttttttca cacccgaaag   2940

tctttaggat ccggaggtgg aggttcagga ggtggaggtt caggaggtgg aggttcactt   3000

aagtatccca atgcctcccc actgctcggc tccagctggg gtggcctgat ccacctgtac   3060

acagccacag ccaggaacag ctaccacctg cagatccaca agaatggcca tgtggatggc   3120

gcaccccatc agaccatcta cagtgccctg atgatcagat cagaggatgc tggctttgtg   3180

gtgattacag gtgtgatgag cagaagatac ctctgcatgg atttcagagg caacattttt   3240

ggatcacact atttcgaccc ggagaactgc aggttccaac accagacgct ggaaaacggg   3300

tacgacgtct accactctcc tcagtatcac ttcctggtca gtctgggccg ggcgaagaga   3360

gccttcctgc caggcatgaa cccacccccg tactcccagt tcctgtcccg gaggaacgag   3420

atccccctaa ttcacttcaa cacccccata ccacggcggc acacccagag cgccgaggac   3480

gactcggagc gggacccccct gaacgtgctg aagccccggg cccggatgac cccggccccg   3540

gcctcctgtt cacaggagct cccgagcgcc gaggacaaca gcccgatggc cagtgaccca   3600

ttaggggtgg tcaggggcgg tcgagtgaac acgcacgctg gggaacggg cccggaaggc   3660

tgccgcccct tcgccaagtt catcggaggt ggaggttcag ccccagaagc agcaggtggt   3720

ccatcagttt ttcttttccc tcccaaaccc aaggatacgc tgatgatctc tcgcacgcct   3780

gaggtgacat gcgtcgtagt agacgtgagc cacgaagatc ccgaggtgaa gttcaattgg   3840

tatgtggacg gagtagaagt gcataacgcg aaaactaagc cgcgcgagga acaatataac   3900

agtacttaca gggtggtatc cgtgctcaca gtcctgcacc aggactggct gaacggtaag   3960

gaatacaagt gcaaagtaag caacaaggca cttcccgcgc ctattgagaa aacaatctcc   4020

aaggcgaagg gacaaccaag agaacctcag gtttacactc tcccgccttc cagggaagag   4080

atgaccaaaa atcaagtttc cctgacttgc ctcgtcaaag gattctaccc ttccgacatt   4140

gctgttgaat gggaaagcaa tggacaacca gagaacaact acaagacaac acccccggtg   4200

ctggatagtg acggatcttt ctttctctac tcaaagctga ccgtggataa gtccaggtgg   4260

cagcagggaa acgtgttttc ctgctctgtc atgcatgaag cgctgcataa tcactatacc   4320

cagaagtctc tgagcttgag cccaggcaag taa                                4353
```

<210> SEQ ID NO 49
<211> LENGTH: 1450
<212> TYPE: PRT
<213> ORGANISM: Artificial Sequence
<220> FEATURE:
<223> OTHER INFORMATION: Description of Artificial Sequence: Synthetic fusion polypeptide derived from human

<400> SEQUENCE: 49

```
Met Pro Ala Ser Ala Pro Pro Arg Arg Pro Arg Pro Pro Pro Pro Ser
1               5                   10                  15

Leu Ser Leu Leu Leu Val Leu Leu Gly Leu Gly Gly Arg Arg Leu Arg
            20                  25                  30

Ala Glu Pro Gly Asp Gly Ala Gln Thr Trp Ala Arg Phe Ser Arg Pro
        35                  40                  45

Pro Ala Pro Glu Ala Ala Gly Leu Phe Gln Gly Thr Phe Pro Asp Gly
    50                  55                  60

Phe Leu Trp Ala Val Gly Ser Ala Ala Tyr Gln Thr Glu Gly Gly Trp
65                  70                  75                  80

Gln Gln His Gly Lys Gly Ala Ser Ile Trp Asp Thr Phe Thr His His
                85                  90                  95

Pro Leu Ala Pro Pro Gly Asp Ser Arg Asn Ala Ser Leu Pro Leu Gly
            100                 105                 110

Ala Pro Ser Pro Leu Gln Pro Ala Thr Gly Asp Val Ala Ser Asp Ser
        115                 120                 125

Tyr Asn Asn Val Phe Arg Asp Thr Glu Ala Leu Arg Glu Leu Gly Val
    130                 135                 140

Thr His Tyr Arg Phe Ser Ile Ser Trp Ala Arg Val Leu Pro Asn Gly
145                 150                 155                 160

Ser Ala Gly Val Pro Asn Arg Glu Gly Leu Arg Tyr Tyr Arg Arg Leu
                165                 170                 175

Leu Glu Arg Leu Arg Glu Leu Gly Val Gln Pro Val Val Thr Leu Tyr
            180                 185                 190

His Trp Asp Leu Pro Gln Arg Leu Gln Asp Ala Tyr Gly Gly Trp Ala
        195                 200                 205

Asn Arg Ala Leu Ala Asp His Phe Arg Asp Tyr Ala Glu Leu Cys Phe
    210                 215                 220

Arg His Phe Gly Gly Gln Val Lys Tyr Trp Ile Thr Ile Asp Asn Pro
225                 230                 235                 240

Tyr Val Val Ala Trp His Gly Tyr Ala Thr Gly Arg Leu Ala Pro Gly
                245                 250                 255

Ile Arg Gly Ser Pro Arg Leu Gly Tyr Leu Val Ala His Asn Leu Leu
            260                 265                 270

Leu Ala His Ala Lys Val Trp His Leu Tyr Asn Thr Ser Phe Arg Pro
        275                 280                 285

Thr Gln Gly Gly Gln Val Ser Ile Ala Leu Ser Ser His Trp Ile Asn
    290                 295                 300

Pro Arg Arg Met Thr Asp His Ser Ile Lys Glu Cys Gln Lys Ser Leu
305                 310                 315                 320

Asp Phe Val Leu Gly Trp Phe Ala Lys Pro Val Phe Ile Asp Gly Asp
                325                 330                 335

Tyr Pro Glu Ser Met Lys Asn Asn Leu Ser Ser Ile Leu Pro Asp Phe
            340                 345                 350

Thr Glu Ser Glu Lys Lys Phe Ile Lys Gly Thr Ala Asp Phe Phe Ala
        355                 360                 365

Leu Cys Phe Gly Pro Thr Leu Ser Phe Gln Leu Leu Asp Pro His Met
    370                 375                 380

Lys Phe Arg Gln Leu Glu Ser Pro Asn Leu Arg Gln Leu Leu Ser Trp
385                 390                 395                 400

Ile Asp Leu Glu Phe Asn His Pro Gln Ile Phe Ile Val Glu Asn Gly
                405                 410                 415
```

```
Trp Phe Val Ser Gly Thr Thr Lys Arg Asp Asp Ala Lys Tyr Met Tyr
            420                 425                 430

Tyr Leu Lys Lys Phe Ile Met Glu Thr Leu Lys Ala Ile Lys Leu Asp
        435                 440                 445

Gly Val Asp Val Ile Gly Tyr Thr Ala Trp Ser Leu Met Asp Gly Phe
    450                 455                 460

Glu Trp His Arg Gly Tyr Ser Ile Arg Arg Gly Leu Phe Tyr Val Asp
465                 470                 475                 480

Phe Leu Ser Gln Asp Lys Met Leu Leu Pro Lys Ser Ser Ala Leu Phe
                485                 490                 495

Tyr Gln Lys Leu Ile Glu Lys Asn Gly Phe Pro Pro Leu Pro Glu Asn
            500                 505                 510

Gln Pro Leu Glu Gly Thr Phe Pro Cys Asp Phe Ala Trp Gly Val Val
        515                 520                 525

Asp Asn Tyr Ile Gln Val Asp Thr Thr Leu Ser Gln Phe Thr Asp Leu
    530                 535                 540

Asn Val Tyr Leu Trp Asp Val His His Ser Lys Arg Leu Ile Lys Val
545                 550                 555                 560

Asp Gly Val Val Thr Lys Lys Arg Lys Ser Tyr Cys Val Asp Phe Ala
                565                 570                 575

Ala Ile Gln Pro Gln Ile Ala Leu Leu Gln Glu Met His Val Thr His
            580                 585                 590

Phe Arg Phe Ser Leu Asp Trp Ala Leu Ile Leu Pro Leu Gly Asn Gln
        595                 600                 605

Ser Gln Val Asn His Thr Ile Leu Gln Tyr Tyr Arg Cys Met Ala Ser
    610                 615                 620

Glu Leu Val Arg Val Asn Ile Thr Pro Val Val Ala Leu Trp Gln Pro
625                 630                 635                 640

Met Ala Pro Asn Gln Gly Leu Pro Arg Leu Leu Ala Arg Gln Gly Ala
                645                 650                 655

Trp Glu Asn Pro Tyr Thr Ala Leu Ala Phe Ala Glu Tyr Ala Arg Leu
            660                 665                 670

Cys Phe Gln Glu Leu Gly His His Val Lys Leu Trp Ile Thr Met Asn
        675                 680                 685

Glu Pro Tyr Thr Arg Asn Met Thr Tyr Ser Ala Gly His Asn Leu Leu
    690                 695                 700

Lys Ala His Ala Leu Ala Trp His Val Tyr Asn Glu Lys Phe Arg His
705                 710                 715                 720

Ala Gln Asn Gly Lys Ile Ser Ile Ala Leu Gln Ala Asp Trp Ile Glu
                725                 730                 735

Pro Ala Cys Pro Phe Ser Gln Lys Asp Lys Glu Val Ala Glu Arg Val
            740                 745                 750

Leu Glu Phe Asp Ile Gly Trp Leu Ala Glu Pro Ile Phe Gly Ser Gly
        755                 760                 765

Asp Tyr Pro Trp Val Met Arg Asp Trp Leu Asn Gln Arg Asn Asn Phe
    770                 775                 780

Leu Leu Pro Tyr Phe Thr Glu Asp Glu Lys Lys Leu Ile Gln Gly Thr
785                 790                 795                 800

Phe Asp Phe Leu Ala Leu Ser His Tyr Thr Thr Ile Leu Val Asp Ser
                805                 810                 815

Glu Lys Glu Asp Pro Ile Lys Tyr Asn Asp Tyr Leu Glu Val Gln Glu
            820                 825                 830
```

```
Met Thr Asp Ile Thr Trp Leu Asn Ser Pro Ser Gln Val Ala Val Val
        835                 840                 845

Pro Trp Gly Leu Arg Lys Val Leu Asn Trp Leu Lys Phe Lys Tyr Gly
    850                 855                 860

Asp Leu Pro Met Tyr Ile Ile Ser Asn Gly Ile Asp Asp Gly Leu His
865                 870                 875                 880

Ala Glu Asp Asp Gln Leu Arg Val Tyr Tyr Met Gln Asn Tyr Ile Asn
                885                 890                 895

Glu Ala Leu Lys Ala His Ile Leu Asp Gly Ile Asn Leu Cys Gly Tyr
            900                 905                 910

Phe Ala Tyr Ser Phe Asn Asp Arg Thr Ala Pro Arg Phe Gly Leu Tyr
        915                 920                 925

Arg Tyr Ala Ala Asp Gln Phe Glu Pro Lys Ala Ser Met Lys His Tyr
    930                 935                 940

Arg Lys Ile Ile Asp Ser Asn Gly Phe Pro Gly Pro Glu Thr Leu Glu
945                 950                 955                 960

Arg Phe Cys Pro Glu Glu Phe Thr Val Cys Thr Glu Cys Ser Phe Phe
                965                 970                 975

His Thr Arg Lys Ser Leu Gly Ser Gly Gly Gly Gly Ser Gly Gly Gly
            980                 985                 990

Gly Ser Gly Gly Gly Gly Ser Leu  Lys Tyr Pro Asn Ala  Ser Pro Leu
        995                 1000                1005

Leu Gly  Ser Ser Trp Gly Gly  Leu Ile His Leu Tyr  Thr Ala Thr
    1010                1015                1020

Ala Arg  Asn Ser Tyr His Leu  Gln Ile His Lys Asn  Gly His Val
    1025                1030                1035

Asp Gly  Ala Pro His Gln Thr  Ile Tyr Ser Ala Leu  Met Ile Arg
    1040                1045                1050

Ser Glu  Asp Ala Gly Phe Val  Val Ile Thr Gly Val  Met Ser Arg
    1055                1060                1065

Arg Tyr  Leu Cys Met Asp Phe  Arg Gly Asn Ile Phe  Gly Ser His
    1070                1075                1080

Tyr Phe  Asp Pro Glu Asn Cys  Arg Phe Gln His Gln  Thr Leu Glu
    1085                1090                1095

Asn Gly  Tyr Asp Val Tyr His  Ser Pro Gln Tyr His  Phe Leu Val
    1100                1105                1110

Ser Leu  Gly Arg Ala Lys Arg  Ala Phe Leu Pro Gly  Met Asn Pro
    1115                1120                1125

Pro Pro  Tyr Ser Gln Phe Leu  Ser Arg Arg Asn Glu  Ile Pro Leu
    1130                1135                1140

Ile His  Phe Asn Thr Pro Ile  Pro Arg Arg His Thr  Gln Ser Ala
    1145                1150                1155

Glu Asp  Asp Ser Glu Arg Asp  Pro Leu Asn Val Leu  Lys Pro Arg
    1160                1165                1170

Ala Arg  Met Thr Pro Ala Pro  Ala Ser Cys Ser Gln  Glu Leu Pro
    1175                1180                1185

Ser Ala  Glu Asp Asn Ser Pro  Met Ala Ser Asp Pro  Leu Gly Val
    1190                1195                1200

Val Arg  Gly Gly Arg Val Asn  Thr His Ala Gly Gly  Thr Gly Pro
    1205                1210                1215

Glu Gly  Cys Arg Pro Phe Ala  Lys Phe Ile Gly Gly  Gly Gly Ser
    1220                1225                1230

Ala Pro  Glu Ala Ala Gly Gly  Pro Ser Val Phe Leu  Phe Pro Pro
```

```
    1235                1240                1245

Lys Pro  Lys Asp Thr Leu Met  Ile Ser Arg Thr Pro  Glu Val Thr
    1250                1255                1260

Cys Val  Val Val Asp Val Ser  His Glu Asp Pro Glu  Val Lys Phe
    1265                1270                1275

Asn Trp  Tyr Val Asp Gly Val  Glu Val His Asn Ala  Lys Thr Lys
    1280                1285                1290

Pro Arg  Glu Glu Gln Tyr Asn  Ser Thr Tyr Arg Val  Val Ser Val
    1295                1300                1305

Leu Thr  Val Leu His Gln Asp  Trp Leu Asn Gly Lys  Glu Tyr Lys
    1310                1315                1320

Cys Lys  Val Ser Asn Lys Ala  Leu Pro Ala Pro Ile  Glu Lys Thr
    1325                1330                1335

Ile Ser  Lys Ala Lys Gly Gln  Pro Arg Glu Pro Gln  Val Tyr Thr
    1340                1345                1350

Leu Pro  Pro Ser Arg Glu Glu  Met Thr Lys Asn Gln  Val Ser Leu
    1355                1360                1365

Thr Cys  Leu Val Lys Gly Phe  Tyr Pro Ser Asp Ile  Ala Val Glu
    1370                1375                1380

Trp Glu  Ser Asn Gly Gln Pro  Glu Asn Asn Tyr Lys  Thr Thr Pro
    1385                1390                1395

Pro Val  Leu Asp Ser Asp Gly  Ser Phe Phe Leu Tyr  Ser Lys Leu
    1400                1405                1410

Thr Val  Asp Lys Ser Arg Trp  Gln Gln Gly Asn Val  Phe Ser Cys
    1415                1420                1425

Ser Val  Met His Glu Ala Leu  His Asn His Tyr Thr  Gln Lys Ser
    1430                1435                1440

Leu Ser  Leu Ser Pro Gly Lys
    1445                1450
```

```
<210> SEQ ID NO 50
<211> LENGTH: 1449
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 50

atgttggggg cccgcctcag gctctgggtc tgtgccttgt gcagcgtctg cagcatgagc      60

gtcctcagag cctatcccaa tgcctcccca ctgctcggct ccagctgggg tggcctgatc     120

cacctgtaca cagccacagc caggaacagc taccacctgc agatccacaa gaatggccat     180

gtggatggcg caccccatca gaccatctac agtgccctga tgatcagatc agaggatgct     240

ggctttgtgg tgattacagg tgtgatgagc agaagatacc tctgcatgga tttcagaggc     300

aacatttttg gatcacacta tttcgacccg gagaactgca ggttccaaca ccagacgctg     360

gaaaacgggt acgacgtcta ccactctcct cagtatcact tcctggtcag tctgggccgg     420

gcgaagagag ccttcctgcc aggcatgaac ccaccccgt actcccagtt cctgtcccgg      480

aggaacgaga tcccctaat tcacttcaac accccatac cacggcggca cacccagagc       540

gccgaggacg actcggagcg ggacccccctg aacgtgctga agccccgggc ccggatgacc    600

ccggccccgg cctcctgttc acaggagctc ccgagcgccg aggacaacag cccgatggcc     660

agtgacccat taggggtggt caggggcggt cgagtgaaca cgcacgctgg gggaacgggc     720
```

```
ccggaaggct gccgcccctt cgccaagttc atcggaggtg gaggttcaaa aacccacacg    780

tgtcctcctt gtcctgcccc agaagcagca ggtggtccat cagtttttct tttccctccc    840

aaacccaagg atacgctgat gatctctcgc acgcctgagg tgacatgcgt cgtagtagac    900

gtgagccacg aagatcccga ggtgaagttc aattggtatg tggacggagt agaagtgcat    960

aacgcgaaaa ctaagccgcg cgaggaacaa tataacagta cttacagggt ggtatccgtg   1020

ctcacagtcc tgcaccagga ctggctgaac ggtaaggaat acaagtgcaa agtaagcaac   1080

aaggcacttc ccgcgcctat tgagaaaaca atctccaagg cgaagggaca accaagagaa   1140

cctcaggttt acactctccc gccttccagg gaagagatga ccaaaaatca agtttccctg   1200

acttgcctcg tcaaaggatt ctacccttcc gacattgctg ttgaatggga aagcaatgga   1260

caaccagaga acaactacaa gacaacaccc ccggtgctgg atagtgacgg atctttcttt   1320

ctctactcaa agctgaccgt ggataagtcc aggtggcagc agggaaacgt gttttcctgc   1380

tctgtcatgc atgaagcgct gcataatcac tatacccaga agtctctgag cttgagccca   1440

ggcaagtaa                                                           1449
```

```
<210> SEQ ID NO 51
<211> LENGTH: 482
<212> TYPE: PRT
<213> ORGANISM: Artificial Sequence
<220> FEATURE:
<223> OTHER INFORMATION: Description of Artificial Sequence: Synthetic
      fusion polypeptide derived from human

<400> SEQUENCE: 51

Met Leu Gly Ala Arg Leu Arg Leu Trp Val Cys Ala Leu Cys Ser Val
1               5                   10                  15

Cys Ser Met Ser Val Leu Arg Ala Tyr Pro Asn Ala Ser Pro Leu Leu
            20                  25                  30

Gly Ser Ser Trp Gly Gly Leu Ile His Leu Tyr Thr Ala Thr Ala Arg
        35                  40                  45

Asn Ser Tyr His Leu Gln Ile His Lys Asn Gly His Val Asp Gly Ala
    50                  55                  60

Pro His Gln Thr Ile Tyr Ser Ala Leu Met Ile Arg Ser Glu Asp Ala
65                  70                  75                  80

Gly Phe Val Val Ile Thr Gly Val Met Ser Arg Arg Tyr Leu Cys Met
                85                  90                  95

Asp Phe Arg Gly Asn Ile Phe Gly Ser His Tyr Phe Asp Pro Glu Asn
            100                 105                 110

Cys Arg Phe Gln His Gln Thr Leu Glu Asn Gly Tyr Asp Val Tyr His
        115                 120                 125

Ser Pro Gln Tyr His Phe Leu Val Ser Leu Gly Arg Ala Lys Arg Ala
    130                 135                 140

Phe Leu Pro Gly Met Asn Pro Pro Pro Tyr Ser Gln Phe Leu Ser Arg
145                 150                 155                 160

Arg Asn Glu Ile Pro Leu Ile His Phe Asn Thr Pro Ile Pro Arg Arg
                165                 170                 175

His Thr Gln Ser Ala Glu Asp Asp Ser Glu Arg Asp Pro Leu Asn Val
            180                 185                 190

Leu Lys Pro Arg Ala Arg Met Thr Pro Ala Pro Ala Ser Cys Ser Gln
        195                 200                 205

Glu Leu Pro Ser Ala Glu Asp Asn Ser Pro Met Ala Ser Asp Pro Leu
    210                 215                 220
```

```
Gly Val Val Arg Gly Gly Arg Val Asn Thr His Ala Gly Gly Thr Gly
225                 230                 235                 240

Pro Glu Gly Cys Arg Pro Phe Ala Lys Phe Ile Gly Gly Gly Gly Ser
                245                 250                 255

Lys Thr His Thr Cys Pro Pro Cys Pro Ala Pro Glu Ala Ala Gly Gly
            260                 265                 270

Pro Ser Val Phe Leu Phe Pro Pro Lys Pro Lys Asp Thr Leu Met Ile
        275                 280                 285

Ser Arg Thr Pro Glu Val Thr Cys Val Val Val Asp Val Ser His Glu
    290                 295                 300

Asp Pro Glu Val Lys Phe Asn Trp Tyr Val Asp Gly Val Glu Val His
305                 310                 315                 320

Asn Ala Lys Thr Lys Pro Arg Glu Glu Gln Tyr Asn Ser Thr Tyr Arg
                325                 330                 335

Val Val Ser Val Leu Thr Val Leu His Gln Asp Trp Leu Asn Gly Lys
            340                 345                 350

Glu Tyr Lys Cys Lys Val Ser Asn Lys Ala Leu Pro Ala Pro Ile Glu
        355                 360                 365

Lys Thr Ile Ser Lys Ala Lys Gly Gln Pro Arg Glu Pro Gln Val Tyr
    370                 375                 380

Thr Leu Pro Pro Ser Arg Glu Glu Met Thr Lys Asn Gln Val Ser Leu
385                 390                 395                 400

Thr Cys Leu Val Lys Gly Phe Tyr Pro Ser Asp Ile Ala Val Glu Trp
                405                 410                 415

Glu Ser Asn Gly Gln Pro Glu Asn Asn Tyr Lys Thr Thr Pro Pro Val
            420                 425                 430

Leu Asp Ser Asp Gly Ser Phe Phe Leu Tyr Ser Lys Leu Thr Val Asp
        435                 440                 445

Lys Ser Arg Trp Gln Gln Gly Asn Val Phe Ser Cys Ser Val Met His
    450                 455                 460

Glu Ala Leu His Asn His Tyr Thr Gln Lys Ser Leu Ser Leu Ser Pro
465                 470                 475                 480

Gly Lys
```

<210> SEQ ID NO 52
<211> LENGTH: 1422
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 52

```
atgttggggg cccgcctcag gctctgggtc tgtgccttgt gcagcgtctg cagcatgagc      60

gtcctcagag cctatcccaa tgcctcccca ctgctcggct ccagctgggg tggcctgatc     120

cacctgtaca cagccacagc caggaacagc taccacctgc agatccacaa gaatggccat     180

gtggatggcg caccccatca gaccatctac agtgccctga tgatcagatc agaggatgct     240

ggctttgtgg tgattacagg tgtgatgagc agaagatacc tctgcatgga tttcagaggc     300

aacatttttg gatcacacta tttcgacccg gagaactgca ggttccaaca ccagacgctg     360

gaaaacgggt acgacgtcta ccactctcct cagtatcact tcctggtcag tctgggccgg     420

gcgaagagag ccttcctgcc aggcatgaac ccacccccgt actcccagtt cctgtcccgg     480

aggaacgaga tcccccctaat tcacttcaac acccccatac cacggcggca cacccagagc     540
```

```
gccgaggacg actcggagcg ggaccccctg aacgtgctga agccccgggc ccggatgacc    600

ccggccccgg cctcctgttc acaggagctc ccgagcgccg aggacaacag cccgatggcc    660

agtgacccat taggggtggt caggggcggt cgagtgaaca cgcacgctgg gggaacgggc    720

ccggaaggct gccgcccctt cgccaagttc atcggaggtg gaggttcagc cccagaagca    780

gcaggtggtc catcagtttt tcttttccct cccaaaccca aggatacgct gatgatctct    840

cgcacgcctg aggtgacatg cgtcgtagta gacgtgagcc acgaagatcc cgaggtgaag    900

ttcaattggt atgtggacgg agtagaagtg cataacgcga aaactaagcc gcgcgaggaa    960

caatataaca gtacttacag ggtggtatcc gtgctcacag tcctgcacca ggactggctg   1020

aacggtaagg aatacaagtg caaagtaagc aacaaggcac ttcccgcgcc tattgagaaa   1080

acaatctcca aggcgaaggg acaaccaaga gaacctcagg tttacactct cccgccttcc   1140

agggaagaga tgaccaaaaa tcaagtttcc ctgacttgcc tcgtcaaagg attctaccct   1200

tccgacattg ctgttgaatg ggaaagcaat ggacaaccag agaacaacta caagacaaca   1260

cccccggtgc tggatagtga cggatctttc tttctctact caaagctgac cgtggataag   1320

tccaggtggc agcagggaaa cgtgttttcc tgctctgtca tgcatgaagc gctgcataat   1380

cactataccc agaagtctct gagcttgagc ccaggcaagt aa                      1422
```

<210> SEQ ID NO 53
<211> LENGTH: 473
<212> TYPE: PRT
<213> ORGANISM: Artificial Sequence
<220> FEATURE:
<223> OTHER INFORMATION: Description of Artificial Sequence: Synthetic fusion polypeptide derived from human

<400> SEQUENCE: 53

```
Met Leu Gly Ala Arg Leu Arg Leu Trp Val Cys Ala Leu Cys Ser Val
1               5                   10                  15

Cys Ser Met Ser Val Leu Arg Ala Tyr Pro Asn Ala Ser Pro Leu Leu
            20                  25                  30

Gly Ser Ser Trp Gly Gly Leu Ile His Leu Tyr Thr Ala Thr Ala Arg
        35                  40                  45

Asn Ser Tyr His Leu Gln Ile His Lys Asn Gly His Val Asp Gly Ala
    50                  55                  60

Pro His Gln Thr Ile Tyr Ser Ala Leu Met Ile Arg Ser Glu Asp Ala
65                  70                  75                  80

Gly Phe Val Val Ile Thr Gly Val Met Ser Arg Arg Tyr Leu Cys Met
                85                  90                  95

Asp Phe Arg Gly Asn Ile Phe Gly Ser His Tyr Phe Asp Pro Glu Asn
            100                 105                 110

Cys Arg Phe Gln His Gln Thr Leu Glu Asn Gly Tyr Asp Val Tyr His
        115                 120                 125

Ser Pro Gln Tyr His Phe Leu Val Ser Leu Gly Arg Ala Lys Arg Ala
    130                 135                 140

Phe Leu Pro Gly Met Asn Pro Pro Pro Tyr Ser Gln Phe Leu Ser Arg
145                 150                 155                 160

Arg Asn Glu Ile Pro Leu Ile His Phe Asn Thr Pro Ile Pro Arg Arg
                165                 170                 175

His Thr Gln Ser Ala Glu Asp Asp Ser Glu Arg Asp Pro Leu Asn Val
            180                 185                 190

Leu Lys Pro Arg Ala Arg Met Thr Pro Ala Pro Ala Ser Cys Ser Gln
        195                 200                 205
```

```
Glu Leu Pro Ser Ala Glu Asp Asn Ser Pro Met Ala Ser Asp Pro Leu
    210                 215                 220

Gly Val Val Arg Gly Gly Arg Val Asn Thr His Ala Gly Gly Thr Gly
225                 230                 235                 240

Pro Glu Gly Cys Arg Pro Phe Ala Lys Phe Ile Gly Gly Gly Gly Ser
                245                 250                 255

Ala Pro Glu Ala Ala Gly Gly Pro Ser Val Phe Leu Phe Pro Pro Lys
            260                 265                 270

Pro Lys Asp Thr Leu Met Ile Ser Arg Thr Pro Glu Val Thr Cys Val
        275                 280                 285

Val Val Asp Val Ser His Glu Asp Pro Glu Val Lys Phe Asn Trp Tyr
    290                 295                 300

Val Asp Gly Val Glu Val His Asn Ala Lys Thr Lys Pro Arg Glu Glu
305                 310                 315                 320

Gln Tyr Asn Ser Thr Tyr Arg Val Val Ser Val Leu Thr Val Leu His
                325                 330                 335

Gln Asp Trp Leu Asn Gly Lys Glu Tyr Lys Cys Lys Val Ser Asn Lys
            340                 345                 350

Ala Leu Pro Ala Pro Ile Glu Lys Thr Ile Ser Lys Ala Lys Gly Gln
        355                 360                 365

Pro Arg Glu Pro Gln Val Tyr Thr Leu Pro Pro Ser Arg Glu Glu Met
    370                 375                 380

Thr Lys Asn Gln Val Ser Leu Thr Cys Leu Val Lys Gly Phe Tyr Pro
385                 390                 395                 400

Ser Asp Ile Ala Val Glu Trp Glu Ser Asn Gly Gln Pro Glu Asn Asn
                405                 410                 415

Tyr Lys Thr Thr Pro Pro Val Leu Asp Ser Asp Gly Ser Phe Phe Leu
            420                 425                 430

Tyr Ser Lys Leu Thr Val Asp Lys Ser Arg Trp Gln Gln Gly Asn Val
        435                 440                 445

Phe Ser Cys Ser Val Met His Glu Ala Leu His Asn His Tyr Thr Gln
    450                 455                 460

Lys Ser Leu Ser Leu Ser Pro Gly Lys
465                 470


<210> SEQ ID NO 54
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 54

His His His His His His
1               5
```